United States Patent
Poss et al.

(10) Patent No.: US 9,492,460 B2
(45) Date of Patent: Nov. 15, 2016

(54) CARBAZOLE COMPOUNDS USEFUL AS BROMODOMAIN INHIBITORS

(71) Applicant: Bristol-Myers Squibb Company, Princeton, NJ (US)

(72) Inventors: Michael A. Poss, Lawrenceville, NJ (US); David R. Tortolani, Skillman, NJ (US); Dharmpal S. Dodd, Princeton, NJ (US); Christopher P. Mussari, Princeton, NJ (US); John S. Tokarski, Princeton, NJ (US); Ashvinikumar V. Gavai, Princeton Junction, NJ (US); Yufen Zhao, Pennington, NJ (US); George V. Delucca, Pennington, NJ (US); Daniel O'Malley, New Hope, PA (US); Derek J. Norris, Pennington, NJ (US); Patrice Gill, Levittown, PA (US); Claude A. Quesnelle, Skillman, NJ (US); Wen-Ching Han, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/190,477

(22) Filed: Feb. 26, 2014

(65) Prior Publication Data

US 2014/0256700 A1 Sep. 11, 2014

Related U.S. Application Data

(60) Provisional application No. 61/769,996, filed on Feb. 27, 2013.

(51) Int. Cl.
| | |
|---|---|
| C07D 405/14 | (2006.01) |
| C07D 413/14 | (2006.01) |
| C07D 417/14 | (2006.01) |
| A61K 31/553 | (2006.01) |
| C07D 413/04 | (2006.01) |
| A61K 31/4192 | (2006.01) |
| A61K 31/422 | (2006.01) |
| A61K 31/427 | (2006.01) |
| A61K 31/454 | (2006.01) |
| A61K 31/496 | (2006.01) |
| A61K 31/5355 | (2006.01) |
| A61K 31/5377 | (2006.01) |
| A61K 31/541 | (2006.01) |

(52) U.S. Cl.
CPC ......... *A61K 31/553* (2013.01); *A61K 31/4192* (2013.01); *A61K 31/422* (2013.01); *A61K 31/427* (2013.01); *A61K 31/454* (2013.01); *A61K 31/496* (2013.01); *A61K 31/5355* (2013.01); *A61K 31/5377* (2013.01); *A61K 31/541* (2013.01); *C07D 405/14* (2013.01); *C07D 413/04* (2013.01); *C07D 413/14* (2013.01); *C07D 417/14* (2013.01)

(58) Field of Classification Search
CPC .................................................. C07D 405/14
See application file for complete search history.

(56) References Cited

U.S. PATENT DOCUMENTS

| | | |
|---|---|---|
| 6,177,440 B1 | 1/2001 | Bach et al. |
| 2003/0129448 A1 | 7/2003 | Lin et al. |
| 2012/0071668 A1 | 3/2012 | Suzuki et al. |
| 2013/0026426 A1 | 1/2013 | Harada et al. |

FOREIGN PATENT DOCUMENTS

WO   WO 2010/080474   7/2010

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*
Purandare, et al. Document No. 153:204322, 2010, retrieved from CAPLUS.*
•Demont, et al., Med. Chem. Lett., 5, 2014, 1190-1195.*
Kikugawa, Y. et al., Journal of Organic Chemistry, vol. 66, No. 25, pp. 8612-8615 (2001).
Hewlins, et al., Journal of Chemical Research, vol. 8, pp. 2645-2696 (1986).

* cited by examiner

*Primary Examiner* — Shawquia Jackson
(74) *Attorney, Agent, or Firm* — Elliott Korsen

(57) ABSTRACT

The present invention is directed to carbazole compounds, pharmaceutically acceptable compositions comprising compounds of the invention and methods of using said compositions in the treatment of various disorders.

15 Claims, 1 Drawing Sheet

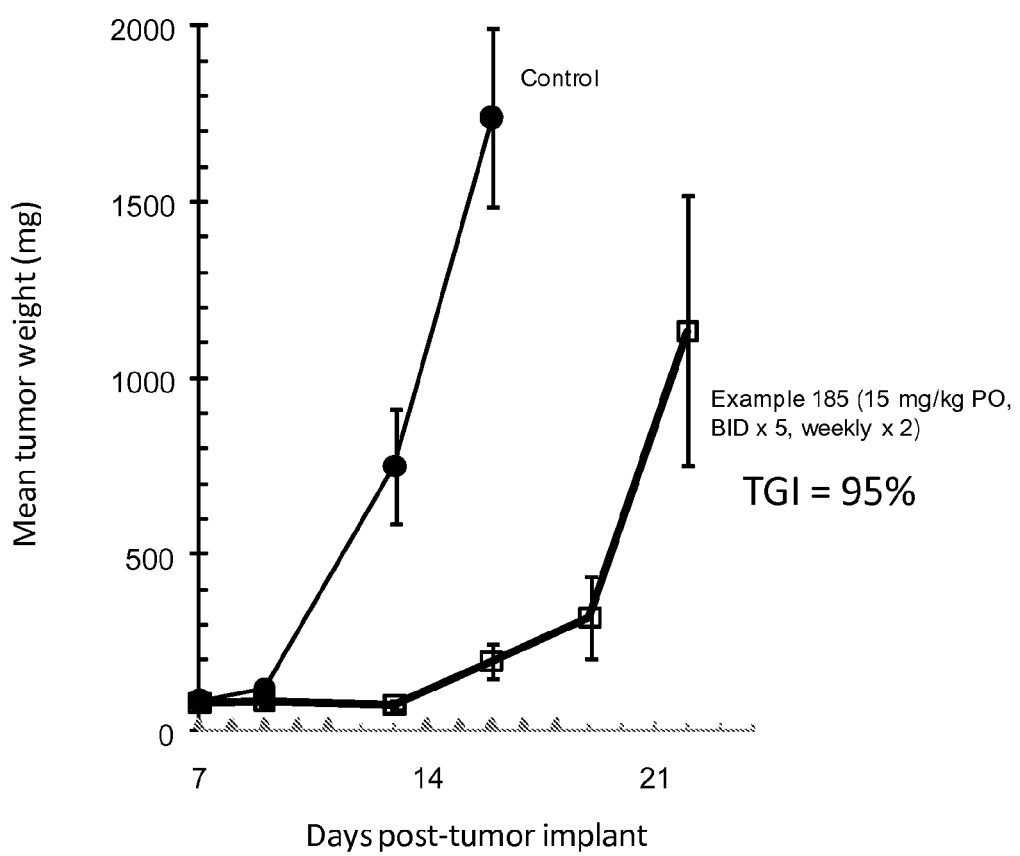

SEQUENCE LISTING

<160> NUMBER OF SEQ ID NOS: 3

<210> SEQ ID NO 1
<211> LENGTH: 21
<212> TYPE: PRT
<213> ORGANISM: Tobacco vein mottling virus

<400> SEQUENCE: 1

Met Gly Ser Ser His His His His His His Ser Ser Gly Glu Thr Val
1               5                   10                  15

Arg Phe Gln Ser Met
            20

<210> SEQ ID NO 2
<211> LENGTH: 39
<212> TYPE: PRT
<213> ORGANISM: Tobacco vein mottling virus

```
-continued

<400> SEQUENCE: 2

Met Gly Ser Ser His His His His His His Ser Ser Gly Glu Thr Val
1               5                   10                  15

Arg Phe Gln Gly Leu Asn Asp Ile Phe Glu Ala Gln Lys Ile Glu Trp
                20                  25                  30

His Glu Asp Thr Gly His Met
            35

<210> SEQ ID NO 3
<211> LENGTH: 21
<212> TYPE: PRT
<213> ORGANISM: Artificial Sequence
<220> FEATURE:
<223> OTHER INFORMATION: Biotinylated histone peptide
<220> FEATURE:
<221> NAME/KEY: MOD_RES
<222> LOCATION: (5)..(5)
<223> OTHER INFORMATION: ACETYLATION
<220> FEATURE:
<221> NAME/KEY: MOD_RES
<222> LOCATION: (8)..(8)
<223> OTHER INFORMATION: ACETYLATION
<220> FEATURE:
<221> NAME/KEY: MOD_RES
<222> LOCATION: (12)..(12)
<223> OTHER INFORMATION: ACETYLATION
<220> FEATURE:
<221> NAME/KEY: MOD_RES
<222> LOCATION: (16)..(16)
<223> OTHER INFORMATION: ACETYLATION

<400> SEQUENCE: 3

Ser Gly Arg Gly Lys Gly Gly Lys Gly Leu Gly Lys Gly Gly Ala Lys
1               5                   10                  15

Arg His Arg Lys Val
            20
```

CARBAZOLE COMPOUNDS USEFUL AS BROMODOMAIN INHIBITORS

This application claims priority from U.S. Provisional Application No. 61/769,996 filed Feb. 27, 2013, the disclosures of which are incorporated herein by reference in their entirety.

FIELD OF THE INVENTION

The invention relates to compounds, pharmaceutical compositions comprising the compounds and to their use in therapy.

BACKGROUND OF THE INVENTION

The genomes of eukaryotic organisms are highly organized within the nucleus of the cell. The long strands of duplex DNA are wrapped around an octomer of histone proteins to form a nucleosome. This basic unit is then further compressed by the aggregation and folding of nucleosomes to form a highly condensed chromatin structure. A range of different states of condensation are possible, and the tightness of this structure varies during the cell cycle, being most compact during the process of cell division. There has been appreciation recently that chromatin templates form a fundamentally important set of gene control mechanisms referred to as epigenetic regulation. By conferring a wide range of specific chemical modifications to histones and DNA (such as acetylation, methylation, phosphorylation, ubiquitinylation and SUMOylation) epigenetic regulators modulate the structure, function and accessibility of our genome, thereby exerting a huge impact in gene expression.

Histone acetylation is most usually associated with the activation of gene transcription, as the modification loosens the interaction of the DNA and the histone octomer by changing the electrostatics. In addition to this physical change, specific proteins bind to acetylated lysine residues within histones to read the epigenetic code. Bromodomains are small (~110 amino acid) distinct domains within proteins that bind to acetylated lysine resides commonly but not exclusively in the context of histones. There is a family of around 50 proteins known to contain bromodomains, and they have a range of functions within the cell. The BET family of bromodomain containing proteins comprises 4 proteins (BRD2, BRD3, BRD4 and BRD-T) which contain tandem bromodomains capable of binding to two acetylated lysine residues in close proximity, increasing tile specificity of the interaction.

BRD2 and BRD3 are reported to associate with histones along actively transcribed genes and may be involved in facilitating transcriptional elongation (Leroy et al, Mol. Cell. 2008 30(1):51-60), while BRD4 appears to be involved in the recruitment of the pTEF-13 complex to inducible genes, resulting in phosphorylation of RNA polymerase and increased transcriptional output (Hargreaves et al, Cell, 2009 138(1): 1294145). All family members have been reported to have some function in controlling or executing aspects of the cell cycle, and have been shown to remain in complex with chromosomes during cell division—suggesting a role in the maintenance of epigenetic memory. In addition some viruses make use of these proteins to tether their genomes to the host cell chromatin, as part of the process of viral replication (You et al Cell, 2004 117(3):349-60).

Recent articles relating to this target include Prinjha et al., Trends in Pharmacological Sciences, March 2012, Vol. 33, No. 3, pp. 146-153; Conway, ACS Med. Chem. Lett., 2012, 3, 691-694 and Hewings et al., J. Med. Chem., 2012, 55, 9393-9413.

Small molecule BET inhibitors that are reported to be in development include GSK-525762 A, OTX-015 as well as others from the University of Oxford and Constellation Pharmaceuticals Inc.

Hundreds of epigenetic effectors have been identified, many of which are chromatin-binding proteins or chromatin-modifying enzymes. These proteins have been associated with a variety of disorders such as neurodegenerative disorders, metabolic diseases, inflammation and cancer. Thus, these compounds which inhibit the binding of a bromodomain with its cognate acetylated proteins, promise new approaches in the treatment of a range of autoimmune and inflammatory diseases or conditions and in the treatment of various types of cancer.

SUMMARY OF THE INVENTION

In a first aspect of the present invention, there is provided a compound of formula (I)

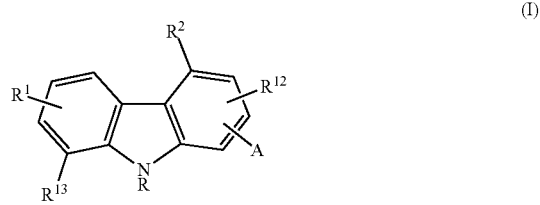

(I)

wherein:

A is optionally substituted heteroaryl or optionally substituted heterocyclo, wherein the substituents are one or more $R^{14}$, $R^{15}$ or $R^{16}$;

R is hydrogen, optionally substituted $(C_1-C_6)$alkyl, optionally substituted $(C_3-C_8)$cycloalkyl$(C_1-C_6)$alkyl, optionally substituted aryl$(C_1-C_6)$alkyl, optionally substituted heteroaryl$(C_1-C_6)$alkyl, optionally substituted heterocyclo$(C_1-C_6)$alkyl, optionally substituted $(C_1-C_6)$alkyl-CO—, optionally substituted aryl-CO—, optionally substituted $(C_3-C_8)$cycloalkyl-CO—, optionally substituted heteroaryl, optionally substituted heterocyclo-CO—, optionally substituted aryl-$SO_2$—, optionally substituted $(C_1-C_6)$alkyl-$SO_2$—, optionally substituted $(C_3-C_8)$cycloalkyl-$SO_2$—, optionally substituted heteroaryl-$SO_2$—, optionally substituted $(C_1-C_6)$alkyl-OCO— or optionally substituted $(C_3-C_8)$cycloalkyl-OCO—; or R is

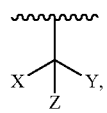

wherein

X and Y are independently selected from hydrogen, optionally substituted $(C_1-C_6)$alkyl, optionally substituted $(C_3-C_8)$cycloalkyl, optionally substituted aryl, optionally substituted heteroaryl or optionally substituted heterocyclo;

Z is hydrogen, halogen, —OH, $(C_1-C_6)$alkyl, $(C_1-C_6)$alkoxy, —$NR^3R^4$, —$CONR^3R^4$, —$OCONR^3R^4$, —$NR^6OCOR^3$, —$NR^6CONR^3R^4$, —$NR^6SO_2NR^3R^4$ or —$NR^6SO_2R^4$;

$R^1$ is halogen, —CN, OH, —NR$^3$R$^4$, —CONR$^3$R$^4$, —COOH, —OCONR$^3$R$^4$, —NHOCOR$^7$, —NHCONR$^7$R$^8$, —NHSO$_2$NR$^7$R$^8$, optionally substituted (C$_1$-C$_6$)alkyl, optionally substituted (C$_2$-C$_6$)alkenyl, optionally substituted (C$_2$-C$_6$)alkynyl, optionally substituted (C$_1$-C$_6$)alkoxy, optionally substituted (C$_3$-C$_8$)cycloalkyl, optionally substituted (C$_3$-C$_8$)cycloalkyl-CO—, optionally substituted (C$_3$-C$_8$)cycloalkyl-SO$_2$—, optionally substituted aryl (C$_1$-C$_6$)alkoxy, optionally substituted (C$_3$-C$_8$)cycloalkyl (C$_1$-C$_6$)alkoxy, optionally substituted heterocyclyl-CO—, optionally substituted heterocyclyl, optionally substituted (C$_1$-C$_6$)alkyl-SO$_2$—, —NHSO$_2$-optionally substituted (C$_1$-C$_6$)alkyl, —NHSO$_2$-optionally substituted heterocyclo, optionally substituted (C$_1$-C$_6$)alkyl-NHSO$_2$— or optionally substituted heterocyclo-NHSO$_2$—;

$R^2$ is H, halogen, —CN, —COOH, —CONR$^7$R$^8$, —NHCOR$^3$R$^4$, —OCONR$^3$R$^4$, —NHCOOR$^3$R$^4$, optionally substituted (C$_1$-C$_6$)alkyl, optionally substituted (C$_2$-C$_6$)alkynyl, optionally substituted (C$_1$-C$_6$)alkoxy, optionally substituted heteroaryl or optionally substituted heterocyclo;

$R^3$ is hydrogen, optionally substituted (C$_1$-C$_6$)alkyl, optionally substituted (C$_3$-C$_8$)cycloalkyl, optionally substituted (C$_2$-C$_6$)alkenyl, optionally substituted (C$_2$-C$_6$)alkynyl, cyano(C$_1$-C$_6$)alkyl, hydroxy(C$_1$-C$_6$)alkyl, optionally substituted aryl, optionally substituted aryl(C$_1$-C$_6$)alkyl, optionally substituted aryloxy(C$_1$-C$_6$)alkyl, optionally substituted (C$_1$-C$_6$)alkyl-SO$_2$—, optionally substituted heterocyclyl, optionally substituted heterocyclyl(C$_1$-C$_6$)alkyl, optionally substituted heteroaryl or optionally substituted heteroaryl (C$_1$-C$_6$)alkyl, $R^4$ is hydrogen, optionally substituted (C$_1$-C$_6$)alkyl or optionally substituted (C$_3$-C$_8$)cycloalkyl;

or $R^3$ and $R^4$ may be taken together with the nitrogen atom to which they are attached to form an optionally substituted (C$_4$-C$_8$)heteroaryl or (C$_4$-C$_8$)heterocyclic ring;

$R^6$ is hydrogen or optionally substituted (C$_1$-C$_6$)alkyl;

$R^7$ and $R^8$ are independently hydrogen, optionally substituted (C$_1$-C$_6$)alkyl, optionally substituted (C$_3$-C$_8$)cycloalkyl, optionally substituted (C$_2$-C$_6$)alkenyl, optionally substituted (C$_2$-C$_6$)alkynyl, cyano(C$_1$-C$_6$)alkyl, hydroxy(C$_1$-C$_6$)alkyl, optionally substituted aryl, optionally substituted aryl(C$_1$-C$_6$)alkyl, optionally substituted aryloxy(C$_1$-C$_6$)alkyl, optionally substituted (C$_1$-C$_6$)alkyl-SO$_2$—, optionally substituted heterocyclyl, optionally substituted heterocyclyl(C$_1$-C$_6$)alkyl, optionally substituted heteroaryl or optionally substituted heteroaryl(C$_1$-C$_6$)alkyl;

or $R^7$ and $R^8$ may be taken together with the nitrogen atom to which they are attached to form an optionally substituted (C$_4$-C$_8$)heteroaryl or (C$_4$-C$_8$)heterocyclic ring;

$R^{12}$ and $R^{13}$ are independently hydrogen, halogen, —CN, OH, —CONR$^3$R$^4$, —NHCOOR$^4$, —NHCONR$^3$R$^4$, —NHCOR$^4$, —NHSO$_2$R$^7$, —SO$_2$NR$^3$R$^4$, —NHSO$_2$NR$^3$R$^4$, —SO$_2$R$^7$, optionally substituted (C$_1$-C$_6$)alkyl, optionally substituted (C$_3$-C$_8$)cycloalkyl, optionally substituted (C$_1$-C$_6$)alkoxy, optionally substituted aryl, optionally substituted heteroaryl or optionally substituted heterocyclo;

$R^{14}$ is hydrogen, optionally substituted (C$_1$-C$_6$)alkyl, (C$_1$-C$_6$)alkoxy, halogen, —CN, —NR$^3$R$^4$, OH, —NHOCOR$^7$, —OCONR$^7$R$^8$, —NHCONR$^7$R$^8$ or —CF$_3$;

$R^{15}$ is hydrogen, optionally substituted (C$_1$-C$_6$)alkyl, (C$_1$-C$_6$)alkoxy, halogen, —CN, —NR$^3$R$^4$, OH, —NHOCOR$^7$, —OCONR$^7$R$^8$, —NHCONR$^7$R$^8$ or —CF$_3$;

$R^{16}$ is hydrogen, optionally substituted (C$_1$-C$_6$)alkyl, (C$_1$-C$_6$)alkoxy, halogen, —CN, —NR$^3$R$^4$, OH, —NHOCOR$^7$, —OCONR$^7$R$^8$, —NHCONR$^7$R$^8$ or —CF$_3$;

with the proviso that only one of $R^{14}$, $R^{15}$ and $R^{16}$ is hydrogen;

and/or a pharmaceutically acceptable salt, tautomer or stereoisomer thereof.

In another aspect, there is provided a pharmaceutical composition comprising a compound of the invention or a pharmaceutically acceptable salt thereof and one or more pharmaceutically acceptable carriers, diluents or excipients.

In another aspect, there is provided a compound of the invention or a pharmaceutically acceptable salt thereof for use in therapy. In particular, for use in the treatment of a disease or condition for which a bromodomain inhibitor is indicated.

In another aspect, there is provided a method of treating autoimmune and inflammatory diseases or conditions which comprises administering to a subject in need thereof a therapeutically effective amount of a bromodomain inhibitor.

In another aspect of the present invention, there is provided a method for treating a bromodomain-containing protein mediated disorder in a patient in need thereof, comprising the step of administering to said patient a compound of the invention.

BRIEF DESCRIPTION OF THE DRAWINGS

The invention is illustrated by reference to the accompanying drawings described below.

FIG. 1 shows the antitumor efficacy of Example 185 against the H187 Human Small Cell Lung Carcinoma.

DETAILED DESCRIPTION OF THE INVENTION

In a first aspect of the present invention, there is provided a compound of formula (I)

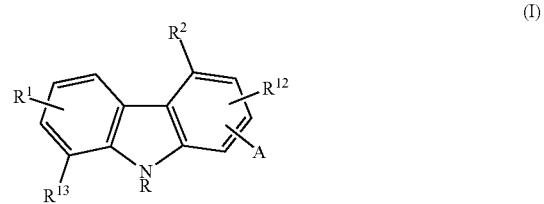

wherein:

A is optionally substituted heteroaryl or optionally substituted heterocyclo, wherein the substituents are one or more $R^{14}$, $R^{15}$ or $R^{16}$;

R is hydrogen, optionally substituted (C$_1$-C$_6$)alkyl, optionally substituted (C$_3$-C$_8$)cycloalkyl(C$_1$-C$_6$)alkyl, optionally substituted aryl(C$_1$-C$_6$)alkyl, optionally substituted heteroaryl(C$_1$-C$_6$)alkyl, optionally substituted heterocyclo(C$_1$-C$_6$)alkyl, optionally substituted (C$_1$-C$_6$)alkyl-CO—, optionally substituted aryl-CO—, optionally substituted (C$_3$-C$_8$)cycloalkyl-CO—, optionally substituted heteroaryl, optionally substituted heterocyclo-CO—, optionally substituted aryl-SO$_2$—, optionally substituted (C$_1$-C$_6$)alkyl-SO$_2$—, optionally substituted (C$_3$-C$_8$)cycloalkyl-SO$_2$—, optionally substituted heteroaryl-SO$_2$—, optionally substituted (C$_1$-C$_6$)alkyl-OCO— or optionally substituted (C$_3$-C$_8$)cycloalkyl-OCO—; or R is

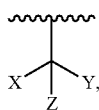

wherein

X and Y are independently selected from hydrogen, optionally substituted ($C_1$-$C_6$)alkyl, optionally substituted ($C_3$-$C_8$)cycloalkyl, optionally substituted aryl, optionally substituted heteroaryl or optionally substituted heterocyclo;

Z is hydrogen, halogen, —OH, ($C_1$-$C_6$)alkyl, ($C_1$-$C_6$) alkoxy, —$NR^3R^4$, —$CONR^3R^4$, —$OCONR^3R^4$, —$NR^6OCOR^3$, —$NR^6CONR^3R^4$, —$NR^6SO_2NR^3R^4$ or —$NR^6SO_2R^4$;

$R^1$ is halogen, —CN, OH, —$NR^3R^4$, —$CONR^3R^4$, —COOH, —$OCONR^3R^4$, —$NHOCOR^7$, —$NHCONR^7R^8$, —$NHSO_2NR^7R^8$, optionally substituted ($C_1$-$C_6$)alkyl, optionally substituted ($C_2$-$C_6$)alkenyl, optionally substituted ($C_2$-$C_6$)alkynyl, optionally substituted ($C_1$-$C_6$)alkoxy, optionally substituted ($C_3$-$C_8$)cycloalkyl, optionally substituted ($C_3$-$C_8$)cycloalkyl-CO—, optionally substituted ($C_3$-$C_8$)cycloalkyl-$SO_2$—, optionally substituted aryl ($C_1$-$C_6$) alkoxy, optionally substituted ($C_3$-$C_8$)cycloalkyl ($C_1$-$C_6$) alkoxy, optionally substituted heterocyclyl-CO—, optionally substituted heterocyclyl, optionally substituted ($C_1$-$C_6$)alkyl-$SO_2$—, —$NHSO_2$-optionally substituted ($C_1$-$C_6$)alkyl, —$NHSO_2$-optionally substituted heterocyclo, optionally substituted ($C_1$-$C_6$)alkyl-$NHSO_2$— or optionally substituted heterocyclo-$NHSO_2$—;

$R^2$ is H, halogen, —CN, —COOH, —$CONR^7R^8$, —$NHCOR^3R^4$, —$OCONR^3R^4$, —$NHCOOR^3R^4$, optionally substituted ($C_1$-$C_6$)alkyl, optionally substituted ($C_2$-$C_6$) alkynyl, optionally substituted ($C_1$-$C_6$)alkoxy, optionally substituted heteroaryl or optionally substituted heterocyclo;

$R^3$ is hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy($C_1$-$C_6$)alkyl, optionally substituted aryl, optionally substituted aryl($C_1$-$C_6$)alkyl, optionally substituted aryloxy($C_1$-$C_6$)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl ($C_1$-$C_6$)alkyl, $R^4$ is hydrogen, optionally substituted ($C_1$-$C_6$)alkyl or optionally substituted ($C_3$-$C_8$)cycloalkyl;

or $R^3$ and $R^4$ may be taken together with the nitrogen atom to which they are attached to form an optionally substituted ($C_4$-$C_8$)heteroaryl or ($C_4$-$C_8$)heterocyclic ring;

$R^6$ is hydrogen or optionally substituted ($C_1$-$C_6$)alkyl;

$R^7$ and $R^8$ are independently hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy($C_1$-$C_6$)alkyl, optionally substituted aryl, optionally substituted aryl($C_1$-$C_6$)alkyl, optionally substituted aryloxy($C_1$-$C_6$)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl($C_1$-$C_6$)alkyl;

or $R^7$ and $R^8$ may be taken together with the nitrogen atom to which they are attached to form an optionally substituted ($C_4$-$C_8$)heteroaryl or ($C_4$-$C_8$)heterocyclic ring;

$R^{12}$ and $R^{13}$ are independently hydrogen, halogen, —CN, OH, —$CONR^3R^4$, —$NHCOOR^4$, —$NHCONR^3R^4$, —$NHCOR^4$, —$NHSO_2R^7$, —$SO_2NR^3R^4$, —$NHSO_2NR^3R^4$, —$SO_2R^7$, optionally substituted ($C_1$-$C_6$)alkyl, optionally substituted ($C_3$-$C_8$)cycloalkyl, optionally substituted ($C_1$-$C_6$)alkoxy, optionally substituted aryl, optionally substituted heteroaryl or optionally substituted heterocyclo;

$R^{14}$ is hydrogen, optionally substituted ($C_1$-$C_6$)alkyl, ($C_1$-$C_6$)alkoxy, halogen, —CN, —$NR^3R^4$, OH, —$NHOCOR^7$, —$OCONR^7R^8$, —$NHCONR^7R^8$ or —$CF_3$;

$R^{15}$ is hydrogen, optionally substituted ($C_1$-$C_6$)alkyl, ($C_1$-$C_6$)alkoxy, halogen, —CN, —$NR^3R^4$, OH, —$NHOCOR^7$, —$OCONR^7R^8$, —$NHCONR^7R^8$ or —$CF_3$;

$R^{16}$ is hydrogen, optionally substituted ($C_1$-$C_6$)alkyl, ($C_1$-$C_6$)alkoxy, halogen, —CN, —$NR^3R^4$, OH, —$NHOCOR^7$, —$OCONR^7R^8$, —$NHCONR^7R^8$ or —$CF_3$;

with the proviso that only one of $R^{14}$, $R^{15}$ and $R^{16}$ is hydrogen;

and/or a pharmaceutically acceptable salt, tautomer or stereoisomer thereof.

In a second aspect within the scope of the first aspect of the invention, there is provided a compound of formula (II)

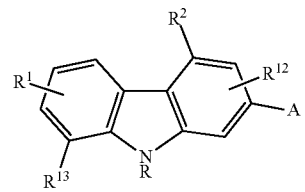

(II)

wherein:

A is optionally substituted heteroaryl or optionally substituted heterocyclo, wherein the substituents are one or more $R^{14}$, $R^{15}$ or $R^{16}$;

R is hydrogen, optionally substituted ($C_1$-$C_6$)alkyl, optionally substituted ($C_3$-$C_8$)cycloalkyl($C_1$-$C_6$)alkyl, optionally substituted aryl($C_1$-$C_6$)alkyl, optionally substituted heteroaryl($C_1$-$C_6$)alkyl, optionally substituted heterocyclo($C_1$-$C_6$)alkyl, optionally substituted ($C_1$-$C_6$)alkyl-CO—, optionally substituted aryl-CO—, optionally substituted ($C_3$-$C_8$)cycloalkyl-CO—, optionally substituted heteroaryl, optionally substituted heterocyclo-CO—, optionally substituted aryl-$SO_2$—, optionally substituted ($C_1$-$C_6$)alkyl-$SO_2$—, optionally substituted ($C_3$-$C_8$)cycloalkyl-$SO_2$—, optionally substituted heteroaryl-$SO_2$—, optionally substituted ($C_1$-$C_6$)alkyl-OCO— or optionally substituted ($C_3$-$C_8$)cycloalkyl-OCO—; or R is

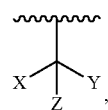

wherein

X and Y are independently selected from hydrogen, optionally substituted ($C_1$-$C_6$)alkyl, optionally substituted ($C_3$-$C_8$)cycloalkyl, optionally substituted aryl, optionally substituted heteroaryl or optionally substituted heterocyclo;

Z is hydrogen, halogen, —OH, ($C_1$-$C_6$)alkyl, ($C_1$-$C_6$) alkoxy, —$NR^3R^4$, —$CONR^3R^4$, —$OCONR^3R^4$, —$NR^6OCOR^3$, —$NR^6CONR^3R^4$, —$NR^6SO_2NR^3R^4$ or —$NR^6SO_2R^4$;

$R^1$ is halogen, —CN, OH, —$NR^3R^4$, —$CONR^3R^4$, —COOH, —$OCONR^3R^4$, —$NHOCOR^7$, —$NHCONR^7R^8$, —$NHSO_2NR^7R^8$, optionally substituted ($C_1$-$C_6$)alkyl, optionally substituted ($C_2$-$C_6$)alkenyl, optionally substituted ($C_2$-$C_6$)alkynyl, optionally substituted ($C_1$-$C_6$)alkoxy, optionally substituted ($C_3$-$C_8$)cycloalkyl, optionally substituted ($C_3$-$C_8$)cycloalkyl-CO—, optionally substituted ($C_3$-$C_8$)cycloalkyl-$SO_2$—, optionally substituted aryl ($C_1$-$C_6$)alkoxy, optionally substituted ($C_3$-$C_8$)cycloalkyl ($C_1$-$C_6$)alkoxy, optionally substituted heterocyclyl-CO—, optionally substituted heterocyclyl, optionally substituted ($C_1$-$C_6$)alkyl-$SO_2$—, —$NHSO_2$-optionally substituted ($C_1$-$C_6$)alkyl, —$NHSO_2$-optionally substituted heterocyclo, optionally substituted ($C_1$-$C_6$)alkyl-$NHSO_2$— or optionally substituted heterocyclo-$NHSO_2$—;

$R^2$ is H, halogen, —CN, —COOH, —$CONR^7R^8$, —$NHCOR^3R^4$, —$OCONR^3R^4$, —$NHCOOR^3R^4$, optionally substituted ($C_1$-$C_6$)alkyl, optionally substituted ($C_2$-$C_6$)alkynyl, optionally substituted ($C_1$-$C_6$)alkoxy, optionally substituted heteroaryl or optionally substituted heterocyclo;

$R^3$ is hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy($C_1$-$C_6$)alkyl, optionally substituted aryl, optionally substituted aryl($C_1$-$C_6$)alkyl, optionally substituted aryloxy($C_1$-$C_6$)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl($C_1$-$C_6$)alkyl, $R^4$ is hydrogen, optionally substituted ($C_1$-$C_6$)alkyl or optionally substituted ($C_3$-$C_8$)cycloalkyl;

or $R^3$ and $R^4$ may be taken together with the nitrogen atom to which they are attached to form an optionally substituted ($C_4$-$C_8$)heteroaryl or ($C_4$-$C_8$)heterocyclic ring;

$R^6$ is hydrogen or optionally substituted ($C_1$-$C_6$)alkyl;

$R^7$ and $R^8$ are independently hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy($C_1$-$C_6$)alkyl, optionally substituted aryl, optionally substituted aryl($C_1$-$C_6$)alkyl, optionally substituted aryloxy($C_1$-$C_6$)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl($C_1$-$C_6$)alkyl;

or $R^7$ and $R^8$ may be taken together with the nitrogen atom to which they are attached to form an optionally substituted ($C_4$-$C_8$)heteroaryl or ($C_4$-$C_8$)heterocyclic ring;

$R^{12}$ and $R^{13}$ are independently hydrogen, halogen, —CN, OH, —$CONR^3R^4$, —$NHCOOR^4$, —$NHCONR^3R^4$, —$NHCOR^4$, —$NHSO_2R^7$, —$SO_2NR^3R^4$, —$NHSO_2NR^3R^4$, —$SO_2R^7$, optionally substituted ($C_1$-$C_6$)alkyl, optionally substituted ($C_3$-$C_8$)cycloalkyl, optionally substituted ($C_1$-$C_6$)alkoxy, optionally substituted aryl, optionally substituted heteroaryl or optionally substituted heterocyclo;

$R^{14}$ is hydrogen, optionally substituted ($C_1$-$C_6$)alkyl, ($C_1$-$C_6$)alkoxy, halogen, —CN, —$NR^3R^4$, OH, —$NHOCOR^7$, —$OCONR^7R^8$, —$NHCONR^7R^8$ or —$CF_3$;

$R^{15}$ is hydrogen, optionally substituted ($C_1$-$C_6$)alkyl, ($C_1$-$C_6$)alkoxy, halogen, —CN, —$NR^3R^4$, OH, —$NHOCOR^7$, —$OCONR^7R^8$, —$NHCONR^7R^8$ or —$CF_3$;

$R^{16}$ is hydrogen, optionally substituted ($C_1$-$C_6$)alkyl, ($C_1$-$C_6$)alkoxy, halogen, —CN, —$NR^3R^4$, OH, —$NHOCOR^7$, —$OCONR^7R^8$, —$NHCONR^7R^8$ or —$CF_3$;

with the proviso that only one of $R^{14}$, $R^{15}$ and $R^{16}$ is hydrogen;

and/or a pharmaceutically acceptable salt, tautomer or stereoisomer thereof.

In a third aspect within the scope of the first and second aspects of the invention, there is provided a compound of formula (III)

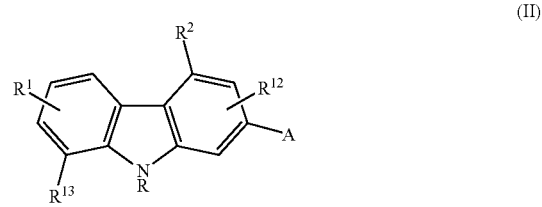

(II)

wherein:

A is optionally substituted heteroaryl or optionally substituted heterocyclo, wherein the substituents are one or more $R^{14}$, $R^{15}$ or $R^{16}$;

R is hydrogen, optionally substituted ($C_1$-$C_6$)alkyl, optionally substituted ($C_3$-$C_8$)cycloalkyl($C_1$-$C_6$)alkyl, optionally substituted aryl($C_1$-$C_6$)alkyl, optionally substituted heteroaryl($C_1$-$C_6$)alkyl, optionally substituted heterocyclo($C_1$-$C_6$)alkyl, optionally substituted ($C_1$-$C_6$)alkyl-CO—, optionally substituted aryl-CO—, optionally substituted ($C_3$-$C_8$)cycloalkyl-CO—, optionally substituted heteroaryl, optionally substituted heterocyclo-CO—, optionally substituted aryl-$SO_2$—, optionally substituted ($C_1$-$C_6$)alkyl-$SO_2$—, optionally substituted ($C_3$-$C_8$)cycloalkyl-$SO_2$—, optionally substituted heteroaryl-$SO_2$—, optionally substituted ($C_1$-$C_6$)alkyl-OCO— or optionally substituted ($C_3$-$C_8$)cycloalkyl-OCO—; or R is

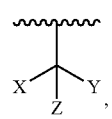

wherein

X and Y are independently selected from hydrogen, optionally substituted ($C_1$-$C_6$)alkyl, optionally substituted ($C_3$-$C_8$)cycloalkyl, optionally substituted aryl, optionally substituted heteroaryl or optionally substituted heterocyclo;

Z is hydrogen, halogen, —OH, ($C_1$-$C_6$)alkyl, ($C_1$-$C_6$)alkoxy, —$NR^3R^4$, —$CONR^3R^4$, —$OCONR^3R^4$, —$NR^6OCOR^3$, —$NR^6CONR^3R^4$, —$NR^6SO_2NR^3R^4$ or —$NR^6SO_2R^4$;

$R^1$ is halogen, —CN, OH, —$NR^3R^4$, —$CONR^3R^4$, —COOH, —$OCONR^3R^4$, —$NHOCOR^7$, —$NHCONR^7R^8$, —$NHSO_2NR^7R^8$, optionally substituted ($C_1$-$C_6$)alkyl, optionally substituted ($C_2$-$C_6$)alkenyl, optionally substituted ($C_2$-$C_6$)alkynyl, optionally substituted ($C_1$-$C_6$)alkoxy, optionally substituted ($C_3$-$C_8$)cycloalkyl, optionally substituted ($C_3$-$C_8$)cycloalkyl-CO—, optionally substituted ($C_3$-$C_8$)cycloalkyl-$SO_2$—, optionally substituted aryl ($C_1$-$C_6$)alkoxy, optionally substituted ($C_3$-$C_8$)cycloalkyl ($C_1$-$C_6$)alkoxy, optionally substituted heterocyclyl-CO—, optionally substituted heterocyclyl, optionally substituted ($C_1$-$C_6$)alkyl-$SO_2$—, —$NHSO_2$-optionally substituted ($C_1$-$C_6$)alkyl, —$NHSO_2$-optionally substituted heterocyclo, optionally substituted ($C_1$-$C_6$)alkyl-$NHSO_2$— or optionally substituted heterocyclo-$NHSO_2$—;

$R^2$ is H, halogen, —CN, —COOH, —CONR$^7$R$^8$, —NHCOR$^3$R$^4$, —OCONR$^3$R$^4$, —NHCOOR$^3$R$^4$, optionally substituted ($C_1$-$C_6$)alkyl, optionally substituted ($C_2$-$C_6$) alkynyl, optionally substituted ($C_1$-$C_6$)alkoxy, optionally substituted heteroaryl or optionally substituted heterocyclo;

$R^3$ is hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy($C_1$-$C_6$)alkyl, optionally substituted aryl, optionally substituted aryl($C_1$-$C_6$)alkyl, optionally substituted aryloxy($C_1$-$C_6$)alkyl, optionally substituted ($C_1$-$C_6$)alkyl-SO$_2$—, optionally substituted heterocyclyl, optionally substituted heterocyclyl($C_1$-$C_6$)alkyl, optionally substituted heteroaryl or optionally substituted heteroaryl ($C_1$-$C_6$)alkyl, $R^4$ is hydrogen, optionally substituted ($C_1$-$C_6$)alkyl or optionally substituted ($C_3$-$C_8$)cycloalkyl;

or $R^3$ and $R^4$ may be taken together with the nitrogen atom to which they are attached to form an optionally substituted ($C_4$-$C_8$)heteroaryl or ($C_4$-$C_8$)heterocyclic ring;

$R^6$ is hydrogen or optionally substituted ($C_1$-$C_6$)alkyl;

$R^7$ and $R^8$ are independently hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy ($C_1$-$C_6$)alkyl, optionally substituted aryl, optionally substituted aryl($C_1$-$C_6$)alkyl, optionally substituted aryloxy($C_1$-$C_6$)alkyl, optionally substituted ($C_1$-$C_6$)alkyl-SO$_2$—, optionally substituted heterocyclyl, optionally substituted heterocyclyl($C_1$-$C_6$)alkyl, optionally substituted heteroaryl or optionally substituted heteroaryl($C_1$-$C_6$)alkyl;

or $R^7$ and $R^8$ may be taken together with the nitrogen atom to which they are attached to form an optionally substituted ($C_4$-$C_8$)heteroaryl or ($C_4$-$C_8$)heterocyclic ring;

$R^{12}$ is hydrogen, halogen, —CN, optionally substituted ($C_1$-$C_6$)alkyl or optionally substituted ($C_1$-$C_6$)alkoxy;

$R^{13}$ is hydrogen, halogen, —CN, OH, —CONR$^3$R$^4$, —NHCOOR$^4$, —NHCONR$^3$R$^4$, —NHCOR$^4$, —NHSO$_2$R$^7$, —SO$_2$NR$^3$R$^4$, —NHSO$_2$NR$^3$R$^4$, —SO$_2$R$^7$, optionally substituted ($C_1$-$C_6$)alkyl, optionally substituted ($C_3$-$C_8$)cycloalkyl, optionally substituted ($C_1$-$C_6$)alkoxy, optionally substituted aryl, optionally substituted heteroaryl or optionally substituted heterocyclo;

$R^{14}$ is hydrogen, optionally substituted ($C_1$-$C_6$)alkyl, ($C_1$-$C_6$)alkoxy, halogen, —CN, —NR$^3$R$^4$, OH, —NHOCOR$^7$, —OCONR$^7$R$^8$, —NHCONR$^7$R$^8$ or —CF$_3$;

$R^{15}$ is hydrogen, optionally substituted ($C_1$-$C_6$)alkyl, ($C_1$-$C_6$)alkoxy, halogen, —CN, —NR$^3$R$^4$, OH, —NHOCOR$^7$, —OCONR$^7$R$^8$, —NHCONR$^7$R$^8$ or —CF$_3$;

$R^{16}$ is hydrogen, optionally substituted ($C_1$-$C_6$)alkyl, ($C_1$-$C_6$)alkoxy, halogen, —CN, —NR$^3$R$^4$, OH, —NHOCOR$^7$, —OCONR$^7$R$^8$, —NHCONR$^7$R$^8$ or —CF$_3$;

with the proviso that only one of $R^{14}$, $R^{15}$ and $R^{16}$ is hydrogen;

and/or a pharmaceutically acceptable salt, tautomer or stereoisomer thereof.

In a fourth aspect within the scope of the first, second and third aspects of the invention, there is provided a compound of formula (III)

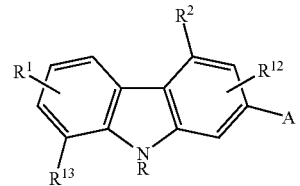

(II)

wherein:

A is optionally substituted heteroaryl or optionally substituted heterocyclo, wherein the substituents are one or more $R^{14}$, $R^{15}$ or $R^{16}$;

R is hydrogen, optionally substituted ($C_1$-$C_6$)alkyl, optionally substituted ($C_3$-$C_8$)cycloalkyl($C_1$-$C_6$)alkyl, optionally substituted aryl($C_1$-$C_6$)alkyl, optionally substituted heteroaryl($C_1$-$C_6$)alkyl, optionally substituted heterocyclo($C_1$-$C_6$)alkyl, optionally substituted ($C_1$-$C_6$)alkyl-CO—, optionally substituted aryl-CO—, optionally substituted ($C_3$-$C_8$)cycloalkyl-CO—, optionally substituted heteroaryl, optionally substituted heterocyclo-CO—, optionally substituted aryl-SO$_2$—, optionally substituted ($C_1$-$C_6$)alkyl-SO$_2$—, optionally substituted ($C_3$-$C_8$)cycloalkyl-SO$_2$—, optionally substituted heteroaryl-SO$_2$—, optionally substituted ($C_1$-$C_6$)alkyl-OCO— or optionally substituted ($C_3$-$C_8$)cycloalkyl-OCO—; or R is

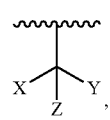

wherein

X and Y are independently selected from hydrogen, optionally substituted ($C_1$-$C_6$)alkyl, optionally substituted ($C_3$-$C_8$)cycloalkyl, optionally substituted aryl, optionally substituted heteroaryl or optionally substituted heterocyclo;

Z is hydrogen, halogen, —OH, ($C_1$-$C_6$)alkyl, ($C_1$-$C_6$) alkoxy, —NR$^3$R$^4$, —CONR$^3$R$^4$, —OCONR$^3$R$^4$, —NR$^6$OCOR$^3$, —NR$^6$CONR$^3$R$^4$, —NR$^6$SO$_2$NR$^3$R$^4$ or —NR$^6$SO$_2$R$^4$;

$R^1$ is halogen, —CN, OH, —NR$^3$R$^4$, —CONR$^3$R$^4$, —COOH, —OCONR$^3$R$^4$, —NHOCOR$^7$, —NHCONR$^7$R$^8$, —NHSO$_2$NR$^7$R$^8$, optionally substituted ($C_1$-$C_6$)alkyl, optionally substituted ($C_2$-$C_6$)alkenyl, optionally substituted ($C_2$-$C_6$)alkynyl, optionally substituted ($C_1$-$C_6$)alkoxy, optionally substituted ($C_3$-$C_8$)cycloalkyl, optionally substituted ($C_3$-$C_8$)cycloalkyl-CO—, optionally substituted ($C_3$-$C_8$)cycloalkyl-SO$_2$—, optionally substituted aryl ($C_1$-$C_6$) alkoxy, optionally substituted ($C_3$-$C_8$)cycloalkyl ($C_1$-$C_6$) alkoxy, optionally substituted heterocyclyl-CO—, optionally substituted heterocyclyl, optionally substituted ($C_1$-$C_6$)alkyl-SO$_2$—, —NHSO$_2$-optionally substituted ($C_1$-$C_6$)alkyl, —NHSO$_2$-optionally substituted heterocyclo, optionally substituted ($C_1$-$C_6$)alkyl-NHSO$_2$— or optionally substituted heterocyclo-NHSO$_2$—;

$R^2$ is H, halogen, —CN, —COOH, —CONR$^7$R$^8$, —NHCOR$^3$R$^4$, —OCONR$^3$R$^4$, —NHCOOR$^3$R$^4$, optionally substituted ($C_1$-$C_6$)alkyl, optionally substituted ($C_2$-$C_6$) alkynyl, optionally substituted ($C_1$-$C_6$)alkoxy, optionally substituted heteroaryl or optionally substituted heterocyclo;

$R^3$ is hydrogen, optionally substituted ($C_1$-$C_6$)alkyl, optionally substituted ($C_3$-$C_8$)cycloalkyl, optionally substituted (C₂-C₆)alkenyl, optionally substituted (C₂-C₆)alkynyl, cyano(C₁-C₆)alkyl, hydroxy(C₁-C₆)alkyl, optionally substituted aryl, optionally substituted aryl(C₁-C₆)alkyl, optionally substituted aryloxy(C₁-C₆)alkyl, optionally substituted (C₁-C₆)alkyl-SO₂—, optionally substituted heterocyclyl, optionally substituted heterocyclyl(C₁-C₆)alkyl, optionally substituted heteroaryl or optionally substituted heteroaryl (C₁-C₆)alkyl, R⁴ is hydrogen, optionally substituted (C₁-C₆)alkyl or optionally substituted (C₃-C₈)cycloalkyl;

or R³ and R⁴ may be taken together with the nitrogen atom to which they are attached to form an optionally substituted (C₄-C₈)heteroaryl or (C₄-C₈)heterocyclic ring;

R⁶ is hydrogen or optionally substituted (C₁-C₆)alkyl;

R⁷ and R⁸ are independently hydrogen, optionally substituted (C₁-C₆)alkyl, optionally substituted (C₃-C₈)cycloalkyl, optionally substituted (C₂-C₆)alkenyl, optionally substituted (C₂-C₆)alkynyl, cyano(C₁-C₆)alkyl, hydroxy (C₁-C₆)alkyl, optionally substituted aryl, optionally substituted aryl(C₁-C₆)alkyl, optionally substituted aryloxy(C₁-C₆)alkyl, optionally substituted (C₁-C₆)alkyl-SO₂—, optionally substituted heterocyclyl, optionally substituted heterocyclyl(C₁-C₆)alkyl, optionally substituted heteroaryl or optionally substituted heteroaryl(C₁-C₆)alkyl;

or R⁷ and R⁸ may be taken together with the nitrogen atom to which they are attached to form an optionally substituted (C₄-C₈)heteroaryl or (C₄-C₈)heterocyclic ring;

R¹² is hydrogen, halogen, —CN, optionally substituted (C₁-C₆)alkyl or optionally substituted (C₁-C₆)alkoxy;

R¹³ is hydrogen, halogen, —CN, optionally substituted (C₁-C₆)alkoxy, —NHSO₂R⁷ or —SO₂R⁷;

R¹⁴ is hydrogen, optionally substituted (C₁-C₆)alkyl, (C₁-C₆)alkoxy, halogen, —CN, —NR³R⁴, OH, —NHOCOR⁷, —OCONR⁷R⁸, —NHCONR⁷R⁸ or —CF₃;

R¹⁵ is hydrogen, optionally substituted (C₁-C₆)alkyl, (C₁-C₆)alkoxy, halogen, —CN, —NR³R⁴, OH, —NHOCOR⁷, —OCONR⁷R⁸, —NHCONR⁷R⁸ or —CF₃;

R¹⁶ is hydrogen, optionally substituted (C₁-C₆)alkyl, (C₁-C₆)alkoxy, halogen, —CN, —NR³R⁴, OH, —NHOCOR⁷, —OCONR⁷R⁸, —NHCONR⁷R⁸ or —CF₃;

with the proviso that only one of R¹⁴, R¹⁵ and R¹⁶ is hydrogen;

and/or a pharmaceutically acceptable salt, tautomer or stereoisomer thereof.

In another aspect of the invention, there is provided a compound of formula (II)

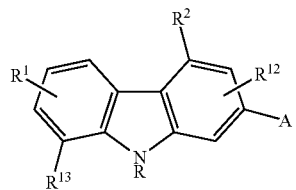

(II)

wherein:

A is optionally substituted heteroaryl or optionally substituted heterocyclo, wherein the substituents are one or more R¹⁴, R¹⁵ or R¹⁶;

R is hydrogen, optionally substituted (C₁-C₆)alkyl, optionally substituted (C₃-C₈)cycloalkyl(C₁-C₆)alkyl, optionally substituted aryl(C₁-C₆)alkyl, optionally substituted heteroaryl(C₁-C₆)alkyl, optionally substituted heterocyclo(C₁-C₆)alkyl, optionally substituted (C₁-C₆)alkyl-CO—, optionally substituted aryl-CO—, optionally substituted (C₃-C₈)cycloalkyl-CO—, optionally substituted heteroaryl, optionally substituted heterocyclo-CO—, optionally substituted aryl-SO₂—, optionally substituted (C₁-C₆)alkyl-SO₂—, optionally substituted (C₃-C₈)cycloalkyl-SO₂—, optionally substituted heteroaryl-SO₂—, optionally substituted (C₁-C₆)alkyl-OCO— or optionally substituted (C₃-C₈)cycloalkyl-OCO—; or R is

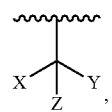

wherein

X and Y are independently selected from hydrogen, optionally substituted (C₁-C₆)alkyl, optionally substituted (C₃-C₈)cycloalkyl, optionally substituted aryl, optionally substituted heteroaryl or optionally substituted heterocyclo;

Z is hydrogen, halogen, —OH, (C₁-C₆)alkyl, (C₁-C₆) alkoxy, —NR³R⁴, —CONR³R⁴, —OCONR³R⁴, —NR⁶OCOR³, —NR⁶CONR³R⁴, —NR⁶SO₂NR³R⁴ or —NR⁶SO₂R⁴;

R¹ is halogen, —CN, OH, —NR³R⁴, —CONR³R⁴, —COOH, —OCONR³R⁴, —NHOCOR⁷, —NHCONR⁷R⁸, —NHSO₂NR⁷R⁸, optionally substituted (C₁-C₆)alkyl, optionally substituted (C₂-C₆)alkenyl, optionally substituted (C₂-C₆)alkynyl, optionally substituted (C₁-C₆)alkoxy, optionally substituted (C₃-C₈)cycloalkyl, optionally substituted (C₃-C₈)cycloalkyl-CO—, optionally substituted (C₃-C₈)cycloalkyl-SO₂—, optionally substituted aryl (C₁-C₆) alkoxy, optionally substituted (C₃-C₈)cycloalkyl (C₁-C₆) alkoxy, optionally substituted heterocyclyl-CO—, optionally substituted heterocyclyl, optionally substituted (C₁-C₆)alkyl-SO₂—, —NHSO₂-optionally substituted (C₁-C₆)alkyl, —NHSO₂-optionally substituted heterocyclo, optionally substituted (C₁-C₆)alkyl-NHSO₂— or optionally substituted heterocyclo-NHSO₂—;

R² is H, halogen, —CN, —COOH, —CONR⁷R⁸, —NHCOR³R⁴, —OCONR³R⁴, —NHCOOR³R⁴, optionally substituted (C₁-C₆)alkyl, optionally substituted (C₂-C₆) alkynyl, optionally substituted (C₁-C₆)alkoxy, optionally substituted heteroaryl or optionally substituted heterocyclo;

R³ is hydrogen, optionally substituted (C₁-C₆)alkyl, optionally substituted (C₃-C₈)cycloalkyl, optionally substituted (C₂-C₆)alkenyl, optionally substituted (C₂-C₆)alkynyl, cyano(C₁-C₆)alkyl, hydroxy(C₁-C₆)alkyl, optionally substituted aryl, optionally substituted aryl(C₁-C₆)alkyl, optionally substituted aryloxy(C₁-C₆)alkyl, optionally substituted (C₁-C₆)alkyl-SO₂—, optionally substituted heterocyclyl, optionally substituted heterocyclyl(C₁-C₆)alkyl, optionally substituted heteroaryl or optionally substituted heteroaryl (C₁-C₆)alkyl, R⁴ is hydrogen, optionally substituted (C₁-C₆)alkyl or optionally substituted (C₃-C₈)cycloalkyl;

or R³ and R⁴ may be taken together with the nitrogen atom to which they are attached to form an optionally substituted (C₄-C₈)heteroaryl or (C₄-C₈)heterocyclic ring;

R⁶ is hydrogen or optionally substituted (C₁-C₆)alkyl;

R⁷ and R⁸ are independently hydrogen, optionally substituted (C₁-C₆)alkyl, optionally substituted (C₃-C₈)cycloalkyl, optionally substituted (C₂-C₆)alkenyl, optionally substituted (C₂-C₆)alkynyl, cyano(C₁-C₆)alkyl, hydroxy (C₁-C₆)alkyl, optionally substituted aryl, optionally substituted aryl($C_1$-$C_6$)alkyl, optionally substituted aryloxy($C_1$-$C_6$)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl($C_1$-$C_6$)alkyl;

or $R^7$ and $R^8$ may be taken together with the nitrogen atom to which they are attached to form an optionally substituted ($C_4$-$C_8$)heteroaryl or ($C_4$-$C_8$)heterocyclic ring;

$R^{12}$ is hydrogen, halogen, —CN, optionally substituted ($C_1$-$C_6$)alkyl or optionally substituted ($C_1$-$C_6$)alkoxy;

$R^{13}$ is hydrogen, halogen, —CN, optionally substituted ($C_1$-$C_6$)alkoxy, —$NHSO_2R^7$ or —$SO_2R^7$;

$R^{14}$ is hydrogen or optionally substituted ($C_1$-$C_6$)alkyl;

$R^{15}$ is hydrogen or optionally substituted ($C_1$-$C_6$)alkyl;

$R^{16}$ is hydrogen or optionally substituted ($C_1$-$C_6$)alkyl;

with the proviso that only one of $R^{14}$, $R^{15}$ and $R^{16}$ is hydrogen;

and/or a pharmaceutically acceptable salt, tautomer or stereoisomer thereof.

In another aspect of the invention, there is provided a compound of formula (II)

(II)

[Structure: carbazole with $R^1$, $R^2$, $R^{12}$, $R^{13}$, A, N–R substituents]

wherein:

A is optionally substituted heteroaryl or optionally substituted heterocyclo, wherein the substituents are one or more $R^{14}$, $R^{15}$ or $R^{16}$;

R is hydrogen, optionally substituted ($C_1$-$C_6$)alkyl, optionally substituted ($C_3$-$C_8$)cycloalkyl($C_1$-$C_6$)alkyl, optionally substituted aryl($C_1$-$C_6$)alkyl, optionally substituted heteroaryl($C_1$-$C_6$)alkyl, optionally substituted heterocyclo($C_1$-$C_6$)alkyl, optionally substituted ($C_1$-$C_6$)alkyl-CO—, optionally substituted aryl-CO—, optionally substituted ($C_3$-$C_8$)cycloalkyl-CO—, optionally substituted heteroaryl, optionally substituted heterocyclo-CO—, optionally substituted aryl-$SO_2$—, optionally substituted ($C_1$-$C_6$)alkyl-$SO_2$—, optionally substituted ($C_3$-$C_8$)cycloalkyl-$SO_2$—, optionally substituted heteroaryl-$SO_2$—, optionally substituted ($C_1$-$C_6$)alkyl-OCO— or optionally substituted ($C_3$-$C_8$)cycloalkyl-OCO—; or R is

[Structure showing X, Y, Z branching from central atom with wavy bond]

wherein

X and Y are independently selected from hydrogen, optionally substituted ($C_1$-$C_6$)alkyl, optionally substituted ($C_3$-$C_8$)cycloalkyl, optionally substituted aryl, optionally substituted heteroaryl or optionally substituted heterocyclo;

Z is hydrogen, halogen, —OH, ($C_1$-$C_6$)alkyl, ($C_1$-$C_6$)alkoxy, —$NR^3R^4$, —$CONR^3R^4$, —$OCONR^3R^4$, —$NR^6OCOR^3$, —$NR^6CONR^3R^4$, —$NR^6SO_2NR^3R^4$ or —$NR^6SO_2R^4$;

$R^1$ is halogen, —CN, OH, —$NR^3R^4$, —$CONR^3R^4$, —COOH, —$OCONR^3R^4$, —$NHOCOR^7$, —$NHCONR^7R^8$, —$NHSO_2NR^7R^8$, optionally substituted ($C_1$-$C_6$)alkyl, optionally substituted ($C_2$-$C_6$)alkenyl, optionally substituted ($C_2$-$C_6$)alkynyl, optionally substituted ($C_1$-$C_6$)alkoxy, optionally substituted ($C_3$-$C_8$)cycloalkyl, optionally substituted ($C_3$-$C_8$)cycloalkyl-CO—, optionally substituted ($C_3$-$C_8$)cycloalkyl-$SO_2$—, optionally substituted aryl ($C_1$-$C_6$) alkoxy, optionally substituted ($C_3$-$C_8$)cycloalkyl ($C_1$-$C_6$) alkoxy, optionally substituted heterocyclyl-CO—, optionally substituted heterocyclyl, optionally substituted ($C_1$-$C_6$)alkyl-$SO_2$—, —$NHSO_2$-optionally substituted ($C_1$-$C_6$)alkyl, —$NHSO_2$-optionally substituted heterocyclo, optionally substituted ($C_1$-$C_6$)alkyl-$NHSO_2$— or optionally substituted heterocyclo-$NHSO_2$—;

$R^2$ is H, —CN, —COOH or —$CONR^7R^8$;

$R^3$ is hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy($C_1$-$C_6$)alkyl, optionally substituted aryl, optionally substituted aryl($C_1$-$C_6$)alkyl, optionally substituted aryloxy($C_1$-$C_6$)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl ($C_1$-$C_6$)alkyl, $R^4$ is hydrogen, optionally substituted ($C_1$-$C_6$)alkyl or optionally substituted ($C_3$-$C_8$)cycloalkyl;

or $R^3$ and $R^4$ may be taken together with the nitrogen atom to which they are attached to form an optionally substituted ($C_4$-$C_8$)heteroaryl or ($C_4$-$C_8$)heterocyclic ring;

$R^6$ is hydrogen or optionally substituted ($C_1$-$C_6$)alkyl;

$R^7$ and $R^8$ are independently hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy ($C_1$-$C_6$)alkyl, optionally substituted aryl, optionally substituted aryl($C_1$-$C_6$)alkyl, optionally substituted aryloxy($C_1$-$C_6$)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl($C_1$-$C_6$)alkyl;

or $R^7$ and $R^8$ may be taken together with the nitrogen atom to which they are attached to form an optionally substituted ($C_4$-$C_8$)heteroaryl or ($C_4$-$C_8$)heterocyclic ring;

$R^{12}$ is hydrogen, halogen, —CN, optionally substituted ($C_1$-$C_6$)alkyl or optionally substituted ($C_1$-$C_6$)alkoxy;

$R^{13}$ is hydrogen, halogen, —CN, optionally substituted ($C_1$-$C_6$)alkoxy, —$NHSO_2R^7$ or —$SO_2R^7$;

$R^{14}$ is hydrogen or optionally substituted ($C_1$-$C_6$)alkyl;

$R^{15}$ is hydrogen or optionally substituted ($C_1$-$C_6$)alkyl;

$R^{16}$ is hydrogen or optionally substituted ($C_1$-$C_6$)alkyl;

with the proviso that only one of $R^{14}$, $R^{15}$ and $R^{16}$ is hydrogen;

and/or a pharmaceutically acceptable salt, tautomer or stereoisomer thereof.

In another aspect of the invention, there is provided a compound of the formula (II)

[Structure: carbazole with $R^1$, $R^2$, $R^{12}$, $R^{13}$, A, N–R substituents]

wherein:

A is optionally substituted heteroaryl or optionally substituted heterocyclo, wherein the substituents are one or more $R^{14}$, $R^{15}$ or $R^{16}$;

R is hydrogen, optionally substituted $(C_1-C_6)$alkyl, optionally substituted $(C_3-C_8)$cycloalkyl$(C_1-C_6)$alkyl, optionally substituted aryl$(C_1-C_6)$alkyl, optionally substituted heteroaryl$(C_1-C_6)$alkyl, optionally substituted heterocyclo$(C_1-C_6)$alkyl, optionally substituted $(C_1-C_6)$alkyl-CO—, optionally substituted aryl-CO—, optionally substituted $(C_3-C_8)$cycloalkyl-CO—, optionally substituted heteroaryl, optionally substituted heterocyclo-CO—, optionally substituted aryl-SO$_2$—, optionally substituted $(C_1-C_6)$alkyl-SO$_2$—, optionally substituted $(C_3-C_8)$cycloalkyl-SO$_2$—, optionally substituted heteroaryl-SO$_2$—, optionally substituted $(C_1-C_6)$alkyl-OCO— or optionally substituted $(C_3-C_8)$cycloalkyl-OCO—; or R is

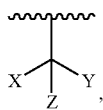

wherein

X and Y are independently selected from hydrogen, optionally substituted $(C_1-C_6)$alkyl, optionally substituted $(C_3-C_8)$cycloalkyl, optionally substituted aryl, optionally substituted heteroaryl or optionally substituted heterocyclo;

Z is hydrogen, halogen, —OH, $(C_1-C_6)$alkyl, $(C_1-C_6)$alkoxy, —NR$^3$R$^4$, —CONR$^3$R$^4$, —OCONR$^3$R$^4$, —NR$^6$OCOR$^3$, —NR$^6$CONR$^3$R$^4$, —NR$^6$SO$_2$NR$^3$R$^4$ or —NR$^6$SO$_2$R$^4$;

$R^1$ is optionally substituted $(C_1-C_6)$alkyl, optionally substituted $(C_1-C_6)$alkyl-SO$_2$—, optionally substituted $(C_3-C_8)$cycloalkyl-CO—, optionally substituted $(C_3-C_8)$cycloalkyl-SO$_2$— or optionally substituted heterocyclyl-CO—;

$R^2$ is H, —CN, —COOH or —CONR$^7$R$^8$;

$R^3$ is hydrogen, optionally substituted $(C_1-C_6)$alkyl, optionally substituted $(C_3-C_8)$cycloalkyl, optionally substituted $(C_2-C_6)$alkenyl, optionally substituted $(C_2-C_6)$alkynyl, cyano$(C_1-C_6)$alkyl, hydroxy$(C_1-C_6)$alkyl, optionally substituted aryl, optionally substituted aryl$(C_1-C_6)$alkyl, optionally substituted aryloxy$(C_1-C_6)$alkyl, optionally substituted $(C_1-C_6)$alkyl-SO$_2$—, optionally substituted heterocyclyl, optionally substituted heterocyclyl$(C_1-C_6)$alkyl, optionally substituted heteroaryl or optionally substituted heteroaryl $(C_1-C_6)$alkyl, $R^4$ is hydrogen, optionally substituted $(C_1-C_6)$alkyl or optionally substituted $(C_3-C_8)$cycloalkyl;

or $R^3$ and $R^4$ may be taken together with the nitrogen atom to which they are attached to form an optionally substituted $(C_4-C_8)$heteroaryl or $(C_4-C_8)$heterocyclic ring;

$R^6$ is hydrogen or optionally substituted $(C_1-C_6)$alkyl;

$R^7$ and $R^8$ are independently hydrogen, optionally substituted $(C_1-C_6)$alkyl, optionally substituted $(C_3-C_8)$cycloalkyl, optionally substituted $(C_2-C_6)$alkenyl, optionally substituted $(C_2-C_6)$alkynyl, cyano$(C_1-C_6)$alkyl, hydroxy$(C_1-C_6)$alkyl, optionally substituted aryl, optionally substituted aryl$(C_1-C_6)$alkyl, optionally substituted aryloxy$(C_1-C_6)$alkyl, optionally substituted $(C_1-C_6)$alkyl-SO$_2$—, optionally substituted heterocyclyl, optionally substituted heterocyclyl$(C_1-C_6)$alkyl, optionally substituted heteroaryl or optionally substituted heteroaryl$(C_1-C_6)$alkyl;

or $R^7$ and $R^8$ may be taken together with the nitrogen atom to which they are attached to form an optionally substituted $(C_4-C_8)$heteroaryl or $(C_4-C_8)$heterocyclic ring;

$R^{12}$ is hydrogen, halogen, —CN, optionally substituted $(C_1-C_6)$alkyl or optionally substituted $(C_1-C_6)$alkoxy;

$R^{13}$ is hydrogen, halogen, —CN, optionally substituted $(C_1-C_6)$alkoxy, —NHSO$_2$R$^7$ or —SO$_2$R$^7$;

$R^{14}$ is hydrogen or optionally substituted $(C_1-C_6)$alkyl;

$R^{15}$ is hydrogen or optionally substituted $(C_1-C_6)$alkyl;

$R^{16}$ is hydrogen or optionally substituted $(C_1-C_6)$alkyl;

with the proviso that only one of $R^{14}$, $R^{15}$ and $R^{16}$ is hydrogen;

and/or a pharmaceutically acceptable salt, tautomer or stereoisomer thereof.

In another aspect of the invention, there is provided a compound of the formula

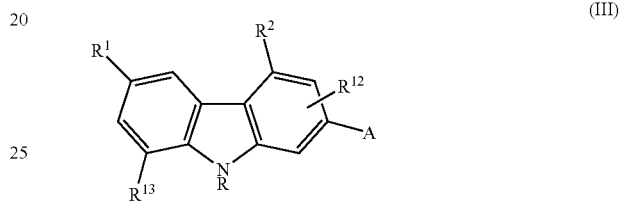

(III)

wherein:

A is optionally substituted heteroaryl or optionally substituted heterocyclo, wherein the substituents are one or more $R^{14}$, $R^{15}$ or $R^{16}$;

R is hydrogen, optionally substituted $(C_1-C_6)$alkyl, optionally substituted $(C_3-C_8)$cycloalkyl$(C_1-C_6)$alkyl, optionally substituted aryl$(C_1-C_6)$alkyl, optionally substituted heteroaryl$(C_1-C_6)$alkyl, optionally substituted heterocyclo$(C_1-C_6)$alkyl, optionally substituted $(C_1-C_6)$alkyl-CO—, optionally substituted aryl-CO—, optionally substituted $(C_3-C_8)$cycloalkyl-CO—, optionally substituted heteroaryl, optionally substituted heterocyclo-CO—, optionally substituted aryl-SO$_2$—, optionally substituted $(C_1-C_6)$alkyl-SO$_2$—, optionally substituted $(C_3-C_8)$cycloalkyl-SO$_2$—, optionally substituted heteroaryl-SO$_2$—, optionally substituted $(C_1-C_6)$alkyl-OCO— or optionally substituted $(C_3-C_8)$cycloalkyl-OCO—; or R is

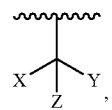

wherein

X and Y are independently selected from hydrogen, optionally substituted $(C_1-C_6)$alkyl, optionally substituted $(C_3-C_8)$cycloalkyl, optionally substituted aryl, optionally substituted heteroaryl or optionally substituted heterocyclo;

Z is hydrogen, halogen, —OH, $(C_1-C_6)$alkyl, $(C_1-C_6)$alkoxy, —NR$^3$R$^4$, —CONR$^3$R$^4$, —OCONR$^3$R$^4$, —NR$^6$OCOR$^3$, —NR$^6$CONR$^3$R$^4$, —NR$^6$SO$_2$NR$^3$R$^4$ or —NR$^6$SO$_2$R$^4$;

$R^1$ is optionally substituted $(C_1-C_6)$alkyl, optionally substituted $(C_1-C_6)$alkyl-SO$_2$—, optionally substituted $(C_3-C_8)$cycloalkyl-CO—, optionally substituted $(C_3-C_8)$cycloalkyl-SO$_2$— or optionally substituted heterocyclyl-CO—;

$R^2$ is H, —CN, —COOH or —CONR$^7$R$^8$;

$R^3$ is hydrogen, optionally substituted (C$_1$-C$_6$)alkyl, optionally substituted (C$_3$-C$_8$)cycloalkyl, optionally substituted (C$_2$-C$_6$)alkenyl, optionally substituted (C$_2$-C$_6$)alkynyl, cyano(C$_1$-C$_6$)alkyl, hydroxy(C$_1$-C$_6$)alkyl, optionally substituted aryl, optionally substituted aryl(C$_1$-C$_6$)alkyl, optionally substituted aryloxy(C$_1$-C$_6$)alkyl, optionally substituted (C$_1$-C$_6$)alkyl-SO$_2$—, optionally substituted heterocyclyl, optionally substituted heterocyclyl(C$_1$-C$_6$)alkyl, optionally substituted heteroaryl or optionally substituted heteroaryl (C$_1$-C$_6$)alkyl, $R^4$ is hydrogen, optionally substituted (C$_1$-C$_6$)alkyl or optionally substituted (C$_3$-C$_8$)cycloalkyl;

or $R^3$ and $R^4$ may be taken together with the nitrogen atom to which they are attached to form an optionally substituted (C$_4$-C$_8$)heteroaryl or (C$_4$-C$_8$)heterocyclic ring;

$R^6$ is hydrogen or optionally substituted (C$_1$-C$_6$)alkyl;

$R^7$ and $R^8$ are independently hydrogen, optionally substituted (C$_1$-C$_6$)alkyl, optionally substituted (C$_3$-C$_8$)cycloalkyl, optionally substituted (C$_2$-C$_6$)alkenyl, optionally substituted (C$_2$-C$_6$)alkynyl, cyano(C$_1$-C$_6$)alkyl, hydroxy (C$_1$-C$_6$)alkyl, optionally substituted aryl, optionally substituted aryl(C$_1$-C$_6$)alkyl, optionally substituted aryloxy(C$_1$-C$_6$)alkyl, optionally substituted (C$_1$-C$_6$)alkyl-SO$_2$—, optionally substituted heterocyclyl, optionally substituted heterocyclyl(C$_1$-C$_6$)alkyl, optionally substituted heteroaryl or optionally substituted heteroaryl(C$_1$-C$_6$)alkyl;

or $R^7$ and $R^8$ may be taken together with the nitrogen atom to which they are attached to form an optionally substituted (C$_4$-C$_8$)heteroaryl or (C$_4$-C$_8$)heterocyclic ring;

$R^{12}$ is hydrogen, halogen, —CN, optionally substituted (C$_1$-C$_6$)alkyl or optionally substituted (C$_1$-C$_6$)alkoxy;

$R^{13}$ is hydrogen, halogen, —CN, optionally substituted (C$_1$-C$_6$)alkoxy, —NHSO$_2$R$^7$ or —SO$_2$R$^7$;

$R^{14}$ is hydrogen or optionally substituted (C$_1$-C$_6$)alkyl;

$R^{15}$ is hydrogen or optionally substituted (C$_1$-C$_6$)alkyl;

$R^{16}$ is hydrogen or optionally substituted (C$_1$-C$_6$)alkyl;

with the proviso that only one of $R^{14}$, $R^{15}$ and $R^{16}$ is hydrogen;

and/or a pharmaceutically acceptable salt, tautomer or stereoisomer thereof.

In another aspect of the invention, there is provided a compound of the formula (III)

wherein:

A is optionally substituted heteroaryl or optionally substituted heterocyclo, wherein the substituents are one or more $R^{14}$, $R^{15}$ or $R^{16}$;

R is optionally substituted (C$_1$-C$_6$)alkyl, optionally substituted (C$_3$-C$_8$)cycloalkyl(C$_1$-C$_6$)alkyl, optionally substituted aryl(C$_1$-C$_6$)alkyl, optionally substituted (C$_1$-C$_6$)alkyl-SO$_2$— or optionally substituted (C$_1$-C$_6$)alkyl-OCO—; or R is wherein X and Y are independently selected from hydrogen, optionally substituted (C$_1$-C$_6$)alkyl, optionally substituted (C$_3$-C$_8$)cycloalkyl, optionally substituted aryl, optionally substituted heteroaryl or optionally substituted heterocyclo;

Z is hydrogen, halogen, —OH, (C$_1$-C$_6$)alkyl, (C$_1$-C$_6$) alkoxy, —NR$^3$R$^4$, —CONR$^3$R$^4$, —OCONR$^3$R$^4$, —NR$^6$OCOR$^3$, —NR$^6$CONR$^3$R$^4$, —NR$^6$SO$_2$NR$^3$R$^4$ or —NR$^6$SO$_2$R$^4$;

$R^1$ is optionally substituted (C$_1$-C$_6$)alkyl, optionally substituted (C$_1$-C$_6$)alkyl-SO$_2$—, optionally substituted (C$_3$-C$_8$) cycloalkyl-CO—, optionally substituted (C$_3$-C$_8$)cycloalkyl-SO$_2$— or optionally substituted heterocyclyl-CO—;

$R^2$ is H, —CN, —COOH or —CONR$^7$R$^8$;

$R^3$ is hydrogen, optionally substituted (C$_1$-C$_6$)alkyl, optionally substituted (C$_3$-C$_8$)cycloalkyl, optionally substituted (C$_2$-C$_6$)alkenyl, optionally substituted (C$_2$-C$_6$)alkynyl, cyano(C$_1$-C$_6$)alkyl, hydroxy(C$_1$-C$_6$)alkyl, optionally substituted aryl, optionally substituted aryl(C$_1$-C$_6$)alkyl, optionally substituted aryloxy(C$_1$-C$_6$)alkyl, optionally substituted (C$_1$-C$_6$)alkyl-SO$_2$—, optionally substituted heterocyclyl, optionally substituted heterocyclyl(C$_1$-C$_6$)alkyl, optionally substituted heteroaryl or optionally substituted heteroaryl (C$_1$-C$_6$)alkyl, $R^4$ is hydrogen, optionally substituted (C$_1$-C$_6$)alkyl or optionally substituted (C$_3$-C$_8$)cycloalkyl;

or $R^3$ and $R^4$ may be taken together with the nitrogen atom to which they are attached to form an optionally substituted (C$_4$-C$_8$)heteroaryl or (C$_4$-C$_8$)heterocyclic ring;

$R^6$ is hydrogen or optionally substituted (C$_1$-C$_6$)alkyl;

$R^7$ and $R^8$ are independently hydrogen, optionally substituted (C$_1$-C$_6$)alkyl, optionally substituted (C$_3$-C$_8$)cycloalkyl, optionally substituted (C$_2$-C$_6$)alkenyl, optionally substituted (C$_2$-C$_6$)alkynyl, cyano(C$_1$-C$_6$)alkyl, hydroxy (C$_1$-C$_6$)alkyl, optionally substituted aryl, optionally substituted aryl(C$_1$-C$_6$)alkyl, optionally substituted aryloxy(C$_1$-C$_6$)alkyl, optionally substituted (C$_1$-C$_6$)alkyl-SO$_2$—, optionally substituted heterocyclyl, optionally substituted heterocyclyl(C$_1$-C$_6$)alkyl, optionally substituted heteroaryl or optionally substituted heteroaryl(C$_1$-C$_6$)alkyl;

or $R^7$ and $R^8$ may be taken together with the nitrogen atom to which they are attached to form an optionally substituted (C$_4$-C$_8$)heteroaryl or (C$_4$-C$_8$)heterocyclic ring;

$R^{12}$ is hydrogen, halogen, —CN, optionally substituted (C$_1$-C$_6$)alkyl or optionally substituted (C$_1$-C$_6$)alkoxy;

$R^{13}$ is hydrogen, halogen, —CN, optionally substituted (C$_1$-C$_6$)alkoxy, —NHSO$_2$R$^7$ or —SO$_2$R$^7$;

$R^{14}$ is hydrogen or optionally substituted (C$_1$-C$_6$)alkyl;

$R^{15}$ is hydrogen or optionally substituted (C$_1$-C$_6$)alkyl;

$R^{16}$ is hydrogen or optionally substituted (C$_1$-C$_6$)alkyl;

with the proviso that only one of $R^{14}$, $R^{15}$ and $R^{16}$ is hydrogen;

and/or a pharmaceutically acceptable salt, tautomer or stereoisomer thereof.

In another aspect of the invention, there is provided a compound of the formula

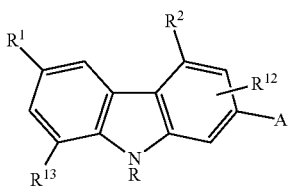
(III)

wherein:
A is

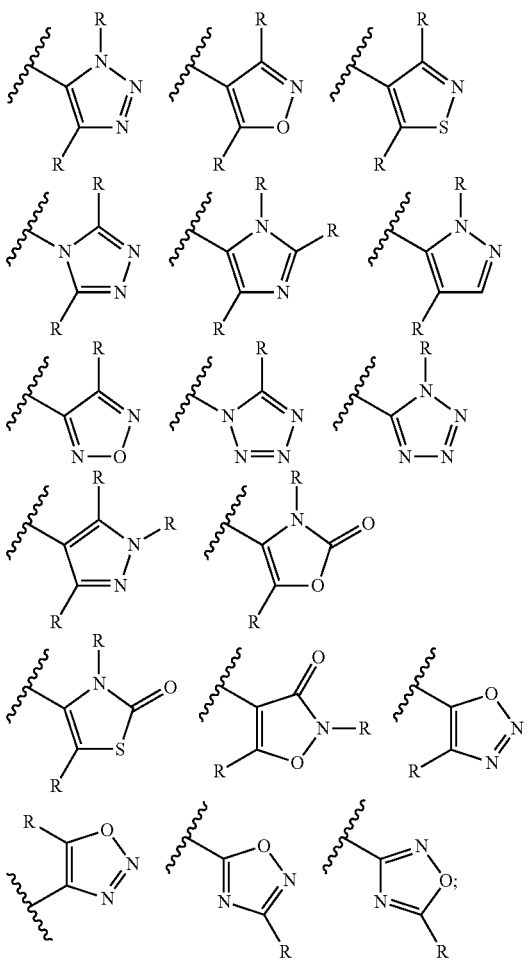

R is optionally substituted (C$_1$-C$_6$)alkyl, optionally substituted (C$_3$-C$_8$)cycloalkyl(C$_1$-C$_6$)alkyl, optionally substituted aryl(C$_1$-C$_6$)alkyl, optionally substituted (C$_1$-C$_6$)alkyl-SO$_2$— or optionally substituted (C$_1$-C$_6$)alkyl-OCO—; or
R is wherein
X and Y are independently selected from hydrogen, optionally substituted (C$_1$-C$_6$)alkyl, optionally substituted (C$_3$-C$_8$)cycloalkyl, optionally substituted aryl, optionally substituted heteroaryl or optionally substituted heterocyclo;

Z is hydrogen, halogen, —OH, (C$_1$-C$_6$)alkyl, (C$_1$-C$_6$)alkoxy, —NR$^3$R$^4$, —CONR$^3$R$^4$, —OCONR$^3$R$^4$, —NR$^6$OCOR$^3$, —NR$^6$CONR$^3$R$^4$, —NR$^6$SO$_2$NR$^3$R$^4$ or —NR$^6$SO$_2$R$^4$;

R$^1$ is optionally substituted (C$_1$-C$_6$)alkyl, optionally substituted (C$_1$-C$_6$)alkyl-SO$_2$—, optionally substituted (C$_3$-C$_8$)cycloalkyl-CO—, optionally substituted (C$_3$-C$_8$)cycloalkyl-SO$_2$— or optionally substituted heterocyclyl-CO—;

R$^2$ is H, —CN, —COOH or —CONR$^7$R$^8$;

R$^3$ is hydrogen, optionally substituted (C$_1$-C$_6$)alkyl, optionally substituted (C$_3$-C$_8$)cycloalkyl, optionally substituted (C$_2$-C$_6$)alkenyl, optionally substituted (C$_2$-C$_6$)alkynyl, cyano(C$_1$-C$_6$)alkyl, hydroxy(C$_1$-C$_6$)alkyl, optionally substituted aryl, optionally substituted aryl(C$_1$-C$_6$)alkyl, optionally substituted aryloxy(C$_1$-C$_6$)alkyl, optionally substituted (C$_1$-C$_6$)alkyl-SO$_2$—, optionally substituted heterocyclyl, optionally substituted heterocyclyl(C$_1$-C$_6$)alkyl, optionally substituted heteroaryl or optionally substituted heteroaryl (C$_1$-C$_6$)alkyl, R$^4$ is hydrogen, optionally substituted (C$_1$-C$_6$)alkyl or optionally substituted (C$_3$-C$_8$)cycloalkyl;

or R$^3$ and R$^4$ may be taken together with the nitrogen atom to which they are attached to form an optionally substituted (C$_4$-C$_8$)heteroaryl or (C$_4$-C$_8$)heterocyclic ring;

R$^6$ is hydrogen or optionally substituted (C$_1$-C$_6$)alkyl;

R$^7$ and R$^8$ are independently hydrogen, optionally substituted (C$_1$-C$_6$)alkyl, optionally substituted (C$_3$-C$_8$)cycloalkyl, optionally substituted (C$_2$-C$_6$)alkenyl, optionally substituted (C$_2$-C$_6$)alkynyl, cyano(C$_1$-C$_6$)alkyl, hydroxy (C$_1$-C$_6$)alkyl, optionally substituted aryl, optionally substituted aryl(C$_1$-C$_6$)alkyl, optionally substituted aryloxy(C$_1$-C$_6$)alkyl, optionally substituted (C$_1$-C$_6$)alkyl-SO$_2$—, optionally substituted heterocyclyl, optionally substituted heterocyclyl(C$_1$-C$_6$)alkyl, optionally substituted heteroaryl or optionally substituted heteroaryl(C$_1$-C$_6$)alkyl;

or R$^7$ and R$^8$ may be taken together with the nitrogen atom to which they are attached to form an optionally substituted (C$_4$-C$_8$)heteroaryl or (C$_4$-C$_8$)heterocyclic ring;

R$^{12}$ is hydrogen, halogen, —CN, optionally substituted (C$_1$-C$_6$)alkyl or optionally substituted (C$_1$-C$_6$)alkoxy;

R$^{13}$ is hydrogen, halogen, —CN, optionally substituted (C$_1$-C$_6$)alkoxy, —NHSO$_2$R$^7$ or —SO$_2$R$^7$;

R$^{14}$ is hydrogen or optionally substituted (C$_1$-C$_6$)alkyl;

R$^{15}$ is hydrogen or optionally substituted (C$_1$-C$_6$)alkyl;

R$^{16}$ is hydrogen or optionally substituted (C$_1$-C$_6$)alkyl;

with the proviso that only one of R$^{14}$, R$^{15}$ and R$^{16}$ is hydrogen;

and/or a pharmaceutically acceptable salt, tautomer or stereoisomer thereof.

In another aspect, there is provided a compound selected from the exemplified examples within the scope of the first aspect, or a pharmaceutically acceptable salt, tautomer or stereoisomer thereof.

In another aspect, there is provided a compound selected from any subset list of compounds within the scope of any of the above aspects.

One embodiment of the invention provides compounds wherein A is optionally substituted isoxazole, preferably substituted with one or more C$_1$-C$_6$ alkyl groups.

Another embodiment of the invention provides compounds wherein A is and R¹⁴, R¹⁵ and R¹⁶ are as defined above.

Another embodiment of the invention provides compounds wherein R¹ is optionally substituted heterocyclyl-CO—.

Another embodiment of the invention provides compounds wherein R¹ is optionally substituted $(C_3-C_8)$cycloalkyl-CO—.

Another embodiment of the invention provides compounds wherein R¹ is optionally substituted $(C_3-C_8)$cycloalkyl-SO₂—.

Another embodiment of the invention provides compounds wherein R¹ is optionally substituted $C_1-C_6$ alkyl-SO₂—.

Another embodiment of the invention provides compounds wherein R¹ is optionally substituted $C_1-C_6$ alkyl.

Another embodiment of the invention provides compounds wherein R is optionally substituted $C_1-C_6$ alkyl.

Another embodiment of the invention provides compounds that when R is optionally substituted $C_1-C_6$ alkyl, the substituents are two aryl groups, such as phenyl.

Another embodiment of the invention provides compounds that when R is optionally substituted $C_1-C_6$ alkyl, the substituents are one aryl group and one heterocyclo group.

Another embodiment of the invention provides compounds wherein R is optionally substituted $(C_3-C_8)$cycloalkyl $(C_1-C_6)$alkyl.

Another embodiment of the invention provides compounds wherein R is optionally substituted aryl $(C_1-C_6)$alkyl.

Another embodiment of the invention provides compounds wherein R is optionally substituted benzyl.

Another embodiment of the invention provides compounds wherein R is optionally substituted $C_1-C_6$ alkyl-SO₂.

Another embodiment of the invention provides compounds wherein R is optionally substituted $C_1-C_6$ alkyl-OCO—.

Another embodiment of the invention provides compounds wherein R is optionally substituted $C_1-C_6$ alkyl-CO—.

Another embodiment of the invention provides compounds wherein R² is —CONR⁷R⁸, where R⁷ and R⁸ are preferably hydrogen or $C_1-C_6$ alkyl.

Another embodiment of the invention provides compounds wherein R² is COOH.

Another embodiment of the invention provides compounds wherein R² is —CN.

In another embodiment, the compounds of the invention have $IC_{50}$ values ≤7.5 µM.

In another embodiment, the compounds of the invention have $IC_{50}$ values ≤500 nm In another embodiment, the compounds of the invention have $IC_{50}$ values ≤50 nm.

In another embodiment, there are disclosed the following compounds of the invention:

2-(3,5-dimethyl-4-isoxazolyl)-6-(4-morpholinylcarbonyl)-9H-carbazole;

2-(3,5-dimethyl-4-isoxazolyl)-6-((cis-2,6-dimethyl-4-morpholinyl)carbonyl)-9-ethyl-9H-carbazole;

2-(dimethyl-1,2-oxazol-4-yl)-6-[(2R,6S)-2,6-dimethylmorpholine-4-carbonyl]-9-propyl-9H-carbazole;

2-(dimethyl-1,2-oxazol-4-yl)-6-[(2R,6S)-2,6-dimethylmorpholine-4-carbonyl]-9-(2-methylpropyl)-9H-carbazole;

9-(cyclopropylmethyl)-2-(dimethyl-1,2-oxazol-4-yl)-6[(2R,6S)-2,6-dimethylmorpholine-4-carbonyl]-9H-carbazole;

2-(dimethyl-1,2-oxazol-4-yl)-6-[(2R,6S)-2,6-dimethylmorpholine-4-carbonyl]-9-(2-fluoroethyl)-9H-carbazole;

9-(2,2-difluoroethyl)-2-(dimethyl-1,2-oxazol-4-yl)-6-[(2R,6S)-2,6-dimethylmorpholine-4-carbonyl]-9H-carbazole;

2-(dimethyl-1,2-oxazol-4-yl)-6-[(2R,6S)-2,6-dimethylmorpholine-4-carbonyl]-9-(2-methoxyethyl)-9H-carbazole;

9-benzyl-2-(dimethyl-1,2-oxazol-4-yl)-6-[(2R,6S)-2,6-dimethylmorpholine-4-carbonyl]-9H-carbazole;

2-(dimethyl-1,2-oxazol-4-yl)-6-[(2R,6S)-2,6-dimethylmorpholine-4-carbonyl]-9-(2-phenylethyl)-9H-carbazole;

9-[(2-chlorophenyl)methyl]-2-(dimethyl-1,2-oxazol-4-yl)-6-[(2R,6S)-2,6-dimethylmorpholine-4-carbonyl]-9H-carbazole;

9-[(4-chlorophenyl)methyl]-2-(dimethyl-1,2-oxazol-4-yl)-6-[(2R,6S)-2,6-dimethylmorpholine-4-carbonyl]-9H-carbazole;

9-[(3-chlorophenyl)methyl]-2-(dimethyl-1,2-oxazol-4-yl)-6-[(2R,6S)-2,6-dimethylmorpholine-4-carbonyl]-9H-carbazole;

2-(dimethyl-1,2-oxazol-4-yl)-6-[(2R,6S)-2,6-dimethylmorpholine-4-carbonyl]-9-[(3-methoxyphenyl)methyl]-9H-carbazole;

2-(dimethyl-1,2-oxazol-4-yl)-6-[(2R,6S)-2,6-dimethylmorpholine-4-carbonyl]-9-[(2-methoxyphenyl)methyl]-9H-carbazole;

2-(dimethyl-1,2-oxazol-4-yl)-6-[(2R,6S)-2,6-dimethylmorpholine-4-carbonyl]-9-[(2-fluorophenyl)methyl]-9H-carbazole;

2-(dimethyl-1,2-oxazol-4-yl)-6-[(2R,6S)-2,6-dimethylmorpholine-4-carbonyl]-9-[(3-fluorophenyl)methyl]-9H-carbazole;

2-(dimethyl-1,2-oxazol-4-yl)-6-[(2R,6S)-2,6-dimethylmorpholine-4-carbonyl]-9-[(4-fluorophenyl)methyl]-9H-carbazole;

2-(dimethyl-1,2-oxazol-4-yl)-6-[(2R,6S)-2,6-dimethylmorpholine-4-carbonyl]-9-[(2-methylphenyl)methyl]-9H-carbazole;

2-(dimethyl-1,2-oxazol-4-yl)-6-[(2R,6S)-2,6-dimethylmorpholine-4-carbonyl]-9-[(3-methylphenyl)methyl]-9H-carbazole;

2-(dimethyl-1,2-oxazol-4-yl)-6-[(2R,6S)-2,6-dimethylmorpholine-4-carbonyl]-9-[(4-methylphenyl)methyl]-9H-carbazole;

9-(cyclopropylmethyl)-2-(3,5-dimethyl-4-isoxazolyl)-6-(4-morpholinylcarbonyl)-9H-carbazole;

2-(3,5-dimethyl-4-isoxazolyl)-6-((cis-2,6-dimethyl-4-morpholinyl)carbonyl)-9-(methylsulfonyl)-9H-carbazole;

9-benzoyl-2-(3,5-dimethyl-4-isoxazolyl)-6-((cis-2,6-dimethyl-4-morpholinyl)carbonyl)-9H-carbazole;

2-(3,5-dimethyl-4-isoxazolyl)-6-((cis-2,6-dimethyl-4-morpholinyl)carbonyl)-9H-carbazole-4-carboxamide;

9-(cyclobutylmethyl)-2-(3,5-dimethyl-4-isoxazolyl)-6-((cis-2,6-dimethyl-4-morpholinyl)carbonyl)-9H-carbazole-4-carboxamide;

2-(dimethyl-1,2-oxazol-4-yl)-6-[(2R,6S)-2,6-dimethylmorpholine-4-carbonyl]-9-(1,3-thiazol-4-ylmethyl)-9H-carbazole-4-carboxamide;

2-(dimethyl-1,2-oxazol-4-yl)-6-[(2R,6S)-2,6-dimethylmorpholine-4-carbonyl]-9-[(4-methyl-1,3-thiazol-2-yl)methyl]-9H-carbazole-4-carboxamide;

2-(dimethyl-1,2-oxazol-4-yl)-6-[(2R,6S)-2,6-dimethylmorpholine-4-carbonyl]-9-(1,3-oxazol-2-ylmethyl)-9H-carbazole-4-carboxamide;

2-(dimethyl-1,2-oxazol-4-yl)-6-[(2R,6S)-2,6-dimethylmorpholine-4-carbonyl]-9-(1,3-thiazol-2-ylmethyl)-9H-carbazole-4-carboxamide;

2-(dimethyl-1,2-oxazol-4-yl)-6-[(2R,6S)-2,6-dimethylmorpholine-4-carbonyl]-9-[(2-fluorophenyl)methyl]-9H-carbazole-4-carboxamide;

2-(dimethyl-1,2-oxazol-4-yl)-6-[(2R,6S)-2,6-dimethylmorpholine-4-carbonyl]-9-[(4-fluorophenyl)methyl]-9H-carbazole-4-carboxamide;

9-[(2-chlorophenyl)methyl]-2-(dimethyl-1,2-oxazol-4-yl)-6-[(2R,6S)-2,6-dimethylmorpholine-4-carbonyl]-9H-carbazole-4-carboxamide;

9-[(3-chlorophenyl)methyl]-2-(dimethyl-1,2-oxazol-4-yl)-6-[(2R,6S)-2,6-dimethylmorpholine-4-carbonyl]-9H-carbazole-4-carboxamide;

9-[(4-chlorophenyl)methyl]-2-(dimethyl-1,2-oxazol-4-yl)-6-[(2R,6S)-2,6-dimethylmorpholine-4-carbonyl]-9H-carbazole-4-carboxamide;

9-[(2,4-difluorophenyl)methyl]-2-(dimethyl-1,2-oxazol-4-yl)-6-[(2R,6S)-2,6-dimethylmorpholine-4-carbonyl]-9H-carbazole-4-carboxamide;

9-[(4-cyanophenyl)methyl]-2-(dimethyl-1,2-oxazol-4-yl)-6-[(2R,6S)-2,6-dimethylmorpholine-4-carbonyl]-9H-carbazole-4-carboxamide;

2-(dimethyl-1,2-oxazol-4-yl)-6-[(2R,6S)-2,6-dimethylmorpholine-4-carbonyl]-9-(pyrimidin-4-ylmethyl)-9H-carbazole-4-carboxamide;

2-(dimethyl-1,2-oxazol-4-yl)-6-[(2R,6S)-2,6-dimethylmorpholine-4-carbonyl]-9-(1-phenylethyl)-9H-carbazole-4-carboxamide;

2-(dimethyl-1,2-oxazol-4-yl)-6-[(2R,6S)-2,6-dimethylmorpholine-4-carbonyl]-9-[(2-methoxyphenyl)methyl]-9H-carbazole-4-carboxamide;

9-[(2,3-difluorophenyl)methyl]-2-(dimethyl-1,2-oxazol-4-yl)-6-[(2R,6S)-2,6-dimethylmorpholine-4-carbonyl]-9H-carbazole-4-carboxamide;

9-[(2,5-difluorophenyl)methyl]-2-(dimethyl-1,2-oxazol-4-yl)-6-[(2R,6S)-2,6-dimethylmorpholine-4-carbonyl]-9H-carbazole-4-carboxamide;

9-[(2-cyanophenyl)methyl]-2-(dimethyl-1,2-oxazol-4-yl)-6-[(2R,6S)-2,6-dimethylmorpholine-4-carbonyl]-9H-carbazole-4-carboxamide;

9-[(3-cyanophenyl)methyl]-2-(dimethyl-1,2-oxazol-4-yl)-6-[(2R,6S)-2,6-dimethylmorpholine-4-carbonyl]-9H-carbazole-4-carboxamide;

2-(3,5-dimethylisoxazol-4-yl)-6-(cis-2,6-dimethylmorpholine-4-carbonyl)-9-(phenylsulfonyl)-9H-carbazole-4-carboxamide;

9-benzoyl-2-(3,5-dimethylisoxazol-4-yl)-6-(cis-2,6-dimethylmorpholine-4-carbonyl)-9H-carbazole-4-carboxamide;

9-benzyl-2-(3,5-dimethyl-4-isoxazolyl)-6-(4-morpholinylcarbonyl)-9H-carbazole-4-carboxamide;

9-benzyl-7-(dimethyl-1,2-oxazol-4-yl)-3-N,3-N-dimethyl-9H-carbazole-3,5-dicarboxamide;

9-benzyl-2-(dimethyl-1,2-oxazol-4-yl)-6-(3,3-dimethylmorpholine-4-carbonyl)-9H-carbazole-4-carboxamide;

9-benzyl-2-(dimethyl-1,2-oxazol-4-yl)-6-(4-ethylpiperidine-1-carbonyl)-9H-carbazole-4-carboxamide;

9-benzyl-2-(dimethyl-1,2-oxazol-4-yl)-6-(4-hydroxy-4-methylpiperidine-1-carbonyl)-9H-carbazole-4-carboxamide;

9-benzyl-2-(dimethyl-1,2-oxazol-4-yl)-6-(3-methoxyazetidine-1-carbonyl)-9H-carbazole-4-carboxamide;

9-benzyl-2-(dimethyl-1,2-oxazol-4-yl)-6-(3-hydroxyazetidine-1-carbonyl)-9H-carbazole-4-carboxamide;

9-benzyl-2-(dimethyl-1,2-oxazol-4-yl)-6-(2-methylazetidine-1-carbonyl)-9H-carbazole-4-carboxamide;

9-benzyl-2-(dimethyl-1,2-oxazol-4-yl)-6-(2-methylmorpholine-4-carbonyl)-9H-carbazole-4-carboxamide;

9-benzyl-2-(dimethyl-1,2-oxazol-4-yl)-6-(1,4-oxazepane-4-carbonyl)-9H-carbazole-4-carboxamide;

9-benzyl-2-(dimethyl-1,2-oxazol-4-yl)-6-[(2S)-2-methylmorpholine-4-carbonyl]-9H-carbazole-4-carboxamide;

9-benzyl-2-(dimethyl-1,2-oxazol-4-yl)-6-(3,3-dimethylpyrrolidine-1-carbonyl)-9H-carbazole-4-carboxamide;

9-benzyl-2-(dimethyl-1,2-oxazol-4-yl)-6-[(3S)-3-fluoropyrrolidine-1-carbonyl]-9H-carbazole-4-carboxamide;

9-benzyl-2-(dimethyl-1,2-oxazol-4-yl)-6-[(3R)-3-fluoropyrrolidine-1-carbonyl]-9H-carbazole-4-carboxamide;

9-benzyl-6-(3,3-difluoropyrrolidine-1-carbonyl)-2-(dimethyl-1,2-oxazol-4-yl)-9H-carbazole-4-carboxamide;

9-benzyl-2-(dimethyl-1,2-oxazol-4-yl)-6-[(2R)-2-methylmorpholine-4-carbonyl]-9H-carbazole-4-carboxamide;

9-benzyl-2-(dimethyl-1,2-oxazol-4-yl)-6-(4-hydroxy-2,2,6,6-tetramethylpiperidine-1-carbonyl)-9H-carbazole-4-carboxamide;

9-benzyl-2-(dimethyl-1,2-oxazol-4-yl)-6-(4-hydroxy-2-methylpiperidine-1-carbonyl)-9H-carbazole-4-carboxamide;

9-benzyl-2-(dimethyl-1,2-oxazol-4-yl)-6-(3-fluoroazetidine-1-carbonyl)-9H-carbazole-4-carboxamide;

9-benzyl-2-(dimethyl-1,2-oxazol-4-yl)-6-(pyrrolidine-1-carbonyl)-9H-carbazole-4-carboxamide;

9-benzyl-2-(dimethyl-1,2-oxazol-4-yl)-6-(4-hydroxypiperidine-1-carbonyl)-9H-carbazole-4-carboxamide;

9-benzyl-2-(dimethyl-1,2-oxazol-4-yl)-6-[4-(hydroxymethyl)piperidine-1-carbonyl]-9H-carbazole-4-carboxamide;

9-benzyl-2-(dimethyl-1,2-oxazol-4-yl)-6-(2,6-dimethylmorpholine-4-carbonyl)-9H-carbazole-4-carboxamide;

9-benzyl-2-(dimethyl-1,2-oxazol-4-yl)-6-(4-methoxypiperidine-1-carbonyl)-9H-carbazole-4-carboxamide;
6-(azetidine-1-carbonyl)-9-benzyl-2-(dimethyl-1,2-oxazol-4-yl)-9H-carbazole-4-carboxamide;
9-benzyl-2-(dimethyl-1,2-oxazol-4-yl)-6-(3,3-dimethylpiperidine-1-carbonyl)-9H-carbazole-4-carboxamide;
9-benzyl-2-(dimethyl-1,2-oxazol-4-yl)-6-(2-methylpiperidine-1-carbonyl)-9H-carbazole-4-carboxamide;
9-benzyl-2-(dimethyl-1,2-oxazol-4-yl)-6-(4-methylpiperidine-1-carbonyl)-9H-carbazole-4-carboxamide;
9-benzyl-2-(dimethyl-1,2-oxazol-4-yl)-6-(4-methylpiperazine-1-carbonyl)-9H-carbazole-4-carboxamide;
9-benzyl-7-(dimethyl-1,2-oxazol-4-yl)-3-N-[2-(morpholin-4-yl)ethyl]-9H-carbazole-3,5-dicarboxamide;
9-benzyl-2-(dimethyl-1,2-oxazol-4-yl)-6-(4,4-dimethyl-1,3-oxazolidine-3-carbonyl)-9H-carbazole-4-carboxamide;
9-benzyl-6-(3,3-difluoroazetidine-1-carbonyl)-2-(dimethyl-1,2-oxazol-4-yl)-9H-carbazole-4-carboxamide;
9-(2,6-difluorobenzyl)-2-(3,5-dimethyl-4-isoxazolyl)-6-(((3S)-3-fluoro-1-pyrrolidinyl)carbonyl)-9H-carbazole-4-carboxamide;
9-[(4-chlorophenyl)methyl]-2-(dimethyl-1,2-oxazol-4-yl)-6-[(3S)-3-fluoropyrrolidine-1-carbonyl]-9H-carbazole-4-carboxamide;
2-(dimethyl-1,2-oxazol-4-yl)-9-[(3-fluorophenyl)methyl]-6-[(3S)-3-fluoropyrrolidine-1-carbonyl]-9H-carbazole-4-carboxamide;
2-(dimethyl-1,2-oxazol-4-yl)-6-[(3S)-3-fluoropyrrolidine-1-carbonyl]-9-[(2-methoxyphenyl)methyl]-9H-carbazole-4-carboxamide;
2-(dimethyl-1,2-oxazol-4-yl)-6-[(3S)-3-fluoropyrrolidine-1-carbonyl]-9-[(4-methyl-1,3-thiazol-2-yl)methyl]-9H-carbazole-4-carboxamide;
2-(dimethyl-1,2-oxazol-4-yl)-6-[(3S)-3-fluoropyrrolidine-1-carbonyl]-9-(1-phenylethyl)-9H-carbazole-4-carboxamide;
2-(3,5-dimethyl-4-isoxazolyl)-6-((3-fluoro-1-azetidinyl)carbonyl)-9-(1-phenylethyl)-9H-carbazole-4-carboxamide;
9-[(4-chloro-3-fluorophenyl)methyl]-2-(dimethyl-1,2-oxazol-4-yl)-6-(3-fluoroazetidine-1-carbonyl)-9H-carbazole-4-carboxamide;
9-[(4-chloro-2-fluorophenyl)methyl]-2-(dimethyl-1,2-oxazol-4-yl)-6-(3-fluoroazetidine-1-carbonyl)-9H-carbazole-4-carboxamide;
2-(dimethyl-1,2-oxazol-4-yl)-6-(3-fluoroazetidine-1-carbonyl)-9-{1-[3-(trifluoromethyl)phenyl]ethyl}-9H-carbazole-4-carboxamide;
2-(dimethyl-1,2-oxazol-4-yl)-6-(3-fluoroazetidine-1-carbonyl)-9-{1-[2-(trifluoromethyl)phenyl]ethyl}-9H-carbazole-4-carboxamide;
9-(cyclobutylmethyl)-2-(dimethyl-1,2-oxazol-4-yl)-6-(3-fluoroazetidine-1-carbonyl)-9H-carbazole-4-carboxamide;
2-(dimethyl-1,2-oxazol-4-yl)-6-(3-fluoroazetidine-1-carbonyl)-9-[1-(4-fluorophenyl)ethyl]-9H-carbazole-4-carboxamide;
9-(cyclopropylmethyl)-2-(dimethyl-1,2-oxazol-4-yl)-6-(3-fluoroazetidine-1-carbonyl)-9H-carbazole-4-carboxamide;
2-(dimethyl-1,2-oxazol-4-yl)-6-(3-fluoroazetidine-1-carbonyl)-9-[(4-fluorophenyl)methyl]-9H-carbazole-4-carboxamide;
9-(1-(4-chlorophenyl)ethyl)-2-(3,5-dimethyl-4-isoxazolyl)-6-((3-fluoro-1-azetidinyl)carbonyl)-9H-carbazole-4-carboxamide;
9-(4-chlorobenzyl)-6-((3,3-difluoro-1-azetidinyl)carbonyl)-2-(3,5-dimethyl-4-isoxazolyl)-9H-carbazole-4-carboxamide;
6-((3,3-difluoro-1-azetidinyl)carbonyl)-2-(3,5-dimethyl-4-isoxazolyl)-9-(1-phenylethyl)-9H-carbazole-4-carboxamide, racemic;
6-((3,3-difluoro-1-azetidinyl)carbonyl)-2-(3,5-dimethyl-4-isoxazolyl)-9-(1-phenylethyl)-9H-carbazole-4-carboxamide, Enantiomer 1;
6-((3,3-difluoro-1-azetidinyl)carbonyl)-2-(3,5-dimethyl-4-isoxazolyl)-9-(1-phenylethyl)-9H-carbazole-4-carboxamide, Enantiomer 2;
6-((3,3-difluoro-1-azetidinyl)carbonyl)-2-(3,5-dimethyl-4-isoxazolyl)-N-methyl-9H-carbazole-4-carboxamide;
9-(4-chlorobenzyl)-6-(3,3-difluoroazetidine-1-carbonyl)-2-(3,5-dimethylisoxazol-4-yl)-N-methyl-9H-carbazole-4-carboxamide;
2-(3,5-dimethyl-4-isoxazolyl)-6-((3-fluoro-1-azetidinyl)carbonyl)-N-methyl-9H-carbazole-4-carboxamide;
9-(4-chlorobenzyl)-2-(3,5-dimethylisoxazol-4-yl)-6-(3-fluoroazetidine-1-carbonyl)-N-methyl-9H-carbazole-4-carboxamide;
2-(dimethyl-1,2-oxazol-4-yl)-6-(3-fluoroazetidine-1-carbonyl)-9-[(4-fluorophenyl)methyl]-N-methyl-9H-carbazole-4-carboxamide;
2-(dimethyl-1,2-oxazol-4-yl)-6-(3-fluoroazetidine-1-carbonyl)-9-[(3-fluorophenyl)methyl]-N-methyl-9H-carbazole-4-carboxamide;
9-[(2,6-difluorophenyl)methyl]-2-(dimethyl-1,2-oxazol-4-yl)-6-(3-fluoroazetidine-1-carbonyl)-N-methyl-9H-carbazole-4-carboxamide;
9-[(2,4-difluorophenyl)methyl]-2-(dimethyl-1,2-oxazol-4-yl)-6-(3-fluoroazetidine-1-carbonyl)-N-methyl-9H-carbazole-4-carboxamide;
9-[(2,3-difluorophenyl)methyl]-2-(dimethyl-1,2-oxazol-4-yl)-6-(3-fluoroazetidine-1-carbonyl)-N-methyl-9H-carbazole-4-carboxamide;
9-[(4-cyanophenyl)methyl]-2-(dimethyl-1,2-oxazol-4-yl)-6-(3-fluoroazetidine-1-carbonyl)-N-methyl-9H-carbazole-4-carboxamide;
9-[(4-chloro-3-fluorophenyl)methyl]-2-(dimethyl-1,2-oxazol-4-yl)-6-(3-fluoroazetidine-1-carbonyl)-N-methyl-9H-carbazole-4-carboxamide;
9-[(4-chloro-2-fluorophenyl)methyl]-2-(dimethyl-1,2-oxazol-4-yl)-6-(3-fluoroazetidine-1-carbonyl)-N-methyl-9H-carbazole-4-carboxamide;
9-[1-(4-chlorophenyl)ethyl]-2-(dimethyl-1,2-oxazol-4-yl)-6-(3-fluoroazetidine-1-carbonyl)-N-methyl-9H-carbazole-4-carboxamide;
2-(dimethyl-1,2-oxazol-4-yl)-6-(3-fluoroazetidine-1-carbonyl)-9-[1-(4-fluorophenyl)ethyl]-N-methyl-9H-carbazole-4-carboxamide;
2-(dimethyl-1,2-oxazol-4-yl)-6-(3-fluoroazetidine-1-carbonyl)-N-methyl-9-(1-phenylethyl)-9H-carbazole-4-carboxamide;
9-(cyclobutylmethyl)-2-(dimethyl-1,2-oxazol-4-yl)-6-(3-fluoroazetidine-1-carbonyl)-N-methyl-9H-carbazole-4-carboxamide;
9-(cyclopropylmethyl)-2-(dimethyl-1,2-oxazol-4-yl)-6-(3-fluoroazetidine-1-carbonyl)-N-methyl-9H-carbazole-4-carboxamide;
2-(3,5-dimethylisoxazol-4-yl)-6-(3-fluoroazetidine-1-carbonyl)-N-methyl-9-(pyridin-2-ylmethyl)-9H-carbazole-4-carboxamide;
9-benzyl-2-(3,5-dimethylisoxazol-4-yl)-6-(cis-2,6-dimethylmorpholine-4-carbonyl)-N-methyl-9H-carbazole-4-carboxamide;

9-benzyl-2-(3,5-dimethylisoxazol-4-yl)-6-(cis-2,6-dimethylmorpholine-4-carbonyl)-N,N-dimethyl-9H-carbazole-4-carboxamide;

6-((3,3-difluoro-1-azetidinyl)carbonyl)-2-(3,5-dimethyl-4-isoxazolyl)-N-methyl-9-(1-phenylethyl)-9H-carbazole-4-carboxamide;

6-((3,3-difluoro-1-azetidinyl)carbonyl)-2-(3,5-dimethyl-4-isoxazolyl)-N,N-dimethyl-9-(1-phenylethyl)-9H-carbazole-4-carboxamide;

2-(3,5-dimethyl-4-isoxazolyl)-6-((3-fluoro-1-azetidinyl)carbonyl)-9-(3-fluorobenzyl)-9H-carbazole-4-carbonitrile;

9-(4-fluorobenzyl)-2-(3-methyl-4-isoxazolyl)-6-(4-morpholinylcarbonyl)-9H-carbazole-4-carboxamide;

9-(4-fluorobenzyl)-2-(5-methylisoxazol-4-yl)-6-(morpholine-4-carbonyl)-9H-carbazole-4-carboxamide;

2-(3,5-dimethyl-4-isoxazolyl)-6-((3-fluoro-1-azetidinyl)carbonyl)-9-(4-fluorobenzyl)-N-propyl-9H-carbazole-4-carboxamide;

N-cyclopropyl-2-(dimethyl-1,2-oxazol-4-yl)-6-(3-fluoroazetidine-1-carbonyl)-9-[(4-fluorophenyl)methyl]-9H-carbazole-4-carboxamide;

2-(dimethyl-1,2-oxazol-4-yl)-N-ethyl-6-(3-fluoroazetidine-1-carbonyl)-9-[(4-fluorophenyl)methyl]-9H-carbazole-4-carboxamide;

2-(dimethyl-1,2-oxazol-4-yl)-6-(3-fluoroazetidine-1-carbonyl)-9-[(4-fluorophenyl)methyl]-N-(propan-2-yl)-9H-carbazole-4-carboxamide;

2-(dimethyl-1,2-oxazol-4-yl)-6-(3-fluoroazetidine-1-carbonyl)-9-[(4-fluorophenyl)methyl]-N-(2-methylpropyl)-9H-carbazole-4-carboxamide;

2-(dimethyl-1,2-oxazol-4-yl)-4,6-bis(3-fluoroazetidine-1-carbonyl)-9-[(4-fluorophenyl)methyl]-9H-carbazole;

9-Benzyl-2-(3,5-dimethyl-4-isoxazolyl)-6-(methylamino)-9H-carbazole-4-carboxamide;

9-benzyl-2-(3,5-dimethylisoxazol-4-yl)-6-(N-methylacetamido)-9H-carbazole-4-carboxamide;

9-benzyl-2-(dimethyl-1,2-oxazol-4-yl)-N-methyl-6-(N-methylacetamido)-9H-carbazole-4-carboxamide;

9-benzyl-2-(dimethyl-1,2-oxazol-4-yl)-N-methyl-6-(methylamino)-9H-carbazole-4-carboxamide;

6-(acetyl(2-fluoroethyl)amino)-9-benzyl-2-(3,5-dimethyl-4-isoxazolyl)-9H-carbazole-4-carboxamide;

6-amino-9-benzyl-2-(3,5-dimethyl-4-isoxazolyl)-9H-carbazole-4-carboxamide;

9-benzyl-2-(3,5-dimethyl-4-isoxazolyl)-6-(2-fluoroethylamino)-9H-carbazole-4-carboxamide;

9-benzyl-2-(dimethyl-1,2-oxazol-4-yl)-6-[(2-hydroxyethyl)amino]-9H-carbazole-4-carboxamide;

9-benzyl-6-[(cyanomethyl)amino]-2-(dimethyl-1,2-oxazol-4-yl)-9H-carbazole-4-carboxamide;

9-benzyl-6-[(2,2-difluoroethyl)amino]-2-(dimethyl-1,2-oxazol-4-yl)-9H-carbazole-4-carboxamide;

9-benzyl-6-[bis(2-hydroxyethyl)amino]-2-(dimethyl-1,2-oxazol-4-yl)-9H-carbazole-4-carboxamide;

9-benzyl-2-(dimethyl-1,2-oxazol-4-yl)-6-(dimethylamino)-N-methyl-9H-carbazole-4-carboxamide;

6-acetamido-9-benzyl-2-(3,5-dimethyl-4-isoxazolyl)-9H-carbazole-4-carboxamide;

9-benzyl-2-(dimethyl-1,2-oxazol-4-yl)-6-methanesulfonamido-9H-carbazole-4-carboxamide;

methyl N-[9-benzyl-5-carbamoyl-7-(dimethyl-1,2-oxazol-4-yl)-9H-carbazol-3-yl]carbamate;

9-benzyl-2-(dimethyl-1,2-oxazol-4-yl)-6-(oxane-4-amido)-9H-carbazole-4-carboxamide;

9-benzyl-2-(dimethyl-1,2-oxazol-4-yl)-6-[(morpholine-4-carbonyl)amino]-9H-carbazole-4-carboxamide;

9-benzyl-2-(dimethyl-1,2-oxazol-4-yl)-6-[(dimethylcarbamoyl)amino]-9H-carbazole-4-carboxamide;

9-benzyl-2-(dimethyl-1,2-oxazol-4-yl)-6-[(methylcarbamoyl)amino]-9H-carbazole-4-carboxamide;

9-benzyl-6-cyclopentaneamido-2-(dimethyl-1,2-oxazol-4-yl)-9H-carbazole-4-carboxamide;

2-(3,5-dimethyl-4-isoxazolyl)-6-(2-oxo-1,3-oxazinan-3-yl)-9H-carbazole-4-carboxamide;

2-(3,5-dimethyl-4-isoxazolyl)-9-(4-fluorobenzyl)-6-(2-oxo-1,3-oxazinan-3-yl)-9H-carbazole-4-carboxamide;

2-(3,5-dimethyl-4-isoxazolyl)-9-(4-fluorobenzyl)-6-(2-oxo-1,3-oxazolidin-3-yl)-9H-carbazole-4-carboxamide;

2-(3,5-dimethyl-4-isoxazolyl)-6-(5,5-dimethyl-2-oxo-1,3-oxazinan-3-yl)-9-(4-fluorobenzyl)-9H-carbazole-4-carboxamide;

2-(3,5-dimethyl-4-isoxazolyl)-N-ethyl-6-(2-oxo-1,3-oxazinan-3-yl)-9H-carbazole-4-carboxamide;

2-(3,5-dimethyl-4-isoxazolyl)-N-ethyl-9-(4-fluorobenzyl)-6-(2-oxo-1,3-oxazinan-3-yl)-9H-carbazole-4-carboxamide;

9-benzyl-2-(3,5-dimethyl-4-isoxazolyl)-6-(2-oxo-1,3-oxazinan-3-yl)-9H-carbazole-4-carboxamide;

9-(4-chlorobenzyl)-2-(3,5-dimethyl-4-isoxazolyl)-6-(2-oxo-1,3-oxazinan-3-yl)-9H-carbazole-4-carboxamide;

2-(3,5-dimethyl-4-isoxazolyl)-6-(2-oxo-1,3-oxazinan-3-yl)-9-(1-phenylethyl)-9H-carbazole-4-carboxamide;

9-(2,5-difluorobenzyl)-2-(3,5-dimethyl-4-isoxazolyl)-6-(2-oxo-1,3-oxazinan-3-yl)-9H-carbazole-4-carboxamide;

9-benzyl-2-(3,5-dimethyl-4-isoxazolyl)-6-(5,5-dimethyl-2-oxo-1,3-oxazinan-3-yl)-9H-carbazole-4-carboxamide;

9-benzyl-2-(3,5-dimethyl-4-isoxazolyl)-6-(2-oxo-1,3-oxazolidin-3-yl)-9H-carbazole-4-carboxamide;

9-(4-chlorobenzyl)-2-(3,5-dimethyl-4-isoxazolyl)-6-(2-oxo-1,3-oxazolidin-3-yl)-9H-carbazole-4-carboxamide;

2-(3,5-dimethyl-4-isoxazolyl)-6-(2-oxo-1,3-oxazolidin-3-yl)-9-(1-phenylethyl)-9H-carbazole-4-carboxamide;

9-(4-chloro-3-fluorobenzyl)-2-(3,5-dimethyl-4-isoxazolyl)-6-(2-oxo-1,3-oxazolidin-3-yl)-9H-carbazole-4-carboxamide;

9-benzyl-2-(3,5-dimethyl-4-isoxazolyl)-N-ethyl-6-(2-oxo-1,3-oxazinan-3-yl)-9H-carbazole-4-carboxamide;

9-(4-chlorobenzyl)-2-(3,5-dimethyl-4-isoxazolyl)-N-ethyl-6-(2-oxo-1,3-oxazinan-3-yl)-9H-carbazole-4-carboxamide;

2-(3,5-dimethyl-4-isoxazolyl)-N-ethyl-6-(2-oxo-1,3-oxazinan-3-yl)-9-(1-phenylethyl)-9H-carbazole-4-carboxamide;

2-(3,5-dimethyl-4-isoxazolyl)-N-methyl-6-(2-oxo-1,3-oxazinan-3-yl)-9H-carbazole-4-carboxamide;

9-benzyl-2-(3,5-dimethyl-4-isoxazolyl)-N-methyl-6-(2-oxo-1,3-oxazinan-3-yl)-9H-carbazole-4-carboxamide;

9-(4-chlorobenzyl)-2-(3,5-dimethyl-4-isoxazolyl)-N-methyl-6-(2-oxo-1,3-oxazinan-3-yl)-9H-carbazole-4-carboxamide;

2-(3,5-dimethyl-4-isoxazolyl)-9-(4-fluorobenzyl)-N-methyl-6-(2-oxo-1,3-oxazinan-3-yl)-9H-carbazole-4-carboxamide;

9-(4-chloro-3-fluorobenzyl)-2-(3,5-dimethyl-4-isoxazolyl)-N-methyl-6-(2-oxo-1,3-oxazinan-3-yl)-9H-carbazole-4-carboxamide;

2-(3,5-dimethyl-4-isoxazolyl)-N-methyl-6-(2-oxo-1,3-oxazinan-3-yl)-9-(1-phenylethyl)-9H-carbazole-4-carboxamide;

2-(3,5-dimethyl-4-isoxazolyl)-6-(1,1-dioxido-2-isothiazolidinyl)-9-(4-fluorobenzyl)-9H-carbazole-4-carboxamide;

2-(3,5-dimethyl-4-isoxazolyl)-6-(1,1-dioxido-1,2-thiazinan-2-yl)-9-(4-fluorobenzyl)-9H-carbazole-4-carboxamide;

2-(3,5-dimethyl-4-isoxazolyl)-6-methoxy-9-(1-phenyl-ethyl)-9H-carbazole-4-carboxamide;
9-benzyl-2-(3,5-dimethyl-4-isoxazolyl)-6-methoxy-9H-carbazole-4-carboxamide;
9-benzyl-2-(3,5-dimethyl-4-isoxazolyl)-6-hydroxy-9H-carbazole-4-carboxamide;
2-(3,5-dimethyl-4-isoxazolyl)-6-methoxy-9-(1-phenyl-ethyl)-9H-carbazole-4-carboxamide, Enantiomer 1;
2-(3,5-dimethyl-4-isoxazolyl)-6-methoxy-9-(1-phenyl-ethyl)-9H-carbazole-4-carboxamide, Enantiomer 2;
9-benzyl-2-(3,5-dimethyl-4-isoxazolyl)-6-(methylsulfonyl)-9H-carbazole-4-carboxamide;
Methyl 9-benzyl-5-cyano-7-(3,5-dimethyl-4-isoxazolyl)-9H-carbazole-2-carboxylate;
Methyl 9-benzyl-5-carbamoyl-7-(3,5-dimethyl-4-isoxazolyl)-9H-carbazole-2-carboxylate;
9-benzyl-2-(3,5-dimethyl-4-isoxazolyl)-7-(1-hydroxy-1-methylethyl)-9H-carbazole-4-carbonitrile;
9-Benzyl-2-(3,5-dimethyl-4-isoxazolyl)-7-(1-hydroxy-1-methylethyl)-9H-carbazole-4-carboxamide;
9-Benzyl-5-cyano-7-(3,5-dimethyl-4-isoxazolyl)-9H-carbazole-2-carboxylic acid;
9-Benzyl-2-(3,5-dimethyl-4-isoxazolyl)-7-(morpholine-4-carbonyl)-9H-carbazole-4-carbonitrile;
9-Benzyl-2-(3,5-dimethyl-4-isoxazolyl)-7-(morpholine-4-carbonyl)-9H-carbazole-4-carboxamide;
9-Benzyl-7-(3,5-dimethyl-4-isoxazolyl)-N~2~-methoxy-N~2~-methyl-9H-carbazole-2,5-dicarboxamide;
9-Benzyl-2-(3,5-dimethyl-4-isoxazolyl)-7-(3-fluorobenzoyl)-9H-carbazole-4-carboxamide;
5-cyano-7-(3,5-dimethyl-4-isoxazolyl)-9-(diphenylmethyl)-9H-carbazole-2-carboxylate;
Methyl 5-carbamoyl-7-(3,5-dimethyl-4-isoxazolyl)-9-(diphenylmethyl)-9H-carbazole-2-carboxylate;
5-Cyano-7-(3,5-dimethyl-4-isoxazolyl)-9-(diphenylmethyl)-9H-carbazole-2-carboxylic acid;
5-Cyano-7-(3,5-dimethyl-4-isoxazolyl)-9-(diphenylmethyl)-9H-carbazole-2-carboxamide;
7-(3,5-Dimethyl-4-isoxazolyl)-9-(diphenylmethyl)-N~2~-,N~2~-dimethyl-9H-carbazole-2,5-dicarboxamide;
2-(3,5-Dimethyl-4-isoxazolyl)-9-(diphenylmethyl)-7-(4-morpholinylcarbonyl)-9H-carbazole-4-carboxamide;
2-(3,5-dimethyl-4-isoxazolyl)-7-(1-hydroxy-1-methylethyl)-9-(tetrahydro-2H-pyran-4-ylmethyl)-9H-carbazole-4-carboxamide;
2-(Dimethyl-1,2-oxazol-4-yl)-7-(2-hydroxypropan-2-yl)-9-[(R)-oxan-4-yl(phenyl)methyl]-9H-carbazole-4-carboxamide, Ent. A;
2-(Dimethyl-1,2-oxazol-4-yl)-7-(2-hydroxypropan-2-yl)-9-[(R)-oxan-4-yl(phenyl)methyl]-9H-carbazole-4-carboxamide, Ent. B;
2-(dimethyl-1,2-oxazol-4-yl)-7-(2-hydroxypropan-2-yl)-9-{4,4,4-trifluoro-1-[2-(trifluoromethyl)phenyl]butyl}-9H-carbazole-4-carboxamide,
2-(dimethyl-1,2-oxazol-4-yl)-7-(2-hydroxypropan-2-yl)-9-{4,4,4-trifluoro-1-[2-(trifluoromethyl)phenyl]butyl}-9H-carbazole-4-carboxamide;
9-[1-(2-chlorophenyl)-4,4,4-trifluorobutyl]-2-(dimethyl-1,2-oxazol-4-yl)-7-(2-hydroxypropan-2-yl)-9H-carbazole-4-carboxamide;
9-[1-(2-chlorophenyl)-4,4,4-trifluorobutyl]-2-(dimethyl-1,2-oxazol-4-yl)-7-(2-hydroxypropan-2-yl)-9H-carbazole-4-carboxamide;
2-(dimethyl-1,2-oxazol-4-yl)-7-(2-hydroxypropan-2-yl)-9-[oxan-4-yl(2,4,6-trifluorophenyl)methyl]-9H-carbazole-4-carboxamide;
2-(dimethyl-1,2-oxazol-4-yl)-7-(2-hydroxypropan-2-yl)-9-[oxan-4-yl(2,4,6-trifluorophenyl)methyl]-9H-carbazole-4-carboxamide;
9-[(2,6-difluorophenyl)(oxan-4-yl)methyl]-2-(dimethyl-1,2-oxazol-4-yl)-7-(2-hydroxypropan-2-yl)-9H-carbazole-4-carboxamide;
9-[(2,6-difluorophenyl)(oxan-4-yl)methyl]-2-(dimethyl-1,2-oxazol-4-yl)-7-(2-hydroxypropan-2-yl)-9H-carbazole-4-carboxamide;
2-(dimethyl-1,2-oxazol-4-yl)-7-(2-hydroxypropan-2-yl)-9-[4,4,4-trifluoro-1-(pyridin-2-yl)butyl]-9H-carbazole-4-carboxamide;
2-(dimethyl-1,2-oxazol-4-yl)-7-(2-hydroxypropan-2-yl)-9-[4,4,4-trifluoro-1-(pyridin-2-yl)butyl]-9H-carbazole-4-carboxamide;
2-(dimethyl-1,2-oxazol-4-yl)-9-[(2-fluorophenyl)(oxan-4-yl)methyl]-7-(2-hydroxypropan-2-yl)-9H-carbazole-4-carboxamide;
2-(dimethyl-1,2-oxazol-4-yl)-9-[(2-fluorophenyl)(oxan-4-yl)methyl]-7-(2-hydroxypropan-2-yl)-9H-carbazole-4-carboxamide;
2-(dimethyl-1,2-oxazol-4-yl)-7-(2-hydroxypropan-2-yl)-9-[(4-methoxyphenyl)(oxan-4-yl)methyl]-9H-carbazole-4-carboxamide;
2-(dimethyl-1,2-oxazol-4-yl)-7-(2-hydroxypropan-2-yl)-9-[(4-methoxyphenyl)(oxan-4-yl)methyl]-9H-carbazole-4-carboxamide;
2-(dimethyl-1,2-oxazol-4-yl)-7-(2-hydroxypropan-2-yl)-9-[(3-methoxyphenyl)(oxan-4-yl)methyl]-9H-carbazole-4-carboxamide;
2-(dimethyl-1,2-oxazol-4-yl)-7-(2-hydroxypropan-2-yl)-9-[(3-methoxyphenyl)(oxan-4-yl)methyl]-9H-carbazole-4-carboxamide;
9-[(2,4-difluorophenyl)(oxan-4-yl)methyl]-2-(dimethyl-1,2-oxazol-4-yl)-7-(2-hydroxypropan-2-yl)-9H-carbazole-4-carboxamide;
9-[(2,4-difluorophenyl)(oxan-4-yl)methyl]-2-(dimethyl-1,2-oxazol-4-yl)-7-(2-hydroxypropan-2-yl)-9H-carbazole-4-carboxamide;
2-(dimethyl-1,2-oxazol-4-yl)-8-fluoro-9-(1,1,1,7,7,7-hexafluoroheptan-4-yl)-7-(2-hydroxypropan-2-yl)-9H-carbazole-4-carboxamide;
(Dimethyl-1,2-oxazol-4-yl)-9-[(4-fluorophenyl)(oxan-4-yl)methyl]-7-(2-hydroxypropan-2-yl)-9H-carbazole-4-carboxamide, Ent. A;
(Dimethyl-1,2-oxazol-4-yl)-9-[(4-fluorophenyl)(oxan-4-yl)methyl]-7-(2-hydroxypropan-2-yl)-9H-carbazole-4-carboxamide, Ent. B;
2-(Dimethyl-1,2-oxazol-4-yl)-9-[(1-fluorocyclobutyl)(phenyl)methyl]-7-(2-hydroxypropan-2-yl)-9H-carbazole-4-carboxamide, Ent. A;
2-(Dimethyl-1,2-oxazol-4-yl)-9-[(1-fluorocyclobutyl)(phenyl)methyl]-7-(2-hydroxypropan-2-yl)-9H-carbazole-4-carboxamide, Ent. B; 2-(Dimethyl-1,2-oxazol-4-yl)-8-fluoro-9-[(4-fluorophenyl)(oxan-4-yl)methyl]-7-(2-hydroxypropan-2-yl)-9H-carbazole-4-carboxamide, Ent. A;
2-(Dimethyl-1,2-oxazol-4-yl)-8-fluoro-9-[(4-fluorophenyl)(oxan-4-yl)methyl]-7-(2-hydroxypropan-2-yl)-9H-carbazole-4-carboxamide, Ent. B;
rel-2-(dimethyl-1,2-oxazol-4-yl)-9-{[(1R,2S,4S)-2-fluoro-7-oxabicyclo[2.2.1]heptan-2-yl]methyl}-7-(2-hydroxypropan-2-yl)-9H-carbazole-4-carboxamide;
9-[(4,4-difluorocyclohexyl)(phenyl)methyl]-2-(dimethyl-1,2-oxazol-4-yl)-8-fluoro-7-(2-hydroxypropan-2-yl)-9H-carbazole-4-carboxamide, Ent. A;

9-[(4,4-difluorocyclohexyl)(phenyl)methyl]-2-(dimethyl-1,2-oxazol-4-yl)-8-fluoro-7-(2-hydroxypropan-2-yl)-9H-carbazole-4-carboxamide, Ent. B;

2-(Dimethyl-1,2-oxazol-4-yl)-7-(2-methoxypropan-2-yl)-9-[(S)-oxan-4-yl(phenyl)methyl]-9H-carbazole-4-carboxamide;

2-(Dimethyl-1,2-oxazol-4-yl)-9-[(S)-oxan-4-yl(phenyl)methyl]-7-(propan-2-yl)-9H-carbazole-4-carboxamide;

2-(dimethyl-1,2-oxazol-4-yl)-8-fluoro-7-(2-hydroxypropan-2-yl)-9-[4,4,4-trifluoro-1-phenylbutyl]-9H-carbazole-4-carboxamide, Ent. A;

2-(dimethyl-1,2-oxazol-4-yl)-8-fluoro-7-(2-hydroxypropan-2-yl)-9-[4,4,4-trifluoro-1-phenylbutyl]-9H-carbazole-4-carboxamide, Ent. B;

2-(1,4-Dimethyl-1H-1,2,3-triazol-5-yl)-7-(2-hydroxypropan-2-yl)-9-(phenyl(tetrahydro-2H-pyran-4-yl)methyl)-9H-carbazole-4-carboxamide, Ent. A;

2-(1,4-Dimethyl-1H-1,2,3-triazol-5-yl)-7-(2-hydroxypropan-2-yl)-9-(phenyl(tetrahydro-2H-pyran-4-yl)methyl)-9H-carbazole-4-carboxamide, Ent. B;

and/or pharmaceutically acceptable salts, tautomers or stereoisomers thereof.

II. Other Embodiments of the Invention

In another embodiment, the invention provides a pharmaceutical composition, comprising a pharmaceutically acceptable carrier and a therapeutically effective amount of at least one of the compounds of the invention or a stereoisomer, a tautomer, a pharmaceutically acceptable salt, or a solvate thereof.

In another embodiment, the invention provides a process for making a compound of the invention or a stereoisomer, a tautomer, a pharmaceutically acceptable salt, or a solvate thereof.

In another embodiment, the invention provides a method for inhibiting activity of a bromodomain-containing protein mediated disorder in a patient in need thereof comprising the step of administering to said patient at least one compound of the invention.

In another embodiment, the invention provides a method for the treatment and/or prophylaxis of various types of cancer, comprising administering to a patient in need of such treatment and/or prophylaxis a therapeutically effective amount of one or more compounds of the invention, alone, or, optionally, in combination with another compound of the invention and/or at least one other type of therapeutic agent.

In another embodiment, the invention provides a method for the treatment and/or prophylaxis of various types of cancer, including without limitation, small cell lung cancer, non-small cell lung cancer, colorectal cancer, multiple myeloma, acute myeloid leukemia (AML), acute lymphoblastic leukemia (ALL), pancreatic cancer, liver cancer, hepatocellular cancer, neuroblastoma, other solid tumors or other hematological cancers.

In another embodiment, the invention provides a method for the treatment and/or prophylaxis of various types of cancer, including without limitation, small cell lung cancer, non-small cell lung cancer, triple-negative breast cancer, colorectal cancer, prostate cancer, melanoma, pancreatic cancer, multiple myeloma, T-acute lymphoblastic leukemia or AML.

In another embodiment, the invention provides a compound of the present invention for use in therapy.

In another embodiment, the invention provides a combined preparation of a compound of the present invention and additional therapeutic agent(s) for simultaneous, separate or sequential use in therapy.

In another embodiment, the invention provides a method of inhibiting a bromodomain-containing protein comprising contacting said protein with any exemplified compound or a pharmaceutically acceptable salt or composition thereof.

III. Therapeutic Applications

The compounds of formula (I) of the invention are bromodomain inhibitors and have potential utility in the treatment of diseases and conditions for which a bromodomain inhibitor is indicated.

In one embodiment there is provided a method for the treatment of a disease or condition, for which a bromodomain inhibitor is indicated, in a subject in need thereof which comprises administering a therapeutically effective amount of compound of formula (I) or a pharmaceutically acceptable salt thereof.

In another embodiment there is provided a method for treatment of a chronic autoimmune and/or inflammatory condition, in a subject in need thereof which comprises administering a therapeutically effective amount of one or more compounds of formula (I) or a pharmaceutically acceptable salt thereof.

In a further embodiment there is provided a method for treatment of cancer in a subject in need thereof which comprises administering a therapeutically effective amount of one or more compounds of formula (I) or a pharmaceutically acceptable salt thereof.

In one embodiment the subject in need thereof is a mammal, particularly a human.

Bromodomain inhibitors are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

Bromodomain inhibitors may be useful in the treatment of a wide variety of chronic autoimmune and inflammatory conditions such as rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, Addison's disease, hypophysitis, thyroiditis, type I diabetes and acute rejection of transplanted organs.

Bromodomain inhibitors may be useful in the treatment of a wide variety of acute inflammatory conditions such as acute gout, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis and acute rejection of transplanted organs.

Bromodomain inhibitors may be useful in the prevention or treatment of diseases or conditions which involve inflammatory responses to infections with bacteria, viruses, fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria, SIRS associated with viral infections such as influenza, herpes zoster, herpes simplex and coronavirus.

Bromodomain inhibitors may be useful in the prevention or treatment of conditions associated with ischaemia-reperfusion injury such as myocardial infarction, cerebrovascular ischaemia (stroke), acute coronary syndromes, renal reperfusion injury, organ transplantation, coronary artery bypass grafting, cardio-pulmonary bypass procedures and pulmonary, renal, hepatic, gastro-intestinal or peripheral limb embolism.

Bromodomain inhibitors may be useful in the treatment of disorders of lipid metabolism via the regulation of APO-A1 such as hypercholesterolemia, atherosclerosis and Alzheimer's disease.

Bromodomain inhibitors may be useful in the treatment of fibrotic conditions such as idiopathic pulmonary fibrosis, renal fibrosis, post-operative stricture, keloid formation, scleroderma and cardiac fibrosis.

Bromodomain inhibitors may be useful in the prevention and treatment of viral infections such as herpes virus, human papilloma virus, adenovirus, poxvirus and other DNA viruses.

Bromodomain inhibitors may also be useful in the treatment of cancer, including hematological, epithelial including lung, breast and colon carcinomas, midline carcinomas, mesenchymal, hepatic, renal and neurological tumours.

In one embodiment the disease or condition for which a bromodomain inhibitor is indicated is selected from diseases associated with systemic inflammatory response syndrome, such as sepsis, burns, pancreatitis, major trauma, hemorrhage and ischemia. In this embodiment, the bromodomain inhibitor would be administered at the point of diagnosis to reduce the incidence of SIRS, the onset of shock, multi-organ dysfunction syndrome, which includes the onset of acute lung injury, ARDS, acute renal, hepatic, cardiac and gastro-intestinal injury and mortality. In another embodiment the bromodomain inhibitor would be administered prior to surgical or other procedures associated with a high risk of sepsis, hemorrhage, extensive tissue damage, SIRS or MODS (multiple organ dysfunction syndrome). In a particular embodiment the disease or condition for which a bromodomain inhibitor is indicated is sepsis, sepsis syndrome, septic shock and endotoxemia. In another embodiment, the bromodomain inhibitor is indicated for the treatment of acute or acute on chronic pancreatitis. In another embodiment the bromodomain inhibitor is indicated for the treatment of burns.

In one embodiment the disease or condition for which a bromodomain inhibitor is indicated is selected from herpes simplex infections and reactivations, cold sores, herpes zoster infections and reactivations, chickenpox, shingles, human papilloma virus, cervical neoplasia, adenovirus infections, including acute respiratory disease, and poxvirus infections such as cowpox and smallpox and African swine fever virus.

The term "diseases or conditions for which a bromodomain inhibitor is indicated" is intended to include any of or all of the above disease states.

In one embodiment, there is provided a method for inhibiting a bromodomain which comprises contacting the bromodomain with a compound of formula (1) or a pharmaceutically acceptable salt thereof.

While it is possible that for use in therapy, a compound of formula (I) as well as pharmaceutically acceptable salts thereof may be administered as the compound itself, it is more commonly presented as a pharmaceutical composition.

Pharmaceutical compositions may be presented in unit dose forms containing a predetermined amount of active ingredient pep unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Types of cancers that may be treated with the compounds of this invention include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

In addition to apoptosis defects found in tumors, defects in the ability to eliminate self-reactive cells of the immune system due to apoptosis resistance are considered to play a key role in the pathogenesis of autoimmune diseases. Autoimmune diseases are characterized in that the cells of the immune system produce antibodies against its own organs and molecules or directly attack tissues resulting in the destruction of the latter. A failure of those self-reactive cells to undergo apoptosis leads to the manifestation of the disease. Defects in apoptosis regulation have been identified in autoimmune diseases such as systemic lupus erythematosus or rheumatoid arthritis.

Thus, according to another embodiment, the invention provides a method of treating an autoimmune disease by providing to a patient in need thereof a compound or composition of the present invention. Examples of such autoimmune diseases include, but are not limited to, collagen diseases such as rheumatoid arthritis, systemic lupus erythematosus. Sharp's syndrome, CREST syndrome (calcinosis, Raynaud's syndrome, esophageal dysmotility, telangiectasia), dermatomyositis, vasculitis (Morbus Wegener's) and Sjogren's syndrome, renal diseases such as Goodpasture's syndrome, rapidly-progressing glomerulonephritis and membrano-proliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotomy, Guillain-Barre syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, malaria and Chagas disease.

Compounds of the invention are useful for the treatment of certain types of cancer by themselves or in combination or co-administration with other therapeutic agents or radiation therapy. Thus, in one embodiment, the compounds of the invention are co-administered with radiation therapy or a second therapeutic agent with cytostatic or antineoplastic activity. Suitable cytostatic chemotherapy compounds include, but are not limited to (i) antimetabolites; (ii) DNA-fragmenting agents, (iii) DNA-crosslinking agents, (iv) intercalating agents (v) protein synthesis inhibitors, (vi) topoisomerase I poisons, such as camptothecin or topotecan; (vii) topoisomerase II poisons, (viii) microtubule-directed agents, (ix) kinase inhibitors (x) miscellaneous investigational agents (xi) hormones and (xii) hormone antagonists. It is contemplated that compounds of the invention may be useful in combination with any known agents falling into the above 12 classes as well as any future agents that are currently in development. In particular, it is contemplated that compounds of the invention may be useful in combination with current Standards of Care as well as any that evolve over the foreseeable future. Specific dosages and dosing regimens would be based on physicians' evolving knowledge and the general skill in the art.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

IV. Pharmaceutical Compositions and Dosing

The invention also provides pharmaceutically acceptable compositions which comprise a therapeutically effective amount of one or more of the compounds of Formula I, formulated together with one or more pharmaceutically acceptable carriers (additives) and/or diluents, and optionally, one or more additional therapeutic agents described above. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained release formulation; (3) topical application, for example, as a cream, ointment, or a controlled release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the patient being treated and the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, troches and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

DEFINITIONS

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

When a substituent is noted as "optionally substituted", the substituents are selected from, for example, substituents such as alkyl, cycloalkyl, aryl, heterocyclo, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g. —SO$_2$NH$_2$, substituted sulfonamido, nitro, cyano, carboxy, carbamyl, e.g. —CONH$_2$, substituted carbamyl e.g. —CONHalkyl, —CONHaryl, —CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl, unless otherwise defined.

For purposes of clarity and in accordance with standard convention in the art, the symbol

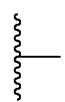

is used in formulas and tables to show the bond that is the point of attachment of the moiety or substituent to the core/nucleus of the structure.

Additionally, for purposes of clarity, where a substituent has a dash (-) that is not between two letters or symbols; this is used to indicate a point of attachment for a substituent. For example, —CONH$_2$ is attached through the carbon atom.

Additionally, for purposes of clarity, when there is no substituent shown at the end of a solid line, this indicates that there is a methyl (CH$_3$) group connected to the bond.

As used herein, the term "alkyl" or "alkylene" is intended to include both branched and straight-chain saturated aliphatic hydrocarbon groups having the specified number of carbon atoms. For example, "$C_1$-$C_6$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "alkenyl" denotes a straight- or branch-chained hydrocarbon radical containing one or more double bonds and typically from 2 to 20 carbon atoms in length. For example, "$C_2$-$C_8$ alkenyl" contains from two to eight carbon atoms. Alkenyl groups include, but are not limited to, for example, ethenyl, propenyl, butenyl, 1-methyl-2-buten-1-yl, heptenyl, octenyl and the like.

The term "alkynyl" denotes a straight- or branch-chained hydrocarbon radical containing one or more triple bonds and typically from 2 to 20 carbon atoms in length. For example, "$C_2$-$C_8$ alkenyl" contains from two to eight carbon atoms. Representative alkynyl groups include, but are not limited to, for example, ethynyl, 1-propynyl, 1-butynyl, heptynyl, octynyl and the like.

The term "alkoxy" or "alkyloxy" refers to an —O-alkyl group. "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

The term "aryl", either alone or as part of a larger moiety such as "aralkyl", "aralkoxy", or "aryloxyalkyl", refers to monocyclic, bicyclic and tricyclic ring systems having a total of five to 15 ring members, wherein at least one ring in the system is aromatic and wherein each ring in the system contains three to seven ring members. In certain embodiments of the invention, "aryl" refers to an aromatic ring system which includes, but not limited to phenyl, biphenyl, indanyl, 1-naphthyl, 2-naphthyl and terahydronaphthyl. The term "aralkyl" or "arylalkyl" refers to an alkyl residue attached to an aryl ring. Non-limiting examples include benzyl, phenethyl and the like. The fused aryls may be connected to another group either at a suitable position on the cycloalkyl ring or the aromatic ring. For example:

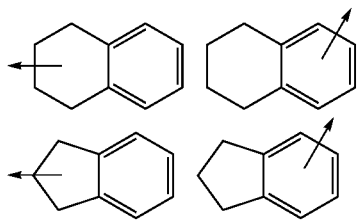

Arrowed lines drawn from the ring system indicate that the bond may be attached to any of the suitable ring atoms.

The term "cycloalkyl" refers to cyclized alkyl groups. $C_{3-6}$ cycloalkyl is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalk-enyl groups. Example cycloalkenyl groups include, but are not limited to, cyclobutenyl, cyclopentenyl, and cyclohexenyl.

The term "cycloalkylalkyl" refers to a cycloalkyl or substituted cycloalkyl bonded to an alkyl group connected to the carbazole core of the compound.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "benzyl," as used herein, refers to a methyl group on which one of the hydrogen atoms is replaced by a phenyl group.

As used herein, the term "heterocycle," "heterocyclyl," or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$ wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "heterocyclylalkyl" refers to a heterocyclyl or substituted heterocyclyl bonded to an alkyl group connected to the carbazole core of the compound.

The term "counter ion" is used to represent a negatively charged species such as chloride, bromide, hydroxide, acetate, and sulfate or a positively charged species such as sodium (Na+), potassium (K+), ammonium ($R_nNH_m+$ where n=0-4 and m=0-4) and the like.

The term "electron withdrawing group" (EWG) refers to a substituent which polarizes a bond, drawing electron density towards itself and away from other bonded atoms. Examples of EWGs include, but are not limited to, $CF_3$, $CF_2CF_3$, CN, halogen, haloalkyl, $NO_2$, sulfone, sulfoxide, ester, sulfonamide, carboxamide, alkoxy, alkoxyether, alkenyl, alkynyl, OH, C(O)alkyl, $CO_2H$, phenyl, heteroaryl, —O-phenyl, and —O-heteroaryl. Preferred examples of EWG include, but are not limited to, $CF_3$, $CF_2CF_3$, CN, halogen, $SO_2(C_{1-4}$ alkyl), $CONH(C_{1-4}$ alkyl), $CON(C_{1-4}$ alkyl)$_2$, and heteroaryl. More preferred examples of EWG include, but are not limited to, $CF_3$ and CN.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. and Greene, T. W. *Protecting Groups in Organic Synthesis*, 4th Edition, Wiley (2007) and *The Peptides Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington: The Science and Practice of Pharmacy*, 22$^{nd}$ Edition, Allen, L. V. Jr., Ed.; Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrugs derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs," A *Textbook of Drug Design and Development*, pp. 113-191, Krosgaard-Larsen, P. et al., eds., Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J (Editor). *Prodrugs and Targeted Delivery (Methods and Principles in Medicinal Chemistry)*, Vol 47, Wiley-VCH, 2011.

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art. Preparation of prodrugs is well known in the art and described in, for example, King, F. D., ed., *Medicinal Chemistry: Principles and Practice*, The Royal Society of Chemistry, Cambridge, UK (2$^{nd}$ edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3$^{rd}$ edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated by reference in their entirety.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Third Edition, Wiley and Sons, 1999).

Compounds of Formula (I) may be prepared by reference to the methods illustrated in the following Schemes. As shown therein the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

Synthesis of the carbazole core of compounds of Formula (I) can be accomplished using a variety of methods known to one of ordinary skill in the art and have been recently reviewed in the literature: Tetrahedron 2012, 6099-6121; Chemical Reviews 2002, 102, 4303-4427. A few examples of alternate synthesis of carbazoles of Formula (I) are summarized in Schemes 1-3 below.

Scheme 1 shows the synthesis of Formula (I) using a Fischer indolization reaction to form the carbazole core.

Scheme 1

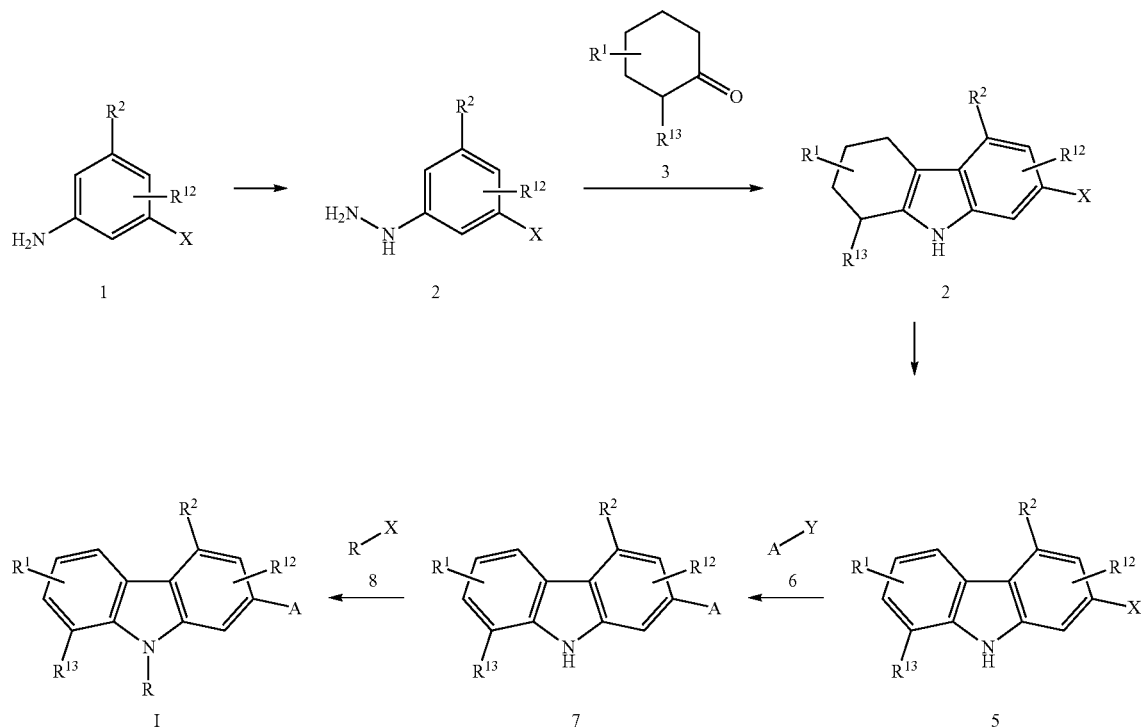

As shown in Scheme 1, a general procedure for the preparation of the compounds of the invention involves starting with the substituted aniline 1. The R and A substituents are defined previously in the text or a functional group that can be converted to the desired final substituent. The substituent X is a leaving group such as a halogen or OH that can be easily converted to a leaving group such as a triflate. The Y is a boronic acid, boronic ester or stannane. The aniline is converted to the corresponding hydrazine typically using aqueous sodium nitrate and concentrated HCl. The product hydrazine-hydrochloride is then condensed with the substituted cyclohexanone 3 using a variety of Fischer Indolization conditions known in the literature. For example, the use of acetic acid at reflux to furnish the Fischer indole product the tetrandrocarbazole 4, which in cases is generated as a mixture of regioisomers. The regioisomers can separated or carried forward as a mixture in subsequent reactions and separated as a later intermediate.

The tetrandrocarbazole 4, can then be converted to the carbazole 5 using a variety of methods known in the literature, for example with the use of oxidizing agent such as DDQ. A Suzuki or Stille reaction between carbazole 5 (where X=halogen) and the aromatic heterocycle A (where Y=Boronic acid, ester, or stannane) using a suitable Pd catalyst, such as PdCl$_2$(dppf), then gives carbazole 7. The Suzuki or Stille partners could be switched such that the carbazole 5 could be the organometallic partner (where X=boronic acid, boronic ester, or stannane) and the aromatic heterocycle A (where Y=halide) is the halogen containing partner.

In the final step, the products of the invention were prepared in a displacement reaction between the carbazole 7 and an the alkylating (or acylating) agent 8, where X is a leaving group such as an halide or mesylate or triflate (or acid chloride, or sulfonyl chloride) in the presence of a base such as potassium carbonate and a catalyst such as 18-crown-6. Alternatively, the carbazole nitrogen can be substituted under Mitsunobu conditions using triphenylphosphine and diisopropyl azodicarboxylate (DIAD) using alkylating agent 8 (where X is OH).

An alternative synthesis of carbazole 7 is shown in Scheme 2. As shown in Scheme 2, a Suzuki reaction between the starting substituted aniline 1 (where X=halogen) and the aromatic heterocycle A (where Y=Boronic acid or ester) using a suitable Pd catalyst, such as PdCl$_2$(dppf), gives the substituted aniline 10. The Suzuki partners could be switched such that the aniline 1 could be the boronic acid partner (where X=boronic acid or boronic ester) and the aromatic heterocycle A (where Y=halide) is the halogen containing partner. The resulting aniline 10 can then undergo a Buchwald N-arylation reaction with a suitably substituted phenyl 11 (where X=halogen) to give the diphenyl aniline 12. The aniline 12 can then undergo a Pd catalyzed cyclization to give the carbazole 7 under a variety of conditions, such as heating with pivalic acid in air in the presence of Pd(Ac)$_2$. The carbazole 7 can then be further used as discussed in Scheme 1.

Scheme 2

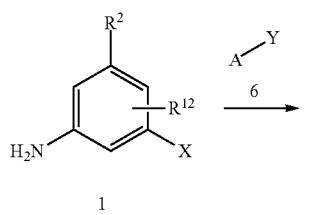

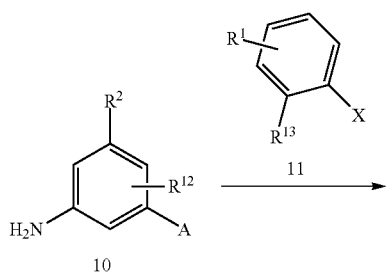

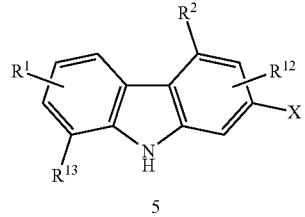

Another alternative synthesis of the carbazole core is the use of the Cadogan reaction as shown in Scheme 3. A Suzuki reaction between the nitrobenzene 14 (where Y=boronic acid or ester) and the substituted phenyl halide 13, where X and $X^1$ are different halides where the $X^1$ is more reactive one (ie. $X^1$=iodide) gives the biphenyl 15. The nitro biphenyl intermediate 15 undergoes a reductive cyclization (Cadogan reaction) in the presence of $Ph_3P$ to give the carbazole 5. The intermediate carbazole 5 can then be further elaborated as outline in Scheme 1.

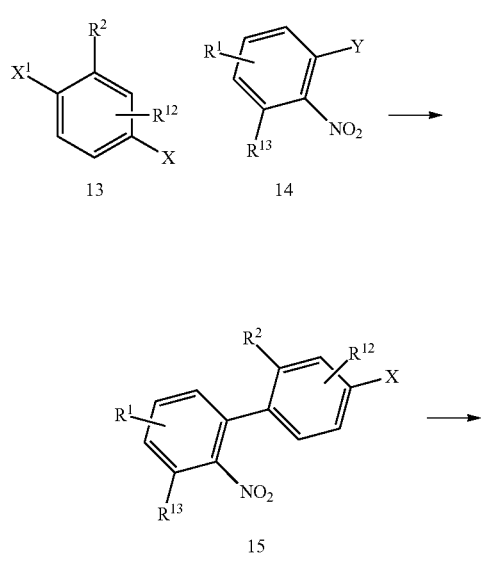

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather is defined by the claims appended hereto.

ABBREVIATIONS

ACN acetonitrile
AcOH acetic acid
$AlMe_3$ trimethyl aluminum
aq aqueous
Bn benzyl
Boc tert-butoxycarbonyl
$Boc_2O$ di-tert-butyl dicarbonate
CBz benzyloxycarbonyl
DCC 1,3-dicyclohexylcarbodiimide
DCM dichloromethane
DDQ 2,3-dichloro-5,6-dicyano-1,4-benzoquinone
DIAD diisopropyl azodicarboxylate
DIEA diisopropylethylamine
DMAP 4-dimethylaminopyridine
DME dimethoxyethane
DMF dimethylformamide
DMSO dimethyl sulfoxide
$Pd(dppf)_2Cl_2$ [1,1'-bis(diphenylphosphino)ferrocene]dichloropalladium(II)
EDC 1-(3-dimethylaminopropyl)-3-ethylcarbodiimide hydrochloride
$Et_2AlCl$ diethyl aluminum chloride
$Et_3N$ triethyl amine
$Et_2O$ diethyl ether
EtOH ethanol
EtOAc ethyl acetate
equiv. equivalent(s)
g gram(s)
h or hr hour(s)
HOBt hydroxybenzotriazole
HPLC high pressure liquid chromatography
iPrOH isopropyl alcohol
KOtBu potassium tert-butoxide
LCMS Liquid Chromatography-Mass Spectroscopy
LDA lithium diisopropylamide
LiHMDS lithium bis(trimethylsilyl)amide
Me methyl
MeI methyl iodide
MeOH methanol
min minute(s)

mL milliliter(s)
mmol millimolar
MTBE methyl t-butyl ether
NaHMDS sodium bis(trimethylsilyl)amide
n-BuLi n-butyl lithium
NH$_4$OAc ammonium acetate
NMP N-methylpyrrolidinone
Pd(OAc)$_2$ palladium acetate
RT or Rt retention time
sat saturated
SFC Supercritical fluid chromatography
t-Bu tertiary butyl
t-BuLi t-butyl lithium
tBuOH tertiary butyl alcohol
tBuOMe tert-butyl methyl ether
TBTU O-(1H-benzotriazol-1-yl)-N,N,N',N'-tetramethyluronium tetrafluoroborate
TCTU O-(1H-6-chlorobenzotriazol-1-yl)-N,N,N',N'-tetramethyluronium tetrafluoroborate
TEA triethylamine
TFA trifluoroacetic acid
Tf$_2$O trifluoromethylsulfonic anhydride
THF tetrahydrofuran
18-Crown-6 [C$_2$H$_4$O]$_6$ IUPAC name—1,4,7,10,13,16-hexaoxacyclooctadecane Example 1

2-(3,5-dimethyl-4-isoxazolyl)-6-(4-morpholinylcarbonyl)-9H-carbazole

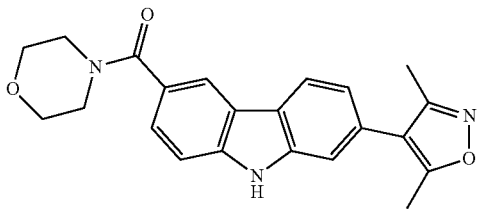 [SMILES: Cc1noc(C)c1-c1ccc2c(c1)[nH]c1ccc(C(=O)N3CCOCC3)cc12]

Step 1: Ethyl 7-bromo-2,3,4,9-tetrahydro-1H-carbazole-3-carboxylate and ethyl 5-bromo-2,3,4,9-tetrahydro-1H-carbazole-3-carboxylate To (3-bromophenyl)hydrazine hydrochloride (940 mg, 4.21 mmol) in AcOH (12 mL) was added ethyl 4-oxocyclohexanecarboxylate (823 mg, 4.84 mmol). The reaction mixture is allowed to reflux for 3 hours. LCMS shows product which is a 1/1 mixture of regioisomers. The reaction mixture is quenched with water, extracted with ethyl acetate, dried and concentrated. 1300 mg (99%) of a 1/1 mixture of ethyl 7-bromo-2,3,4,9-tetrahydro-1H-carbazole-3-carboxylate and ethyl 5-bromo-2,3,4,9-tetrahydro-1H-carbazole-3-carboxylate was isolated.
Column: Waters Acquity SDS BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes. Flow: 1.11 mL/min.
HPLC RT: 1.05, 1.07 min; LCMS: (ES) m/e 322.08 (M+H).

Step 2: Ethyl 7-bromo-9H-carbazole-3-carboxylate and ethyl 5-bromo-9H-carbazole-3-carboxylate To a 1/1 mixture of mixture of ethyl 7-bromo-2,3,4,9-tetrahydro-1H-carbazole-3-carboxylate and ethyl 5-bromo-2,3,4,9-tetrahydro-1H-carbazole-3-carboxylate (1300 mg, 4.03 mmol) in toluene (15 ml) was added DDQ (2430 mg, 10.49 mmol). The reaction mixture is allowed to reflux. After 2 h, LCMS shows consumption of starting material. The solids are filtered off and concentrated to dryness. 1200 mg (94%) of a 1/1 mixture of ethyl 7-bromo-9H-carbazole-3-carboxylate and ethyl 5-bromo-9H-carbazole-3-carboxylate was isolated.
Column: Waters Acquity SDS BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes. Flow: 1.11 mL/min.
HPLC RT: 1.06, 1.07 min; LCMS: (ES) m/e 318.08 (M+H).

Step 3: 7-bromo-9H-carbazole-3-carboxylic acid and 5-bromo-9H-carbazole-3-carboxylic acid To a 1/1 mixture of ethyl 7-bromo-9H-carbazole-3-carboxylate and ethyl 5-bromo-9H-carbazole-3-carboxylate (1.00 g, 3.14 mmol) in THF (5 mL) and EtOH (1 mL) was added sodium hydroxide (1.572 mL, 15.72 mmol). The reaction mixture was stirred at RT for 3 hours. The mixture was concentrated, 1N HCl was added and the precipitate was filtered off 830 mg (91%) of a 1/1 mixture of 7-bromo-9H-carbazole-3-carboxylic acid and 5-bromo-9H-carbazole-3-carboxylic acid was isolated. Column: Waters Acquity SDS BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes. Flow: 1.11 mL/min. HPLC RT: 0.84, 0.88 min; LCMS: (ES) m/e 290.08 (M+H).

Step 4: (7-bromo-9H-carbazol-3-yl)(morpholino)methanone and (5-bromo-9H-carbazol-3-yl)(morpholino)methanone To a 1/1 mixture of 7-bromo-9H-carbazole-3-carboxylic acid and 5-bromo-9H-carbazole-3-carboxylic acid (251 mg, 0.865 mmol) in DMF (5 mL) was added HCTU (344 mg, 2.60 mmol), DMAP (317 mg, 2.60 mmol) and morpholine (452 mg, 5.19 mmol). LCMS showed all product after 1 h. 10% LiCl in water was added and the precipitate was collected. The precipitate was washed with water and air dried to give 260 mg (84%) of a 1/1 mixture of (7-bromo-9H-carbazol-3-yl)(morpholino)methanone and (5-bromo-9H-carbazol-3-yl)(morpholino)methanone.
Column: Waters Acquity SDS BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes. Flow: 1.11 mL/min.
HPLC RT: 0.85, 0.87 min; LCMS: (ES) m/e 359.08 (M+H).

Step 5: (7-(3,5-dimethylisoxazol-4-yl)-9H-carbazol-3-yl)(morpholino) methanone

To a 1/1 mixture of (7-bromo-9H-carbazol-3-yl)(morpholino)methanone and (5-bromo-9H-carbazol-3-yl)(morpholino)methanone (260 mg, 0.724 mmol) and 3,5-dimethyl-4-(4,4,5,5-tetramethyl-1,3,2-dioxaborolan-2-yl)isoxazole (242 mg, 1.086 mmol) was added DMF (3.5 ml). The reaction was degassed and PdCl$_2$(dppf)-CH$_2$Cl$_2$Adduct (29.6 mg, 0.036 mmol) and aqueous phosphoric acid, potassium salt (0.724 ml, 2.171 mmol) were added. The reaction was degassed and heated at 80° C. LCMS showed all product after 2 h. The reaction mixture was cooled, water was added and the precipitate was collected. 140 mg (50%) of a 1/1 mixture of (7-(3,5-dimethylisoxazol-4-yl)-9H-carbazol-3-yl)(morpholino)methanone and (5-(3,5-dimethylisoxazol-4-yl)-9H-carbazol-3-yl)(morpholino)methanone was isolated. The crude material was purified via preparative LC/MS with the following conditions: Column. Waters XBridge C18, 19×150 mm, 5-μm particles; Guard Column. Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 15 minutes, then a 5-minute hold at 100% B; Flow: 20 mL/min. Fractions containing the desired product were combined and dried via centrifugal evaporation.

The yield of (7-(3,5-dimethylisoxazol-4-yl)-9H-carbazol-3-yl)(morpholino)methanone was 4.6 mg, and its estimated purity by LCMS analysis was 99%. Two analytical LC/MS injections were used to determine the final purity.

Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Injection 2 conditions: Column: Waters Acquity UPLC BEH C18, 2.1×50 mm, 1.7-μm particles; MobilePhase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. Proton NMR was acquired in deuterated DMSO.

HPLC RT: 1.256 min; LCMS: (ES) m/e 376.17 (M+H).

Example 2

2-(3,5-dimethyl-4-isoxazolyl)-6-((cis-2,6-dimethyl-4-morpholinyl)carbonyl)-9-ethyl-9H-carbazole

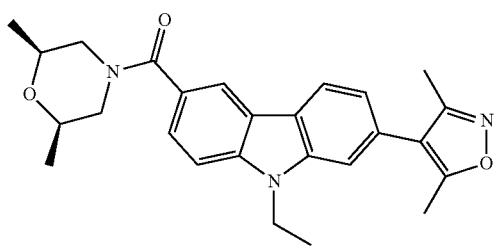 [SMILES: CCn1c2ccc(C(=O)N3C[C@@H](C)O[C@@H](C)C3)cc2c2ccc(-c3c(C)noc3C)cc21]

Step 1: (7-bromo-9H-carbazol-3-yl)(cis-2,6-dimethylmorpholino)methanone and (5-bromo-9H-carbazol-3-yl)(cis-2,6-dimethylmorpholino)methanone To a 1/1 mixture of 7-bromo-9H-carbazole-3-carboxylic acid and 5-bromo-9H-carbazole-3-carboxylic acid (571 mg, 1.968 mmol) (obtained from Example 1 step 3) in DMF (5 mL) was added HCTU (2348 mg, 5.90 mmol), DMAP (721 mg, 5.90 mmol) and cis-2,6-dimethylmorpholine (1360 mg, 11.81 mmol). LCMS showed all product after 1 h. 10% LiCl in water was added and the precipitate was collected. The precipitate was washed with water and air dried to give 760 mg (99%) of a 1/1 mixture of (7-bromo-9H-carbazol-3-yl)(cis-2,6-dimethylmorpholino)methanone and (5-bromo-9H-carbazol-3-yl)(cis-2,6-dimethylmorpholino)methanone.
Column: Waters Acquity SDS BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes. Flow: 1.11 mL/min.

HPLC RT: 1.00 min; LCMS: (ES) m/e 387.08 (M+H).

Step 2. (7-(3,5-dimethylisoxazol-4-yl)-9H-carbazol-3-yl)(cis-2,6-dimethylmorpholino)methanone and (5-(3,5-dimethylisoxazol-4-yl)-9H-carbazol-3-yl)(cis-2,6-dimethylmorpholino)methanone To a 1/1 mixture of (7-bromo-9H-carbazol-3-yl)(cis-2,6-dimethylmorpholino)methanone and (5-bromo-9H-carbazol-3-yl)(cis-2,6-dimethylmorpholino)methanone (760 mg, 1.962 mmol) and 3,5-dimethyl-4-(4,4,5,5-tetramethyl-1,3,2-dioxaborolan-2-yl)isoxazole (657 mg, 2.94 mmol) was added DMF (6.0 ml). The reaction was degassed and then PdCl$_2$(dppf)-CH$_2$Cl$_2$Adduct (80 mg, 0.098 mmol) and aqueous phosphoric acid, potassium salt (1.962 ml, 5.89 mmol) were added. The reaction was degassed again and heated at 80° C. LCMS shows complete conversion to product after 2 h. The reaction mixture was cooled, water was added and the precipitate was collected. 800 mg (99%) of a 1/1 mixture of (7-(3,5-dimethylisoxazol-4-yl)-9H-carbazol-3-yl)(cis-2,6-dimethylmorpholino)methanone and (5-(3,5-dimethylisoxazol-4-yl)-9H-carbazol-3-yl)(cis-2,6-dimethylmorpholino)methanone was isolated.
Column: Waters Acquity SDS BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes. Flow: 1.11 mL/min.

HPLC RT: 0.96, 0.977 min; LCMS: (ES) m/e 404.08 (M+H).

Step 3: (7-(3,5-dimethylisoxazol-4-yl)-9-ethyl-9H-carbazol-3-yl)(cis-2,6-dimethylmorpholino)methanone To 70 mg of a 1/1 mixture of (7-(3,5-dimethylisoxazol-4-yl)-9H-carbazol-3-yl)(cis-2,6-dimethylmorpholino)methanone (35 mg, 0.087 mmol) and (5-(3,5-dimethylisoxazol-4-yl)-9H-carbazol-3-yl)(cis-2,6-dimethylmorpholino)methanone (35 mg, 0.087 mmol) in acetone (1.0 mL) was added potassium carbonate (48.0 mg, 0.347 mmol), 18-crown-6 (2.293 mg, 8.67 μmol) and iodoethane (135 mg, 0.867 mmol). The reaction was allowed to heat to 80° C. for 2 h. The reaction was concentrated to dryness, diluted with DMF, filtered and the crude material was purified via preparative HPLC with the following conditions:
Column: Waters XBridge C18, 19×250 mm, 5-μm particles; Guard Column. Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 10-minute hold at 60% B; Flow: 20 mL/min. Fractions containing the desired product were combined and dried via centrifugal evaporation. The yield of (7-(3,5-dimethylisoxazol-4-yl)-9-ethyl-9H-carbazol-3-yl)(cis-2,6-dimethylmorpholino)methanone was 7.3 mg, and its estimated purity by LCMS analysis was 100%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Injection 2 conditions: Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. Proton NMR was acquired in deuterated DMSO.

HPLC RT: 1.896 min; LCMS: (ES) m/e 432.23 (M+H).

The compounds in Table 1 were prepared in a similar procedure as described for Example 2:

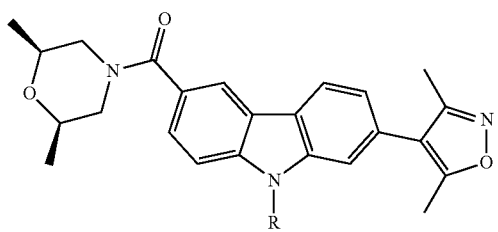

TABLE 1

| Example # | R | HPLC RT (min.) | M + H | HPLC Method |
|---|---|---|---|---|
| 3 | —CH$_2$CH$_2$CH$_3$ | 2.0 | 446.1 | B |
| 4 | —CH$_2$CH(CH$_3$)$_2$ | 2.1 | 460.1 | B |
| 5 | —CH$_2$-Cyclopropyl | 2.0 | 458.2 | B |
| 6 | —CH$_2$CH$_2$F | 1.8 | 450.1 | A |
| 7 | —CH$_2$CHF$_2$ | 1.8 | 468.1 | A |
| 8 | —CH$_2$CH$_2$OCH$_3$ | 1.8 | 462.1 | B |
| 9 | —CH$_2$-phenyl | 2.1 | 494.2 | B |
| 10 | —CH$_2$CH$_2$-phenyl | 2.1 | 508.2 | A |
| 11 | CH$_2$-(2-Cl-phenyl) | 2.2 | 528.2 | A |
| 12 | CH$_2$-(4-Cl-phenyl) | 2.2 | 528.2 | A |
| 13 | CH$_2$-(3-Cl-phenyl) | 2.2 | 528.2 | B |
| 14 | CH$_2$-(3-OMe-phenyl) | 2.1 | 524.2 | A |
| 15 | CH$_2$-(2-OMe-phenyl) | 2.1 | 524.3 | A |
| 16 | CH$_2$-(2-F-phenyl) | 2.1 | 512.1 | B |
| 17 | CH$_2$-(3-F-phenyl) | 2.1 | 512.1 | B |
| 18 | CH$_2$-(4-F-phenyl) | 2.1 | 512.1 | B |
| 19 | CH$_2$-(2-Me-phenyl) | 2.2 | 508.2 | B |
| 20 | CH$_2$-(3-Me-phenyl) | 2.2 | 508.2 | B |
| 21 | CH$_2$-(4-Me-phenyl) | 2.2 | 508.2 | B |

HPLC Conditions for all Samples:
Method A:
Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.
Method B:
Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min.

Example 22

9-(cyclopropylmethyl)-2-(3,5-dimethyl-4-isoxazolyl)-6-(4-morpholinylcarbonyl)-9H-carbazole

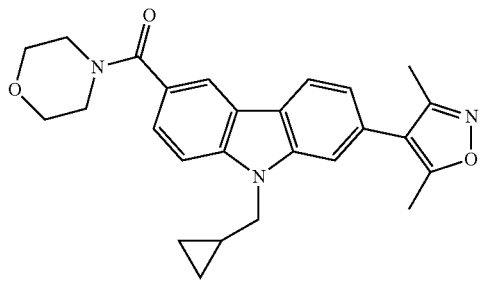 [SMILES: Cc1noc(C)c1-c1ccc2c3cc(C(=O)N4CCOCC4)ccc3n(CC3CC3)c2c1]

To 60 mg of a 1/1 mixture of (7-(3,5-dimethylisoxazol-4-yl)-9H-carbazol-3-yl)(morpholino)methanone (30 mg, 0.080 mmol) and (5-(3,5-dimethylisoxazol-4-yl)-9H-carbazol-3-yl)(morpholino)methanone (30.0 mg, 0.080 mmol) in acetone (1.5 ml) was added potassium carbonate (44.2 mg, 0.320 mmol), 18C6 (2.112 mg, 7.99 mmol) and (bromomethyl)cyclopropane (108 mg, 0.799 mmol). The reaction was allowed to heat to 80° C. for 4 h. The reaction mixture was filtered, concentrated, diluted with DMF and purified via preparative HPLC with the following conditions: Column: Waters XBridge Shield RP18, 19×200 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 25 mL/min. Fractions containing the desired product were combined and dried via centrifugal evaporation.

The material was further purified via preparative HPLC with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-55% B over 25 minutes, then a 15-minute hold at 55% B; Flow: 20 mL/min. Fractions containing the desired product were combined and dried via centrifugal evaporation.

The yield of (9-(cyclopropylmethyl)-7-(3,5-dimethylisoxazol-4-yl)-9H-carbazol-3-yl)(morpholino)methanone was 18.2 mg, and its estimated purity by LCMS analysis was 100%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. Injection 2 conditions: Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. Proton NMR was acquired in deuterated DMSO.

HPLC RT: 1.785 min; LCMS: (ES) m/e 430.21 (M+H).

Example 23

2-(3,5-dimethyl-4-isoxazolyl)-6-((cis-2,6-dimethyl-4-morpholinyl)carbonyl)-9-(methylsulfonyl)-9H-carbazole

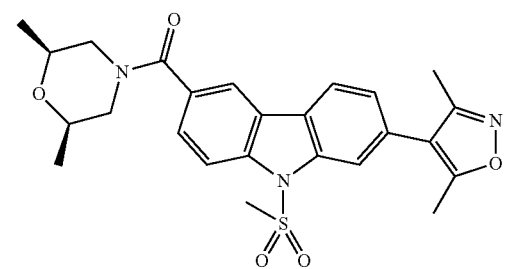 [SMILES: Cc1noc(C)c1-c1ccc2c3cc(C(=O)N4C[C@@H](C)O[C@@H](C)C4)ccc3n(S(C)(=O)=O)c2c1]

To 100 mg of a 1/1 mixture of (7-(3,5-dimethylisoxazol-4-yl)-9H-carbazol-3-yl)(morpholino)methanone (50 mg, 0.124 mmol) and (5-(3,5-dimethylisoxazol-4-yl)-9H-carbazol-3-yl)(morpholino)methanone (50.0 mg, 0.124 mmol) in DMF (1.0 mL) was added 60% sodium hydride (19.83 mg, 0.496 mmol), methanesulfonyl chloride (0.034 mL, 0.434 mmol), 18C6 (3.28 mg, 0.012 mmol). The reaction was allowed to stir at RT. LCMS showed partial completion after ½ hour. The reaction mixture was diluted with DMF, filtered and purified via preparative HPLC with the following conditions: Column: Waters XBridge Shield RP18, 19×250 mm, 5-μm particles; Guard Column: Waters XBridge C18, 19×10 mm, 5-μm particles; Mobile Phase A: 5:95 acetonitrile:water with 0.05% TFA; Mobile Phase B: 95:5 acetonitrile:water with 0.05% TFA; Gradient: 15-55% B over 25 minutes, then a 10-minute hold at 55% B; Flow: 20 mL/min. Fractions containing the desired product were combined and dried via centrifugal evaporation.

The yield of (7-(3,5-dimethylisoxazol-4-yl)-9-(methylsulfonyl)-9H-carbazol-3-yl)(cis-2,6-dimethylmorpholino)methanone was 4.6 mg, and its estimated purity by LCMS analysis was 98%. Two analytical LC/MS injections were used to determine the final purity.

Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Injection 2 conditions: Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. Proton NMR was acquired in deuterated DMSO.

HPLC RT: 1.517 min; LCMS: (ES) m/e 482.17 (M+H).

Example 24

9-benzoyl-2-(3,5-dimethyl-4-isoxazolyl)-6-((cis-2,6-dimethyl-4-morpholinyl)carbonyl)-9H-carbazole

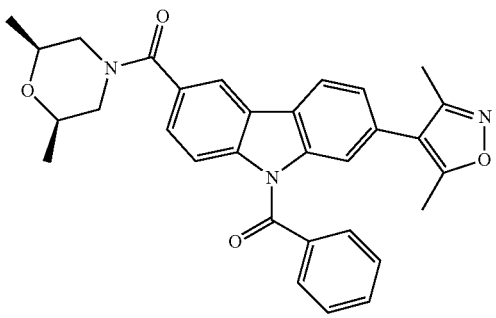 [SMILES: Cc1noc(C)c1-c1ccc2c3cc(C(=O)N4C[C@@H](C)O[C@@H](C)C4)ccc3n(C(=O)c3ccccc3)c2c1]

To 80 mg of a 1/1 mixture of (7-(3,5-dimethylisoxazol-4-yl)-9H-carbazol-3-yl)(cis-2,6-dimethylmorpholino)methanone (40 mg, 0.099 mmol) and (5-(3,5-dimethylisoxazol-4-yl)-9H-carbazol-3-yl)(cis-2,6-dimethylmorpholino)methanone (40.0 mg, 0.099 mmol) in THF (1.0 mL) was added 60% sodium hydride (15.86 mg, 0.397 mmol) and benzoyl chloride (49 mg, 0.397 mmol). The reaction was allowed to stir at RT. LCMS showed partial completion after a ½ hour. The reaction mixture was diluted with DMF, filtered and purified via preparative HPLC with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 25 minutes, then a 10-minute hold at 65% B; Flow: 20 mL/min. Fractions containing the desired product were combined and dried via centrifugal evaporation.

The yield of (9-benzoyl-7-(3,5-dimethylisoxazol-4-yl)-9H-carbazol-3-yl)(cis-2,6-dimethylmorpholino)methanone was 6.7 mg, and its estimated purity by LCMS analysis was 98%. Two analytical LC/MS injections were used to determine the final purity.

Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Injection 2 conditions: Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. Proton NMR was acquired in deuterated DMSO.

Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. HPLC RT: 2.012 min; LCMS: (ES) m/e 508.22 (M+H).

Example 25

2-(3,5-dimethyl-4-isoxazolyl)-6-((cis-2,6-dimethyl-4-morpholinyl)carbonyl)-9H-carbazole-4-carboxamide

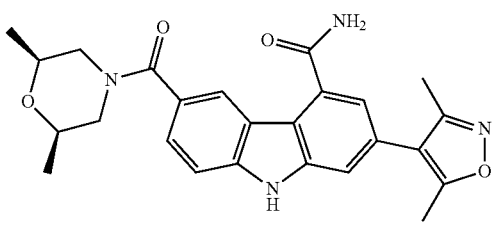 [SMILES: Cc1noc(C)c1-c1cc(C(N)=O)c2c(c1)[nH]c1ccc(C(=O)N3C[C@@H](C)O[C@@H](C)C3)cc12]

Step 1: 3-bromo-5-hydrazinylbenzoic acid dihydrochloride

A solution of sodium nitrite (1.757 g, 25.5 mmol) in $H_2O$, (8 mL) was added dropwise to a cooled (−14° C., ice-salt bath), cream-colored suspension of 3-amino-5-bromobenzoic acid (5.24 g, 24.26 mmol) in conc. HCl (24 mL), such that the temperature did not exceed 0° C. (over 12 min). The light brown-colored solution was stirred at 0° C. for 6 min, and was then added in portions to a cooled (−20° C., isopropanol/dry ice) and rapidly stirred solution of tin (II) chloride (13.80 g, 72.8 mmol) in conc. HCl (8 mL), such that the temperature stayed between −20° C. and −5° C. (over 30 min). In between additions, the flask containing the diazonium intermediate was kept in an ice/salt bath. After completion of the addition, the reaction was stirred for 45 minutes at −10° C. The resulting cream-colored suspension was warmed up to room temperature and stirred at room temperature for 1 hour. The solid was collected by filtration, washed with water and ether and dried to give 6.3 g (85%) of 3-bromo-5-hydrazinylbenzoic acid dihydrochloride.

Column: Waters Acquity SDS BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes. Flow: 1.11 mL/min.

HPLC RT: 0.50 min; LCMS: (ES) m/e 231.08 (M+H).

Step 2: 7-bromo-3-(ethoxycarbonyl)-2,3,4,9-tetrahydro-1H-carbazole-5-carboxylic acid To 3-bromo-5-hydrazinylbenzoic acid hydrochloride (2.71 g, 10.13 mmol) in AcOH (12 mL) was added ethyl 4-oxocyclohexanecarboxylate (1.983 g, 11.65 mmol). The reaction was refluxed for 3 hours. LCMS shows product which is a mixture of regioisomers. The reaction mixture was cooled to room temperature and concentrated to dryness. The product was purified by ISCO eluting with 0-5% MeOH/DCM. The product isomers were separated and 1.90 g (51%) of 7-bromo-3-(ethoxycarbonyl)-2,3,4,9-tetrahydro-1H-carbazole-5-carboxylic acid was isolated.

Column: Waters Acquity SDS BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes. Flow: 1.11 mL/min.

HPLC RT: 0.87 min; LCMS: (ES) m/e 366.08 (M+H).

Step 3: Ethyl 7-bromo-5-carbamoyl-2,3,4,9-tetrahydro-1H-carbazole-3-carboxylate To 7-bromo-3-(ethoxycarbonyl)-2,3,4,9-tetrahydro-1H-carbazole-5-carboxylic acid (1900 mg, 5.19 mmol) in THF (20 mL) and DCM (4.00 mL) was added EDC (3978 mg, 20.75 mmol) and HOBT (3178 mg, 20.75 mmol). The reaction mixture was stirred at room temperature for ¼ hour and then ammonium hydroxide (1.212 mL, 31.1 mmol) was added. The mixture turned into a thick yellow suspension and stirring was continued at room temperature for 3 hours. The reaction mixture was concentrated to a minimal volume and water was added. The reaction mixture was extracted with EtOAc, dried and concentrated to give 1.9 g (99%) of ethyl 7-bromo-5-carbamoyl-2,3,4,9-tetrahydro-1H-carbazole-3-carboxylate.

Column: Waters Acquity SDS BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes. Flow: 1.11 mL/min.
HPLC RT: 0.78 min.; LCMS: (ES) m/e 365.08 (M+H).

Step 4: Ethyl 7-bromo-5-carbamoyl-9H-carbazole-3-carboxylate

In a 500 ml round bottom flask was added THF (100 ml), DDQ (11.21 g, 48.4 mmol) and ethyl 7-bromo-5-carbamoyl-2,3,4,9-tetrahydro-1H-carbazole-3-carboxylate (6.80 g, 18.62 mmol). The reaction mixture was refluxed for 90 minutes. The reaction was concentrated to dryness and then diluted with diluted saturated sodium bicarbonate solution. A white solid precipitated upon stirring and was filtered off, washed with water and then diethyl ether to give ethyl 7-bromo-5-carbamoyl-9H-carbazole-3-carboxylate as a white solid (5.8 g, 85%).

Column: Waters Acquity SDS BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes. Flow: 1.11 mL/min. HPLC RT: 0.80 min; LCMS: (ES) m/e 361.08 (M+H).

Step 5: 7-bromo-5-carbamoyl-9H-carbazole-3-carboxylic acid

To ethyl 7-bromo-5-carbamoyl-9H-carbazole-3-carboxylate (2.00 g, 5.54 mmol) in THF (10 mL) and MeOH (2 mL) was added sodium hydroxide (2.77 mL, 27.7 mmol). The reaction mixture was stirred at room temperature for 6 hours. The reaction mixture was concentrated, added 1N HCl was added and the precipitate was collected to give 1.9 g (95%) of 7-bromo-5-carbamoyl-9H-carbazole-3-carboxylic acid.

Column: Waters Acquity SDS BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes. Flow: 1.11 mL/min. HPLC RT: 0.66 min; LCMS: (ES) m/e 333.08 (M+H).

Step 6: 2-bromo-6-(cis-2,6-dimethylmorpholine-4-carbonyl)-9H-carbazole-4-carboxamide To 7-bromo-5-carbamoyl-9H-carbazole-3-carboxylic acid (2.0 g, 6.00 mmol) in DMF (15 mL) was added HCTU (7.16 g, 18.01 mmol), DMAP (2.200 g, 18.01 mmol) and cis-2,6-dimethylmorpholine (4.15 g, 36.0 mmol). LCMS shows all product after ½ hour. 10% LiCl in water was added and the mixture was extracted with EtOAc. 2.0 g of crude 2-bromo-6-(cis-2,6-dimethylmorpholine-4-carbonyl)-9H-carbazole-4-carboxamide was isolated.

Column: Waters Acquity SDS BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes. Flow: 1.11 mL/min.
HPLC RT: 0.73 min; LCMS: (ES) m/e 430.08 (M+H).

Step 7: 2-(3,5-dimethylisoxazol-4-yl)-6-(cis-2,6-dimethylmorpholine-4-carbonyl)-9H-carbazole-4-carboxamide To 2-bromo-6-(cis-2,6-dimethylmorpholine-4-carbonyl)-9H-carbazole-4-carboxamide (2.0 g, 4.65 mmol), and 3,5-dimethyl-4-(4,4,5,5-tetramethyl-1,3,2-dioxaborolan-2-yl)isoxazole (1.555 g, 6.97 mmol) was added DMF (30 ml). The reaction was degassed and then $PdCl_2(dppf)$-$CH_2Cl_2$ adduct (0.190 g, 0.232 mmol) and aqueous phosphoric acid, potassium salt (4.65 ml, 13.94 mmol) were added. The reaction was degassed and heated at 80° C. for 1 hour. The reaction mixture was cooled, 10% LiCl in water was added and the precipitate formed was collected. 2.0 g of crude 2-(3,5-dimethylisoxazol-4-yl)-6-(cis-2,6-dimethylmorpholine-4-carbonyl)-9H-carbazole-4-carboxamide was isolated.

About 30 mg of the crude material was purified via preparative HPLC with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 25 minutes, then a 5-minute hold at 100% B; Flow: 20 mL/min. Fractions containing the desired product were combined and dried via centrifugal evaporation.

The material was further purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 25 minutes, then a 5-minute hold at 50% B; Flow: 20 mL/min. Fractions containing the desired product were combined and dried via centrifugal evaporation.

The yield of 2-(3,5-dimethylisoxazol-4-yl)-6-(cis-2,6-dimethylmorpholine-4-carbonyl)-9H-carbazole-4-carboxamide was 8.4 mg, and its estimated purity by LCMS analysis was 97%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. Injection 2 conditions: Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow:

1.11 mL/min. Proton NMR was acquired in deuterated 1:1 methanol:chloroform. LCMS: (ES) m/e 447.20 (M+H)

Example 26

9-(cyclobutylmethyl)-2-(3,5-dimethyl-4-isoxazolyl)-6-((cis-2,6-dimethyl-4-morpholinyl)carbonyl)-9H-carbazole-4-carboxamide

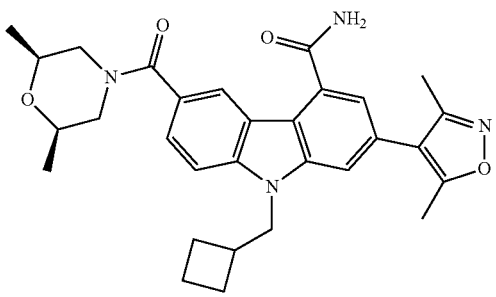 [SMILES: Cc1noc(C)c1-c1cc(C(N)=O)c2c3cc(C(=O)N4C[C@@H](C)O[C@@H](C)C4)ccc3n(CC3CCC3)c2c1]

To 2-(3,5-dimethylisoxazol-4-yl)-6-(cis-2,6-dimethyl-morpholine-4-carbonyl)-9H-carbazole-4-carboxamide (120 mg, 0.269 mmol) was added acetone (1.5 mL), potassium carbonate (149 mg, 1.075 mmol), 18-crown-6 (7.10 mg, 0.027 mmol) and (bromomethyl)cyclobutane (401 mg, 2.69 mmol). The reaction was allowed to heat to 80° C. for 16 hours.

The reaction mixture was filtered and the crude material was purified via preparative HPLC with the following conditions: Column: Waters Xbridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation. The yield of 9-(cyclobutylmethyl)-2-(3,5-dimethylisoxazol-4-yl)-6-(cis-2,6-dimethylmorpholine-4-carbonyl)-9H-carbazole-4-carboxamide was 3.8 mg, and its estimated purity by LCMS analysis was 95%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. Injection 2 conditions: Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. Proton NMR was acquired in deuterated 1:1 methanol:chloroform.

HPLC RT: 1.797 min; LCMS: (ES) m/e 515.27 (M+H).

The compounds in Table 2 were prepared in a similar procedure as described for Example 26:

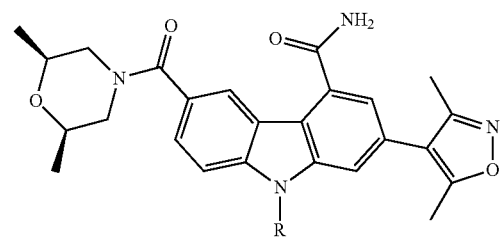

TABLE 2

| Example # | R | HPLC RT (min.) | M + H | HPLC Method |
|---|---|---|---|---|
| 27 | 4-methylthiazole-CH2- | 1.4 | 544.1 | A |
| 28 | 4-methyl-2-thiazolyl-CH2- | 1.5 | 558.1 | B |
| 29 | oxazol-2-yl-CH2- | 1.3 | 528.1 | A |
| 30 | thiazol-2-yl-CH2- | 1.4 | 544.1 | A |
| 31 | 2-fluorobenzyl | 1.7 | 555.2 | B |
| 32 | 4-fluorobenzyl | 1.7 | 555.2 | A |
| 33 | 2-chlorobenzyl | 1.8 | 571.3 | A |
| 34 | 3-chlorobenzyl | 1.8 | 571.2 | B |

TABLE 2-continued

| Example # | R | HPLC RT (min.) | M + H | HPLC Method |
|---|---|---|---|---|
| 35 | 4-chlorobenzyl | 1.8 | 571.2 | A |
| 36 | 2,4-difluorobenzyl | 1.7 | 573.2 | A |
| 37 | 4-cyanobenzyl | 1.6 | 562.2 | A |
| 38 | pyrimidin-4-ylmethyl | 1.2 | 539.2 | A |
| 39 | 1-phenylethyl | 1.7 | 551.3 | A |
| 40 | 2-methoxybenzyl | 1.8 | 567.3 | A |
| 41 | 2,3-difluorobenzyl | 1.7 | 573.2 | A |
| 42 | 2,5-difluorobenzyl | 1.7 | 573.2 | A |
| 43 | 2-cyanobenzyl | 1.6 | 562.2 | A |
| 44 | 3-cyanobenzyl | 1.6 | 562.2 | A |

Example 45

2-(3,5-dimethylisoxazol-4-yl)-6-(cis-2,6-dimethyl-morpholine-4-carbonyl)-9-(phenylsulfonyl)-9H-carbazole-4-carboxamide To 2-(3,5-dimethylisoxazol-4-yl)-6-(cis-2,6-dimethylmorpholine-4-carbonyl)-9H-carbazole-4-carboxamide (100 mg, 0.224 mmol) in DMF (1.0 mL) was added sodium hydride (35.8 mg, 0.896 mmol) and benzenesulfonyl chloride (138 mg, 0.784 mmol). The reaction was allowed to stir at room temperature for ½ hour. The reaction was quenched with water, filtered and the crude material was purified via preparative HPLC with the following conditions: Column: Waters XBridge C18, 19×200 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 20 minutes, then a 5-minute hold at 100% B; Flow: 20 mL/min. Fractions containing the desired product were combined and dried via centrifugal evaporation. The yield of 2-(3,5-dimethylisoxazol-4-yl)-6-(cis-2,6-dimethylmorpholine-4-carbonyl)-9-(phenylsulfonyl)-9H-carbazole-4-carboxamide was 1.6 mg and its estimated purity by LCMS analysis was 91%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. Injection 2 conditions: Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. Proton NMR was acquired in deuterated DMSO.

HPLC RT: 1.79 min; LCMS: (ES) m/e 587.189 (M+H).

Example 46

9-benzoyl-2-(3,5-dimethylisoxazol-4-yl)-6-(cis-2,6-dimethylmorpholine-4-carbonyl)-9H-carbazole-4-carboxamide

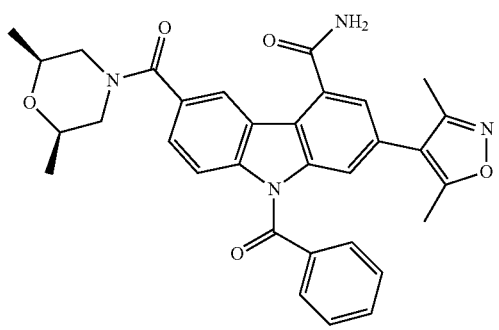 [SMILES: Cc1noc(C)c1-c1cc(C(N)=O)c2c3cc(C(=O)N4C[C@@H](C)O[C@@H](C)C4)ccc3n(C(=O)c3ccccc3)c2c1]

To 2-(3,5-dimethylisoxazol-4-yl)-6-(cis-2,6-dimethylmorpholine-4-carbonyl)-9H-carbazole-4-carboxamide (150 mg, 0.336 mmol) in DMF (1.0 mL) was added sodium hydride (53.7 mg, 1.344 mmol) and benzoyl chloride (165 mg, 1.176 mmol). The reaction was allowed to stir at room temperature for ½ hour. The reaction was quenched with water, filtered and the crude material was purified via preparative HPLC using the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation. The yield of 9-benzoyl-2-(3,5-dimethylisoxazol-4-yl)-6-(cis-2,6-dimethylmorpholine-4-carbonyl)-9H-carbazole-4-carboxamide was 1.1 mg, and its estimated purity by LCMS analysis was 94%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. Injection 2 conditions: Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75 minute hold at 100% B; Flow: 1.11 mL/min. Proton NMR was acquired in deuterated DMSO.

HPLC RT: 1.635 min; LCMS: (ES) m/e 551.23 (M+H).

Example 47

9-benzyl-2-(3,5-dimethyl-4-isoxazolyl)-6-(4-morpholinylcarbonyl)-9H-carbazole-4-carboxamide

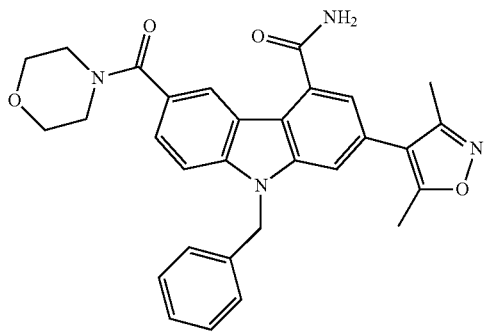 [SMILES: Cc1noc(C)c1-c1cc(C(N)=O)c2c3cc(C(=O)N4CCOCC4)ccc3n(Cc3ccccc3)c2c1]

Step 1: Ethyl 5-carbamoyl-7-(3,5-dimethylisoxazol-4-yl)-9H-carbazole-3-carboxylate To ethyl 7-bromo-5-carbamoyl-9H-carbazole-3-carboxylate (1.5 g, 4.15 mmol) and 3,5-dimethyl-4-(4,4,5,5-tetramethyl-1,3,2-dioxaborolan-2-yl)isoxazole (1.390 g, 6.23 mmol) was added DMF (15 ml). The reaction was degassed and then PdCl$_2$(dppf)-CH$_2$Cl$_2$ adduct (0.170 g, 0.208 mmol) and aqueous phosphoric acid, potassium salt (4.15 ml, 12.46 mmol) were added. The reaction was degassed and heated at 80° C. for 1 hour. The reaction was cooled, 10% LiCl in water was added and the precipitate was collected 1.57 g (99%) of ethyl 5-carbamoyl-7-(3,5-dimethylisoxazol-4-yl)-9H-carbazole-3-carboxylate was isolated.
Column: Waters Acquity SDS BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes. Flow: 1.11 mL/min.

HPLC RT: 0.82 min; LCMS: (ES) m/e 378.08 (M+H).

Step 2: Ethyl 9-benzyl-5-carbamoyl-7-(3,5-dimethylisoxazol-4-yl)-9H-carbazole-3-carboxylate To ethyl 5-carbamoyl-7-(3,5-dimethylisoxazol-4-yl)-9H-carbazole-3-carboxylate (566 mg, 1.500 mmol) was added acetone (1.0 mL), potassium carbonate (829 mg, 6.00 mmol), 18-crown-6 (39.6 mg, 0.150 mmol) and (bromomethyl)benzene (385 mg, 2.250 mmol). The reaction was heated to 80° C. for 2 hours. The reaction was concentrated to dryness to give ethyl 9-benzyl-5-carbamoyl-7-(3,5-dimethylisoxazol-4-yl)-9H-carbazole-3-carboxylate.
Column: Waters Acquity SDS BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes. Flow: 1.11 mL/min.

HPLC RT: 1.01 min; LCMS: (ES) m/e 468.08 (M+H).

Step 3: 9-benzyl-5-carbamoyl-7-(3,5-dimethylisoxazol-4-yl)-9H-carbazole-3-carboxylic acid To ethyl 9-benzyl-5-carbamoyl-7-(3,5-dimethylisoxazol-4-yl)-9H-carbazole-3-carboxylate (600 mg, 1.283 mmol) in THF (10 mL) and MeOH (2 mL) was added 10 N sodium hydroxide (0.642 mL, 6.42 mmol). The reaction was allowed to stir at 60° C. for 1 hour. The reaction mixture was concentrated to dryness, and 1N HCl was added to give 500 mg (88% 2 steps) of 9-benzyl-5-carbamoyl-7-(3,5-dimethylisoxazol-4-yl)-9H-carbazole-3-carboxylic acid.
Column: Waters Acquity SDS BEH C18, 2.1×50 mm, 1.7-µm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes. Flow: 1.11 mL/min.
HPLC RT: 0.89 min; LCMS: (ES) m/e 440.08 (M+H).

Step 4: 9-benzyl-2-(3,5-dimethylisoxazol-4-yl)-6-(morpholine-4-carbonyl)-9H-carbazole-4-carboxamide To 9-benzyl-5-carbamoyl-7-(3,5-dimethylisoxazol-4-yl)-9H-carbazole-3-carboxylic acid (30 mg, 0.068 mmol) in DMF (1.0 mL) was added HCTU (81 mg, 0.205 mmol), DMAP (25.02 mg, 0.205 mmol) and morpholine (35.7 mg, 0.410 mmol) and stirred at room temperature for ½ hour. The reaction mixture was diluted with DMF, filtered and the crude material was purified via preparative HPLC with the following conditions: Column: Waters XBridge C18, 19×150 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of 9-benzyl-2-(3,5-dimethylisoxazol-4-yl)-6-(morpholine-4-carbonyl)-9H-carbazole-4-carboxamide was 2.5 mg, and its estimated purity by LCMS analysis was 84%. Two analytical LC/MS injections were used to determine the final purity. Injection 1 conditions: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. Injection 2 conditions: Column: Waters Acquity UPLC BEH C18, 2.1×50 mm, 1.7-µm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. Proton NMR was acquired in deuterated DMSO.
HPLC RT: 1.541 min; LCMS: (ES) m/e 509.22 (M+H).
The compounds in Table 3 were prepared in a similar procedure as described for Example 47:

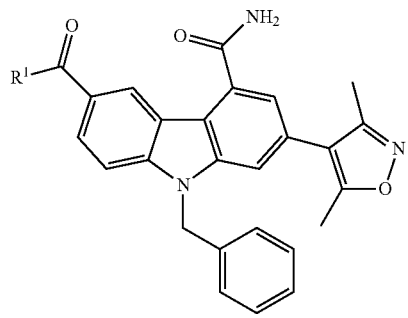

TABLE 3

| Example # | $R^1$ | HPLC RT (min.) | M + H | HPLC Method |
|---|---|---|---|---|
| 48 | —N(CH$_3$)$_2$ | 1.5 | 467 | B |
| 49 | 2,2-dimethylmorpholinyl | 1.7 | 537.1 | A |
| 50 | 4-ethylpiperidinyl | 2.0 | 535 | A |
| 51 | 4-hydroxy-4-methylpiperidinyl | 1.5 | 537 | B |
| 52 | 3-methoxyazetidinyl | 1.6 | 509 | A |
| 53 | 3-hydroxyazetidinyl | 1.4 | 495.1 | A |
| 54 | 2-methylazetidinyl | 1.6 | 493 | B |
| 55 | 2-methylmorpholinyl | 1.6 | 523 | B |
| 56 | 1,4-oxazepanyl | 1.5 | 523 | B |
| 57 | (2S)-2-methylmorpholinyl | 1.6 | 523 | A |

TABLE 3-continued

| Example # | R¹ | HPLC RT (min.) | M + H | HPLC Method |
|---|---|---|---|---|
| 58 | 3,3-dimethylpyrrolidinyl | 1.8 | 521 | B |
| 59 | (S)-3-fluoropyrrolidinyl | 1.6 | 511.1 | A |
| 60 | (R)-3-fluoropyrrolidinyl | 1.6 | 511 | A |
| 61 | 3,3-difluoropyrrolidinyl | 1.7 | 529 | A |
| 62 | (S)-2-methylmorpholinyl | 1.6 | 523 | B |
| 63 | 2,2,6,6-tetramethyl-4-hydroxypiperidinyl | 1.5 | 579 | B |
| 64 | 2-methyl-4-hydroxypiperidinyl | 1.6 | 534 | A |
| 65 | 3-fluoroazetidinyl | 1.6 | 497 | A |
| 66 | pyrrolidinyl | 1.6 | 493 | A |
| 67 | 4-hydroxypiperidinyl | 1.4 | 523.2 | B |
| 68 | 4-(hydroxymethyl)piperidinyl | 1.5 | 537.2 | A |
| 69 | 2,6-dimethylmorpholinyl | 1.7 | 537 | B |
| 70 | 4-methoxypiperidinyl | 1.6 | 537 | |
| 71 | azetidinyl | 1.5 | 479 | B |
| 72 | 3,3-dimethylpiperidinyl | 1.9 | 535 | B |
| 73 | 2-methylpiperidinyl | 1.8 | 521 | B |
| 74 | 4-methylpiperidinyl | 1.9 | 521 | A |
| 75 | 4-methylpiperazinyl | 1.4 | 523.3 | A |
| 76 | 2-morpholinoethylamino | 1.4 | 552 | |
| 77 | 4,4-dimethyloxazolidin-3-yl | 1.7 | 523.2 | B |
| 78 | 3,3-difluoroazetidinyl | 1.7 | 515.2 | A |

Example 79

9-(2,6-difluorobenzyl)-2-(3,5-dimethyl-4-isoxazolyl)-6-(((3S)-3-fluoro-1-pyrrolidinyl)carbonyl)-9H-carbazole-4-carboxamide

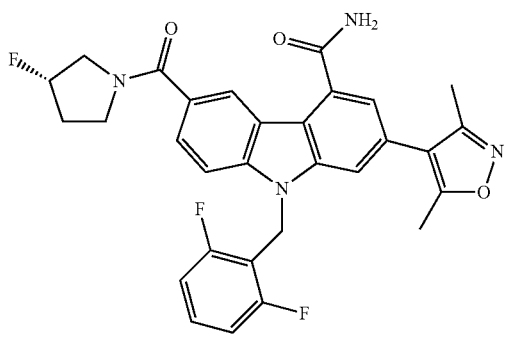 [SMILES: Cc1noc(C)c1-c1cc(C(N)=O)c2c3cc(C(=O)N4CC[C@H](F)C4)ccc3n(Cc3c(F)cccc3F)c2c1]

Step 1: 5-carbamoyl-7-(3,5-dimethylisoxazol-4-yl)-9H-carbazole-3-carboxylic acid To ethyl 5-carbamoyl-7-(3,5-dimethylisoxazol-4-yl)-9H-carbazole-3-carboxylate (1.57 g, 4.16 mmol) in THF (10 mL) and MeOH (2 mL) was added sodium hydroxide (2.080 mL, 20.80 mmol). The reaction was allowed to stir at 60° C. for 6 hours. The reaction mixture was concentrated to dryness, and 1N HCl was added. The precipitate was collected and 1.4 g (96%) of 5-carbamoyl-7-(3,5-dimethylisoxazol-4-yl)-9H-carbazole-3-carboxylic acid was isolated.

Column: Waters Acquity SDS BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes. Flow: 1.11 mL/min.

HPLC RT: 0.70 min; LCMS: (ES) m/e 350.08 (M+H).

Step 2: (S)-2-(3,5-dimethylisoxazol-4-yl)-6-(3-fluoropyrrolidine-1-carbonyl)-9H-carbazole-4-carboxamide To 5-carbamoyl-7-(3,5-dimethylisoxazol-4-yl)-9H-carbazole-3-carboxylic acid (325 mg, 0.930 mmol) in DMF (5.0 mL) was added HCTU (1110 mg, 2.79 mmol), DMAP (341 mg, 2.79 mmol) and (S)-3-fluoropyrrolidine (332 mg, 3.72 mmol) and stirred for 1 hour. Water was added and the precipitate was collected To give 380 mg (97%) of (S)-2-(3,5-dimethylisoxazol-4-yl)-6-(3-fluoropyrrolidine-1-carbonyl)-9H-carbazole-4-carboxamide.

Column: Waters Acquity SDS BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes. Flow: 1.11 mL/min.

HPLC RT: 0.74 min; LCMS: (ES) m/e 421.08 (M+H).

Step 3: (S)-9-(2,6-difluorobenzyl)-2-(3,5-dimethylisoxazol-4-yl)-6-(3-fluoropyrrolidine-1-carbonyl)-9H-carbazole-4-carboxamide To (S)-2-(3,5-dimethylisoxazol-4-yl)-6-(3-fluoropyrrolidine-1-carbonyl)-9H-carbazole-4-carboxamide (60 mg, 0.143 mmol) in DMF (1.0 mL) was added cesium carbonate (186 mg, 0.571 mmol), 18-crown-6 (3.77 mg, 0.014 mmol) and 2-(bromomethyl)-1,3-difluorobenzene (177 mg, 0.856 mmol). The reaction was heated at 80° C. for 2 hours. The reaction mixture was filtered and the crude material was purified via preparative HPLC using the following conditions:

Column: Waters XBridge Shield RP18, 19×200 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 20 minutes, then a 5-minute hold at 100% B; Flow: 25 mL/min. Fractions containing the desired product were combined and dried via centrifugal evaporation. The yield of (S)-9-(2,6-difluorobenzyl)-2-(3,5-dimethylisoxazol-4-yl)-6-(3-fluoropyrrolidine-1-carbonyl)-9H-carbazole-4-carboxamide was 10.8 mg, and its estimated purity by LCMS analysis was 98%. Two analytical LC/MS injections were used to determine the final purity.

Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Injection 2 conditions: Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. Proton NMR was acquired in deuterated 1:1 methanol:chloroform.

HPLC RT: 1.600 min; LCMS: (ES) m/e 547.20 (M+H).

The compounds in Table 4 were prepared in a similar procedure as described for Example 80:

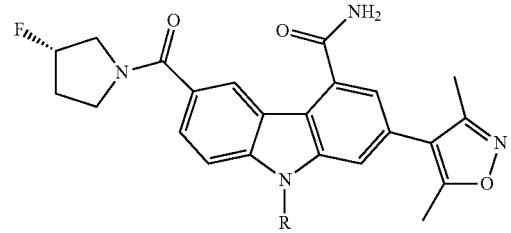

TABLE 4

| Example. # | R | HPLC RT (min.) | M + H | HPLC Method |
|---|---|---|---|---|
| 80 | ~~~⟨⟩-Cl (para) | 1.8 | 545.1 | A |
| 81 | ~~~⟨⟩-F (meta) | 1.6 | 529.2 | A |

TABLE 4-continued

| Example. # | R | HPLC RT (min.) | M + H | HPLC Method |
|---|---|---|---|---|
| 82 | (2-methoxybenzyl) | 1.7 | 541.2 | A |
| 83 | (4-methylthiazol-2-ylmethyl) | 1.4 | 532.2 | A |
| 84 | (1-phenylethyl) | 1.7 | 525.2 | A |

Example 85

2-(3,5-dimethyl-4-isoxazolyl)-6-((3-fluoro-1-azetidinyl)carbonyl)-9-(1-phenylethyl)-9H-carbazole-4-carboxamide

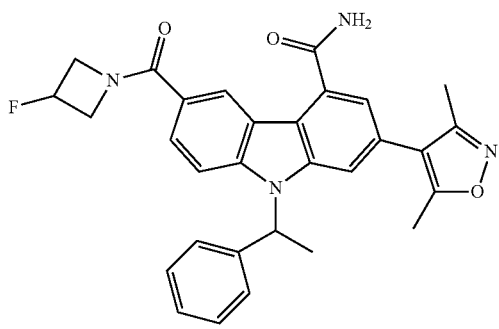 [SMILES: Cc1noc(C)c1-c1cc(C(N)=O)c2c3cc(C(=O)N4CC(F)C4)ccc3n(C(C)c3ccccc3)c2c1]

Step 1: 2-(3,5-dimethylisoxazol-4-yl)-6-(3-fluoroazetidine-1-carbonyl)-9H-carbazole-4-carboxamide To 5-carbamoyl-7-(3,5-dimethylisoxazol-4-yl)-9H-carbazole-3-carboxylic acid (320 mg, 0.916 mmol) in DMF (5.0 mL) was added HCTU (1093 mg, 2.75 mmol), DMAP (336 mg, 2.75 mmol) and 3-fluoroazetidine, 1.0HCl (307 mg, 2.75 mmol). LCMS showed a complete reaction after 1 hour. Water was added and the precipitate was collected to give 330 mg of 2-(3,5-dimethylisoxazol-4-yl)-6-(3-fluoroazetidine-1-carbonyl)-9H-carbazole-4-carboxamide.

Column: Waters Acquity SDS BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes. Flow: 1.11 mL/min.

HPLC RT: 0.73 min; LCMS: (ES) m/e 407.08 (M+H).

Step 2: 2-(3,5-dimethylisoxazol-4-yl)-6-(3-fluoroazetidine-1-carbonyl)-9-(1-phenylethyl)-9H-carbazole-4-carboxamide To 2-(3,5-dimethylisoxazol-4-yl)-6-(3-fluoroazetidine-1-carbonyl)-9H-carbazole-4-carboxamide (130 mg, 0.320 mmol) in acetone (1.0 mL) was added potassium carbonate (177 mg, 1.279 mmol), 18-crown-6 (8.45 mg, 0.032 mmol) and (1-bromoethyl)benzene (355 mg, 1.919 mmol). The reaction was then heated at 80° C. for 6 hours. The reaction was concentrated, diluted with DMF, filtered and the crude material was purified via preparative HPLC using the following conditions:

Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation. The yield of 2-(3,5-dimethylisoxazol-4-yl)-6-(3-fluoroazetidine-1-carbonyl)-9-(1-phenylethyl)-9H-carbazole-4-carboxamide was 31.9 mg, and its estimated purity by LCMS analysis was 98%. Two analytical LC/MS injections were used to determine the final purity.

Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Injection 2 conditions: Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. Proton NMR was acquired in deuterated DMSO.

HPLC RT: 1.660 min; LCMS: (ES) m/e 511.21 (M+H).

The compounds in Table 5 were prepared in a similar procedure as described for Example 85:

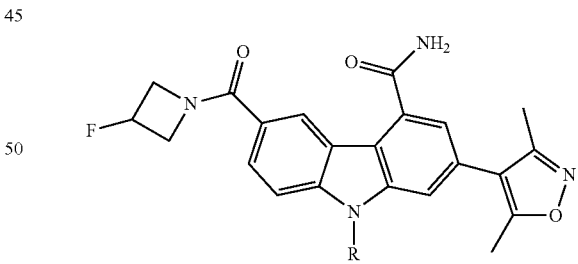

TABLE 5

| Example No. | R | HPLC RT (min.) | M + H | HPLC Method |
|---|---|---|---|---|
| 86 | (3-fluoro-4-chlorobenzyl) | 1.8 | 549.2 | A |

TABLE 5-continued

| Example No. | R | HPLC RT (min.) | M + H | HPLC Method |
|---|---|---|---|---|
| 87 | 4-Cl, 2-F benzyl (CH with wavy bonds) | 1.8 | 549.2 | A |
| 88 | 3-CF3 phenyl (CH(CH3)) | 1.8 | 579.2 | A |
| 89 | 2-CF3 phenyl (CH(CH3)) | 1.7 | 579.2 | A |
| 90 | cyclobutylmethyl | 1.6 | 475.2 | A |
| 91 | 4-F phenyl (CH(CH3)) | 1.7 | 529.1 | A |
| 92 | cyclopropylmethyl | 1.5 | 461.1 | A |
| 93 | 4-F benzyl | 1.5 | 515 | A |

Example 94

9-(1-(4-chlorophenyl)ethyl)-2-(3,5-dimethyl-4-isoxazolyl)-6-((3-fluoro-1-azetidinyl)carbonyl)-9H-carbazole-4-carboxamide

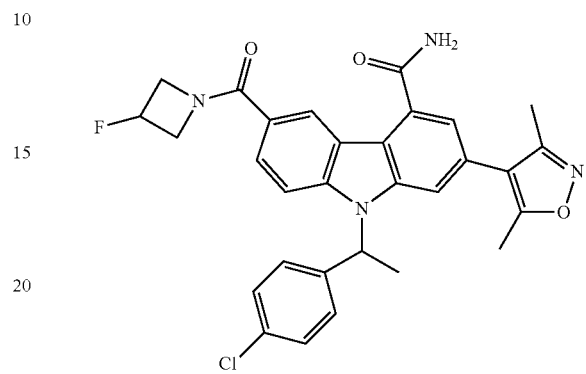

To 2-(3,5-dimethylisoxazol-4-yl)-6-(3-fluoroazetidine-1-carbonyl)-9H-carbazole-4-carboxamide (75 mg, 0.185 mmol) in a small vial was added triphenylphosphine (194 mg, 0.738 mmol), DIAD (0.144 mL, 0.738 mmol), THF (1.5 mL) and 1-(4-chlorophenyl)ethanol (116 mg, 0.738 mmol). The reaction was allowed to stir at room temperature for 1½ hours. The reaction mixture was concentrated to dryness, diluted with DMF, filtered and the crude material was purified via preparative HPLC using the following conditions:

Column: Waters XBridge Shield RP18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation. The yield of 9-(1-(4-chlorophenyl)ethyl)-2-(3,5-dimethylisoxazol-4-yl)-6-(3-fluoroazetidine-1-carbonyl)-9H-carbazole-4-carboxamide was 16.1 mg, and its estimated purity by LCMS analysis was 98%. Two analytical LC/MS injections were used to determine the final purity.

Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Injection 2 conditions: Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. Proton NMR was acquired in deuterated DMSO.

HPLC RT: 1.825 min; LCMS: (ES) m/e 545.18 (M+H).

Example 95

9-(4-chlorobenzyl)-6-((3,3-difluoro-1-azetidinyl) carbonyl)-2-(3,5-dimethyl-4-isoxazolyl)-9H-carbazole-4-carboxamide

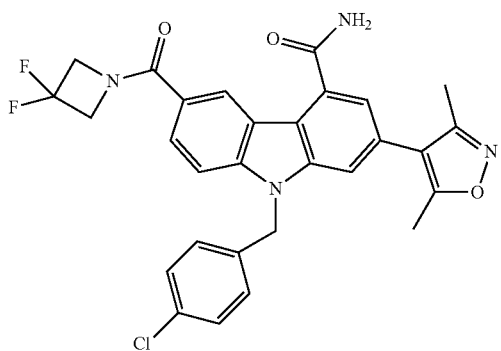 [SMILES: Cc1noc(C)c1-c1cc(C(N)=O)c2c3cc(C(=O)N4CC(F)(F)C4)ccc3n(Cc3ccc(Cl)cc3)c2c1]

Step 1: 6-(3,3-difluoroazetidine-1-carbonyl)-2-(3,5-dimethylisoxazol-4-yl)-9H-carbazole-4-carboxamide To 5-carbamoyl-7-(3,5-dimethylisoxazol-4-yl)-9H-carbazole-3-carboxylic acid (320 mg, 0.916 mmol) in DMF (5.0 mL) was added HCTU (1093 mg, 2.75 mmol), DMAP (336 mg, 2.75 mmol) and 3,3-difluoroazetidine, 1.0HCl (356 mg, 2.75 mmol) and stirred for 1 hour. Water was added and the precipitate was collected to give 330 mg (85%) of 6-(3,3-difluoroazetidine-1-carbonyl)-2-(3,5-dimethylisoxazol-4-yl)-9H-carbazole-4-carboxamide.

Column: Waters Acquity SDS BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes. Flow: 1.11 mL/min.

HPLC RT: 0.78 min; LCMS: (ES) m/e 425.08 (M+H).

Step 2: 9-(4-chlorobenzyl)-6-(3,3-difluoroazetidine-1-carbonyl)-2-(3,5-dimethylisoxazol-4-yl)-9H-carbazole-4-carboxamide To 6-(3,3-difluoroazetidine-1-carbonyl)-2-(3,5-dimethylisoxazol-4-yl)-9H-carbazole-4-carboxamide (60 mg, 0.141 mmol) in DMF (1.0 mL) was added cesium carbonate (184 mg, 0.566 mmol), 18-crown-6 (3.74 mg, 0.014 mmol) and 1-(bromomethyl)-4-chlorobenzene (174 mg, 0.848 mmol). The reaction was heated to 80° C. for 1 hour. The reaction mixture was filtered and the crude material was purified via preparative HPLC with the following conditions: Column: Waters XBridge C18, 19×200 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-100% B over 20 minutes, then a 5-minute hold at 100% B; Flow: 20 mL/min. Fractions containing the desired product were combined and dried via centrifugal evaporation. The yield of 9-(4-chlorobenzyl)-6-(3,3-difluoroazetidine-1-carbonyl)-2-(3,5-dimethylisoxazol-4-yl)-9H-carbazole-4-carboxamide was 14.2 mg, and its estimated purity by LCMS analysis was 99%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. Injection 2 conditions: Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. Proton NMR was acquired in deuterated DMSO.

Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

HPLC RT: 1.811 min; LCMS: (ES) m/e 549.15 (M+H).

Example 96

6-((3,3-difluoro-1-azetidinyl)carbonyl)-2-(3,5-dimethyl-4-isoxazolyl)-9-(1-phenylethyl)-9H-carbazole-4-carboxamide

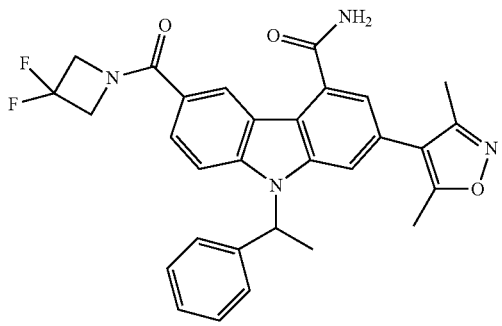 [SMILES: Cc1noc(C)c1-c1cc(C(N)=O)c2c3cc(C(=O)N4CC(F)(F)C4)ccc3n(C(C)c3ccccc3)c2c1]

To 6-(3,3-difluoroazetidine-1-carbonyl)-2-(3,5-dimethylisoxazol-4-yl)-9H-carbazole-4-carboxamide (227 mg, 0.535 mmol) in acetone (3.0 mL) was added potassium carbonate (296 mg, 2.139 mmol), 18-crown-6 (14.14 mg, 0.053 mmol) and (1-bromoethyl)benzene (594 mg, 3.21 mmol). The reaction was heated to 80° C. for 6 hours. The reaction mixture was concentrated. 10% LiCl was added and the reaction mixture was extracted with EtOAc. The reaction mixture was dried and concentrated to give crude product. The crude material was purified via preparative HPLC using the following conditions:

Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation. The yield of 6-(3,3-difluoroazetidine-1-carbonyl)-2-(3,5-dimethylisoxazol-4-yl)-9-(1-phenylethyl)-9H-carbazole-4-carboxamide was 22.5 mg, and its estimated purity by LCMS analysis was 99%. Two analytical LC/MS injections were used to determine the final purity.

Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Injection 2 conditions: Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. Proton NMR was acquired in deuterated DMSO. Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

HPLC RT: 1.757 min. LCMS: (ES) m/e 529.20 (M+H).

The enantiomers were then separated to give chiral isomers 1 and 2.

Example 97

6-((3,3-difluoro-1-azetidinyl)carbonyl)-2-(3,5-dimethyl-4-isoxazolyl)-9-(1-phenylethyl)-9H-carbazole-4-carboxamide Enantiomer 1

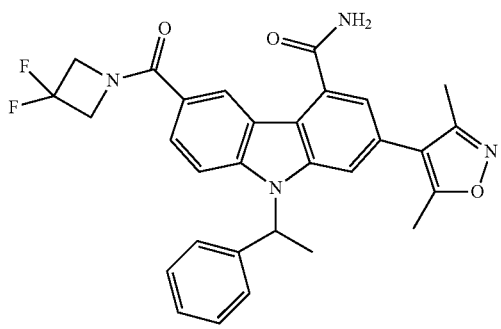 [SMILES: Cc1noc(C)c1-c1cc(C(N)=O)c2c3cc(C(=O)N4CC(F)(F)C4)ccc3n(C(C)c3ccccc3)c2c1]

Isomer 1:
A sample of racemic 6-(3,3-difluoroazetidine-1-carbonyl)-2-(3,5-dimethylisoxazol-4-yl)-9-(1-phenylethyl)-9H-carbazole-4-carboxamide from Example 96 was resolved using preparative chiral SFC HPLC:

Instrument: Berger SFC MGII; Column: Chiral OJ-H 25×3 cm ID, 5 μm; Flow rate: 85 mL/min; Mobile Phase: 80/20 CO₂/MeOH w/0.1% DEA; Detector Wavelength: 220 nm; The first peak from the column gave 6-(3,3-difluoroazetidine-1-carbonyl)-2-(3,5-dimethylisoxazol-4-yl)-9-(1-phenylethyl)-9H-carbazole-4-carboxamide.
Chiral HPLC Analytical Chromatographic Conditions:
Instrument: Berger analytical SFC (LVL-L4021 Lab); Column: Chiral OJ-H 250×4.6 mm ID, 5 μm; Flow rate: 2.0 mL/min; Mobile Phase: 80/20 CO2/MeOH w/0.1% DEA. Chiral HPLC RT: 11.01 min Column: Waters Acquity SDS BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes. Flow: 1.11 mL/min.

HPLC RT: 0.94 min; LCMS: (ES) m/e 529.08 (M+H).

Example 98

6-((3,3-difluoro-1-azetidinyl)carbonyl)-2-(3,5-dimethyl-4-isoxazolyl)-9-(1-phenylethyl)-9H-carbazole-4-carboxamide Enantiomer 2

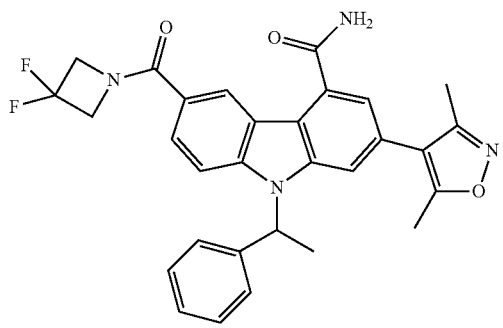 [SMILES: Cc1noc(C)c1-c1cc(C(N)=O)c2c3cc(C(=O)N4CC(F)(F)C4)ccc3n(C(C)c3ccccc3)c2c1]

Isomer 2:
A sample of racemic 6-(3,3-difluoroazetidine-1-carbonyl)-2-(3,5-dimethylisoxazol-4-yl)-9-(1-phenylethyl)-9H-carbazole-4-carboxamide from Example 96 was resolved using preparative chiral SFC HPLC:
Instrument: Berger SFC MGII; Column: Chiral OJ-H 25×3 cm ID, 5 μm; Flow rate: 85 mL/min; Mobile Phase: 80/20 CO₂/MeOH w/0.1% DEA; Detector Wavelength: 220 nm; The second peak from the column gave 6-(3,3-difluoroazetidine-1-carbonyl)-2-(3,5-dimethylisoxazol-4-yl)-9-(1-phenylethyl)-9H-carbazole-4-carboxamide. Enantiomer 2.
Chiral HPLC Analytical Chromatographic Conditions:
Instrument: Berger analytical SFC (LVL-L4021 Lab); Column: Chiral OJ-H 250×4.6 mm ID, 5 μm; Flow rate: 2.0 mL/min; Mobile Phase: 80/20 CO2/MeOH w/0.1% DEA. Chiral HPLC RT: 13.93 min Column: Waters Acquity SDS BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes. Flow: 1.11 mL/min.

HPLC RT: 0.94 min; LCMS: (ES) m/e 529.08 (M+H).

Example 99

6-((3,3-difluoro-1-azetidinyl)carbonyl)-2-(3,5-dimethyl-4-isoxazolyl)-N-methyl-9H-carbazole-4-carboxamide

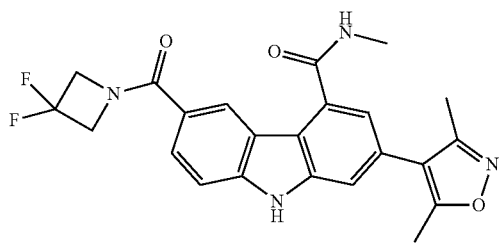 [SMILES: CNC(=O)c1cc(-c2c(C)noc2C)cc2[nH]c3ccc(C(=O)N4CC(F)(F)C4)cc3c12]

Step 1: Ethyl 7-bromo-5-(methylcarbamoyl)-2,3,4, 9-tetrahydro-1H-carbazole-3-carboxylate To 7-bromo-3-(ethoxycarbonyl)-2,3,4,9-tetrahydro-1H-carbazole-5-carboxylic acid (3.53 g, 9.64 mmol) in THF (30 mL) and DCM (6 ml) was added EDC (5.54 g, 28.9 mmol) and HOBT (4.43 g, 28.9 mmol). The reaction was stirred at room temperature for ¼ hour. Methanamine, 1.0HCl (2.60 g, 38.6 mmol) and DIEA (10.10 mL, 57.8 mmol) were added and stirring was continued at room temperature for 3 hours. The reaction mixture was concentrated, water was added and the precipitate was collected. The precipitate was washed with water and 3.6 g (99%) of ethyl 7-bromo-5-(methylcarbamoyl)-2,3,4,9-tetrahydro-1H-carbazole-3-carboxylate was isolated.

Column: Waters Acquity SDS BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes. Flow: 1.11 mL/min.

HPLC RT: 0.85 min; LCMS: (ES) m/e 379.08 (M+H).

Step 2: Ethyl 7-bromo-5-(methylcarbamoyl)-9H-carbazole-3-carboxylate

To ethyl 7-bromo-5-(methylcarbamoyl)-2,3,4,9-tetrahydro-1H-carbazole-3-carboxylate (3.6 g, 9.49 mmol) in THF (50 ml) was added DDQ (5.72 g, 24.68 mmol). The reaction was heated to reflux. LCMS showed complete reaction after ¾ hours. The reaction mixture was concentrated to dryness and saturated sodium bicarbonate and water were added. The mixture was stirred for ½ hour. The precipitate was collected, washed with water and air dried. 3.42 g (96%) of ethyl 7-bromo-5-(methylcarbamoyl)-9H-carbazole-3-carboxylate was isolated.

Column: Waters Acquity SDS BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes. Flow: 1.11 mL/min.

HPLC RT: 0.72 min; LCMS: (ES) m/e 375.08 (M+H).

Step 3: Ethyl 7-(3,5-dimethylisoxazol-4-yl)-5-(methylcarbamoyl)-9H-carbazole-3-carboxylate To ethyl 7-bromo-5-(methylcarbamoyl)-9H-carbazole-3-carboxylate (3.42 g, 9.11 mmol) and 3,5-dimethyl-4-(4,4,5, 5-tetramethyl-1,3,2-dioxaborolan-2-yl)isoxazole (3.05 g, 13.67 mmol) was added DMF (30 ml). The reaction was degassed and then $PdCl_2(dppf)\cdot CH_2Cl_2$ adduct (0.372 g, 0.456 mmol) and aqueous phosphoric acid, potassium salt (9.11 ml, 27.3 mmol) were added. The reaction was degassed and heated at 80° C. for 2 hours. The reaction mixture was cooled, 10% LiCl in water was added and the precipitate was collected. 3.57 g (99%) of ethyl 7-(3,5-dimethylisoxazol-4-yl)-5-(methylcarbamoyl)-9H-carbazole-3-carboxylate was isolated.

Column: Waters Acquity SDS BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes. Flow: 1.11 mL/min.

HPLC RT: 0.86 min; LCMS: (ES) m/e 392.08 (M+H.

Step 4: 7-(3,5-dimethylisoxazol-4-yl)-5-(methylcarbamoyl)-9H-carbazole-3-carboxylic acid To ethyl 7-(3,5-dimethylisoxazol-4-yl)-5-(methylcarbamoyl)-9H-carbazole-3-carboxylate (3.57 g, 9.12 mmol) in THF (20 mL) and MeOH (4 mL) was added sodium hydroxide (4.56 mL, 45.6 mmol). The reaction was allowed to stir at room temperature for 16 hours and then heated to 70 C for 2 hours. The reaction mixture was concentrated to a minimal volume. 1 N HCl was added and the precipitate was collected. The precipitate was washed and dried to give 3.2 g (97%) of 7-(3,5-dimethylisoxazol-4-yl)-5-(methylcarbamoyl)-9H-carbazole-3-carboxylic acid.

Column: Waters Acquity SDS BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes. Flow: 1.11 mL/min.

HPLC RT: 0.71 min; LCMS: (ES) m/e 364.08 (M+H).

Step 5: 6-((3,3-difluoro-1-azetidinyl)carbonyl)-2-(3, 5-dimethyl-4-isoxazolyl)-N-methyl-9H-carbazole-4-carboxamide To 7-(3,5-dimethylisoxazol-4-yl)-5-(methylcarbamoyl)-9H-carbazole-3-carboxylic acid (500 mg, 1.376 mmol) in DMF (5.0 mL) was added HCTU (1231 mg, 3.10 mmol), DMAP (378 mg, 3.10 mmol) and 3,3-difluoroazetidine, 1.0HCl (401 mg, 3.10 mmol) and stirred for 1 hour. Water was added and the precipitate was collected. 330 mg (55%) of 6-(3,3-difluoroazetidine-1-carbonyl)-2-(3,5-dimethylisoxazol-4-yl)-N-methyl-9H-carbazole-4-carboxamide was isolated.

The crude material was purified via preparative HPLC using the following conditions:

Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-100% B over 25 minutes, then a 5-minute hold at 100% B; Flow: 20 mL/min. Fractions containing the desired product were combined and dried via centrifugal evaporation. The yield of 6-((3,3-difluoro-1-azetidinyl)carbonyl)-2-(3,5-dimethyl-4-isoxazolyl)-N-methyl-9H-carbazole-4-carboxamide was 13.7 mg, and its estimated purity by LCMS analysis was 99%. Two analytical LC/MS injections were used to determine the final purity.

Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Injection 2 conditions: Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. Proton NMR was acquired in deuterated DMSO.

Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

HPLC RT: 1.299 min; LCMS: (ES) m/e 439.16 (M+H).

Example 100

9-(4-chlorobenzyl)-6-(3,3-difluoroazetidine-1-carbonyl)-2-(3,5-dimethylisoxazol-4-yl)-N-methyl-9H-carbazole-4-carboxamide

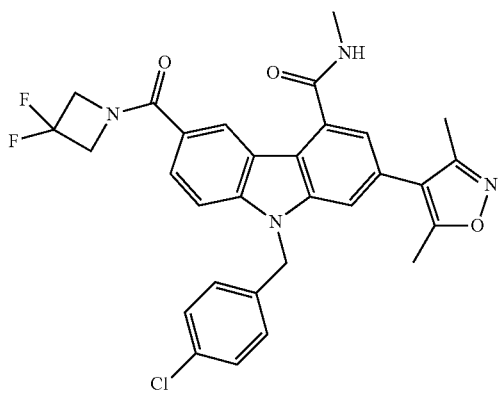 [SMILES: CNC(=O)c1cc(-c2c(C)noc2C)cc2c1c1cc(C(=O)N3CC(F)(F)C3)ccc1n2Cc1ccc(Cl)cc1]

To 6-(3,3-difluoroazetidine-1-carbonyl)-2-(3,5-dimethylisoxazol-4-yl)-N-methyl-9H-carbazole-4-carboxamide (Example 16) (60 mg, 0.137 mmol) in a vial was added potassium carbonate (76 mg, 0.547 mmol), 18-crown-6 (3.62 mg, 0.014 mmol), acetone (1 mL) and 1-(bromomethyl)-4-chlorobenzene (169 mg, 0.821 mmol). The reaction was allowed to heat to 80° C. for 3 hours. The reaction mixture was concentrated to dryness, diluted with DMF, filtered and the crude material was purified via preparative HPLC using the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min. Fractions containing the desired product were combined and dried via centrifugal evaporation. The yield of 9-(4-chlorobenzyl)-6-(3,3-difluoroazetidine-1-carbonyl)-2-(3,5-dimethylisoxazol-4-yl)-N-methyl-9H-carbazole-4-carboxamide was 18.2 mg, and its estimated purity by LCMS analysis was 98%. Two analytical LC/MS injections were used to determine the final purity. Injection 1 conditions: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. Injection 2 conditions: Column: Waters Acquity UPLC BEH C18, 2.1×50 mm, 1.7-µm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. Proton NMR was acquired in deuterated DMSO. Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

HPLC RT: 1.871 min; LCMS: (ES) m/e 563.17 (M+H).

Example 101

2-(3,5-dimethyl-4-isoxazolyl)-6-((3-fluoro-1-azetidinyl)carbonyl)-N-methyl-9H-carbazole-4-carboxamide

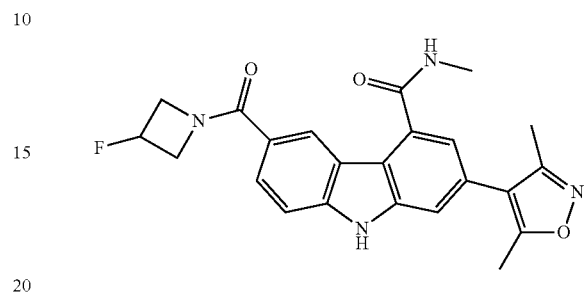

Step 1: Ethyl 7-bromo-5-(methylcarbamoyl)-2,3,4,9-tetrahydro-1H-carbazole-3-carboxylate To 7-bromo-3-(ethoxycarbonyl)-2,3,4,9-tetrahydro-1H-carbazole-5-carboxylic acid (3.53 g, 9.64 mmol) in THF (30 mL) and DCM (6 ml) was added EDC (5.54 g, 28.9 mmol) and HOBT (4.43 g, 28.9 mmol). The reaction was stirred at room temperature for ¼ hour. Methanamine, 1.0HCl (2.60 g, 38.6 mmol) and DIEA (10.10 mL, 57.8 mmol) were added and stirring was continued at room temperature for 3 hours. The reaction mixture was concentrated, water was added and the precipitate was collected. The precipitate was washed with water and 3.6 g (99%) of ethyl 7-bromo-5-(methylcarbamoyl)-2,3,4,9-tetrahydro-1H-carbazole-3-carboxylate was isolated.

Step 2: Ethyl 7-bromo-5-(methylcarbamoyl)-9H-carbazole-3-carboxylate

To ethyl 7-bromo-5-(methylcarbamoyl)-2,3,4,9-tetrahydro-1H-carbazole-3-carboxylate (3.6 g, 9.49 mmol) in THF (50 ml) was added DDQ (5.72 g, 24.68 mmol). The reaction was heated to reflux for ¾ hours. The reaction mixture was concentrated to dryness and saturated sodium bicarbonate and water were added. The mixture was stirred for ½ hour. The precipitate was collected, washed with water and air dried. 3.42 g (96%) of ethyl 7-bromo-5-(methylcarbamoyl)-9H-carbazole-3-carboxylate was isolated.

Step 3: Ethyl 7-(3,5-dimethylisoxazol-4-yl)-5-(methylcarbamoyl)-9H-carbazole-3-carboxylate To ethyl 7-bromo-5-(methylcarbamoyl)-9H-carbazole-3-carboxylate (3.42 g, 9.11 mmol) and 3,5-dimethyl-4-(4,4,5,5-tetramethyl-1,3,2-dioxaborolan-2-yl)isoxazole (3.05 g, 13.67 mmol) was added DMF (30 ml). The reaction was degassed and then PdCl$_2$(dppf)-CH$_2$Cl$_2$ adduct (0.372 g, 0.456 mmol) and aqueous phosphoric acid, potassium salt (9.11 ml, 27.3 mmol) were added. The reaction was degassed and heated at 80° C. for 2 hours. The reaction mixture was cooled, 10% LiCl in water was added and the precipitate was collected. 3.57 g (99%) of ethyl 7-(3,5-dimethylisoxazol-4-yl)-5-(methylcarbamoyl)-9H-carbazole-3-carboxylate was isolated.

Step 4: 7-(3,5-dimethylisoxazol-4-yl)-5-(methylcarbamoyl)-9H-carbazole-3-carboxylic acid To ethyl 7-(3,5-dimethylisoxazol-4-yl)-5-(methylcarbamoyl)-9H-carbazole-3-carboxylate (3.57 g, 9.12 mmol) in THF (20 mL) and MeOH (4 mL) was added sodium hydroxide (4.56 mL, 45.6 mmol). The reaction was allowed to stir at room temperature for 16 hours and then heated to 70 C for 2 hours. The reaction mixture was concentrated to a minimal volume. 1 N HCl was added and the precipitate was collected. The precipitate was washed and dried to give 3.2 g (97%) of 7-(3,5-dimethylisoxazol-4-yl)-5-(methylcarbamoyl)-9H-carbazole-3-carboxylic acid.

Step 5: 2-(3,5-dimethyl-4-isoxazolyl)-6-((3-fluoro-1-azetidinyl)carbonyl)-N-methyl-9H-carbazole-4-carboxamide To 7-(3,5-dimethylisoxazol-4-yl)-5-(methylcarbamoyl)-9H-carbazole-3-carboxylic acid (632 mg, 1.739 mmol) in DMF (5.0 mL) was added HCTU (1556 mg, 3.91 mmol), DMAP (478 mg, 3.91 mmol) and 3-fluoroazetidine, 1.0HCl (437 mg, 3.91 mmol) and stirred for 1 hour. Water was added and the precipitate was collected. 680 mg (93%) of 2-(3,5-dimethyl-4-isoxazolyl)-6-((3-fluoro-1-azetidinyl)carbonyl)-N-methyl-9H-carbazole-4-carboxamide was isolated. A 60 mg aliquot of this compound was purified via preparative HPLC using the following conditions: Column: Waters Xbridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 0-100% B over 25 minutes, then a 5-minute hold at 100% B; Flow: 20 mL/min. Fractions containing the desired product were combined and dried via centrifugal evaporation. The yield of 2-(3,5-dimethylisoxazol-4-yl)-6-(3-fluoroazetidine-1-carbonyl)-N-methyl-9H-carbazole-4-carboxamide was 12.0 mg, and its estimated purity by LCMS analysis was 99%. Two analytical LC/MS injections were used to determine the final purity. Injection 1 conditions: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. Injection 2 conditions: Column: Waters Acquity UPLC BEH C18, 2.1×50 mm, 1.7-µm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. Proton NMR was acquired in deuterated DMSO.

Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. HPLC RT: 1.197 min; LCMS: (ES) m/e 421.17 (M+H).

Example 102

9-(4-chlorobenzyl)-2-(3,5-dimethylisoxazol-4-yl)-6-(3-fluoroazetidine-1-carbonyl)-N-methyl-9H-carbazole-4-carboxamide

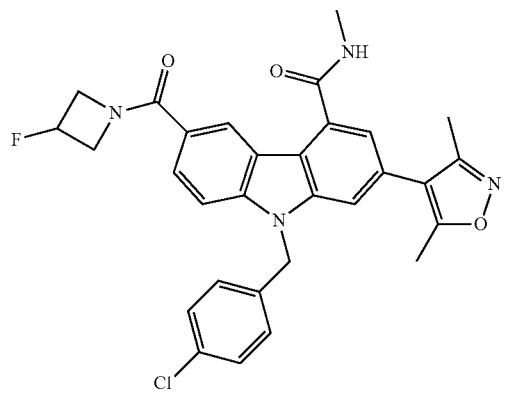 [SMILES: CNC(=O)c1cc(-c2c(C)noc2C)cc2c1c1cc(C(=O)N3CC(F)C3)ccc1n2Cc1ccc(Cl)cc1]

To 2-(3,5-dimethylisoxazol-4-yl)-6-(3-fluoroazetidine-1-carbonyl)-N-methyl-9H-carbazole-4-carboxamide (60 mg, 0.143 mmol) in a vial was added potassium carbonate (79 mg, 0.571 mmol), 18-crown-6 (3.77 mg, 0.014 mmol), acetone (1 mL) and 1-(bromomethyl)-4-chlorobenzene (176 mg, 0.856 mmol). The reaction was heated to 80° C. for 2 hours. The reaction mixture was concentrated to dryness, diluted with DMF, filtered and submitted for purification.

The crude material was purified via preparative HPLC using the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation. The yield of 9-(4-chlorobenzyl)-2-(3,5-dimethylisoxazol-4-yl)-6-(3-fluoroazetidine-1-carbonyl)-N-methyl-9H-carbazole-4-carboxamide was 18.3 mg, and its estimated purity by LCMS analysis was 99%. Two analytical LC/MS injections were used to determine the final purity.

Injection 1 conditions: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Injection 2 conditions: Column: Waters Acquity UPLC BEH C18, 2.1×50 mm, 1.7-µm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. Proton NMR was acquired in deuterated DMSO.

Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

HPLC RT: 1.774 min; LCMS: (ES) m/e 545.18 (M+H).

The compounds in Table 6 were prepared in a similar procedure as described for Example 102:

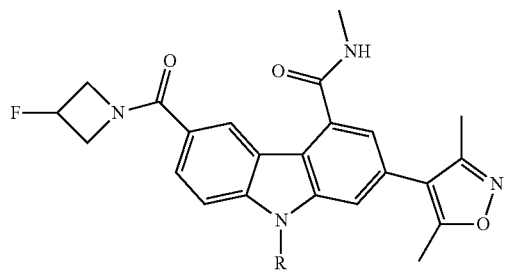

TABLE 6

| Example No. | R | HPLC RT (min.) | M + H | HPLC Method |
|---|---|---|---|---|
| 103 | 4-F-benzyl | 1.7 | 529.2 | A |
| 104 | 3-F-benzyl | 1.7 | 529.2 | A |
| 105 | 2,6-diF-benzyl | 1.6 | 547.2 | A |
| 106 | 2,4-diF-benzyl | 1.7 | 547.2 | A |
| 107 | 2,3-diF-benzyl | 1.7 | 547.2 | A |
| 108 | 4-CN-benzyl | 1.6 | 536.2 | A |
| 109 | 3-F-4-Cl-benzyl | 1.8 | 563.2 | A |
| 110 | 4-Cl-2-F-benzyl | 1.8 | 563.2 | A |
| 111 | 1-(4-Cl-phenyl)ethyl | 1.9 | 559.2 | A |
| 112 | 1-(4-F-phenyl)ethyl | 1.6 | 543 | A |
| 113 | 1-phenylethyl | 1.6 | 525.2 | A |
| 114 | cyclobutylmethyl | 1.7 | 489.1 | A |
| 115 | cyclopropylmethyl | 1.5 | 475.1 | A |

Example 116

2-(3,5-dimethylisoxazol-4-yl)-6-(3-fluoroazetidine-1-carbonyl)-N-methyl-9-(pyridin-2-ylmethyl)-9H-carbazole-4-carboxamide

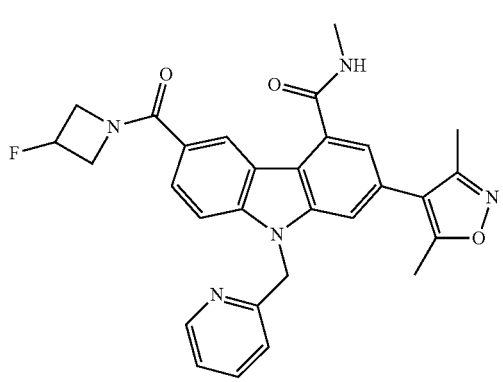 [SMILES: CNC(=O)c1cc(-c2c(C)noc2C)cc2c1c1cc(C(=O)N3CC(F)C3)ccc1n2Cc1ccccn1]

To 2-(3,5-dimethylisoxazol-4-yl)-6-(3-fluoroazetidine-1-carbonyl)-N-methyl-9H-carbazole-4-carboxamide (71 mg, 0.169 mmol) in a small vial was added triphenylphosphine (177 mg, 0.675 mmol), DIAD (0.131 mL, 0.675 mmol), THF (1.5 mL) and pyridin-2-ylmethanol (73.7 mg, 0.675 mmol). The reaction was allowed to stir at room temperature for 1½ hours. The reaction mixture was concentrated to dryness, diluted with DMF, filtered and submitted for purification.

The crude material was purified via preparative HPLC using the following conditions: Column: Waters XBridge C18, 19×250 mm, 5-μm particles; Mobile Phase A: 5:95 acetonitrile:water with 0.05% TFA; Mobile Phase B: 95:5 acetonitrile:water with 0.05% TFA; Gradient: 5-100% B over 25 minutes, then a 5-minute hold at 100% B; Flow: 20 mL/min. Fractions containing the desired product were combined and dried via centrifugal evaporation. The yield of 2-(3,5-dimethylisoxazol-4-yl)-6-(3-fluoroazetidine-1-carbonyl)-N-methyl-9-(pyridin-2-ylmethyl)-9H-carbazole-4-carboxamide was 6.1 mg, and its estimated purity by LCMS analysis was 88%. Two analytical LC/MS injections were used to determine the final purity.

Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Injection 2 conditions: Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. Proton NMR was acquired in deuterated DMSO.

Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

HPLC RT: 1.320 min; LCMS: (ES) m/e 498.19 (M+H).

Example 117

9-benzyl-2-(3,5-dimethylisoxazol-4-yl)-6-(cis-2,6-dimethylmorpholine-4-carbonyl)-N-methyl-9H-carbazole-4-carboxamide

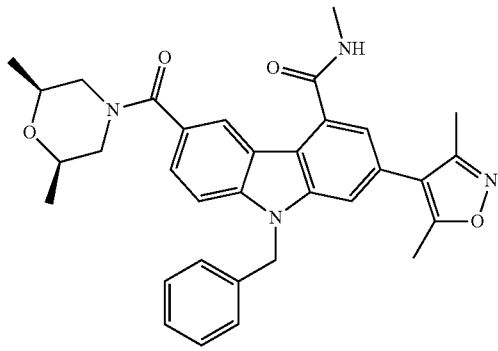 [SMILES: CNC(=O)c1cc(-c2c(C)noc2C)cc2c1c1cc(C(=O)N3C[C@@H](C)O[C@@H](C)C3)ccc1n2Cc1ccccc1]

To 9-benzyl-2-(3,5-dimethylisoxazol-4-yl)-6-(cis-2,6-dimethylmorpholine-4-carbonyl)-9H-carbazole-4-carboxamide (80 mg, 0.149 mmol) in DMF (1.0 mL) was added sodium hydride (13.12 mg, 0.328 mmol). The reaction was allowed to stir at room temperature for 15 minutes then iodomethane (0.012 mL, 0.179 mmol) was added and after 15 minutes, the reaction was quenched with water, diluted with DMF and the mono and di-alkylated products were separated and purified via preparative HPLC using the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation. The yield of 9-benzyl-2-(3,5-dimethylisoxazol-4-yl)-6-(cis-2,6-dimethylmorpholine-4-carbonyl)-N-methyl-9H-carbazole-4-carboxamide was 5.7 mg, and its estimated purity by LCMS analysis was 94%. Two analytical LC/MS injections were used to determine the final purity.

Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Injection 2 conditions: Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. Proton NMR was acquired in deuterated DMSO.

Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

HPLC RT: 1.727 min; LCMS: (ES) m/e 551.27 (M+H).

Example 118

9-benzyl-2-(3,5-dimethylisoxazol-4-yl)-6-(cis-2,6-dimethylmorpholine-4-carbonyl)-N,N-dimethyl-9H-carbazole-4-carboxamide

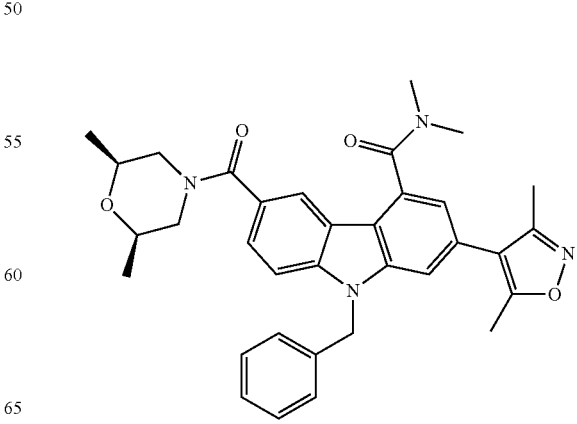

The crude material (from Example 117) was purified via preparative HPLC using the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation. The yield of 9-benzyl-2-(3,5-dimethylisoxazol-4-yl)-6-(cis-2,6-dimethylmorpholine-4-carbonyl)-N,N-dimethyl-9H-carbazole-4-carboxamide was 3.7 mg, and its estimated purity by LCMS analysis was 96%. Two analytical LC/MS injections were used to determine the final purity.

Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Injection 2 conditions: Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. Proton NMR was acquired in deuterated DMSO. Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

HPLC RT: 1.789 min; LCMS: (ES) m/e 565.28 (M+H).

Example 119

6-((3,3-difluoro-1-azetidinyl)carbonyl)-2-(3,5-dimethyl-4-isoxazolyl)-N-methyl-9-(1-phenylethyl)-9H-carbazole-4-carboxamide

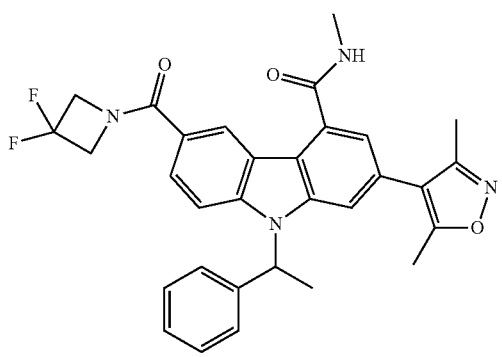 [SMILES: CNC(=O)c1cc(-c2c(C)noc2C)cc2c1c1cc(C(=O)N3CC(F)(F)C3)ccc1n2C(C)c1ccccc1]

To 6-(3,3-difluoroazetidine-1-carbonyl)-2-(3,5-dimethylisoxazol-4-yl)-9-(1-phenylethyl)-9H-carbazole-4-carboxamide (220 mg, 0.416 mmol) in DMF (1.0 mL) was added sodium hydride (36.6 mg, 0.916 mmol). The reaction was allowed to stir at room temperature for 15 minutes then iodomethane (0.036 mL, 0.562 mmol) was added. After 15 minutes the reaction was quenched with water, diluted with DMF and submitted for isolation of the mono and di-alkylated products.

The crude material was purified via preparative HPLC using the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation. The yield of 6-((3,3-difluoro-1-azetidinyl)carbonyl)-2-(3,5-dimethyl-4-isoxazolyl)-N-methyl-9-(1-phenylethyl)-9H-carbazole-4-carboxamide was 5.3 mg, and its estimated purity by LCMS analysis was 94%. Two analytical LC/MS injections were used to determine the final purity.

Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Injection 2 conditions: Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. Proton NMR was acquired in deuterated DMSO.

Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

HPLC RT: 1.819 min
LCMS: (ES) m/e 543.22 (M+H)

Example 120

6-((3,3-difluoro-1-azetidinyl)carbonyl)-2-(3,5-dimethyl-4-isoxazolyl)-N,N-dimethyl-9-(1-phenylethyl)-9H-carbazole-4-carboxamide

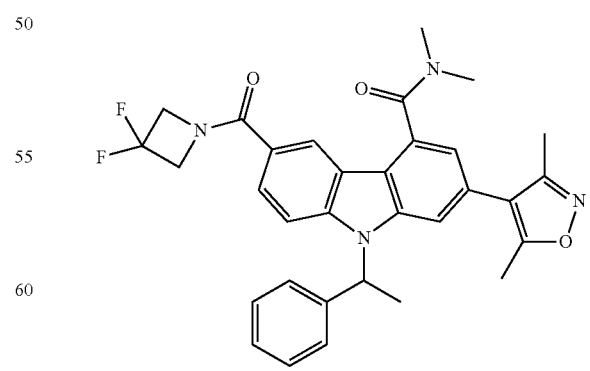

The crude material (from Example 119) was purified via preparative HPLC using the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation. The yield of 6-((3,3-difluoro-1-azetidinyl)carbonyl)-2-(3,5-dimethyl-4-isoxazolyl)-N,N-dimethyl-9-(1-phenylethyl)-9H-carbazole-4-carboxamide was 15.5 mg, and its estimated purity by LCMS analysis was 98%. Two analytical LC/MS injections were used to determine the final purity.

Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Injection 2 conditions: Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. Proton NMR was acquired in deuterated DMSO.

Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

HPLC RT: 1.877 min; LCMS: (ES) m/e 557.24 (M+H).

Example 121

2-(3,5-dimethyl-4-isoxazolyl)-6-((3-fluoro-1-azetidinyl)carbonyl)-9-(3-fluorobenzyl)-9H-carbazole-4-carbonitrile

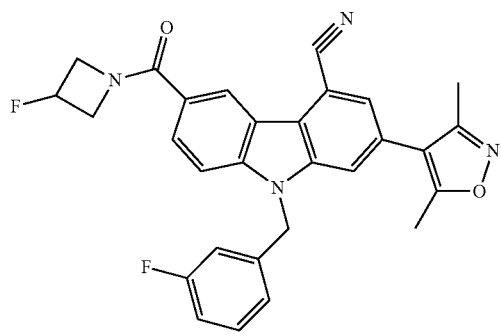 [SMILES: Cc1noc(C)c1-c1cc(C#N)c2c3cc(C(=O)N4CC(F)C4)ccc3n(Cc3cccc(F)c3)c2c1]

To 2-(3,5-dimethylisoxazol-4-yl)-6-(3-fluoroazetidine-1-carbonyl)-9-(3-fluorobenzyl)-9H-carbazole-4-carboxamide (62 mg, 0.121 mmol) in a vial was added DCM (1 mL) and Burgess reagent (28.7 mg, 0.121 mmol). The reaction was allowed to stir at room temperature for ½ hour. The reaction was concentrated, diluted with DMF and was purified via preparative HPLC using the following conditions: Column: Waters XBridge C18, 19×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 10 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-75% B over 25 minutes, then a 15-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 25 minutes, then a 5-minute hold at 100% B; Flow: 20 mL/min. Fractions containing the desired product were combined and dried via centrifugal evaporation. The yield of 2-(3,5-dimethyl-4-isoxazolyl)-6-((3-fluoro-1-azetidinyl)carbonyl)-9-(3-fluorobenzyl)-9H-carbazole-4-carbonitrile was 9.1 mg, and its estimated purity by LCMS analysis was 100%. Two analytical LC/MS injections were used to determine the final purity.

Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Injection 2 conditions: Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. Proton NMR was acquired in deuterated DMSO.

Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

HPLC RT: 1.89 min; LCMS: (ES) m/e 497.171 (M+H).

Example 122

9-(4-fluorobenzyl)-2-(3-methyl-4-isoxazolyl)-6-(4-morpholinylcarbonyl)-9H-carbazole-4-carboxamide

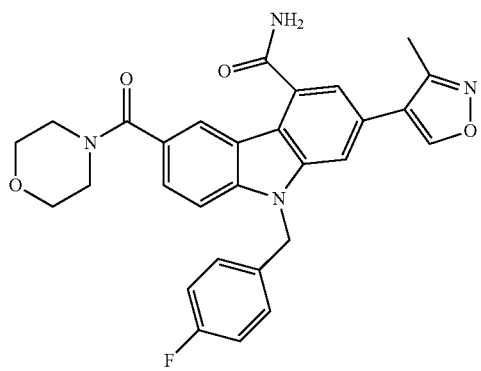 [SMILES: Cc1nocc1-c1cc(C(N)=O)c2c3cc(C(=O)N4CCOCC4)ccc3n(Cc3ccc(F)cc3)c2c1]

Step 1: 2-bromo-6-(morpholine-4-carbonyl)-9H-carbazole-4-carboxamide

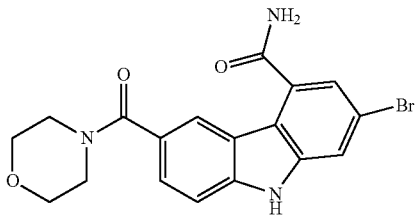 [SMILES: NC(=O)c1cc(Br)cc2[nH]c3ccc(C(=O)N4CCOCC4)cc3c12]

To a mixture of 7-bromo-5-carbamoyl-9H-carbazole-3-carboxylic acid (450 mg, 1.351 mmol) and TBTU in DMF (7.5 mL) was added TEA (0.235 mL, 1.688 mmol) followed by morpholine (0.235 mL, 2.70 mmol). The reaction was stirred for 1 h, diluted with ethyl acetate (100 mL), poured into a separatory funnel and washed with 1 N aq. HCl (1×20 mL), aq. 10% LiCl solution (2×25 mL) and sat. aq. NaCl solution (1×25 mL). The organic layer was dried (Na$_2$SO$_4$), filtered and concentrated in vacuo to give a solid. The crude product was dissolved in a small amount of DCM and charged to a 12 g ISCO silica gel column which was eluted over a 15 min gradient with 0%-5% MeOH/DCM to give 2-bromo-6-(morpholine-4-carbonyl)-9H-carbazole-4-carboxamide (400 mg, 76%). MS (ES) 402 (M+1).

Step 2: 2-bromo-9-(4-fluorobenzyl)-6-(morpholine-4-carbonyl)-9H-carbazole-4-carboxamide

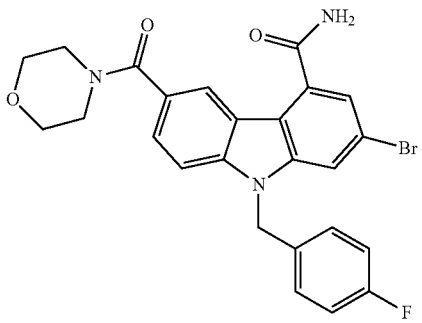 [SMILES: NC(=O)c1cc(Br)cc2c1c1cc(C(=O)N3CCOCC3)ccc1n2Cc1ccc(F)cc1]

A mixture of 2-bromo-6-(morpholine-4-carbonyl)-9H-carbazole-4-carboxamide (175 mg, 0.435 mmol), 1-(chloromethyl)-4-fluorobenzene (0.258 mL, 2.175 mmol), 18-crown-6 (10 mg, 0.435 mmol) and K$_2$CO$_3$ (241 mg, 1.740 mmol) in acetone (2 mL) were heated at 55° C. for 12 h. The reaction was filtered through a pad of celite and the pad rinsed with DCM. The filtrate was concentrated, and the crude product was dissolved in a small amount of DCM and charged to a 4 g ISCO column silica gel which was eluted over a 10 min gradient with 5%-100% DCM/EtOAc, to give pure 2-bromo-9-(4-fluorobenzyl)-6-(morpholine-4-carbonyl)-9H-carbazole-4-carboxamide (50 mg, 22.5%). MS (ES) 511 (M+1).

Step 3: 9-(4-fluorobenzyl)-6-(morpholine-4-carbonyl)-2-(4,4,5,5-tetramethyl-1,3,2-dioxaborolan-2-yl)-9H-carbazole-4-carboxamide

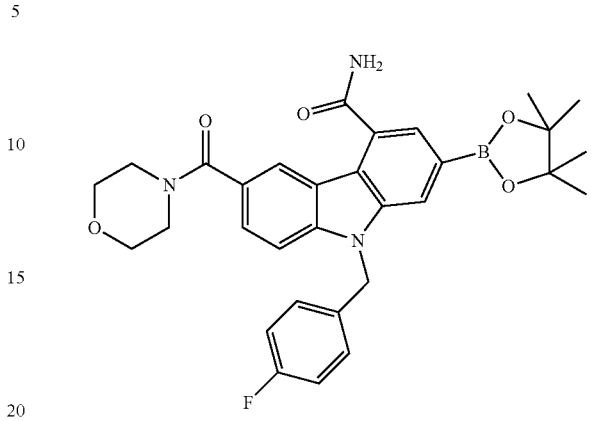

To a mixture of 2-bromo-9-(4-fluorobenzyl)-6-(morpholine-4-carbonyl)-9H-carbazole-4-carboxamide (50 mg, 0.098 mmol), 4,4,4',4',5,5,5',5'-octamethyl-2,2'-bi(1,3,2-dioxaborolane) (31.1 mg, 0.122 mmol), potassium acetate (24.04 mg, 0.245 mmol) and PdCl$_2$(dppf)-CH$_2$Cl$_2$ adduct (4.00 mg, 4.90 µmol) in a screw cap vial was added dioxane (1 mL). The vial was fitted with a teflon lined septum cap. The system was evacuated under vacuum (via a needle from a nitrogen/vacuum manifold line) and backfilled with nitrogen gas. The procedure was repeated three times. The needle was removed and the vial sealed and heated at 100° C. for 2 h. The reaction was cooled and filtered through a plug of celite and the celite pad rinsed with DCM (~5 mL). Next, the filtrate was concentrated in vacuo to give crude 9-(4-fluorobenzyl)-6-(morpholine-4-carbonyl)-2-(4,4,5,5-tetramethyl-1,3,2-dioxaborolan-2-yl)-9H-carbazole-4-carboxamide which was used as is in the next coupling step. MS (ES) 558 (M+1).

Step 4: 9-(4-fluorobenzyl)-2-(3-methyl-4-isoxazolyl)-6-(4-morpholinylcarbonyl)-9H-carbazole-4-carboxamide To a mixture of crude 9-(4-fluorobenzyl)-6-(morpholine-4-carbonyl)-2-(4,4,5,5-tetramethyl-1,3,2-dioxaborolan-2-yl)-9H-carbazole-4-carboxamide (25 mg, 0.045 mmol), 4-bromo-3-methylisoxazole (10.90 mg, 0.067 mmol) or 4-iodo-5-methylisoxazole (14.06 mg, 0.067 mmol), and PdCl$_2$(dppf)-CH$_2$Cl$_2$adduct (1.831 mg, 2.242 µmol) in a screw cap vial was added THF (0.5 mL), followed by a 3N aqueous solution of tripotassium phosphate (0.037 mL, 0.112 mmol). The vial was fitted with a teflon lined septum cap and evacuated under vacuum (via a needle from a nitrogen/vacuum manifold line) and backfilled with nitrogen gas. The procedure was repeated three times. The needle was removed and the vials were sealed and heated at 70° C. for 6 h. The reaction was cooled and diluted with 1.5 mL of DMF. The mixtures were filtered through a 0.45 micron nylon membrane syringe filter and purified on Prep HPLC using a Waters XBridge C18 column, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-100% B over 25 minutes, then a 5-minute hold at 100% B; Flow: 20 mL/min to give 9-(4-fluorobenzyl)-2-(3-methyl-4-isoxazolyl)-6-(4-morpholinylcarbonyl)-9H-carbazole-4-carboxamide (8 mg, 38%). MS (ES) 523 (M+1). HPLC retention time, 1.42 min.

Analytical column. Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min).

$^1$H NMR (500 MHz, DMSO-$d_6$) δ 9.25 (s, 1H), 8.57 (d, J=1.8 Hz, 1H), 8.16 (s, 1H), 7.96 (d, J=1.2 Hz, 1H), 7.77 (d, J=8.5 Hz, 2H), 7.57 (dd, J=8.5, 1.2 Hz, 1H), 7.54 (d, J=1.2 Hz, 1H), 7.28 (dd, J=8.5, 5.5 Hz, 2H), 7.16-7.10 (m, 2H), 5.80 (s, 2H), 3.66 (br. s., 4H), 3.57 (br. s., 4H), 2.44 (s, 3H).

Example 123

9-(4-fluorobenzyl)-2-(5-methylisoxazol-4-yl)-6-(morpholine-4-carbonyl)-9H-carbazole-4-carboxamide

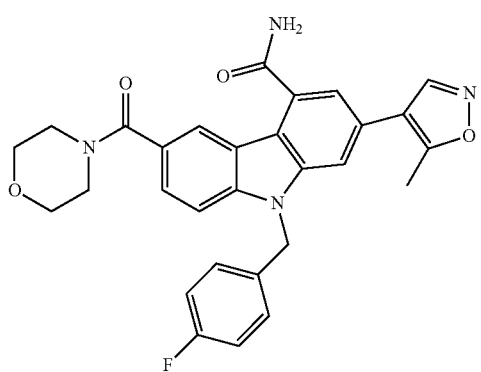 [SMILES: Cc1oncc1-c1cc(C(N)=O)c2c3cc(C(=O)N4CCOCC4)ccc3n(Cc3ccc(F)cc3)c2c1]

Reaction of crude 9-(4-fluorobenzyl)-6-(morpholine-4-carbonyl)-2-(4,4,5,5-tetramethyl-1,3,2-dioxaborolan-2-yl)-9H-carbazole-4-carboxamide (25 mg, 0.045 mmol) with 4-iodo-5-methylisoxazole (14.06 mg, 0.067 mmol) using the same conditions described for the preparation of Example 121 yielded 9-(4-fluorobenzyl)-2-(5-methylisoxazol-4-yl)-6-(morpholine-4-carbonyl)-9H-carbazole-4-carboxamide (13 mg, 57%). MS (ES) 513 (M+1). HPLC retention time, 1.47 min.

$^1$H NMR (500 MHz, methanol-$d_4$/CDCl$_3$) δ 8.65 (br. s, 1H), 8.58 (br. s, 1H), 7.63 (d, J=1.5 Hz, 1H), 7.59-7.54 (m, 3H), 7.14 (dd, J=8.4, 5.4 Hz, 2H), 6.99 (t, J=8.7 Hz, 2H), 5.66 (s, 2H), 3.80 (br. s., 8H), 2.58 (s, 3H).

Example 124

2-(3,5-dimethyl-4-isoxazolyl)-6-((3-fluoro-1-azetidinyl)carbonyl)-9-(4-fluorobenzyl)-N-propyl-9H-carbazole-4-carboxamide

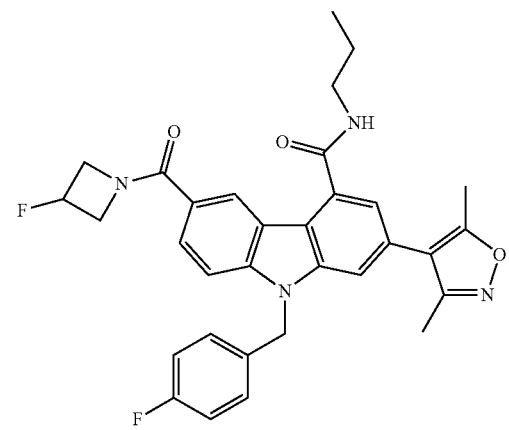 [SMILES: CCCNC(=O)c1cc(-c2c(C)noc2C)cc2c1c1cc(C(=O)N3CC(F)C3)ccc1n2Cc1ccc(F)cc1]

Step 1: 5-tert-butyl 3-ethyl 7-bromo-9H-carbazole-3,5-dicarboxylate

In a 40 ml reaction vial was added 7-bromo-3-(ethoxycarbonyl)-2,3,4,9-tetrahydro-1H-carbazole-5-carboxylic acid (0.752 g, 2.053 mmol) in THF (6 mL) to give a solution, which was cooled to 0° C. over 15 minutes. Tert-butyl 2,2,2-trichloroacetimidate (0.735 mL, 4.11 mmol) was added slowly over 3 minutes. The reaction was stirred for 15 minutes at 0° C. Boron trifluoride etherate (0.026 mL, 0.205 mmol) was then added. The reaction was allowed to warm to room temperature as the bath warmed overnight. After 18 hours, the reaction mixture was clear. To this solution was added NaHCO$_3$ (0.863 g, 10.27 mmol) solid and the reaction was stirred for 30 minutes. The reaction was then filtered over Na$_2$SO$_4$ and washed with THF (50 ml). The filtrate was concentrated in-vacuo and purified by flash chromatography (ISCO) using MeOH/DCM as the eluent. Following concentration of the fractions, collected 5-tert-butyl 3-ethyl 7-bromo-9H-carbazole-3,5-dicarboxylate (3) (0.32 g, 37%). LC-MS (M+1=423).

Step 2: Ethyl 5-tert-butyl 3-ethyl 7-bromo-9H-carbazole-3,5-dicarboxylate

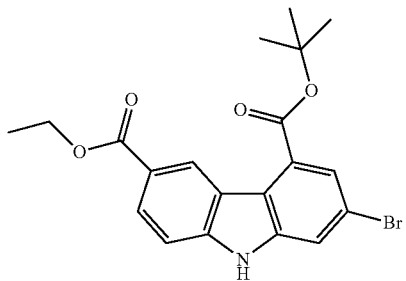 [SMILES: CCOC(=O)c1ccc2[nH]c3cc(Br)cc(C(=O)OC(C)(C)C)c3c2c1]

In a 40 ml reaction vial was added THF (100 ml), DDQ (2.139 g, 9.23 mmol) and 5-tert-butyl 3-ethyl 7-bromo-2,3,4,9-tetrahydro-1H-carbazole-3,5-dicarboxylate (1.500 g, 3.55 mmol). Let reflux for 90 minutes. LCMS shows all product and DDQ byproducts. The reaction was concentrated to dryness and then diluted with diluted saturated sodium bicarbonate solution. A white solid began precipitating upon stirring. The solid was filtered off, washed with water and then diethyl ether. Collected ethyl 5-tert-butyl 3-ethyl 7-bromo-9H-carbazole-3,5-dicarboxylate as a white solid (0.95 g, 65%). LC-MS (M+1=419).

Step 3: 5-tert-butyl 3-ethyl 7-(3,5-dimethylisoxazol-4-yl)-9H-carbazole-3,5-dicarboxylate

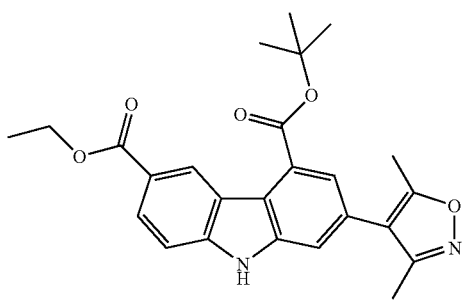 [SMILES: CCOC(=O)c1ccc2[nH]c3cc(-c4c(C)noc4C)cc(C(=O)OC(C)(C)C)c3c2c1]

To 5-tert-butyl 3-ethyl 7-bromo-9H-carbazole-3,5-dicarboxylate (0.500 g, 1.195 mmol), 3,5-dimethyl-4-(4,4,5,5-tetramethyl-1,3,2-dioxaborolan-2-yl)isoxazole (0.347 g, 1.554 mmol), and PdCl$_2$(dppf)-CH$_2$Cl$_2$ adduct (0.039 g, 0.060 mmol) was added 3.0 M potassium phosphate solution (1.195 ml, 3.59 mmol) and THF (3.98 ml). The reaction was capped with a teflon-lined cap and was degassed 3× with nitrogen gas and heated at 65° C. for 30 minutes. The reaction was complete. The reaction was then concentrated, taken up in water (75 ml) and triturated for 20 minutes. The solid was filtered off, washed with water and dried through a stream of air overnight. The product was collected as a whitish solid (0.48 g, 92%). LC-MS (M+1=435).

Step 4: 5-tert-butyl 3-ethyl 7-(3,5-dimethylisoxazol-4-yl)-9-(4-fluorobenzyl)-9H-carbazole-3,5-dicarboxylate

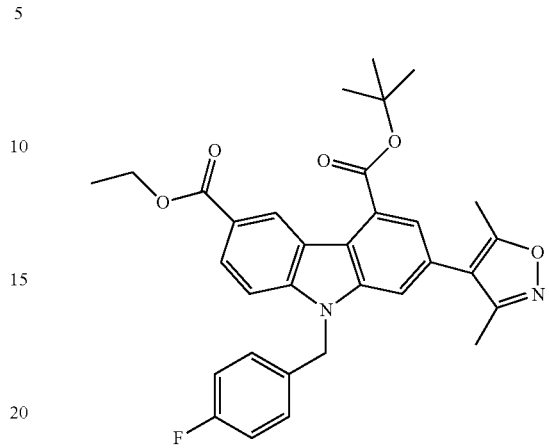

To 5-tert-butyl 3-ethyl 7-(3,5-dimethylisoxazol-4-yl)-9H-carbazole-3,5-dicarboxylate (0.455 g, 1.047 mmol) was added acetone (1.0 mL), potassium carbonate (0.579 g, 4.19 mmol), 10 mg of 18-crown-6 and 1-(chloromethyl)-4-fluorobenzene (0.227 g, 1.571 mmol). The reaction was allowed to heat to 80° C. for 2 hrs. The reaction was then concentrated to dryness. To the residue was added ethyl acetate/water and the layers were separated. The aqueous was extracted 2 times with ethyl acetate. The organics were collected, dried over Na$_2$SO$_4$, filtered and concentrated. The residue was taken up in 2 ml of DCM and purified on a 24 gram ISCO column using 0-100% ethyl acetate/heptane. Following concentration of the fractions, 5-tert-butyl 3-ethyl 7-(3,5-dimethylisoxazol-4-yl)-9-(4-fluorobenzyl)-9H-carbazole-3,5-dicarboxylate was collected as a clear oil (0.495 g, 87%). LC-MS (M+1=543). $^1$H NMR (400 MHz, methanol-d$_4$) δ 9.54 (d, J=1.1 Hz, 1H), 8.23 (dd, J=8.7, 1.7 Hz, 1H), 7.70-7.66 (m, 2H), 7.38 (dd, J=8.8, 5.5 Hz, 1H), 7.20 (dd, J=9.0, 5.3 Hz, 2H), 7.11-6.99 (m, 2H), 5.76 (s, 2H), 4.46 (q, J=7.1 Hz, 2H), 2.41 (s, 3H), 2.24 (s, 3H), 1.83-1.75 (m, 9H), 1.48 (t, J=7.2 Hz, 3H).

Step 5: 5-(tert-butoxycarbonyl)-7-(3,5-dimethylisoxazol-4-yl)-9-(4-fluorobenzyl)-9H-carbazole-3-carboxylic acid

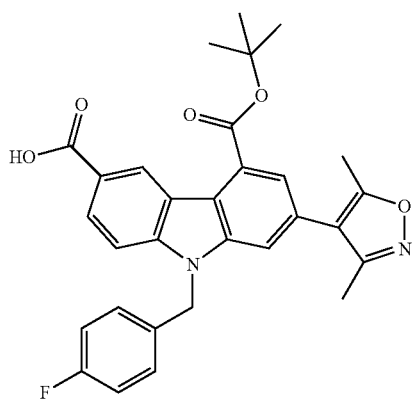 [SMILES: Cc1noc(C)c1-c1cc(C(=O)OC(C)(C)C)c2c3cc(C(=O)O)ccc3n(Cc3ccc(F)cc3)c2c1]

To a 40 ml reaction vial was added 5-tert-butyl 3-ethyl 7-(3,5-dimethylisoxazol-4-yl)-9-(4-fluorobenzyl)-9H-carbazole-3,5-dicarboxylate (0.350 g, 0.645 mmol), THF, MeOH and 20% NaOH (0.645 g, 3.23 mmol) solution. The reaction was heated at 75° C. for 4 hrs. LC shows complete saponification. The volatiles were removed and ice was added to the flask. The suspension was acidified with concentrated HCl and the solids were filtered and washed repeatedly with water. The filter cake was allowed to dry over night under a stream of air. The 5-(tert-butoxycarbonyl)-7-(3,5-dimethylisoxazol-4-yl)-9-(4-fluorobenzyl)-9H-carbazole-3-carboxylic acid was collected as a white solid (0.13 g, 39%). LC-MS (M+1=515).

Step 6: tert-butyl 2-(3,5-dimethylisoxazol-4-yl)-6-(3-fluoroazetidine-1-carbonyl)-9-(4-fluorobenzyl)-9H-carbazole-4-carboxylate

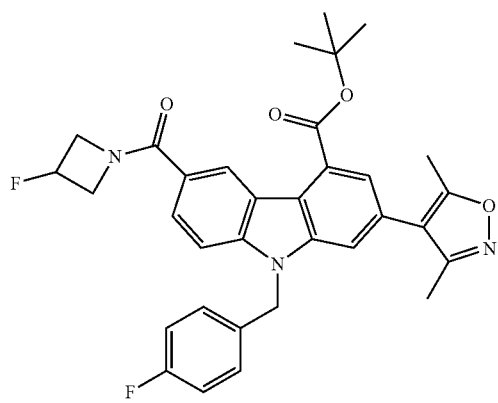 [SMILES: Cc1noc(C)c1-c1cc(C(=O)OC(C)(C)C)c2c3cc(C(=O)N4CC(F)C4)ccc3n(Cc3ccc(F)cc3)c2c1]

To 5-(tert-butoxycarbonyl)-7-(3,5-dimethylisoxazol-4-yl)-9-(4-fluorobenzyl)-9H-carbazole-3-carboxylic acid (250 mg, 0.486 mmol) in DMF (5.0 mL) was added HCTU (628 mg, 1.579 mmol), DMAP (193 mg, 1.579 mmol) and 3-fluoroazetidine, 1.0HCl (176 mg, 1.579 mmol). LCMS shows complete reaction after 1 hour. Water was added and a white precipitate formed. The solid was filtered off and collected. The solid was then dissolved in minimal amount of DCM and purified on a 24 gram ISCO column using 0-100% ethyl acetae/heptane. Following concentration of the fractions, tert-butyl 2-(3,5-dimethylisoxazol-4-yl)-6-(3-fluoroazetidine-1-carbonyl)-9-(4-fluorobenzyl)-9H-carbazole-4-carboxylate was collected as a white solid (0.105 g, 38%). LC-MS (M+1=572).

Step 7: 2-(3,5-dimethylisoxazol-4-yl)-6-(3-fluoroazetidine-1-carbonyl)-9-(4-fluorobenzyl)-9H-carbazole-4-carboxylic acid

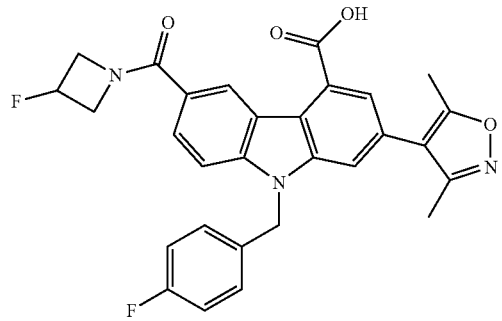 [SMILES: Cc1noc(C)c1-c1cc(C(=O)O)c2c3cc(C(=O)N4CC(F)C4)ccc3n(Cc3ccc(F)cc3)c2c1]

To a 2 dram vial was added tert-butyl 2-(3,5-dimethylisoxazol-4-yl)-6-(3-fluoroazetidine-1-carbonyl)-9-(4-fluorobenzyl)-9H-carbazole-4-carboxylate (0.095 g, 0.166 mmol), DCM (1 mL) and TFA (0.128 mL, 1.662 mmol). The reaction was stirred at room temperature for 1 hour. LC shows complete conversion to product. The reaction was concentrated, diluted with 2 ml of ether and filtered to give 2-(3,5-dimethylisoxazol-4-yl)-6-(3-fluoroazetidine-1-carbonyl)-9-(4-fluorobenzyl)-9H-carbazole-4-carboxylic acid (0.081 g, 95%) as a light brown solid. LC-MS (M+1=516).

Step 8: 2-(3,5-dimethyl-4-isoxazolyl)-6-((3-fluoro-1-azetidinyl)carbonyl)-9-(4-fluorobenzyl)-N-propyl-9H-carbazole-4-carboxamide To 2-(3,5-dimethylisoxazol-4-yl)-6-(3-fluoroazetidine-1-carbonyl)-9-(4-fluorobenzyl)-9H-carbazole-4-carboxylic acid (0.020 g, 0.039 mmol) in DMF (1 mL) was added HCTU (0.035 g, 0.087 mmol), DMAP (10.66 mg, 0.087 mmol) and propan-1-amine (8.34 mg, 0.087 mmol). LCMS shows complete reaction after 1 hour. The reaction was then concentrated, diluted with MeOH, and filtered through a 0.45 um nylon membrane syringe filter. Next, the crude material was purified via preparative LC/MS using the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 15 minutes, then a 5-minute hold at 100% B; Flow: 20 mL/min. Fractions containing the desired product were combined and dried via centrifugal evaporation to give 2-(3,5-dimethyl-4-isoxazolyl)-6-((3-fluoro-1-azetidinyl)carbonyl)-9-(4-fluorobenzyl)-N-propyl-9H-carbazole-4-carboxamide (10.9 mg, 49%). Two analytical LC/MS injections were used to determine the final purity. Injection 1 conditions: HPLC Ret. Time=1.76 min., column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. (HPLC Ret. Time$^{Method\ b}$). MS (ES): m/z=557 [M+H]$^+$. Injection 2 conditions: HPLC Ret. Time=1.76 min., column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. (HPLC Ret. Time$^{Method\ c}$). MS (ES): m/z=557 [M+H]$^+$.

The compounds listed in Table 7 were prepared using the same procedure for Example 124 with the appropriate amine reactant in the final step.

TABLE 7

| Example No. | Structure | Name | [M + H]$^+$ | Ret time | HPLC Method |
|---|---|---|---|---|---|
| 125 | 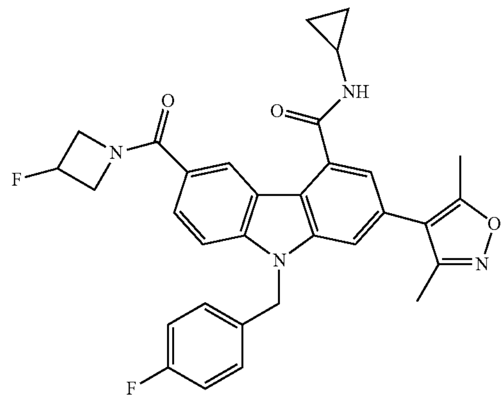 [SMILES: Cc1noc(C)c1-c1cc(C(=O)NC2CC2)c2c3cc(C(=O)N4CC(F)C4)ccc3n(Cc3ccc(F)cc3)c2c1] | N-cyclopropyl-2-(3,5-dimethyl-4-isoxazolyl)-6-((3-fluoro-1-azetidinyl)carbonyl)-9-(4-fluorobenzyl)-9H-carbazole-4-carboxamide | 555 | 1.680 | B |
| 126 | 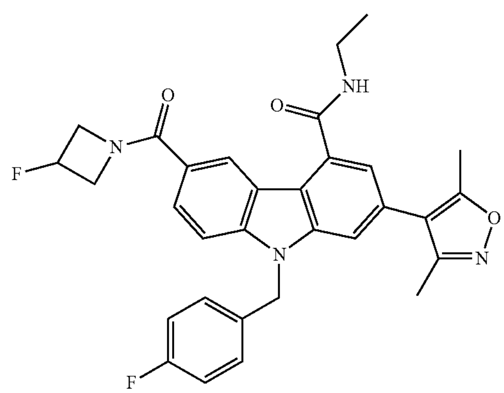 [SMILES: CCNC(=O)c1cc(-c2c(C)noc2C)cc2c1c1cc(C(=O)N3CC(F)C3)ccc1n2Cc1ccc(F)cc1] | 2-(3,5-dimethyl-4-isoxazolyl)-N-ethyl-6-((3-fluoro-1-azetidinyl)carbonyl)-9-(4-fluorobenzyl)-9H-carbazole-4-carboxamide | 543 | 1.744 | B |
| 127 | 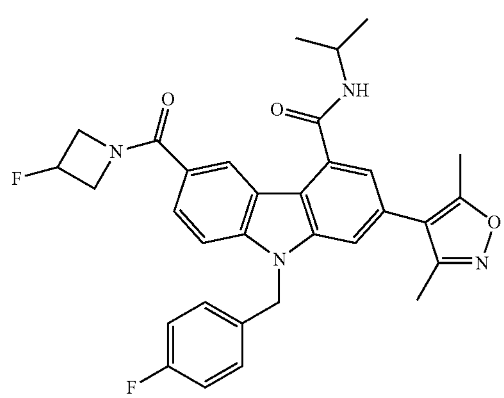 [SMILES: Cc1noc(C)c1-c1cc(C(=O)NC(C)C)c2c3cc(C(=O)N4CC(F)C4)ccc3n(Cc3ccc(F)cc3)c2c1] | 2-(3,5-dimethyl-4-isoxazolyl)-6-((3-fluoro-1-azetidinyl)carbonyl)-9-(4-fluorobenzyl)-N-isopropyl-9H-carbazole-4-carboxamide | 557 | 1.750 | B |

US 9,492,460 B2

111 112

TABLE 7-continued

| Example No. | Structure | Name | [M + H]+ | Ret time | HPLC Method |
|---|---|---|---|---|---|
| 128 | 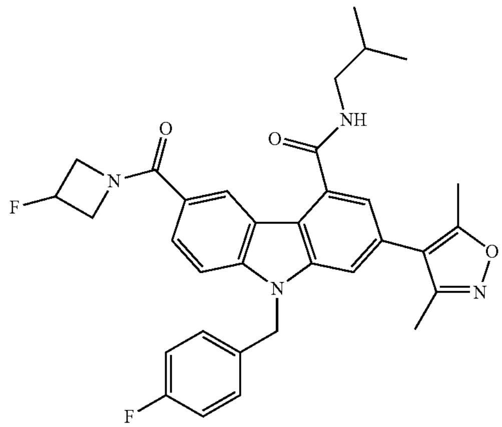 [SMILES: Cc1noc(C)c1-c1cc(C(=O)NCC(C)C)c2c3cc(C(=O)N4CC(F)C4)ccc3n(Cc3ccc(F)cc3)c2c1] | 2-(3,5-dimethyl-4-isoxazolyl)-6-((3-fluoro-1-azetidinyl)carbonyl)-9-(4-fluorobenzyl)-N-isobutyl-9H-carbazole-4-carboxamide | 571 | 1.850 | B |
| 129 | 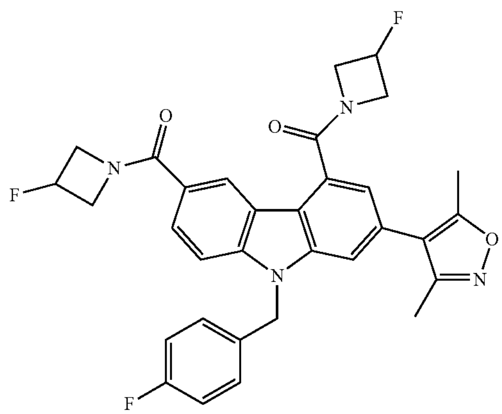 [SMILES: Cc1noc(C)c1-c1cc(C(=O)N2CC(F)C2)c2c3cc(C(=O)N4CC(F)C4)ccc3n(Cc3ccc(F)cc3)c2c1] | 2-(3,5-dimethyl-4-isoxazolyl)-4,6-bis((3-fluoro-1-azetidinyl)carbonyl)-9-(4-fluorobenzyl)-9H-carbazole | 573 | 1.792 | B |

Example 130

9-Benzyl-2-(3,5-dimethyl-4-isoxazolyl)-6-(methyl-amino)-9H-carbazole-4-carboxamide

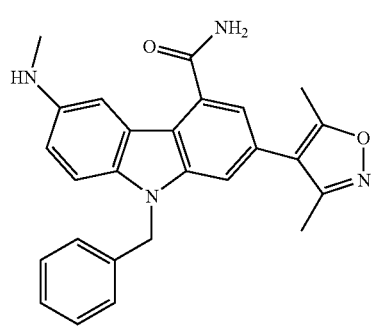 [SMILES: CNc1ccc2c(c1)c1c(C(N)=O)cc(-c3c(C)noc3C)cc1n2Cc1ccccc1]

Step 1: 9-benzyl-7-bromo-5-carbamoyl-9H-carbazole-3-carboxylic acid

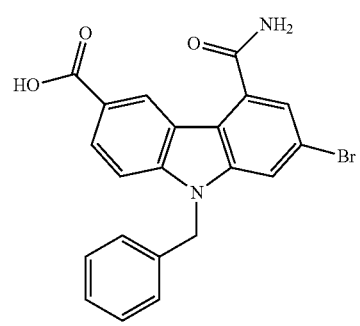 [SMILES: NC(=O)c1cc(Br)cc2c1c1cc(C(=O)O)ccc1n2Cc1ccccc1]

To ethyl 7-bromo-5-carbamoyl-9H-carbazole-3-carboxylate (1.000 g, 2.77 mmol) was added acetone (1.0 mL), potassium carbonate (1.531 g, 11.07 mmol), 18-crown-6 (0.073 g, 0.277 mmol) and (bromomethyl)benzene (0.710 g, 4.15 mmol). The reaction was allowed to heat to 80° C. for 2 hrs. LCMS shows consumption of starting material after 2 h. The reaction was then concentrated to dryness. The resulting material, ethyl 9-benzyl-7-bromo-5-carbamoyl-9H-carbazole-3-carboxylate was transferred to a 250 ml round bottom flask using water (20 ml)/THF (50 ml)/MeOH (10 ml). To the solution was added 10 ml of a 25% NaOH solution. The reaction was then refluxed for 4 hrs. LC shows complete saponification. The volatiles were removed and ice was added to the flask. The suspension was acidified with conc. HCl and the solids were filtered and washed repeatedly with water. The filter cake was allowed to dry over night under a stream of air. 9-benzyl-7-bromo-5-carbamoyl-9H-carbazole-3-carboxylic acid collected as a white solid (1.05 g, 90%). LC-MS (M+1=423). $^1$H NMR (400 MHz, DMSO-d$_6$) δ 9.05 (s, 1H), 8.20 (br. S., 1H), 8.11-8.01 (m, 2H), 7.81 (br. S., 1H), 7.70 (d, J=8.6 Hz, 1H), 7.49 (d, J=1.5 Hz, 1H), 7.34-7.20 (m, 3H), 7.13 (d, J=7.0 Hz, 2H), 5.78 (s, 2H).

Step 2: 4-methoxybenzyl 9-benzyl-7-bromo-5-carbamoyl-9H-carbazol-3-ylcarbamate

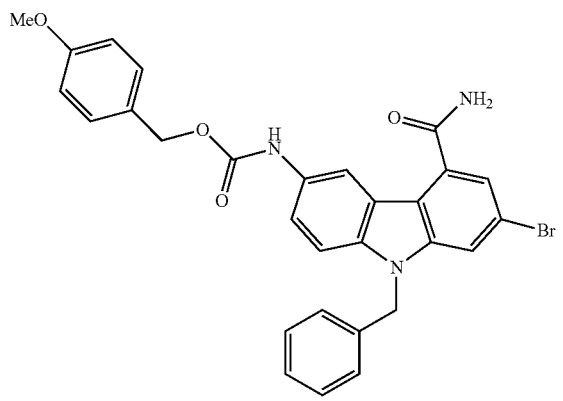 [SMILES: COc1ccc(COC(=O)Nc2ccc3c(c2)c2c(C(N)=O)cc(Br)cc2n3Cc2ccccc2)cc1]

9-benzyl-7-bromo-5-carbamoyl-9H-carbazole-3-carboxylic acid (0.170 g, 0.402 mmol) was mixed with molecular seives 4 A (0.100 g, 0.402 mmol) in dioxane (2.008 ml). To the mixture was added Et$_3$N (0.138 ml, 0.992 mmol) and diphenyl phosphorazidate (0.214 ml, 0.992 mmol). The mixture was stirred at 55° C. for 2 hours. LCMS showed the formation of isocyanate (OMe adduct). Next, (4-methoxyphenyl)methanol (0.277 g, 2.008 mmol) was added to the mixture, and the reaction was stirred at 80° C. for 16 hours. LCMS showed formation of the desired product. The mixture was concentrated, diluted with DCM and purified on a 24 gram ISCO column using 0-100% ethyl acetate/heptane. Following concentration of the fractions, 4-methoxybenzyl 9-benzyl-7-bromo-5-carbamoyl-9H-carbazol-3-ylcarbamate was collected as an off-white solid (0.19 g, 85%). LC-MS (M+1=522).

Step 3: 4-methoxybenzyl 9-benzyl-7-bromo-5-carbamoyl-9H-carbazol-3-yl(methyl)carbamate

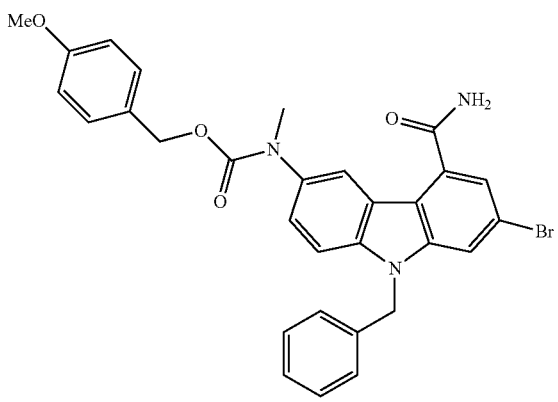 [SMILES: COc1ccc(COC(=O)N(C)c2ccc3c(c2)c2c(C(N)=O)cc(Br)cc2n3Cc2ccccc2)cc1]

To a 40 ml reaction vial was added 4-methoxybenzyl (9-benzyl-7-bromo-5-carbamoyl-9H-carbazol-3-yl)carbamate (0.095 g, 0.170 mmol), Cs$_2$CO$_3$ (0.166 g, 0.510 mmol) and acetone (2.5 ml). The reaction was cooled to 5° C. and iodomethane (0.011 ml, 0.179 mmol) was added via syringe. The reaction was stirred at 5° C. for 1 hour, and then stirred at room temperature overnight. LC shows 10% conversion. Next, the reaction was stirred at 50° C. for 3 hours. LC shows 30% conversion. Additional MeI was added and the reaction was heated at 50° C. for 1 hour. LC shows 70% mono-alkylated product together with the di-alkylated amide. The reaction was concentrated, diluted with water and a yellowish solid was filtered off and 4-methoxybenzyl 9-benzyl-7-bromo-5-carbamoyl-9H-carbazol-3-yl(methyl) carbamate was collected as a mixture of mono- and di-alkylated products (0.060 g, 62%). LC-MS (M+1=573).

Step 4: 4-methoxybenzyl 9-benzyl-5-carbamoyl-7-(3,5-dimethylisoxazol-4-yl)-9H-carbazol-3-yl(methyl)carbamate

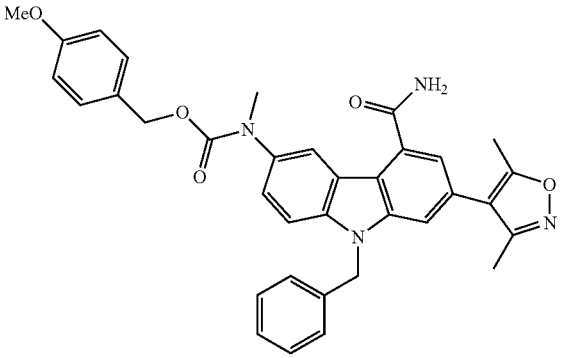 [SMILES: COc1ccc(COC(=O)N(C)c2ccc3c(c2)c2c(C(N)=O)cc(-c4c(C)noc4C)cc2n3Cc2ccccc2)cc1]

To 4-methoxybenzyl (9-benzyl-7-bromo-5-carbamoyl-9H-carbazol-3-yl)(methyl)carbamate (0.490 g, 0.856 mmol), 3,5-dimethyl-4-(4,4,5,5-tetramethyl-1,3,2-dioxaborolan-2-yl)isoxazole (0.191 g, 0.856 mmol), PdCl₂(dppf)-CH₂Cl₂ adduct (0.558 g, 0.856 mmol) was added 3.0 M potassium phosphate solution (0.856 ml, 2.57 mmol) and THF (2.85 ml). The reaction was capped with a teflon-lined cap and degassed. Next, the reaction was heated at 65° C. for 30 minutes, after which the reaction was judged to be complete. The reaction was concentrated, taken up in water (75 ml) and triturated for 20 minutes. The solid was filtered off, washed with water and dried through a stream of air overnight. The product was collected as a off-white solid (0.42 g, 83%). LC-MS (M+1=589).

Step 5: 9-benzyl-2-(3,5-dimethyl-4-isoxazolyl)-6-(methylamino)-9H-carbazole-4-carboxamide

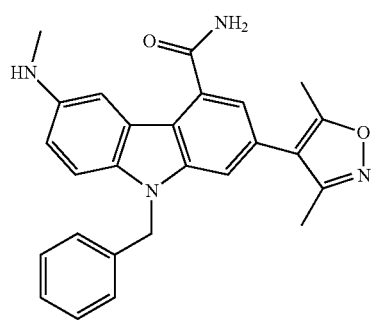 [SMILES: CNc1ccc2c(c1)c1c(C(N)=O)cc(-c3c(C)noc3C)cc1n2Cc1ccccc1]

To a 20 ml reaction vial was added 4-methoxybenzyl (9-benzyl-5-carbamoyl-7-(3,5-dimethylisoxazol-4-yl)-9H-carbazol-3-yl)(methyl)carbamate (0.040 g, 0.068 mmol), DCM (1 mL), anisole (0.074 mL, 0.680 mmol) and TFA (0.052 mL, 0.680 mmol) dropwise. The reaction was stirred for 15 minutes at room temperature. LCMS shows complete conversion to product. The sample was concentrated and stirred with 10 ml of 7N NH₃/MeOH for 15 minutes. Ether was added and the solid was triturated overnight. Following filtration, a tan solid was collected and washed with ether. The solid was dried through a stream of air for 2 hours to give 9-benzyl-2-(3,5-dimethyl-4-isoxazolyl)-6-(methylamino)-9H-carbazole-4-carboxamide (0.024 g, 83%). LC-MS (M+1=425).

Example 131

9-benzyl-2-(3,5-dimethylisoxazol-4-yl)-6-(N-methylacetamido)-9H-carbazole-4-carboxamide

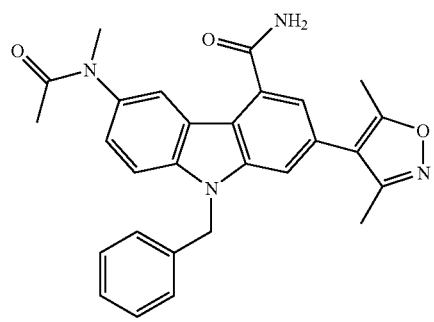 [SMILES: CC(=O)N(C)c1ccc2c(c1)c1c(C(N)=O)cc(-c3c(C)noc3C)cc1n2Cc1ccccc1]

To a 2 dram vial was added 9-benzyl-2-(3,5-dimethylisoxazol-4-yl)-6-(methylamino)-9H-carbazole-4-carboxamide (0.040 g, 0.094 mmol), DCM (0.5 mL), pyridine (0.037 g, 0.471 mmol) and, acetyl chloride (0.074 g, 0.942 mmol) dropwise. The reaction was stirred at room temperature for 10 minutes then diluted with 1N HCl and extracted 2× with DCM. The organics were collected and dried over Na₂SO₄, filtered and concentrated. The crude product was purified via preparative LCMS with the following conditions: Column: Waters XBridge C18, 19×150 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 5-100% B over 15 minutes, then a 5-minute hold at 100% B; Flow: 20 mL/min. Fractions containing the desired product were combined and dried via centrifugal evaporation to give 9-benzyl-2-(3,5-dimethylisoxazol-4-yl)-6-(N-methylacetamido)-9H-carbazole-4-carboxamide (0.8 mg, 1.7%). Two analytical LC/MS injections were used to determine the final purity.

Injection 1 conditions: HPLC Ret. Time=1.49 min., Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. (HPLC Ret. Time$^{Method\ b}$). MS (ES): m/z=467 [M+H]⁺.

Injection 2 conditions: HPLC Ret. Time=1.46 min., column: Waters Acquity UPLC BEH C18, 2.1×50 mm, 1.7-µm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. (HPLC Ret. Time$^{Method\ c}$). MS (ES): m/z=467 [M+H]⁺.

The compounds listed in Table 8 were prepared using the same procedure outlined for the preparation of Compound 131.

TABLE 8

| Example No. | Structure | Name | [M + H]⁺ | Ret time | HPLC Method |
|---|---|---|---|---|---|
| 132 | 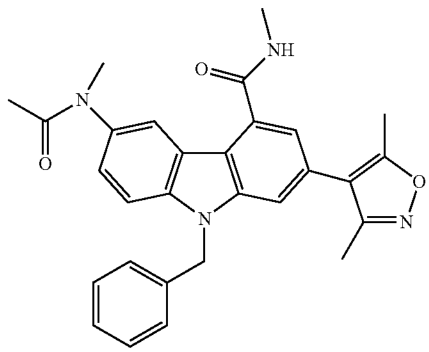 [SMILES: CNC(=O)c1cc(-c2c(C)noc2C)cc2c1c1cc(N(C)C(C)=O)ccc1n2Cc1ccccc1] | 6-(acetyl(methyl)amino)-9-benzyl-2-(3,5-dimethyl-4-isoxazolyl)-N-methyl-9H-carbazole-4-carboxamide | 481 | 1.604 | B |
| 133 | 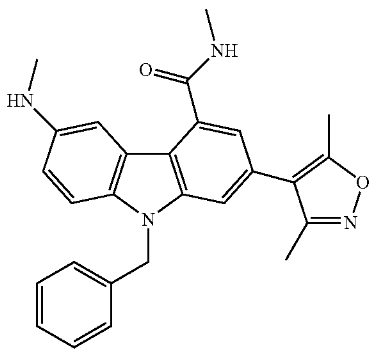 [SMILES: CNC(=O)c1cc(-c2c(C)noc2C)cc2c1c1cc(NC)ccc1n2Cc1ccccc1] | 9-benzyl-2-(3,5-dimethyl-4-isoxazolyl)-N-methyl-6-(methylamino)-9H-carbazole-4-carboxamide | 439 | 1.672 | B |

Example 134

6-(acetyl(2-fluoroethyl)amino)-9-benzyl-2-(3,5-dimethyl-4-isoxazolyl)-9H-carbazole-4-carboxamide

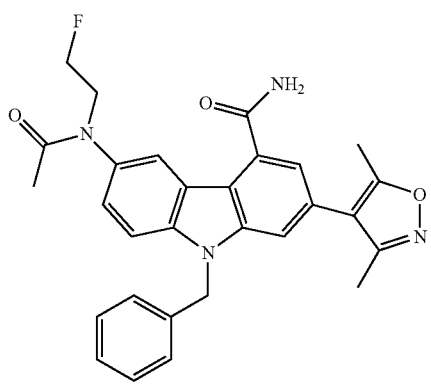 [SMILES: CC(=O)N(CCF)c1ccc2c(c1)c1c(C(N)=O)cc(-c3c(C)noc3C)cc1n2Cc1ccccc1]

The above titled compound was prepared according to the conditions described for the preparation of (131) from 2-fluoro-ethylbromide. The reaction was done at a temperature of 80° C. for 2 hours. The crude material was purified via preparative LCMS using the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 0.05% TFA; Mobile Phase B: 95:5 acetonitrile:water with 0.05% TFA; Gradient: 15-100% B over 25 minutes, then a 5-minute hold at 100% B; Flow: 20 mL/min. Fractions containing the desired product were combined and dried via centrifugal evaporation to give 6-(acetyl(2-fluoroethyl)amino)-9-benzyl-2-(3,5-dimethyl-4-isoxazolyl)-9H-carbazole-4-carboxamide (3.6 mg, 15.7%). (HPLC Ret. Time=1.64 min$^{Method\ b}$). MS (ES): m/z=499 [M+H]⁺.

Example 135

6-amino-9-benzyl-2-(3,5-dimethyl-4-isoxazolyl)-9H-carbazole-4-carboxamide

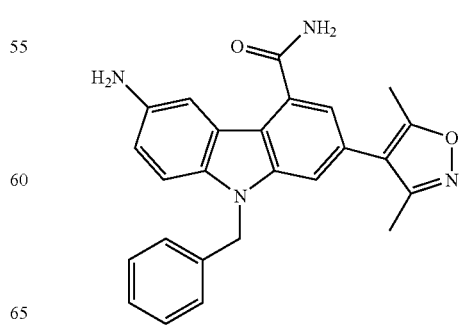

Step 1: 4-methoxybenzyl 9-benzyl-5-carbamoyl-7-(3,5-dimethylisoxazol-4-yl)-9H-carbazol-3-ylcarbamate

Example 136

9-benzyl-2-(3,5-dimethyl-4-isoxazolyl)-6-(2-fluoro-ethylamino)-9H-carbazole-4-carboxamide

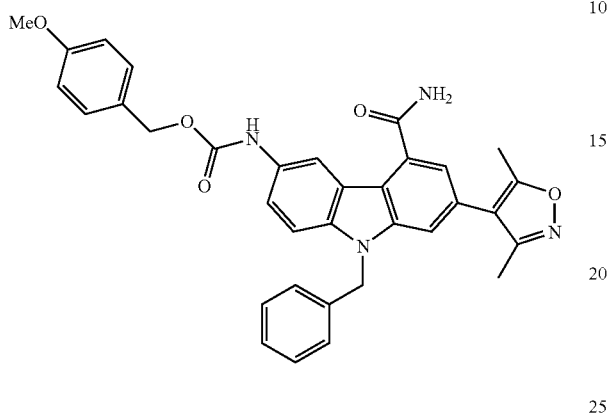

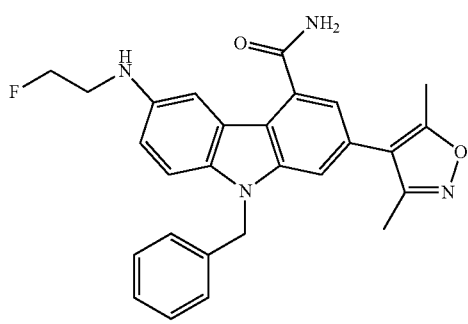 [SMILES: Cc1noc(C)c1-c1cc(C(N)=O)c2c3cc(NCCF)ccc3n(Cc3ccccc3)c2c1]

To 4-methoxybenzyl (9-benzyl-7-bromo-5-carbamoyl-9H-carbazol-3-yl)carbamate (0.500 g, 0.895 mmol), 3,5-dimethyl-4-(4,4,5,5-tetramethyl-1,3,2-dioxaborolan-2-yl) isoxazole (0.260 g, 1.164 mmol), $PdCl_2(dppf)\text{-}CH_2Cl_2$ adduct (0.029 g, 0.045 mmol) was added 3.0 M potassium phosphate solution (0.895 ml, 2.69 mmol) and THF (2.98 ml). The reaction was capped with a teflon-lined cap and was degassed and heated at 65° C. for 30 minutes. The reaction was then concentrated, taken up in water (75 ml) and triturated for 20 minutes. The solid was filtered off, washed with water and dried through a stream of air overnight. The product was collected as an off-white solid (0.475 g, 92%). LC-MS (M+1=575. $^1$H NMR (400 MHz, DMSO-$d_6$) δ 9.68-9.52 (m, 1H), 8.54 (s, 1H), 8.03 (br. s., 1H), 7.75-7.58 (m, 3H), 7.49 (d, J=8.6 Hz, 1H), 7.39 (d, J=8.8 Hz, 2H), 7.31-7.14 (m, 6H), 6.96 (d, J=8.6 Hz, 2H), 5.71 (s, 2H), 5.09 (s, 2H), 3.84-3.71 (m, 3H), 2.42 (s, 3H), 2.24 (s, 3H).

Step 2: 6-amino-9-benzyl-2-(3,5-dimethylisoxazol-4-yl)-9H-carbazole-4-carboxamide To a 20 ml reaction vial was added 4-methoxybenzyl (9-benzyl-5-carbamoyl-7-(3,5-dimethylisoxazol-4-yl)-9H-carbazol-3-yl)carbamate (0.600 g, 1.044 mmol), DCM, anisole (1.141 ml, 10.44 mmol) and TFA (0.804 ml, 10.44 mmol) dropwise. The reaction was stirred for 15 minutes at room temperature. LCMS showed complete conversion to product. The sample was concentrated and stirred with 10 ml of 7 N NH3/MeOH for 15 minutes. Ether was added and the solid was triturated overnight and 6-amino-9-benzyl-2-(3,5-dimethylisoxazol-4-yl)-9H-carbazole-4-carboxamide was filtered off as a light brown solid (0.378 g, 88%). (HPLC Ret. Time=1.498 min.$^{Method\ b}$). MS (ES): m/z=411 [M+H]$^+$.

To a 2 dram vial was added 6-amino-9-benzyl-2-(3,5-dimethylisoxazol-4-yl)-9H-carbazole-4-carboxamide (0.020 g, 0.049 mmol), 1-bromo-2-fluoroethane (0.012 g, 0.097 mmol), sodium carbonate (0.021 g, 0.195 mmol) and DMF (1 mL). The reaction was stirred at 80° C. for 2 hrs. The reaction was then concentrated, diluted with DMSO (1.5 ml) and the crude material was purified via preparative LCMS using the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 0.05% TFA; Mobile Phase B: 95:5 acetonitrile:water with 0.05% TFA; Gradient: 15-100% B over 25 minutes, then a 5-minute hold at 100% B; Flow: 20 mL/min. Fractions containing the desired product were combined and dried via centrifugal evaporation to give 9-benzyl-2-(3,5-dimethylisoxazol-4-yl)-6-(2-fluoroethylamino)-9H-carbazole-4-carboxamide (4.3 mg, 19%). Two analytical LC/MS injections were used to determine the final purity.

Injection 1 conditions: HPLC Ret. Time=1.674 min., column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. (HPLC Ret. Time$^{Method\ b}$). MS (ES): m/z=457 [M+H]$^+$.

Injection 2 conditions: HPLC Ret. Time=1.357 min., column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. (HPLC Ret. Time$^{Method\ c}$). MS (ES): m/z=457 [M+H]$^+$.

The compounds listed in Table 9 were prepared using the same procedure outlined above for the synthesis of Compound 136.

TABLE 9

| Example No. | Structure | Name | [M + H]⁺ | Ret time | HPLC Method |
|---|---|---|---|---|---|
| 137 | 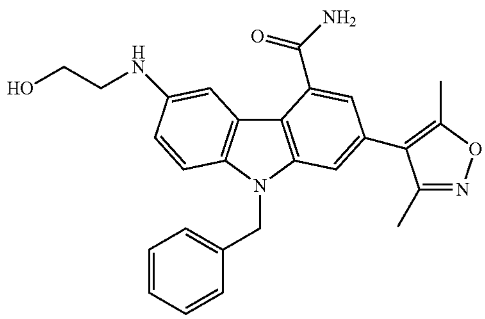 [SMILES: Cc1noc(C)c1-c1cc(C(N)=O)c2c3cc(NCCO)ccc3n(Cc3ccccc3)c2c1] | 9-benzyl-2-(3,5-dimethyl-4-isoxazolyl)-6-((2-hydroxyethyl)amino)-9H-carbazole-4-carboxamide | 455 | 1.302 | B |
| 138 | 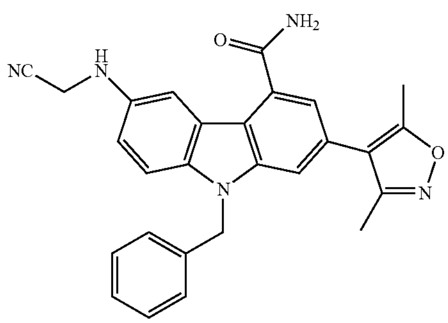 [SMILES: Cc1noc(C)c1-c1cc(C(N)=O)c2c3cc(NCC#N)ccc3n(Cc3ccccc3)c2c1] | 9-benzyl-6-((cyanomethyl)amino)-2-(3,5-dimethyl-4-isoxazolyl)-9H-carbazole-4-carboxamide | 450 | 1.593 | B |
| 139 | 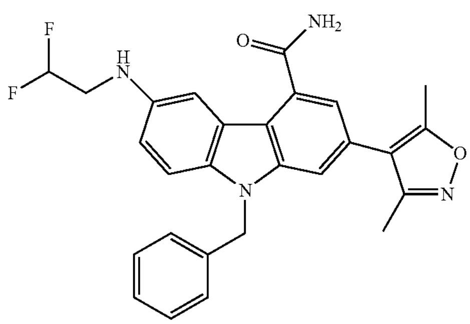 [SMILES: Cc1noc(C)c1-c1cc(C(N)=O)c2c3cc(NCC(F)F)ccc3n(Cc3ccccc3)c2c1] | 9-benzyl-6-((2,2-difluoroethyl)amino)-2-(3,5-dimethyl-4-isoxazolyl)-9H-carbazole-4-carboxamide | 475 | 1.742 | B |
| 140 | 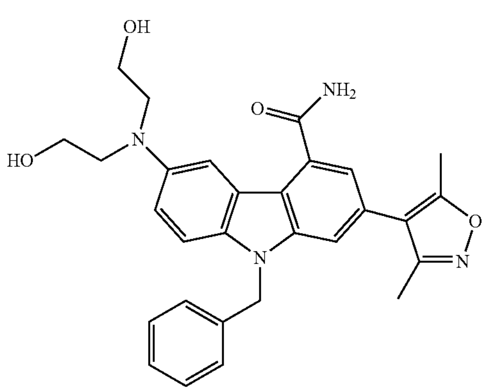 [SMILES: Cc1noc(C)c1-c1cc(C(N)=O)c2c3cc(N(CCO)CCO)ccc3n(Cc3ccccc3)c2c1] | 9-benzyl-6-(bis(2-hydroxyethyl)amino)-2-(3,5-dimethyl-4-isoxazolyl)-9H-carbazole-4-carboxamide | 499 | 1.346 | B |

TABLE 9-continued

| Example No. | Structure | Name | [M + H]+ | Ret time | HPLC Method |
|---|---|---|---|---|---|
| 141 | 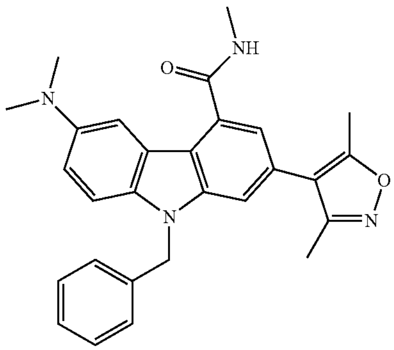 [SMILES: CNC(=O)c1cc(-c2c(C)noc2C)cc2c1c1cc(N(C)C)ccc1n2Cc1ccccc1] | 9-benzyl-6-(dimethylamino)-2-(3,5-dimethyl-4-isoxazolyl)-N-methyl-9H-carbazole-4-carboxamide | 453 | 1.392 | B |

Example 142

6-acetamido-9-benzyl-2-(3,5-dimethyl-4-isoxazolyl)-9H-carbazole-4-carboxamide

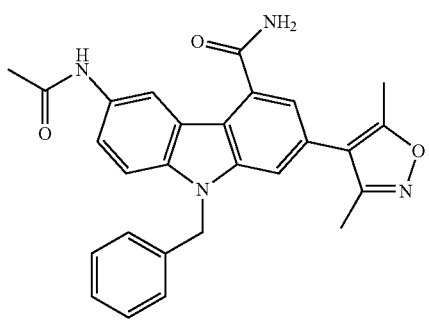 [SMILES: CC(=O)Nc1ccc2c(c1)c1c(C(N)=O)cc(-c3c(C)noc3C)cc1n2Cc1ccccc1]

To a 2 dram vial was added 6-amino-9-benzyl-2-(3,5-dimethylisoxazol-4-yl)-9H-carbazole-4-carboxamide (0.015 g, 0.037 mmol), DCM (0.5 mL), pyridine (0.014 g, 0.183 mmol) and acetyl chloride (8.61 mg, 0.110 mmol) dropwise. The reaction was stirred at room temperature for 10 minutes then concentrated to dryness. The residue was diluted with DMSO, filtered through a 0.45 um nylon membrane syringe filter. The crude material was purified via preparative LCMS with the following conditions: Column: Waters XBridge C18, 19×100 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-100% B over 10 minutes, then a 5-minute hold at 100% B; Flow: 20 mL/min. Fractions containing the desired product were combined and dried via centrifugal evaporation. The material was further purified via preparative LCMS using the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 5-minute hold at 60% B; Flow: 20 mL/min. Fractions containing the desired product were combined and dried via centrifugal evaporation to provide 6-acetamido-9-benzyl-2-(3,5-dimethyl-4-isoxazolyl)-9H-carbazole-4-carboxamide (7.0 mg, 41%). Two analytical LC/MS injections were used to determine the final purity.

Injection 1 conditions: HPLC Ret. Time=1.410 min., column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. (HPLC Ret. Time$^{Method\ b}$). MS (ES): m/z=453 [M+H]+.

Injection 2 conditions: HPLC Ret. Time=1.400 min., column: Waters Acquity UPLC BEH C18, 2.1×50 mm, 1.7-µm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. (HPLC Ret. Time$^{Method\ c}$). MS (ES): m/z=453 [M+H]+.

The compounds listed in Table 10 were prepared using the same procedure with the appropriate acid chloride, carbamoyl chloride or sulfonyl chloride.

TABLE 10

| Example No. | Structure | Name | [M + H]+ | HPLC Ret time | HPLC Method |
|---|---|---|---|---|---|
| 143 | 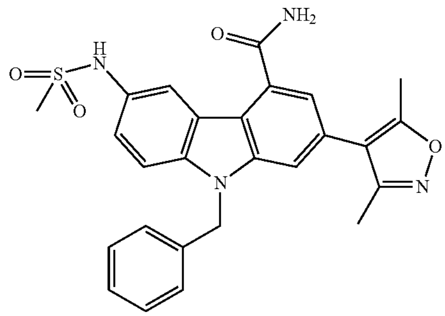 [SMILES: Cc1noc(C)c1-c1cc(C(N)=O)c2c3cc(NS(C)(=O)=O)ccc3n(Cc3ccccc3)c2c1] | 9-benzyl-2-(3,5-dimethyl-4-isoxazolyl)-6-(methylsulfonamido)-9H-carbazole-4-carboxamide | 489 | 1.554 | B |
| 144 | 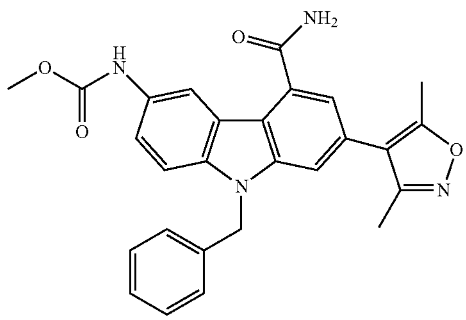 [SMILES: COC(=O)Nc1ccc2c(c1)c1c(C(N)=O)cc(-c3c(C)noc3C)cc1n2Cc1ccccc1] | methyl (9-benzyl-5-carbamoyl-7-(3,5-dimethyl-4-isoxazolyl)-9H-carbazol-3-yl)carbamate | 469 | 1.630 | B |
| 145 | 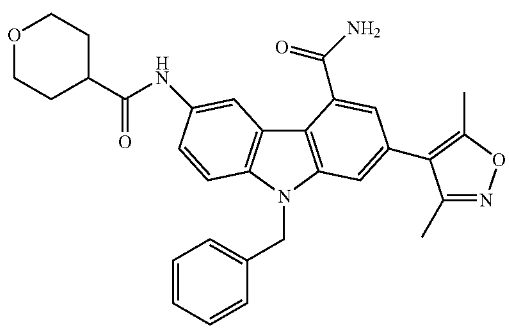 [SMILES: Cc1noc(C)c1-c1cc(C(N)=O)c2c3cc(NC(=O)C4CCOCC4)ccc3n(Cc3ccccc3)c2c1] | 9-benzyl-2-(3,5-dimethyl-4-isoxazolyl)-6-((tetrahydro-2H-pyran-4-ylcarbonyl)amino)-9H-carbazole-4-carboxamide | 523 | 1.555 | B |
| 146 | 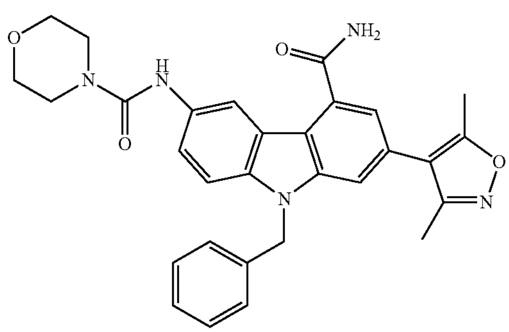 [SMILES: Cc1noc(C)c1-c1cc(C(N)=O)c2c3cc(NC(=O)N4CCOCC4)ccc3n(Cc3ccccc3)c2c1] | 9-benzyl-2-(3,5-dimethyl-4-isoxazolyl)-6-((4-morpholinylcarbonyl)amino)-9H-carbazole-4-carboxamide | 524 | 1.520 | B |

TABLE 10-continued

| Example No. | Structure | Name | [M + H]+ | Ret time | HPLC Method |
|---|---|---|---|---|---|
| 147 | 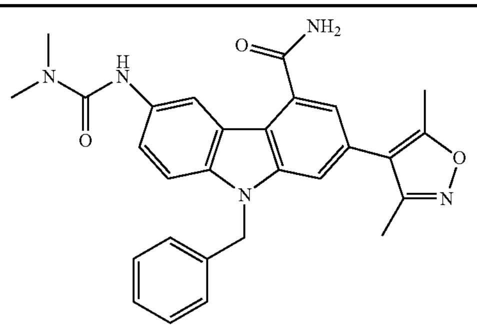 | 9-benzyl-6-((dimethylcarbamoyl)amino)-2-(3,5-dimethyl-4-isoxazolyl)-9H-carbazole-4-carboxamide | 482 | 1.529 | B |
| 148 | 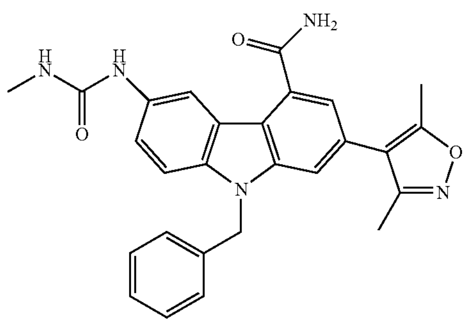 [SMILES: CNC(=O)Nc1ccc2c(c1)c1c(C(N)=O)cc(-c3c(C)noc3C)cc1n2Cc1ccccc1] | 9-benzyl-2-(3,5-dimethyl-4-isoxazolyl)-6-((methylcarbamoyl)amino)-9H-carbazole-4-carboxamide | 468 | 1.466 | B |
| 149 | 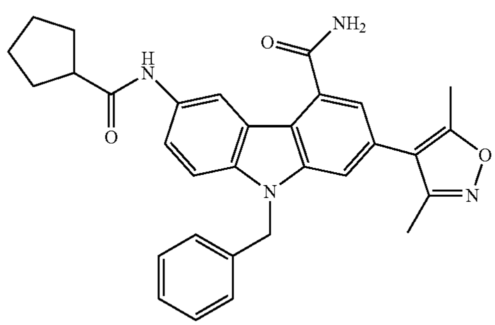 [SMILES: Cc1noc(C)c1-c1cc(C(N)=O)c2c3cc(NC(=O)C4CCCC4)ccc3n(Cc3ccccc3)c2c1] | 9-benzyl-6-((cyclopentylcarbonyl)amino)-2-(3,5-dimethyl-4-isoxazolyl)-9H-carbazole-4-carboxamide | 507 | 1.760 | B |

Example 150

2-(3,5-dimethyl-4-isoxazolyl)-6-(2-oxo-1,3-oxazinan-3-yl)-9H-carbazole-4-carboxamide

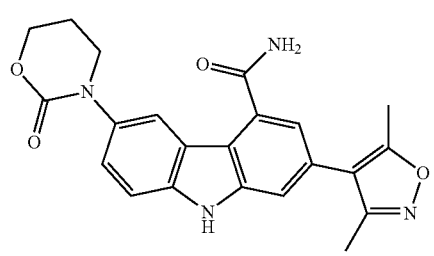 [SMILES: Cc1noc(C)c1-c1cc(C(N)=O)c2c(c1)[nH]c1ccc(N3CCCOC3=O)cc12]

Step 1: 4-methoxybenzyl 5-carbamoyl-7-(3,5-dimethylisoxazol-4-yl)-9H-carbazol-3-ylcarbamate

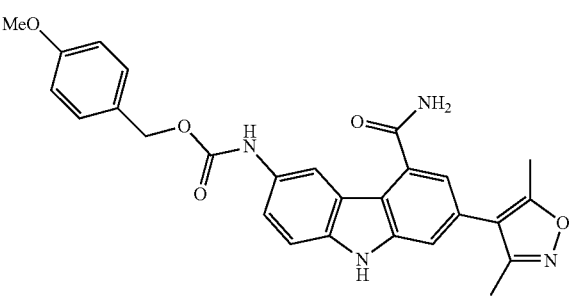 [SMILES: COc1ccc(COC(=O)Nc2ccc3[nH]c4cc(-c5c(C)noc5C)cc(C(N)=O)c4c3c2)cc1]

7-bromo-5-carbamoyl-9H-carbazole-3-carboxylic acid (0.450 g, 1.351 mmol) was mixed with 4 A molecular sieves (0.100 g, 1.351 mmol) in dioxane (10 mL). To the mixture was added Et₃N (0.465 mL, 3.34 mmol) and diphenyl phosphorazidate (0.721 mL, 3.34 mmol). The mixture was then stirred at 55° C. for 2 hours. LCMS showed the formation of isocyanate (OMe adduct). Next, (4-methoxyphenyl)methanol (0.933 g, 6.75 mmol) was added to the mixture, and stirring was continued at 80° C. for 16 hours. LCMS showed formation of the desired product. The mixture was filtered thru celite and washed with DCM/MeOH and then concentrated. To this residue was added water and DCM, and the layers were separated. The organic was dried over Na$_2$SO$_4$, filtered and concentrated. The crude 4-methoxybenzyl (7-bromo-5-carbamoyl-9H-carbazol-3-yl) carbamate was added to a 40 ml reaction vial and 3,5-dimethyl-4-(4,4,5,5-tetramethyl-1,3,2-dioxaborolan-2-yl) isoxazole (0.362 g, 1.621 mmol), PdCl$_2$(dppf)-CH$_2$Cl$_2$ adduct (0.044 g, 0.068 mmol), THF (10 mL) and 3.0M potassium phosphate solution (1.351 mL, 4.05 mmol) were added. The mixture was capped and pump/purged with nitrogen 3 times. The reaction was then heated at 65° C. for 1 hour. LC showed complete reaction. The mixture was concentrated, diluted with DCM and water, and the layers were separated. The organic was collected, dried over Na$_2$SO$_4$, filtered and concentrated. The crude residue was diluted with DCM and purified on a 40 gram ISCO column using 0-100% ethyl acetate/heptane. Following concentration of the fractions, the product was collected as an off-white solid (0.44 g, 67%). LC-MS (M+1=485).

Step 2: 6-amino-2-(3,5-dimethylisoxazol-4-yl)-9H-carbazole-4-carboxamide

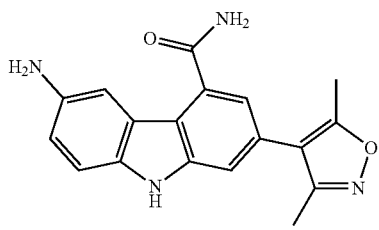 [SMILES: Cc1noc(C)c1-c1cc(C(N)=O)c2c(c1)[nH]c1ccc(N)cc12]

To a 40 ml reaction vial was added 4-methoxybenzyl (5-carbamoyl-7-(3,5-dimethylisoxazol-4-yl)-9H-carbazol-3-yl)carbamate (0.100 g, 0.206 mmol), DCM, anisole (0.022 g, 0.206 mmol) and TFA (0.016 ml, 0.206 mmol) dropwise. The reaction was stirred at room temperature for 30 minutes, and then concentrated. The aniline was treated with 1 ml of NH$_3$/MeOH and concentrated. Next, the crude product was suspended in ether and stirred for 15 minutes. A tan solid was filtered off and washed with ether. After drying, 6-amino-2-(3,5-dimethylisoxazol-4-yl)-9H-carbazole-4-carboxamide was collected as a brownish solid (0.051 g, 77%). LC-MS (M+1=321).

Step 3: 2-(3,5-dimethyl-4-isoxazolyl)-6-(2-oxo-1,3-oxazinan-3-yl)-9H-carbazole-4-carboxamide To a 2 dram vial was added 6-amino-2-(3,5-dimethylisoxazol-4-yl)-9H-carbazole-4-carboxamide (0.240 g, 0.749 mmol), DCM (1 mL), pyridine (0.296 g, 3.75 mmol) and 3-chloropropyl carbonochloridate (0.129 g, 0.824 mmol). The reaction was stirred at room temperature for 0.5 hours. The reaction was then diluted with DCM and washed with water then brine. The organics were dried over Na$_2$SO$_4$, filtered and concentrated. To the residue in a 2 dram vial was added acetone (1 mL) and potassium carbonate (0.414 g, 3.00 mmol). The reaction was sealed and heated at 75° C. overnight. Next, the mixture was concentrated, diluted with DMSO, filtered and purified by HPLC using 40-100% MeOH/Water (Solvent A (90% water, 10% methanol, 0.1% TFA), Solvent B (10% water, 90% methanol, 0.1% TFA), 12 min gradient, 16 minute run, 25 mL/min). Following concentration of the solvent via roto-evaporation, the product was obtained as a tan solid. (75.0 mg, 25%). The final purity was determined by LCMS. Injection conditions: HPLC Ret. Time=0.64 min. Column: Waters Acquity SDS BEH C18, 2.1×50 mm, 1.7-µm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes. Flow: 1.11 mL/min. (HPLC Ret. Time$^{Method\ f}$), MS (ES): m/z=405 [M+H]$^+$.

Example 151

2-(3,5-dimethyl-4-isoxazolyl)-9-(4-fluorobenzyl)-6-(2-oxo-1,3-oxazinan-3-yl)-9H-carbazole-4-carboxamide

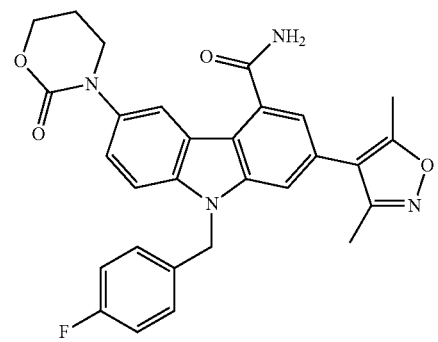 [SMILES: Cc1noc(C)c1-c1cc(C(N)=O)c2c3cc(N4CCCOC4=O)ccc3n(Cc3ccc(F)cc3)c2c1]

To 2-(3,5-dimethyl isoxazol-4-yl)-6-(2-oxo-1,3-oxazinan-3-yl)-9H-carbazole-4-carboxamide (0.013 g, 0.033 mmol) was added acetone (1.0 mL), potassium carbonate (0.018 g, 0.132 mmol), 18-crown-6 (0.869 mg, 3.29 µmol) and 1-(chloromethyl)-4-fluorobenzene (9.51 mg, 0.066 mmol). The reaction was allowed to heat at 80° C. for 2 hours. LCMS showed consumption of starting material. The reaction was concentrated to dryness. Next, 1 ml of DMSO was added and the mixture was filtered through a frit. The solution was purified by HPLC using 40-100% MeOH/water (Solvent A (90% water, 10% methanol, 0.1% TFA), Solvent B (10% water, 90% methanol, 0.1% TFA), 12 min gradient, 16 minute run, 25 mL/min). Following concentration of the solvent via roto-evaporation, the product was obtained as a white solid (8.0 mg, 47%). The final purity was determined by an LCMS injection. Injection conditions: HPLC Ret. Time=0.83 min. Column: Waters Acquity SDS BEH C18, 2.1×50 mm, 1.7-µm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes. Flow: 1.11 mL/min. (HPLC Ret. Time$^{Method\ f}$), MS (ES): m/z=513 [M+H]$^+$. $^1$H NMR (400 MHz, DMSO-d$_6$) δ 8.33 (d, J=2.0 Hz, 1H), 8.10 (s, 1H), 7.77 (d, J=1.3 Hz, 1H), 7.74 (d, J=8.8 Hz, 1H), 7.63 (s, 1H), 7.46 (dd, J=8.7, 2.1 Hz, 1H), 7.34-7.23 (m, 3H), 7.17-7.07 (m, 2H), 5.76 (s, 2H), 4.40 (t, J=5.3 Hz, 2H), 3.70 (t, J=6.2 Hz, 2H), 2.45 (s, 3H), 2.26 (s, 3H), 2.22-2.11 (m, 2H).

Example 152

2-(3,5-dimethyl-4-isoxazolyl)-9-(4-fluorobenzyl)-6-(2-oxo-1,3-oxazolidin-3-yl)-9H-carbazole-4-carboxamide

Example 153

2-(3,5-dimethyl-4-isoxazolyl)-6-(5,5-dimethyl-2-oxo-1,3-oxazinan-3-yl)-9-(4-fluorobenzyl)-9H-carbazole-4-carboxamide

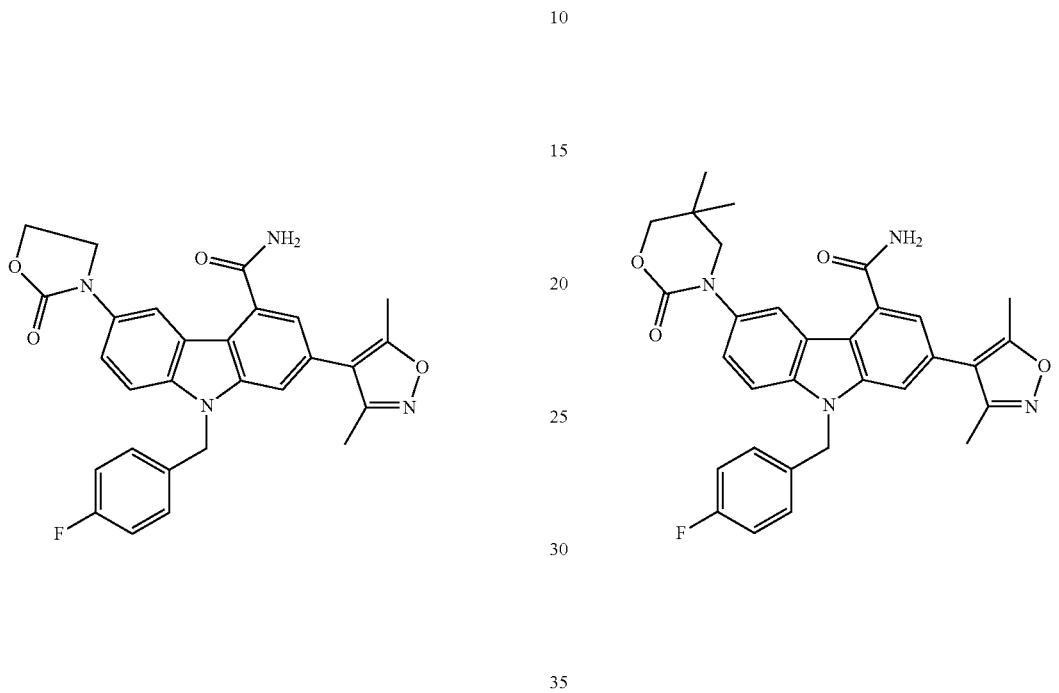

The above titled compound was prepared according to the conditions described for the preparation of Compound 150 from 2-chloroethyl carbonochloridate. The crude material was purified via preparative LCMS with the following conditions: Column: Waters XBridge C18, 19×250 mm, 5-μm particles; Mobile Phase A: 5:95 acetonitrile:water with 0.05% TFA; Mobile Phase B: 95:5 acetonitrile:water with 0.05% TFA; Gradient: 15-50% B over 25 minutes, then a 10-minute hold at 100% B; Flow: 20 mL/min. Fractions containing the desired product were combined and dried via centrifugal evaporation (7.2 mg, 28%). Two analytical LC/MS injections were used to determine the final purity.

Injection 1 conditions: HPLC Ret. Time=1.621 min., column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. (HPLC Ret. Time$^{Method\ b}$). MS (ES): m/z=499 [M+H]$^+$.

Injection 2 conditions: HPLC Ret. Time=1.617 min., column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. (HPLC Ret. Time$^{Method\ c}$). MS (ES): m/z=499 [M+H]$^+$.

The above titled compound was prepared according to the conditions described for the preparation of Compound 150 from 3-chloro-2,2-dimethylpropyl carbonochloridate. The crude material was purified via preparative LCMS using the following conditions: Column: Waters XBridge C18, 19×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 10 minutes, then a 5-minute hold at 100% B; Flow: 20 mL/min. Fractions containing the desired product were combined and dried via centrifugal evaporation (14.6 mg, 51%). Two analytical LC/MS injections were used to determine the final purity.

Injection 1 conditions: HPLC Ret. Time=1.640 min. Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. (HPLC Ret. Time$^{Method\ b}$) MS (ES): m/z=541 [M+H]$^+$.

Injection 2 conditions: HPLC Ret. Time=1.640 min. Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. (HPLC Ret. Time$^{Method\ c}$). MS (ES): m/z=541 [M+H]$^+$.

Example 154

2-(3,5-dimethyl-4-isoxazolyl)-N-ethyl-6-(2-oxo-1,3-oxazinan-3-yl)-9H-carbazole-4-carboxamide

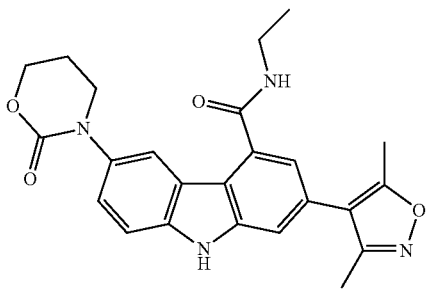 [SMILES: CCNC(=O)c1cc(-c2c(C)noc2C)cc2[nH]c3ccc(N4CCCOC4=O)cc3c12]

Step 1: 7-bromo-5-(ethylcarbamoyl)-9H-carbazole-3-carboxylic acid

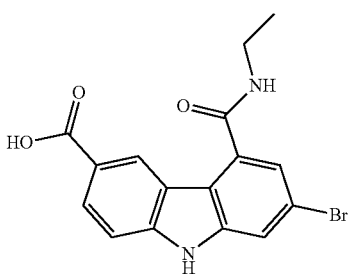 [SMILES: CCNC(=O)c1cc(Br)cc2[nH]c3ccc(C(=O)O)cc3c12]

To ethyl 7-bromo-5-(ethylcarbamoyl)-9H-carbazole-3-carboxylate (0.440 g, 1.130 mmol) was added water (2 ml)/THF (5 ml)//MeOH (1 ml). Next, 1 ml of a 20% NaOH solution was added. The reaction was heated at 70° C. for 4 hours. LC showed complete saponification. The volatiles were removed and ice was added to the flask. The suspension was acidified with concentrated HCl, and the solids were filtered and washed repeatedly with water. The filter cake was allowed to dry over night under a stream of air. The product was collected as an off-white solid (0.36 g, 88%). LC-MS (M+1=362).

Step 2: 2-bromo-N-ethyl-6-(2-oxo-1,3-oxazinan-3-yl)-9H-carbazole-4-carboxamide

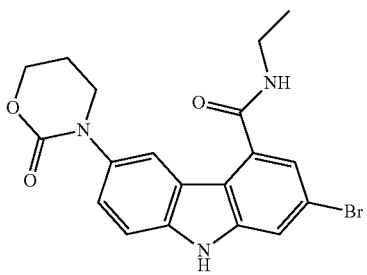 [SMILES: CCNC(=O)c1cc(Br)cc2[nH]c3ccc(N4CCCOC4=O)cc3c12]

7-bromo-5-(ethylcarbamoyl)-9H-carbazole-3-carboxylic acid (0.250 g, 0.692 mmol) was mixed with 4 A molecular sieves (0.100 g, 0.692 mmol) in dioxane (3 mL). To the mixture was added Et$_3$N (0.238 mL, 1.710 mmol) and diphenyl phosphorazidate (0.370 mL, 1.710 mmol). The mixture was stirred at 55° C. for 2 hours. LCMS showed the formation of isocyanate (OMe adduct). Next, 3-chloropropan-1-ol (0.327 g, 3.46 mmol) was added, and the mixture was stirred at 80° C. for 16 hours. LCMS showed formation of the desired product. The mixture was filtered through celite and washed with DCM/MeOH and then concentrated. To the resultant residue was added potassium carbonate (0.383 g, 2.77 mmol) and acetone (7 mL). Next, the reaction (yellow suspension) was heated at 80° C. for 24 hrs. The reaction was concentrated, diluted with 20 ml of water and the solid was filtered off and washed with water to give 2-bromo-N-ethyl-6-(2-oxo-1,3-oxazinan-3-yl)-9H-carbazole-4-carboxamide (0.19 g, 66%) as an off-white solid used without purification in the subsequent step. LC-MS (M+1=417).

Step 3: 2-(3,5-dimethyl-4-isoxazolyl)-N-ethyl-6-(2-oxo-1,3-oxazinan-3-yl)-9H-carbazole-4-carboxamide 2-bromo-N-ethyl-6-(2-oxo-1,3-oxazinan-3-yl)-9H-carbazole-4-carboxamide (0.300 g, 0.721 mmol) was diluted with THF (5 mL) in a 40 ml reaction vial. 3,5-dimethyl-4-(4,4,5,5-tetramethyl-1,3,2-dioxaborolan-2-yl)isoxazole (0.193 g, 0.865 mmol), PdCl$_2$(dppf)-CH$_2$Cl$_2$ adduct (0.023 g, 0.036 mmol), and 3.0 M potassium phosphate solution (0.721 mL, 2.162 mmol) were then added. The mixture was capped and pump/purged with nitrogen 3 times. Next, the reaction was heated at 65° C. for 1 hour. LC showed complete reaction. The mixture was concentrated, diluted with DCM and water, and the layers were separated. The organics were collected, dried over Na$_2$SO$_4$, filtered and concentrated. The crude residue was diluted with DCM (1.5 ml) and purified on a 24 gram ISCO column using 0-15% methanol/DCM. Following concentration of the fractions, 2-(3,5-dimethylisoxazol-4-yl)-N-ethyl-6-(2-oxo-1,3-oxazinan-3-yl)-9H-carbazole-4-carboxamide was collected as an off-white solid (0.090 g, 29%). Two analytical LC/MS injections were used to determine the final purity.

Injection 1 conditions: HPLC Ret. Time=1.110 min. Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. (HPLC Ret. Time$^{Method\ b}$). MS (ES): m/z=433 [M+H]$^+$.

Injection 2 conditions: HPLC Ret. Time=1.120 min. Column: Waters Acquity UPLC BEH C18, 2.1×50 mm, 1.7-µm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. (HPLC Ret. Time$^{Method\ c}$). MS (ES): m/z=433 [M+H]$^+$.

Example 155

2-(3,5-dimethyl-4-isoxazolyl)-N-ethyl-9-(4-fluorobenzyl)-6-(2-oxo-1,3-oxazinan-3-yl)-9H-carbazole-4-carboxamide

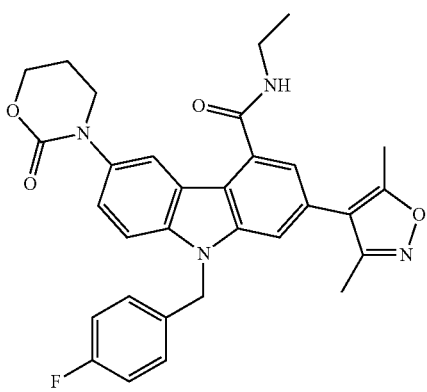 [SMILES: CCNC(=O)c1cc(-c2c(C)noc2C)cc2c1c1cc(N3CCCOC3=O)ccc1n2Cc1ccc(F)cc1]

To 2-(3,5-dimethylisoxazol-4-yl)-N-ethyl-6-(2-oxo-1,3-oxazinan-3-yl)-9H-carbazole-4-carboxamide (0.020 g, 0.046 mmol) was added acetone (1.0 mL), potassium carbonate (0.026 g, 0.185 mmol), 18-crown-6 (1.222 mg, 4.62 mmol) and 1-(bromomethyl)-4-chlorobenzene (0.019 g, 0.092 mmol). The reaction was then heated at 80° C. for 2 hours. LCMS showed consumption of starting material. Next, the reaction was concentrated to dryness. The residue was diluted with DMSO, and filtered through a 0.45 um nylon membrane syringe filter. The crude material was purified via preparative LCMS using the following conditions: Column: Waters XBridge C18, 19×100 mm, 5-μm particles; Guard Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 25 minutes, then a 5-minute hold at 100% B; Flow: 20 mL/min. Fractions containing the desired product were combined and dried via centrifugal evaporation to provide 2-(3,5-dimethylisoxazol-4-yl)-N-ethyl-9-(4-fluorobenzyl)-6-(2-oxo-1,3-oxazinan-3-yl)-9H-carbazole-4-carboxamide (0.6 mg, 2.2%). A single analytical LCMS injection was used to determine the final purity. Injection 1 conditions: HPLC Ret. Time=1.590 min., column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. (HPLC RetRet. Time$^{Method\ b}$). MS (ES): m/z=541 [M+H]$^+$.

The following compounds listed in Table 11 were prepared using the same procedure as outlined in the preparation of Compounds 150 to 155 using the appropriate benzyl bromide or benzyl chloride.

TABLE 11

| Example No. | Structure | Name | [M + H]$^+$ | Ret time | HPLC Method |
|---|---|---|---|---|---|
| 156 | 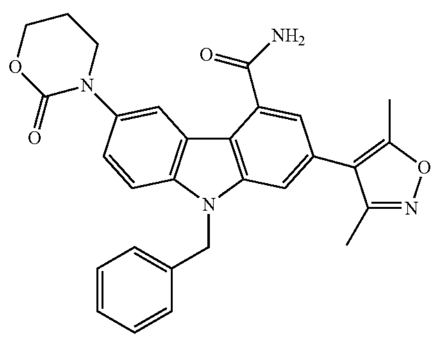 [SMILES: Cc1noc(C)c1-c1cc(C(N)=O)c2c3cc(N4CCCOC4=O)ccc3n(Cc3ccccc3)c2c1] | 9-benzyl-2-(3,5-dimethyl-4-isoxazolyl)-6-(2-oxo-1,3-oxazinan-3-yl)-9H-carbazole-4-carboxamide | 494 | 1.531 | B |
| 157 | 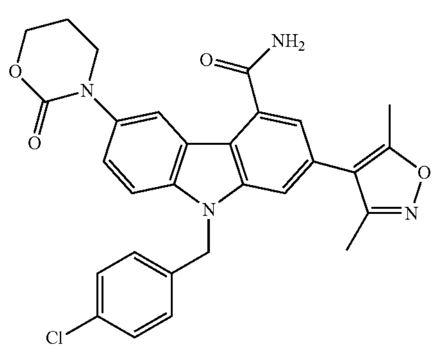 [SMILES: Cc1noc(C)c1-c1cc(C(N)=O)c2c3cc(N4CCCOC4=O)ccc3n(Cc3ccc(Cl)cc3)c2c1] | 9-(4-chlorobenzyl)-2-(3,5-dimethyl-4-isoxazolyl)-6-(2-oxo-1,3-oxazinan-3-yl)-9H-carbazole-4-carboxamide | 529 | 1.580 | B |

TABLE 11-continued

| Example No. | Name | [M + H]+ | Ret time | HPLC Method |
|---|---|---|---|---|
| 158 | 2-(3,5-dimethyl-4-isoxazolyl)-6-(2-oxo-1,3-oxazinan-3-yl)-9-(1-phenylethyl)-9H-carbazole-4-carboxamide | 509 | 1.510 | B |
| 159 | 9-(2,5-difluorobenzyl)-2-(3,5-dimethyl-4-isoxazolyl)-6-(2-oxo-1,3-oxazinan-3-yl)-9H-carbazole-4-carboxamide | 531 | 1.450 | B |
| 160 | 9-benzyl-2-(3,5-dimethyl-4-isoxazolyl)-6-(5,5-dimethyl-2-oxo-1,3-oxazinan-3-yl)-9H-carbazole-4-carboxamide | 523 | 1.660 | B |
| 161 | 9-benzyl-2-(3,5-dimethyl-4-isoxazolyl)-6-(2-oxo-1,3-oxazolidin-3-yl)-9H-carbazole-4-carboxamide | 481 | 1.591 | B |

TABLE 11-continued

| Example No. | Structure | Name | [M + H]+ | Ret time | HPLC Method |
|---|---|---|---|---|---|
| 162 | 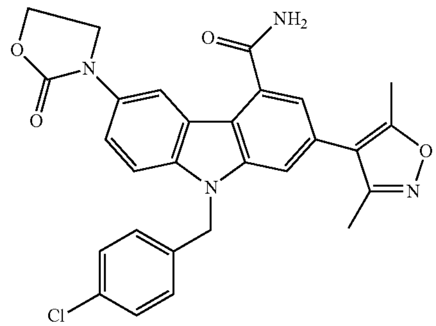 [SMILES: Cc1noc(C)c1-c1cc(C(N)=O)c2c3cc(N4CCOC4=O)ccc3n(Cc3ccc(Cl)cc3)c2c1] | 9-(4-chlorobenzyl)-2-(3,5-dimethyl-4-isoxazolyl)-6-(2-oxo-1,3-oxazolidin-3-yl)-9H-carbazole-4-carboxamide | 515 | 1.737 | B |
| 163 | 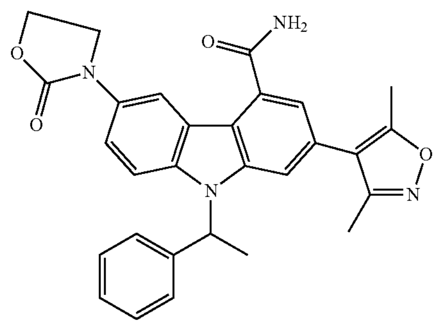 [SMILES: Cc1noc(C)c1-c1cc(C(N)=O)c2c3cc(N4CCOC4=O)ccc3n(C(C)c3ccccc3)c2c1] | 2-(3,5-dimethyl-4-isoxazolyl)-6-(2-oxo-1,3-oxazolidin-3-yl)-9-(1-phenylethyl)-9H-carbazole-4-carboxamide | 495 | 1.688 | B |
| 164 | 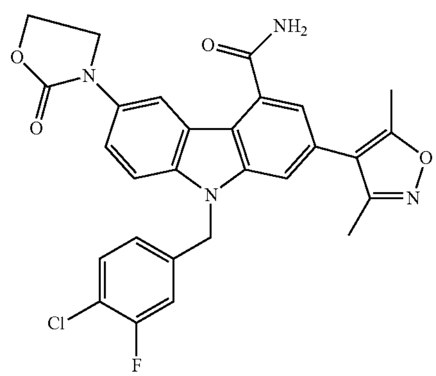 [SMILES: Cc1noc(C)c1-c1cc(C(N)=O)c2c3cc(N4CCOC4=O)ccc3n(Cc3ccc(Cl)c(F)c3)c2c1] | 9-(4-chloro-3-fluorobenzyl)-2-(3,5-dimethyl-4-isoxazolyl)-6-(2-oxo-1,3-oxazolidin-3-yl)-9H-carbazole-4-carboxamide | 533 | 1.287 | B |
| 165 | 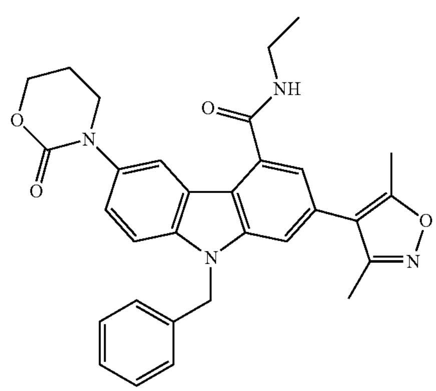 [SMILES: CCNC(=O)c1cc(-c2c(C)noc2C)cc2c1c1cc(N3CCCOC3=O)ccc1n2Cc1ccccc1] | 9-benzyl-2-(3,5-dimethyl-4-isoxazolyl)-N-ethyl-6-(2-oxo-1,3-oxazinan-3-yl)-9H-carbazole-4-carboxamide | 523 | 1.570 | B |

TABLE 11-continued

| Example No. | Structure | Name | [M + H]+ | Ret time | HPLC Method |
|---|---|---|---|---|---|
| 166 | 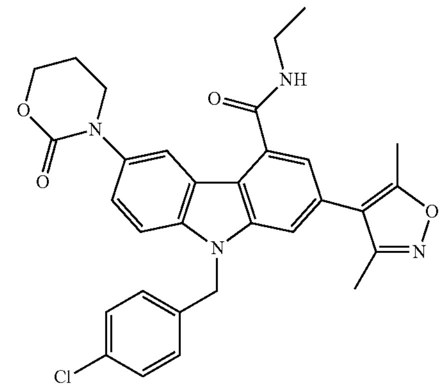 [SMILES: CCNC(=O)c1cc(-c2c(C)noc2C)cc2c1c1cc(N3CCCOC3=O)ccc1n2Cc1ccc(Cl)cc1] | 9-(4-chlorobenzyl)-2-(3,5-dimethyl-4-isoxazolyl)-N-ethyl-6-(2-oxo-1,3-oxazinan-3-yl)-9H-carbazole-4-carboxamide | 557 | 1.700 | B |
| 167 | 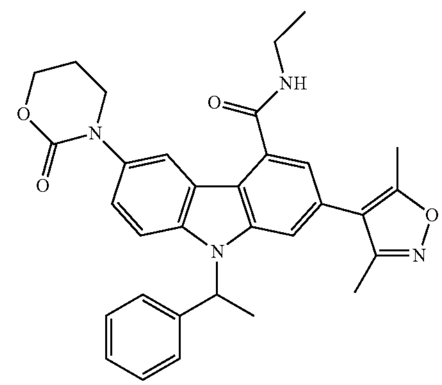 [SMILES: CCNC(=O)c1cc(-c2c(C)noc2C)cc2c1c1cc(N3CCCOC3=O)ccc1n2C(C)c1ccccc1] | 2-(3,5-dimethyl-4-isoxazolyl)-N-ethyl-6-(2-oxo-1,3-oxazinan-3-yl)-(1-phenylethyl)-9H-carbazole-4-carboxamide | 537 | 1.670 | B |
| 168 | 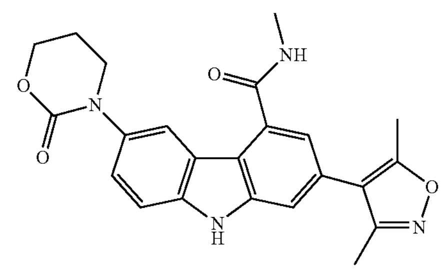 [SMILES: CNC(=O)c1cc(-c2c(C)noc2C)cc2[nH]c3ccc(N4CCCOC4=O)cc3c12] | 2-(3,5-dimethyl-4-isoxazolyl)-N-methyl-6-(2-oxo-1,3-oxazinan-3-yl)-9H-carbazole-4-carboxamide | 419 | 0.98 | B |
| 169 | 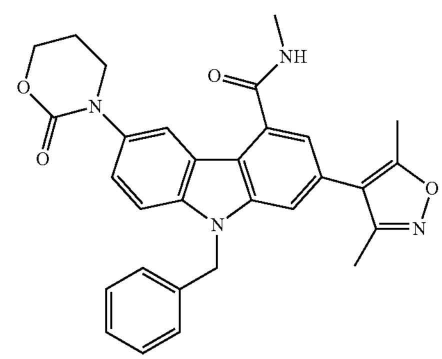 [SMILES: CNC(=O)c1cc(-c2c(C)noc2C)cc2c1c1cc(N3CCCOC3=O)ccc1n2Cc1ccccc1] | 9-benzyl-2-(3,5-dimethyl-4-isoxazolyl)-N-methyl-6-(2-oxo-1,3-oxazinan-3-yl)-9H-carbazole-4-carboxamide | 509 | 1.490 | B |

TABLE 11-continued

| Example No. | Structure | Name | [M + H]+ | Ret time | HPLC Method |
|---|---|---|---|---|---|
| 170 | 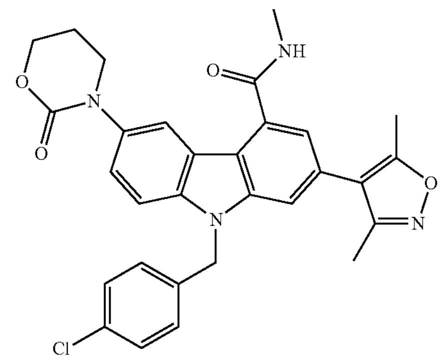 [SMILES: CNC(=O)c1cc(-c2c(C)noc2C)cc2c1c1cc(N3CCCOC3=O)ccc1n2Cc1ccc(Cl)cc1] | 9-(4-chlorobenzyl)-2-(3,5-dimethyl-4-isoxazolyl)-N-methyl-6-(2-oxo-1,3-oxazinan-3-yl)-9H-carbazole-4-carboxamide | 543 | 1.630 | B |
| 171 | 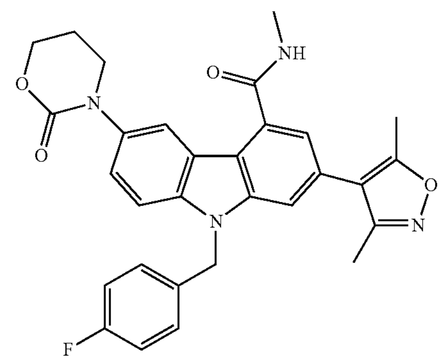 [SMILES: CNC(=O)c1cc(-c2c(C)noc2C)cc2c1c1cc(N3CCCOC3=O)ccc1n2Cc1ccc(F)cc1] | 2-(3,5-dimethyl-4-isoxazolyl)-9-(4-fluorobenzyl)-N-methyl-6-(2-oxo-1,3-oxazinan-3-yl)-9H-carbazole-4-carboxamide | 527 | 1.470 | B |
| 172 | 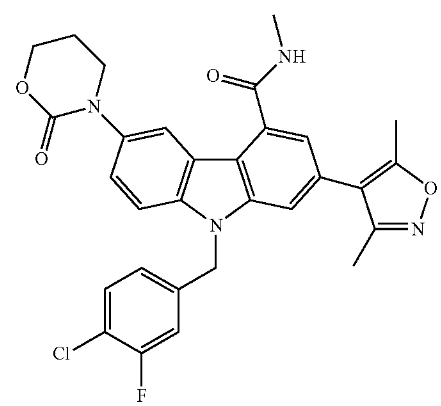 [SMILES: CNC(=O)c1cc(-c2c(C)noc2C)cc2c1c1cc(N3CCCOC3=O)ccc1n2Cc1ccc(Cl)c(F)c1] | 9-(4-chloro-3-fluorobenzyl)-2-(3,5-dimethyl-4-isoxazolyl)-N-methyl-6-(2-oxo-1,3-oxazinan-3-yl)-9H-carbazole-4-carboxamide | 561 | 1.580 | B |
| 173 | 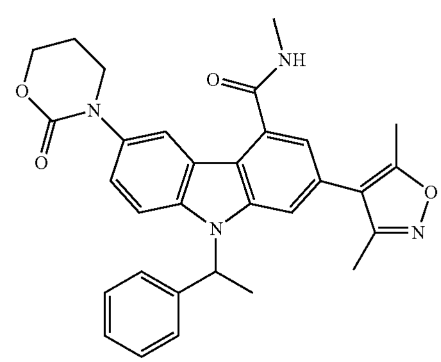 [SMILES: CNC(=O)c1cc(-c2c(C)noc2C)cc2c1c1cc(N3CCCOC3=O)ccc1n2C(C)c1ccccc1] | 2-(3,5-dimethyl-4-isoxazolyl)-N-methyl-6-(2-oxo-1,3-oxazinan-3-yl)-9-(1-phenylethyl)-9H-carbazole-4-carboxamide | | 1.520 | B |

Example 174

2-(3,5-dimethyl-4-isoxazolyl)-6-(1,1-dioxido-2-iso-thiazolidinyl)-9-(4-fluorobenzyl)-9H-carbazole-4-carboxamide

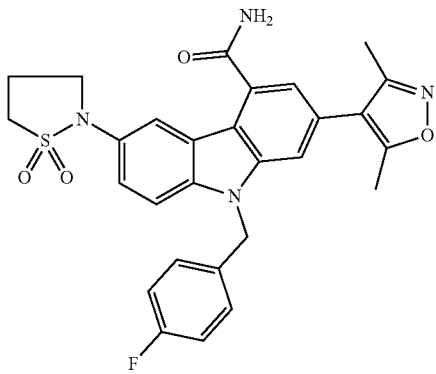 [SMILES: Cc1noc(C)c1-c1cc(C(N)=O)c2c3cc(N4CCCS4(=O)=O)ccc3n(Cc3ccc(F)cc3)c2c1]

To a solution of 6-amino-2-(3,5-dimethylisoxazol-4-yl)-9-(4-fluorobenzyl)-9H-carbazole-4-carboxamide (20 mg, 0.047 mmol) in DCM (1 mL) was added TEA (0.020 mL, 0.140 mmol) followed by the addition of 3-chloropropane-1-sulfonyl chloride (8.51 µl, 0.070 mmol). The reaction was stirred for 30 minutes and concentrated in vacuo to give crude 6-(3-chloropropylsulfonamido)-2-(3,5-dimethylisoxazol-4-yl)-9-(4-fluorobenzyl)-9H-carbazole-4-carboxamide. MS (EI) 569 (M+1).

The crude material was re-dissolved in DMF (0.5 mL) and cesium carbonate (30.4 mg, 0.093 mmol) was added. The mixture was then heated at 75° C. for 2 hours, cooled to room temperature, diluted with DMF (1.5 mL) and filtered through a 0.45 uM nylon membrane syringe filter. The crude material was purified on preparative HPLC using a Waters XBridge C18, 19×250 mm, 5-µm particle column; Mobile Phase A: 5:95 acetonitrile:water with 10 mM ammonium acetate; Mobile Phase B: 95:5 acetonitrile:water with 10 mM ammonium acetate; Gradient: 0-100% B over 25 minutes, then a 5-minute hold at 100% B; Flow: 20 mL/min to give 2-(3,5-dimethyl-4-isoxazolyl)-6-(1,1-dioxido-2-isothiazolidinyl)-9-(4-fluorobenzyl)-9H-carbazole-4-carboxamide (12.5 mg, 0.023 mmol, 50.3% yield). MS (EI) 533 (M+1). HPLC retention time, 1.70 min. Purity assessment was done using: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

$^1$H NMR (500 MHz, DMSO-$d_6$) δ 8.34 (d, J=1.7 Hz, 1H), 8.14 (s, 1H), 7.79-7.72 (m, 2H), 7.70 (br. s., 1H), 7.49 (dd, J=8.8, 2.0 Hz, 1H), 7.30 (s, 1H), 7.27-7.21 (m, 2H), 7.11 (t, J=8.9 Hz, 2H), 5.74 (s, 2H), 3.77 (s, 2H), 3.49 (t, J=7.6 Hz, 2H), 2.43 (br. m, 5H), 2.24 (s, 3H).

Example 175

2-(3,5-dimethyl-4-isoxazolyl)-6-(1,1-dioxido-1,2-thiazinan-2-yl)-9-(4-fluorobenzyl)-9H-carbazole-4-carboxamide

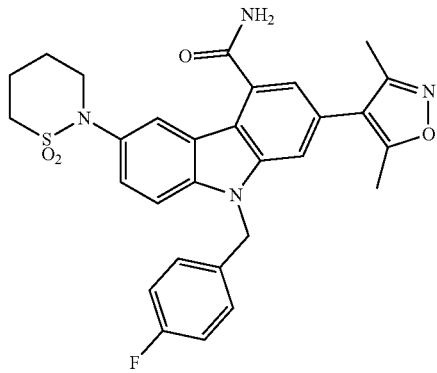 [SMILES: Cc1noc(C)c1-c1cc(C(N)=O)c2c3cc(N4CCCCS4(=O)=O)ccc3n(Cc3ccc(F)cc3)c2c1]

The product was prepared from 6-amino-2-(3,5-dimethylisoxazol-4-yl)-9-(4-fluorobenzyl)-9H-carbazole-4-carboxamide and 4-chlorobutane-1-sulfonyl chloride in 64% yield according to the procedure used for the synthesis of Example 174 above. MS (EI) 547 (M+1). HPLC retention time, 1.80 min.

Purity assessment was done using: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

$^1$H NMR (500 MHz, DMSO-$d_6$) δ 8.43 (d, J=1.8 Hz, 1H), 8.13 (s, 1H), 7.78 (s, 1H), 7.75-7.72 (m, 2H), 7.47 (dd, J=8.9, 2.1 Hz, 1H), 7.33 (d, J=1.2 Hz, 1H), 7.27 (dd, J=8.5, 6.1 Hz, 2H), 7.12 (t, J=9.2 Hz, 2H), 5.76 (s, 2H), 3.72-3.64 (m, 2H), 3.34-3.28 (m, 2H), 2.44 (s, 3H), 2.26 (s, 3H), 2.21 (br. s., 2H), 1.92-1.85 (m, 2H).

Example 176

2-(3,5-dimethyl-4-isoxazolyl)-6-methoxy-9-(1-phenylethyl)-9H-carbazole-4-carboxamide

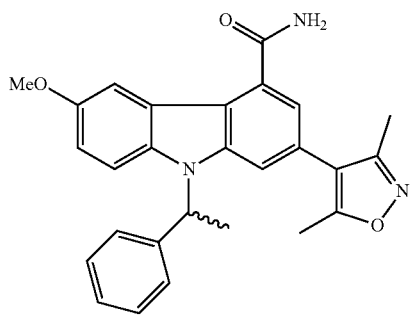 [SMILES: COc1ccc2c(c1)c1c(C(N)=O)cc(-c3c(C)noc3C)cc1n2C(C)c1ccccc1]

Step 1: Methyl-3-amino-5-bromobenzoate

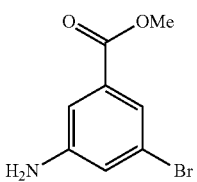

To a solution of 3-amino-5-bromobenzoic acid (2 g, 9.26 mmol) in Diethyl Ether (30 mL) and Methanol (5.00 mL) was added TMS-Diazomethane (2.0 M in Hexanes) (5.55 mL, 11.11 mmol). The reaction was stirred at room temperature for ca. 1 h 15 min, then quenched with AcOH and concentrated. The reaction mixture was transferred to a separatory funnel containing saturated aqueous $NaHCO_3$ solution (25 mL). The aqueous layer was extracted with ethyl acetate (3×25 mL). The combined organic layers were washed with brine (20 mL), dried over $MgSO_4$, filtered, and concentrated to afford methyl-3-amino-5-bromobenzoate (2.1 g, 9.13 mmol, 99% yield) as a colorless solid. $^1$H NMR (400 MHz, DMSO-$d_6$) is consistent with the desired product.

$^1$H NMR (400 MHz, DMSO-$d_6$) δ 7.17 (dd, J=2.2, 1.5 Hz, 1H), 7.14 (t, J=1.7 Hz, 1H), 6.97 (t, J=2.1 Hz, 1H), 5.73 (s, 2H), 3.82 (s, 3H).

LCMS (ESI) m/e 231.9 ((M+H)$^+$, calcd for $C_8H_9BrNO_2$ 231.1).

Step 2: Methyl 3-amino-5-(3,5-dimethylisoxazol-4-yl)benzoate

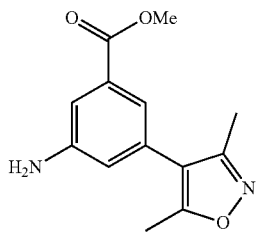 [SMILES: COC(=O)c1cc(N)cc(-c2c(C)noc2C)c1]

To a suspension of methyl 3-amino-5-bromobenzoate (2.1 g, 9.13 mmol) and (3,5-dimethylisoxazol-4-yl)boronic acid (1.415 g, 10.04 mmol) in THF (35 mL), tripotassium phosphate (3M in $H_2O$) (9.13 mL, 27.4 mmol) was added. The solution was degassed with nitrogen. $PdCl_2$(dppf) (0.334 g, 0.456 mmol) was added and the mixture was heated in a pressure vial at 70° C. for 3 hours. LCMS suggested the formation of the desired product. The reaction mixture was transferred to a separatory funnel containing saturated aqueous $NaHCO_3$ solution (25 mL). The aqueous layer was extracted with ethyl acetate (3×25 mL). The combined organic layers were washed with brine (25 mL), dried over $MgSO_4$, filtered, and concentrated.

The residue was purified by column chromatography on silica gel (0%→60% ethyl acetate in hexanes; 80 g column) to afford methyl 3-amino-5-(3,5-dimethylisoxazol-4-yl)benzoate (2.0 g, 8.12 mmol, 89% yield) as a colorless solid.

LCMS (ESI) m/e 247.0 ((M+H)$^+$, calcd for $C_{13}H_{15}N_2O_3$ 247.1).

Step 3: Methyl 3-(3,5-dimethylisoxazol-4-yl)-5-((4-methoxyphenyl)amino)benzoate

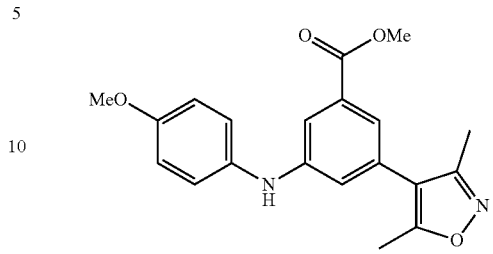

To a suspension of 1-bromo-4-methoxybenzene (0.228 ml, 1.827 mmol), and methyl 3-amino-5-(3,5-dimethylisoxazol-4-yl)benzoate (0.300 g, 1.218 mmol) in toluene (8.12 ml), $Cs_2CO_3$ (0.794 g, 2.436 mmol) was added. The suspension was degassed with bubbling nitrogen for 2 minutes. XPhos Precatalyst (0.048 g, 0.061 mmol) was added and the reaction mixture was heated to 100° C. for 24 h.

LCMS indicated the formation of the desired product along with some unreacted starting material. The reaction mixture was transferred to a separatory funnel containing saturated aqueous $NaHCO_3$ solution (25 mL). The aqueous layer was extracted with ethyl acetate (3×25 mL). The combined organic layers were washed with brine (20 mL), dried over $MgSO_4$, filtered, and concentrated. The residue was purified by column chromatography on silica gel (0%→60% ethyl acetate in hexanes; 40 g column) to afford methyl 3-(3,5-dimethylisoxazol-4-yl)-5-((4-methoxyphenyl)amino)benzoate (230 mg, 0.653 mmol, 53.6% yield) as a colorless solid.

$^1$H NMR (400 MHz, DMSO-$d_6$) δ 8.24 (s, 1H), 7.50-7.43 (m, 1H), 7.21 (s, 1H), 7.12 (d, J=8.8 Hz, 2H), 7.07-7.03 (m, 1H), 6.94 (d, J=8.8 Hz, 2H), 3.84 (s, 3H), 3.75 (s, 3H), 2.41 (s, 3H), 2.22 (s, 3H).

LCMS (ESI) m/e 353.2 ((M+H)$^+$, calcd for $C_{20}H_{21}N_2O_4$ 353.2).

Step 4: Methyl 2-(3,5-dimethylisoxazol-4-yl)-6-methoxy-9H-carbazole-4-carboxylate

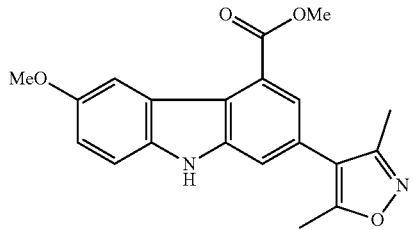 [SMILES: COC(=O)c1cc(-c2c(C)noc2C)cc2[nH]c3ccc(OC)cc3c12]

A mixture of methyl 3-(3,5-dimethylisoxazol-4-yl)-5-((4-methoxyphenyl)amino)benzoate (170 mg, 0.482 mmol), $K_2CO_3$ (13.33 mg, 0.096 mmol) and palladium(II) acetate (21.66 mg, 0.096 mmol) in pivalic acid (1680 μl, 14.47 mmol) was heated to 110° C. in a vial open to air for 18 h. LCMS suggested the consumption of the starting material and formation of the desired product.

The reaction mixture was diluted with methylene chloride and transferred to a separatory funnel containing saturated aqueous $NaHCO_3$ solution (20 mL). The aqueous layer was extracted with methylene chloride (3×20 mL). The combined organic layers were washed with brine (20 mL), dried over MgSO₄, filtered, and concentrated.

The residue was purified by column chromatography on silica gel (0%→80% ethyl acetate in hexanes; 24 g column) to afford methyl 2-(3,5-dimethylisoxazol-4-yl)-6-methoxy-9H-carbazole-4-carboxylate (70 mg, 0.200 mmol, 41.4% yield) as a yellow solid.

NMR studies using 2D-NMR and ¹³C-NMR confirmed that the desired product is the only regioisomer obtained.

¹H NMR (400 MHz, DMSO-d₆) δ 11.57 (s, 1H), 8.25 (d, J=2.6 Hz, 1H), 7.72 (d, J=1.5 Hz, 1H), 7.66 (d, J=1.5 Hz, 1H), 7.50 (d, J=8.8 Hz, 1H), 7.16 (dd, J=8.8, 2.6 Hz, 1H), 4.06-3.99 (m, 3H), 3.86 (s, 3H), 2.47 (s, 3H), 2.29 (s, 3H).

LCMS (ESI) m/e 351.1 ((M+H)⁺, calcd for C₂₀H₁₉N₂O₄ 351.1).

Step 5: Methyl 2-(3,5-dimethylisoxazol-4-yl)-6-methoxy-9-(1-phenylethyl)-9H-carbazole-4-carboxylate

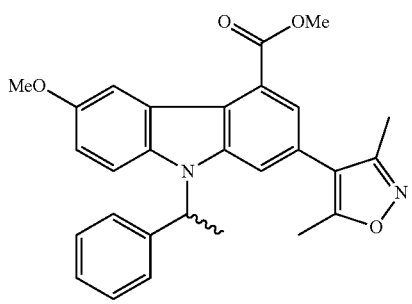 [SMILES: COC(=O)c1cc(-c2c(C)noc2C)cc2c1c1cc(OC)ccc1n2C(C)c1ccccc1]

To a solution of methyl 2-(3,5-dimethylisoxazol-4-yl)-6-methoxy-9H-carbazole-4-carboxylate (30 mg, 0.086 mmol) in DMF (1 mL) cooled to 0° C., NaH (60% in mineral oil) (5.14 mg, 0.128 mmol) was added. The mixture was warmed to room temperature and stirred for 15 min. The mixture turned dark red. The mixture was cooled to 0° C. and (1-bromoethyl)benzene (0.017 mL, 0.128 mmol) was added. The mixture was stirred at RT for 1 h. LCMS indicated the formation of the desired product.

The reaction was cooled to 0° C. and quenched with NH₄Cl solution. The reaction mixture was taken in a separatory funnel containing ammonium chloride solution (10 mL). The aqeuous layer was extracted with EtOAc (2×10 mL). The reaction mixture was taken in a separatory funnel containing ammonium chloride solution (10 mL). The aqeuous layer was extracted with EtOAc (2×10 mL). The combined organic layers were washed with brine (5 mL), dried over MgSO₄, filtered, and concentrated to afford methyl 2-(3,5-dimethylisoxazol-4-yl)-6-methoxy-9-(1-phenylethyl)-9H-carbazole-4-carboxylate (37 mg, 0.081 mmol, 95% yield) as a yellow solid.

LCMS (ESI) m/e 455.1 ((M+H)⁺, calcd for C₂₈H₂₇N₂O₄ 455.2).

Step 6: 2-(3,5-dimethylisoxazol-4-yl)-6-methoxy-9-(1-phenylethyl)-9H-carbazole-4-carboxylic acid

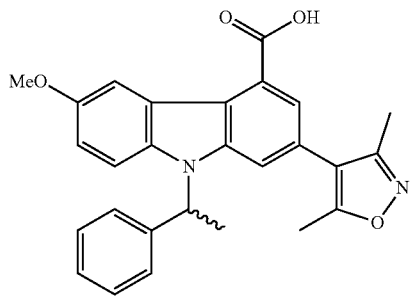 [SMILES: COc1ccc2c(c1)c1c(C(=O)O)cc(-c3c(C)noc3C)cc1n2C(C)c1ccccc1]

A mixture of methyl 2-(3,5-dimethylisoxazol-4-yl)-6-methoxy-9-(1-phenylethyl)-9H-carbazole-4-carboxylate (37 mg, 0.081 mmol) and NaOH (0.163 mL, 0.163 mmol) in Methanol (2 mL) and Water (0.400 mL) was stirred at RT for 3 h. LCMS suggested formation of the desired product.

The solvent was evaporated and the residue was dried in vacuo to afford 2-(3,5-dimethylisoxazol-4-yl)-6-methoxy-9-(1-phenylethyl)-9H-carbazole-4-carboxylic acid (35 mg, 0.079 mmol, 98% yield) as a yellow solid.

LCMS (ESI) m/e 441.2 ((M+H)⁺, calcd for C₂₇H₂₅N₂O₄ 441.2).

Step 7: 2-(3,5-dimethyl-4-isoxazolyl)-6-methoxy-9-(1-phenylethyl)-9H-carbazole-4-carboxamide

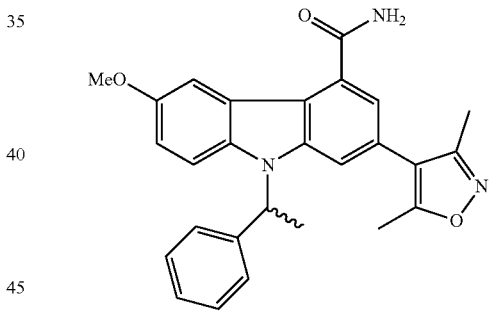

To a solution of 2-(3,5-dimethylisoxazol-4-yl)-6-methoxy-9-(1-phenylethyl)-9H-carbazole-4-carboxylic acid (35 mg, 0.079 mmol), EDC (60.9 mg, 0.318 mmol) and HOBT (48.7 mg, 0.318 mmol) in THF (2 mL) and DCM (0.400 mL), ammonium hydroxide (0.019 mL, 0.477 mmol) was added. The reaction was stirred at room temperature for 2 hours. LCMS suggested consumption of the starting material and formation of the desired product. The solvent was evaporated and water was added to the residue. The precipitate formed was collected and dried to afford 2-(3,5-dimethyl-4-isoxazolyl)-6-methoxy-9-(1-phenylethyl)-9H-carbazole-4-carboxamide (30 mg, 0.067 mmol, 84% yield) as an off white solid.

LCMS (ESI) m/e 440.3 ((M+H)⁺, calcd for C₂₇H₂₆N₃O₃ 440.2).

¹H NMR (400 MHz, CHLOROFORM-d) δ 8.09 (d, J=2.4 Hz, 1H), 7.39-7.35 (m, 2H), 7.34 (d, J=2.2 Hz, 2H), 7.32 (s, 2H), 7.23 (d, J=1.3 Hz, 1H), 7.15 (dd, J=8.9, 2.5 Hz, 1H), 7.03 (d, J=1.3 Hz, 1H), 6.10 (q, J=7.0 Hz, 1H), 3.96 (s, 3H), 2.27 (s, 3H), 2.12 (s, 3H), 2.00 (d, J=7.0 Hz, 3H).

HPLC Purity: 10% B→100% B, C18 XBridge, 3.0×150 mm, 3.5 um, 0.5 mL/min; 98.9% @ 220 nM; 99.5% @ 254 nM HPLC Purity: 10% B→100% B, Phenyl XBridge, 3.0× 150 mm, 3.5 um, 0.5 mL/min; 98.1% @ 220 nM; 99.2% @ 254 nM Solvent A—95/5 water/MeCN with 0.05% TFA
Solvent B—5/95 water/MeCN with 0.05% TFA Example 177

9-benzyl-2-(3,5-dimethyl-4-isoxazolyl)-6-methoxy-9H-carbazole-4-carboxamide

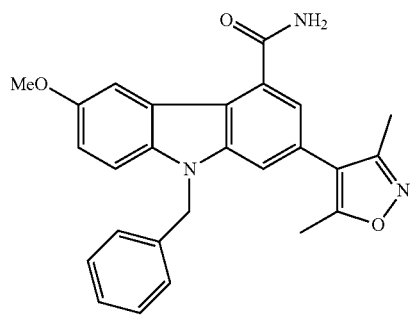

Step 1: Methyl 9-benzyl-2-(3,5-dimethylisoxazol-4-yl)-6-methoxy-9H-carbazole-4-carboxylate

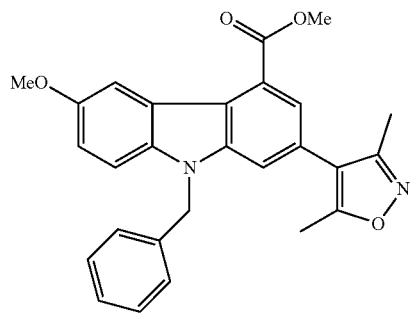 [SMILES: COC(=O)c1cc(-c2c(C)noc2C)cc2c1c1cc(OC)ccc1n2Cc1ccccc1]

To a solution of methyl 2-(3,5-dimethylisoxazol-4-yl)-6-methoxy-9H-carbazole-4-carboxylate (40 mg, 0.114 mmol) in DMF (1 mL) cooled to 0° C., NaH (60%) (6.85 mg, 0.171 mmol) was added. The mixture was warmed to room temperature and stirred for 15 min. The mixture turned dark red. The mixture was cooled to 0° C. and (bromomethyl)benzene (29.3 mg, 0.171 mmol) was added. The mixture was stirred at RT for 1 h. LCMS indicated the formation of the desired product. The reaction was cooled to 0° C. and quenched with NH$_4$Cl solution. The combined organic layers were washed with brine (5 mL), dried over MgSO$_4$, filtered, and concentrated to afford methyl 9-benzyl-2-(3,5-dimethylisoxazol-4-yl)-6-methoxy-9H-carbazole-4-carboxylate (40 mg, 0.091 mmol, 80% yield) as a yellow solid.

LCMS (ESI) m/e 441.3 ((M+H)$^+$, calcd for C$_{27}$H$_{25}$N$_2$O$_4$ 441.2).

Step 2: 9-benzyl-2-(3,5-dimethylisoxazol-4-yl)-6-methoxy-9H-carbazole-4-carboxylic acid

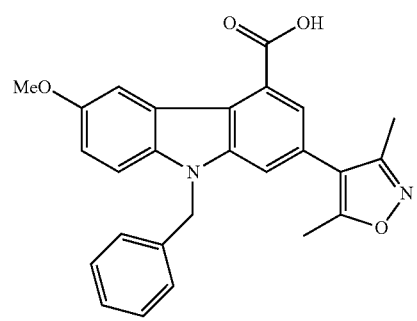 [SMILES: COc1ccc2c(c1)c1c(C(=O)O)cc(-c3c(C)noc3C)cc1n2Cc1ccccc1]

A mixture of methyl 9-benzyl-2-(3,5-dimethylisoxazol-4-yl)-6-methoxy-9H-carbazole-4-carboxylate (40 mg, 0.091 mmol) and NaOH (1N) (0.182 mL, 0.182 mmol) in Methanol (2 mL) was stirred at RT for 2 h. LCMS suggested formation of the desired product. The solvent was evaporated and the residue was dried in vacuo to afford 9-benzyl-2-(3,5-dimethylisoxazol-4-yl)-6-methoxy-9H-carbazole-4-carboxylic acid (38 mg, 0.089 mmol, 98% yield) as the desired product.

LCMS (ESI) m/e 427.3 ((M+H)$^+$, calcd for C$_{26}$H$_{23}$N$_2$O$_4$ 427.2).

Step 3: 9-benzyl-2-(3,5-dimethyl-4-isoxazolyl)-6-methoxy-9H-carbazole-4-carboxamide

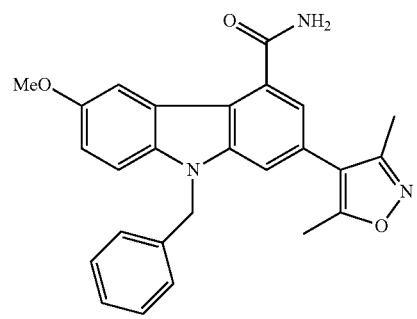 [SMILES: COc1ccc2c(c1)c1c(C(N)=O)cc(-c3c(C)noc3C)cc1n2Cc1ccccc1]

To a solution of 9-benzyl-2-(3,5-dimethylisoxazol-4-yl)-6-methoxy-9H-carbazole-4-carboxylic acid (38 mg, 0.089 mmol), EDC (68.3 mg, 0.356 mmol) and HOBT (54.6 mg, 0.356 mmol) in THF (2 mL) and DCM (0.400 mL), ammonium hydroxide (0.021 mL, 0.535 mmol) was added. The reaction was stirred at room temperature for 2 hours. LCMS suggested consumption of the starting material and formation of the desired product. The solvent was evaporated and water was added to the residue. The precipitate formed was collected and dried to afford 9-benzyl-2-(3,5-dimethyl-4-isoxazolyl)-6-methoxy-9H-carbazole-4-carboxamide (30 mg, 0.068 mmol, 76% yield) as an off white solid.

LCMS (ESI) m/e 426.3 ((M+H)$^+$, calcd for C$_{26}$H$_{24}$N$_3$O$_3$ 426.2).

$^1$H NMR (400 MHz, DMSO-d$_6$) is consistent with the desired product.

HPLC Purity: 10% B→100% B, C18 xbridge, 3.0×150 mm, 3.5 um, 0.5 mL/min; 95.8% @ 220 nM; 99.5% @ 254 nM HPLC Purity: 10% B→100% B, phenyl xbridge, 3.0×150 mm, 3.5 um, 0.5 mL/min; 100% @ 220 nM; 99.8% @ 254 nM Solvent A—95/5 water/MeCN with 0.05% TFA
Solvent B—5/95 water/MeCN with 0.05% TFA Example 178

9-benzyl-2-(3,5-dimethyl-4-isoxazolyl)-6-hydroxy-9H-carbazole-4-carboxamide

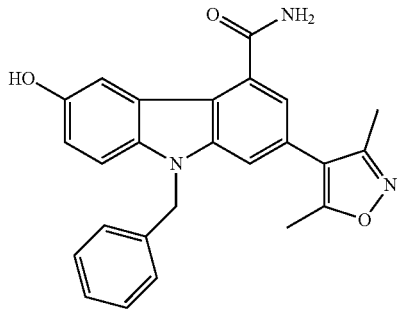 [SMILES: Cc1noc(C)c1-c1cc(C(N)=O)c2c3cc(O)ccc3n(Cc3ccccc3)c2c1]

To a solution of 9-benzyl-2-(3,5-dimethylisoxazol-4-yl)-6-methoxy-9H-carbazole-4-carboxamide (10 mg, 0.024 mmol) in DCM (0.5 mL) at −78° C., boron tribromide (1M in DCM) (0.026 mL, 0.026 mmol) was added. The mixture was stirred at −78 C for 15 min. LCMS indicated no conversion of the starting material to the desired product. Additional boron tribromide (1M in DCM) (0.026 mL, 0.026 mmol) was added and the reaction was again stirred at −78° C. for 15 min. LCMS indicated no conversion of starting material to the desired product. The mixture was allowed to warm to 0° C. After 30 minutes of stirring, LCMS showed conversion of starting material to the desired product. The reaction was quenched with saturated NaHCO$_3$ solution at 0° C. The reaction mixture was transferred to a separatory funnel containing saturated aqueous NaHCO$_3$ solution (15 mL). The aqueous layer was extracted with ethyl acetate (3×10 mL). The combined organic layers were washed with brine (10 mL), dried over MgSO$_4$, filtered, and concentrated to afford 9-benzyl-2-(3,5-dimethyl-4-isoxazolyl)-6-hydroxy-9H-carbazole-4-carboxamide (9 mg, 0.021 mmol, 90% yield) as a yellow solid.

LCMS (ESI) m/e 412.2 ((M+H)$^+$, calcd for $C_{25}H_{22}N_3O_3$ 412.2).

$^1$H NMR (400 MHz, METHANOL-d$_4$)—7.86 (d, J=2.4 Hz, 1H), 7.44 (dd, J=5.2, 3.6 Hz, 2H), 7.27-7.21 (m, 4H), 7.15 (d, J=1.8 Hz, 1H), 7.13 (s, 1H), 7.06 (dd, J=8.7, 2.5 Hz, 1H), 5.64 (s, 2H), 2.38 (s, 3H), 2.22 (s, 3H).

HPLC Purity: 10% B→100% B, C18 xbridge, 3.0×150 mm, 3.5 um, 0.5 mL/min; 95.5% @ 220 nM; 95.8% @ 254 nM HPLC Purity: 10% B→100% B, phenyl xbridge, 3.0×150 mm, 3.5 um, 0.5 mL/min; 97.5% @ 220 nM; 97.6% @ 254 nM Solvent A—95/5 water/MeCN with 0.05% TFA
Solvent B—5/95 water/MeCN with 0.05% TFA Example 179

2-(3,5-dimethyl-4-isoxazolyl)-6-methoxy-9-(1-phenylethyl)-9H-carbazole-4-carboxamide—Enantiomer 1

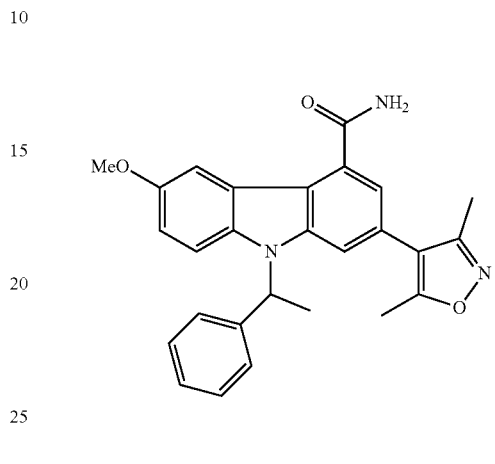

To a solution of 2-(3,5-dimethylisoxazol-4-yl)-6-methoxy-9-(1-phenylethyl)-9H-carbazole-4-carboxylic acid (35 mg, 0.079 mmol), EDC (60.9 mg, 0.318 mmol) and HOBT (48.7 mg, 0.318 mmol) in THF (2 mL) and DCM (0.400 mL), ammonium hydroxide (0.019 mL, 0.477 mmol) was added. The reaction was stirred at room temperature for 2 h. LCMS suggested consumption of the starting material and formation of the desired product. The solvent was evaporated and water was added to the residue. The precipitate formed was collected and dried to afford 2-(3,5-dimethyl-4-isoxazolyl)-6-methoxy-9-(1-phenylethyl)-9H-carbazole-4-carboxamide (30 mg, 0.067 mmol, 84% yield) as an off white solid.

20 mg of the racemate was resolved by preparative SFC chromatography (Berger SFC MGII, Chiral AD-H 25×3 cm ID, 5 μm, 80/20 CO$_2$/MeOH, 85 mL/min). Fractions containing the desired product were concentrated, dried overnight under vacuum to afford 2-(3,5-dimethyl-4-isoxazolyl)-6-methoxy-9-(1-phenylethyl)-9H-carbazole-4-carboxamide—Enantiomer 1 (4.5 mg, 22.2%) as a colorless solid.

Analytical SFC chromatography: (Berger analytical SFC, Chiral AD-H 250×4.6 mm ID, 5 μm, 80/20 CO$_2$/MeOH, 2 mL/min) RT: 8.827 min.

LCMS (ESI) m/e 440.2 ((M+H)$^+$, calcd for $C_{27}H_{26}N_3O_3$ 440.2).

HPLC Purity: 10% B→100% B, C18 xbridge, 3.0×150 mm, 3.5 um, 0.5 mL/min; 100% @ 220 nM; 99.5% @ 254 nM HPLC Purity: 10% B→100% B, phenyl xbridge, 3.0×150 mm, 3.5 um, 0.5 mL/min; 97.3% @ 220 nM; 99.2% @ 254 nM Solvent A—95/5 water/MeCN with 0.05% TFA
Solvent B—5/95 water/MeCN with 0.05% TFA

Example 180

2-(3,5-dimethyl-4-isoxazolyl)-6-methoxy-9-(1-phenylethyl)-9H-carbazole-4-carboxamide—Enantiomer 2

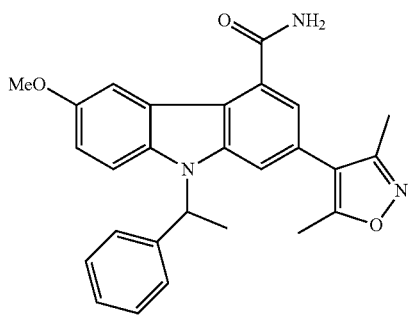

To a solution of 2-(3,5-dimethylisoxazol-4-yl)-6-methoxy-9-(1-phenylethyl)-9H-carbazole-4-carboxylic acid (35 mg, 0.079 mmol), EDC (60.9 mg, 0.318 mmol) and HOBT (48.7 mg, 0.318 mmol) in THF (2 mL) and DCM (0.400 mL), ammonium hydroxide (0.019 mL, 0.477 mmol) was added. The reaction was stirred at room temperature for 2 h. LCMS suggested consumption of the starting material and formation of the desired product. The solvent was evaporated and water was added to the residue. The precipitate formed was collected and dried to afford 2-(3,5-dimethyl-4-isoxazolyl)-6-methoxy-9-(1-phenylethyl)-9H-carbazole-4-carboxamide (30 mg, 0.067 mmol, 84% yield) as an off white solid.

20 mg of the racemate was resolved by preparative SFC chromatography (Berger SFC MGII, Chiral AD-H 25×3 cm ID, 5 μm, 80/20 CO$_2$/MeOH, 85 mL/min). Fractions containing the desired product were concentrated, dried overnight under vacuum to afford 2-(3,5-dimethyl-4-isoxazolyl)-6-methoxy-9-(1-phenylethyl)-9H-carbazole-4-carboxamide Enantiomer 2 (6 mg, 29.7%) as a colorless solid.

Analytical SFC chromatography: (Berger analytical SFC, Chiral AD-H 250×4.6 mm ID, 5 μm, 80/20 CO$_2$/MeOH, 2 mL/min). RT: 11.046 min.

LCMS (ESI) m/e 440.2 ((M+H)$^+$, calcd for C$_{27}$H$_{26}$N$_3$O$_3$ 440.2).

HPLC Purity: 10% B→100% B, C18 xbridge, 3.0×150 mm, 3.5 um, 0.5 mL/min; 100% @ 220 nM; 95.7% @ 254 nM HPLC Purity: 10% B→100% B, phenyl xbridge, 3.0×150 mm, 3.5 um, 0.5 mL/min; 100% @ 220 nM; 100% @ 254 nM Solvent A—95/5 water/MeCN with 0.05% TFA
Solvent B—5/95 water/MeCN with 0.05% TFA

Example 181

9-benzyl-2-(3,5-dimethyl-4-isoxazolyl)-6-(methylsulfonyl)-9H-carbazole-4-carboxamide

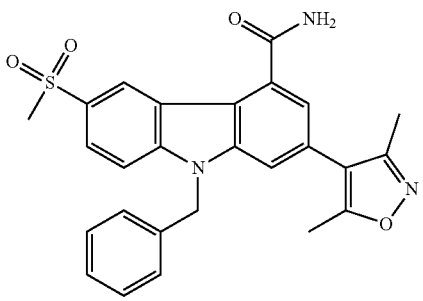 [SMILES: Cc1noc(C)c1-c1cc(C(N)=O)c2c3cc(S(C)(=O)=O)ccc3n(Cc3ccccc3)c2c1]

Step 1: 3-(3,5-dimethylisoxazol-4-yl)-5-((4-(methylsulfonyl)phenyl)amino)benzoate

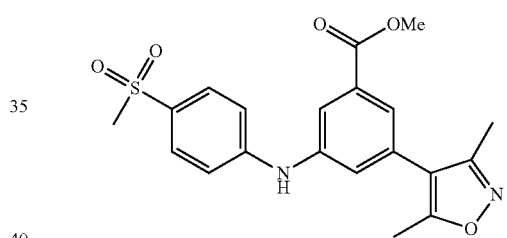

A mixture of 1-bromo-4-(methylsulfonyl)benzene (71.6 mg, 0.305 mmol), methyl 3-amino-5-(3,5-dimethylisoxazol-4-yl)benzoate (50 mg, 0.203 mmol), XPhos precatalyst (7.99 mg, 10.15 μmol) and Cs$_2$CO$_3$ (66.2 mg, 0.203 mmol) in toluene (2 mL) was deoxygenated by bubbling N$_2$ for 3 min. The mixture was then heated in a closed vial overnight. The mixture was cooled to RT. The mixture was directly loaded on a solid load cartridge, and purified by flash silica gel chromatography (4 g, EtOAc/hexane=0-100%) to give 42 mg of 3-(3,5-dimethylisoxazol-4-yl)-5-((4-(methylsulfonyl)phenyl)amino)benzoate (42 mg, 52%).

HPLC RT=2.287 min (Chromolith SpeedROD column 4.6×50 mm eluting with 10-90% aqueous methanol over 4 minutes containing 0.1% TFA, 4 mL/min, monitoring at 220 nm.)

LCMS: M+1=401

$^1$H NMR (400 MHz, CHLOROFORM-d) δ 7.92-7.80 (m, 3H), 7.66 (t, J=1.4 Hz, 1H), 7.24 (t, J=1.9 Hz, 1H), 7.18-7.10 (m, 2H), 6.46 (s, 1H), 3.97 (s, 3H), 3.08 (s, 3H), 2.46 (s, 3H), 2.31 (s, 3H).

Step 2: Methyl 2-(3,5-dimethylisoxazol-4-yl)-6-(methylsulfonyl)-9H-carbazole-4-carboxylate

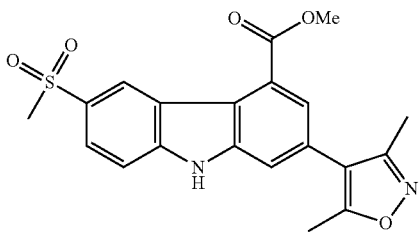 [SMILES: COC(=O)c1cc(-c2c(C)noc2C)cc2[nH]c3ccc(S(C)(=O)=O)cc3c12]

A mixture of methyl 3-(3,5-dimethylisoxazol-4-yl)-5-((4-(methylsulfonyl)phenyl)amino)benzoate (42 mg, 0.105 mmol), K2CO3 (1.450 mg, 10.49 mmol) and palladium(II) acetate (2.355 mg, 10.49 mmol) in pivalic acid (365 µl, 3.15 mmol) was heated to 110° C. in a vial open to air for 20 h. The reaction was then cooled to RT. Next, the reaction mixture was diluted with methylene chloride and transferred to a separatory funnel containing saturated aqueous NaHCO₃ solution. The aqueous layer was extracted with methylene chloride 3 times. The combined organic layers were washed with brine, dried over MgSO₄ and concentrated. The residue was purified by flash column chromatography on silica gel (4 g, EtOAc/hexane=0-60%) to afford methyl 2-(3,5-dimethylisoxazol-4-yl)-6-(methylsulfonyl)-9H-carbazole-4-carboxylate (8.5 mg, 20%) as a yellow solid.

HPLC Peak RT=2.338 minute (Chromolith SpeedROD column 4 6×50 mm eluting with 10-90% aqueous methanol over 4 minutes containing 0.1% TFA, 4 mL/min, monitoring at 220 nm.)

LCMS: M+1=399

¹H NMR (400 MHz, CHLOROFORM-d) δ 9.61 (d, J=1.8 Hz, 1H), 9.09 (s, 1H), 8.06 (dd, J=8.6, 1.8 Hz, 1H), 7.90 (d, J=1.5 Hz, 1H), 7.63-7.59 (m, 2H), 4.10 (s, 3H), 3.21 (s, 3H), 2.49 (s, 3H), 2.35 (s, 3H)

Step 3: 9-benzyl-2-(3,5-dimethylisoxazol-4-yl)-6-(methylsulfonyl)-9H-carbazole-4-carboxylic acid

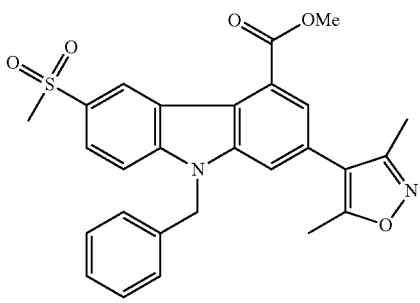 [SMILES: COC(=O)c1cc(-c2c(C)noc2C)cc2c1c1cc(S(C)(=O)=O)ccc1n2Cc1ccccc1]

To a solution of methyl 2-(3,5-dimethylisoxazol-4-yl)-6-(methylsulfonyl)-9H-carbazole-4-carboxylate (8.5 mg, 0.021 mmol) and Cs2CO3 (13.90 mg, 0.043 mmol) in DMF (0.3 mL) was added benzyl bromide (3.81 µl, 0.032 mmol). The mixture was stirred at RT for 2 h. Water was added, and the solution was extracted with EtOAc two times. The combined extracts were combined and concentrated to dryness. The residue was dissolved in a mixed solvent of THF (0.25 ml)/MeOH (0.25 mL), and 1N NaOH (0.043 mL, 0.043 mmol) was added. The mixture was stirred at RT overnight. The reaction was concentrated to dryness, then water and a few drops of 1N HCl were added. The resulting mixture was sonicated, and the solid was collected by filtration, rinsed with water, and dried to give (8.3 mg, 82%) as a white solid.

HPLC Peak RT=2.650 minute (Chromolith SpeedROD column 4 6×50 mm eluting with 10-90% aqueous methanol over 4 minutes containing 0.1% TFA, 4 mL/min, monitoring at 220 nm.)

LCMS: M+1=475

Step 4: 9-benzyl-2-(3,5-dimethyl-4-isoxazolyl)-6-(methylsulfonyl)-9H-carbazole-4-carboxamide

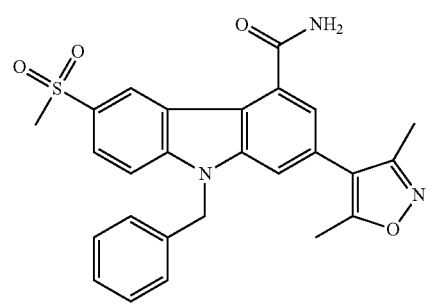 [SMILES: Cc1noc(C)c1-c1cc(C(N)=O)c2c3cc(S(C)(=O)=O)ccc3n(Cc3ccccc3)c2c1]

To a mixture of 9-benzyl-2-(3,5-dimethylisoxazol-4-yl)-6-(methylsulfonyl)-9H-carbazole-4-carboxylic acid (8.3 mg, 0.017 mmol), HOBT (10.71 mg, 0.070 mmol) and EDC (13.41 mg, 0.070 mmol) in THF (1 mL) was added 2N ammonia in IPA (0.379 µl, 0.017 mmol). The reaction was stirred at RT overnight. Water was added, and the mixture was extracted with EtOAc. The organic layer was separated and washed with saturated NaHCO₃, dried and concentrated. The residue was treated with a small amount of MeOH, and the solid was collected by filtration, rinsed with MeOH, and dried to give 9-benzyl-2-(3,5-dimethyl-4-isoxazolyl)-6-(methylsulfonyl)-9H-carbazole-4-carboxamide (3.8 mg, 45%) as a white solid.

HPLC Peak RT=2.243 minutes. (Chromolith SpeedROD column 4 6×50 mm eluting with 10-90% aqueous methanol over 4 minutes containing 0.1% TFA, 4 mL/min, monitoring at 220 nm.)

LCMS (m+1)=474.

¹H NMR (400 MHz, CHLOROFORM-d) δ 9.24 (d, J=1.3 Hz, 1H), 8.10 (dd, J=8.7, 1.9 Hz, 1H), 7.61 (d, J=8.8 Hz, 1H), 7.42 (d, J=1.3 Hz, 1H), 7.35 (d, J=1.3 Hz, 1H), 7.33 (d, J=1.5 Hz, 3H), 7.15-7.10 (m, 2H), 5.64 (s, 2H), 3.18 (s, 3H), 2.37 (s, 3H), 2.22 (s, 3H).

Example 182

Methyl 9-benzyl-5-cyano-7-(3,5-dimethyl-4-isoxazolyl)-9H-carbazole-2-carboxylate

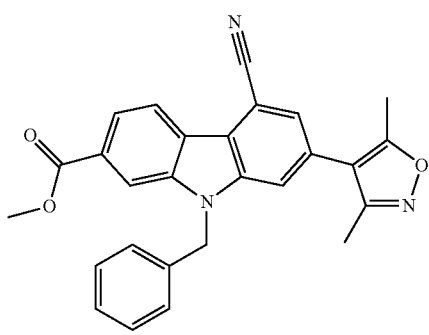 [SMILES: COC(=O)c1ccc2c3c(C#N)cc(-c4c(C)noc4C)cc3n(Cc3ccccc3)c2c1]

Step 1: Methyl 4'-bromo-2'-cyano-2-nitro-[1,1'-biphenyl]-4-carboxylate

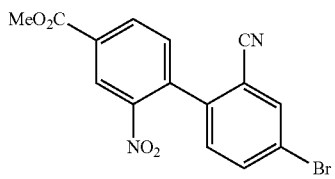 [SMILES: COC(=O)c1ccc(-c2ccc(Br)cc2C#N)c([N+](=O)[O-])c1]

A mixture of 5-bromo-2-iodobenzonitrile (3.0 g, 9.74 mmol), (4-(methoxycarbonyl)-2-nitrophenyl)boronic acid (2.192 g, 9.74 mmol), tripotassium phosphate (14.61 mL, 29.2 mmol) and PdCl$_2$(dppf)-CH$_2$Cl$_2$ adduct (0.796 g, 0.974 mmol) in tetrahydrofuran (20 mL) was added to a 200 ml round bottom flask. Nitrogen was bubbled through the mixture for a few minutes and then it was sealed with a septum cap, evacuated and flushed with nitrogen several times. Next, the mixture was stirred at room temperature. After 4 hours, another 1.1 gram of (4-(methoxycarbonyl)-2-nitrophenyl)boronic acid was added and stirring was continued at room temperature overnight. Analysis by LCMS showed reaction complete. The mixture was diluted with ethyl acetate and washed several times with water. Next, it was concentrated to give a black residue. The residue was chromatographed on an ISCO Companion 220 g silica gel column and eluted with EtOAc/Hexane gradient (20-50%) to give methyl 4'-bromo-2'-cyano-2-nitro-[1,1'-biphenyl]-4-carboxylate (2.85 g, 7.89 mmol, 81% yield) as a tan solid.

LCMS: Waters Sunfire C18 2.1×30 mm 2.5 u (4 min grad) 0-100% B. Flow Rate=1 ml/min. Inj. Vol.=3 uL. Oven Temp.=40C. Solvent A: 10% MeOH-90% H$_2$O-0.1% TFA. Solvent B: 90% MeOH-10% H2O—0.1% TFA. LCMS: RT=3.21 min; (ES): m/z (M+H)$^+$=361.04, 363.04

$^1$H NMR (400 MHz, Chloroform-d) δ 8.82 (d, J=1.8 Hz, 1H), 8.39 (dd, J=7.9, 1.8 Hz, 1H), 7.93 (d, J=2.0 Hz, 1H), 7.82 (dd, J=8.3, 2.1 Hz, 1H), 7.53 (d, J=7.9 Hz, 1H), 7.25 (d, J=8.4 Hz, 1H), 4.03 (s, 3H).

Step 2: Methyl 7-bromo-5-cyano-9H-carbazole-2-carboxylate

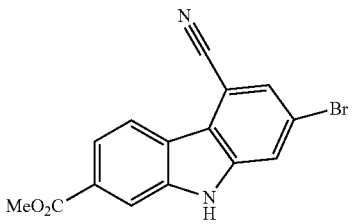 [SMILES: COC(=O)c1ccc2c(c1)[nH]c1cc(Br)cc(C#N)c12]

A mixture of methyl 4'-bromo-2'-cyano-2-nitro-[1,1'-biphenyl]-4-carboxylate (100 mg, 0.277 mmol) and triphenylphosphine (363 mg, 1.384 mmol) in 1,2-dichlorobenzene (0.5 mL) was sealed in a small vial and heated in a heating block at 170° C. for 8 hours. The resulting dark mixture was directly loaded onto a silica gel column (w/DCM) and chromatographed on an ISCO Companion 40 g silica gel column and eluted with EtOAc/Hexane gradient (0-100%) to give methyl 7-bromo-5-cyano-9H-carbazole-2-carboxylate (41 mg, 0.125 mmol, 45.0% yield) as a tan solid.

LCMS: Waters Sunfire C18 2.1×30 mm 2.5 u (4 min grad) 0-100% B. Flow Rate=1 ml/min. Inj. Vol.=3 uL. Oven Temp.=40° C. Solvent A: 10% MeOH-90% H$_2$O-0.1% TFA. Solvent B: 90% MeOH-10% H$_2$O-0.1% TFA. LCMS: RT=3.77 min; (ES): m/z (M+H)$^+$=327.08, 329.08

$^1$H NMR (400 MHz, Methanol-d$_4$) δ 8.47 (dd, J=8.4, 0.7 Hz, 1H), 8.18-8.10 (m, 1H), 7.91 (dd, J=8.4, 1.5 Hz, 1H), 7.83 (d, J=1.5 Hz, 1H), 7.59 (d, J=1.5 Hz, 1H), 3.93 (s, 3H).

Step 3: Methyl 9-benzyl-7-bromo-5-cyano-9H-carbazole-2-carboxylate

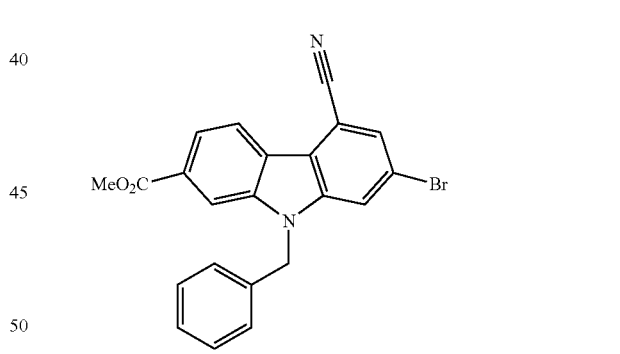

A mixture of methyl 7-bromo-5-cyano-9H-carbazole-2-carboxylate (0.58 g, 1.762 mmol) and Cs$_2$CO$_3$ (1.148 g, 3.52 mmol) in DMF (5 mL) was treated with (bromomethyl)benzene (0.362 g, 2.115 mmol) and stirred at room temperature for 4 hours. The mixture was then diluted with ethyl acetate and washed with water and concentrated to give a dark residue. The dark residue was dissolved in DCM and chromatographed on an ISCO Companion 40 g silica gel column and eluted with EtOAc/Hexane gradient (20-50%) to give methyl 9-benzyl-7-bromo-5-cyano-9H-carbazole-2-carboxylate (515 mg, 1.228 mmol, 70% yield)) as an off-white solid.

LCMS: Waters Sunfire C18 2.1×30 mm 2.5 u (4 min grad) 0-100% B. Flow Rate=1 ml/min. Inj. Vol.=3 uL. Oven Temp.=40° C. Solvent A: 10% MeOH-90% H$_2$O-0.1% TFA.

Solvent B: 90% MeOH-10% H$_2$O-0.1% TFA. LCMS: RT=4.18 min; (ES): m/z (M+H)$^+$=419.01, 421.01.

$^1$H NMR (400 MHz, Chloroform-d) δ 8.66 (dd, J=8.4, 0.4 Hz, 1H), 8.20 (s, 1H), 8.07 (dd, J=8.4, 1.3 Hz, 1H), 7.76 (d, J=1.5 Hz, 1H), 7.70 (d, J=1.5 Hz, 1H), 7.34-7.29 (m, 3H), 7.09 (dd, J=7.3, 2.2 Hz, 2H), 5.59 (s, 2H), 3.98 (s, 3H).

Step 4: Methyl 9-benzyl-5-cyano-7-(3,5-dimethyl-4-isoxazolyl)-9H-carbazole-2-carboxylate A mixture of methyl 9-benzyl-7-bromo-5-cyano-9H-carbazole-2-carboxylate (31 mg, 0.074 mmol), 3,5-dimethyl-4-(4,4,5,5-tetramethyl-1,3,2-dioxaborolan-2-yl)isoxazole (33.0 mg, 0.148 mmol), PdCl2(dppf)-CH$_2$Cl$_2$ adduct (6.04 mg, 7.39 μmol), and 2 M aqueous tripotassium phosphate (0.111 mL, 0.222 mmol) in tetrahydrofuran (2 mL) was added to a vial, and nitrogen was bubbled through the solution for a few minutes. The vial was sealed with a septum, and evacuated and nitrogen purged a few times. The reaction vial was then heated in a heating block at 85° C. for 6 hours. Analysis by LCMS showed complete reaction. The vial was removed from the heating block and let cool to room temperature. The reaction mixture was diluted with ethyl acetate, washed with water and concentrated to give a dark residue. The residue was chromatographed on an ISCO Companion 40 g silica gel column and eluted with EtOAc/Hexane gradient (20-100%) to give methyl 9-benzyl-5-cyano-7-(3,5-dimethyl-4-isoxazolyl)-9H-carbazole-2-carboxylate (22 mg, 0.049 mmol, 66.3% yield) as a white solid.

LCMS: Waters Sunfire C18 2.1×30 mm 2.5 u (4 min grad) 0-100% B. Flow Rate=1 ml/min. Inj. Vol.=3 uL. Oven Temp.=40° C. Solvent A: 10% MeOH-90% H$_2$O-0.1% TFA. Solvent B: 90% MeOH-10% H$_2$O-0.1% TFA. LCMS: RT=3.92 min; (ES): m/z (M+H)$^+$=436.15

HPLC Purity: 95/5 to 5/95 H$_2$O/CH$_3$CN/0.05% TFA, flow=0.5 mL/min, gradient=15 min Sunfire C$_{18}$ 3.5 um, 3.0×150 mm: RT=14.497 min; Purity @220 nm: 97.8%; @254 nm: 100%

Xbridge Phenyl 3.5 um, 3.0×150 mm: RT=13.177 min; Purity @220 nm: 95%; @254 nm: 94.9%

$^1$H NMR (400 MHz, Chloroform-d) δ 8.71 (d, J=8.4 Hz, 1H), 8.29 (s, 1H), 8.09 (dd, J=8.4, 1.3 Hz, 1H), 7.46 (d, J=1.1 Hz, 1H), 7.38 (d, J=1.3 Hz, 1H), 7.35-7.28 (m, 3H), 7.13 (dd, J=7.4, 2.1 Hz, 2H), 5.64 (s, 2H), 4.00 (s, 3H), 2.34 (s, 3H), 2.19 (s, 3H).

Example 183

Methyl 9-benzyl-5-carbamoyl-7-(3,5-dimethyl-4-isoxazolyl)-9H-carbazole-2-carboxylate

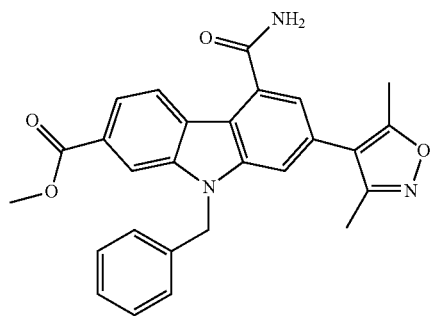 [SMILES: COC(=O)c1ccc2c3c(C(N)=O)cc(-c4c(C)noc4C)cc3n(Cc3ccccc3)c2c1]

A solution of methyl 9-benzyl-5-cyano-7-(3,5-dimethyl-isoxazol-4-yl)-9H-carbazole-2-carboxylate (110 mg, 0.253 mmol) in DMSO (5 mL) was treated with K$_2$CO$_3$ (105 mg, 0.758 mmol) and then with drop wise addition of 50% aqueous hydrogen peroxide (0.464 mL, 7.58 mmol). The resulting mixture was stirred at room temperature until LCMS analysis showed reaction complete. The mixture was diluted with water and extracted with ethyl acetate. After concentration, the crude product was chromatographed on an ISCO Companion 40 g silica gel column and eluted with EtOAc/Hexane gradient (60-100%) to give methyl 9-benzyl-5-carbamoyl-7-(3,5-dimethyl-4-isoxazolyl)-9H-carbazole-2-carboxylate (38 mg, 32% yield) as an off-white solid.

LCMS: Waters Sunfire C18 2.1×30 mm 2.5 u (4 min grad) 0-100% B. Flow Rate=1 ml/min. Inj. Vol.=3 uL. Oven Temp.=40° C. Solvent A: 10% MeOH-90% H$_2$O-0.1% TFA. Solvent B: 90% MeOH-10% H$_2$O-0.1% TFA. LCMS: RT=3.22 min; (ES): m/z (M+H)$^+$=454.15.

HPLC Purity: 95/5 to 5/95 H$_2$O/CH$_3$CN/0.05% TFA, flow=0.5 mL/min, gradient=15 min Sunfire C$_{18}$ 3.5 um, 3.0×150 mm: RT=11.116 min; Purity @220 nm: 97.9%; @254 nm: 96.8%

Xbridge Phenyl 3.5 um, 3.0×150 mm: RT=10.748 min; Purity @220 nm: 94.6%; @254 nm: 95.4%

$^1$H NMR (400 MHz, DMSO-d$_6$) δ 8.51 (d, J=8.4 Hz, 1H), 8.28 (s, 1H), 8.13 (br. s., 1H), 7.82 (dd, J=8.4, 1.3 Hz, 1H), 7.79 (s, 1H), 7.71 (br. s., 1H), 7.33 (d, J=1.3 Hz, 1H), 7.30-7.20 (m, 3H), 7.15 (d, J=6.8 Hz, 2H), 5.86 (s, 2H), 3.89 (s, 3H), 2.42 (s, 3H), 2.23 (s, 3H).

Example 184

9-benzyl-2-(3,5-dimethyl-4-isoxazolyl)-7-(1-hydroxy-1-methylethyl)-9H-carbazole-4-carbonitrile

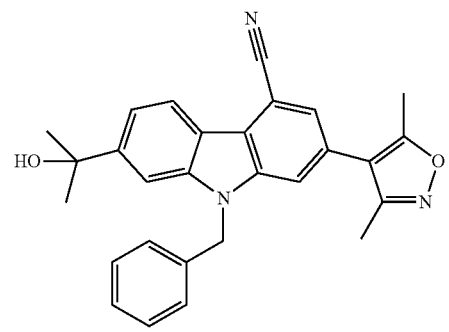 [SMILES: Cc1noc(C)c1-c1cc(C#N)c2c3ccc(C(C)(C)O)cc3n(Cc3ccccc3)c2c1]

A solution of methyl 9-benzyl-5-cyano-7-(3,5-dimethyl-isoxazol-4-yl)-9H-carbazole-2-carboxylate (60 mg, 0.138 mmol) in tetrahydrofuran (5 mL) was cooled in a dry-ice/acetone bath at −78° C. and treated drop wise with a solution of 1.6 M methyl lithium in diethyl ether (0.431 mL, 0.689 mmol). The resulting black solution was then stirred in bath at −78° C. After 90 minutes, the mixture was removed from the bath and allowed to stir at room temperature for 30 minutes and then poured into 1 N HCl and extracted with ethyl acetate. The combined organic fractions were washed with water and concentrated to give a yellow solid. The crude material was chromatographed on an ISCO Companion 40 g silica gel column and eluted with EtOAc/Hexane gradient (20-100%) to give 9-benzyl-2-(3,5-dimethyl-4-isoxazolyl)-7-(1-hydroxy-1-methylethyl)-9H-carbazole-4-carbonitrile (3.8 mg, 0.083 mmol, 60.2% yield) as a light yellow solid. LCMS4: Waters Acquity SDS. Column: BEH C18 2.1×50 mm 1.7 u (1.6 min grad) 2-98% B. Flow Rate=0.8 ml/min. Solvent A: H$_2$O-0.1% TFA. Solvent B: Acetonitrile-0.1% TFA. LCMS: RT=1.05 min; (ES): m/z (M+H)$^+$=436.4

LVL-L3405-LCMS: Waters Sunfire C18 2.1×30 mm 2.5 u (4 min grad) 0-100% B. Flow Rate=1 ml/min. Inj. Vol.=3 uL. Oven Temp.=40° C. Solvent A: 10% MeOH-90% H$_2$O-0.1% TFA. Solvent B: 90% MeOH-10% H$_2$O-0.1% TFA. LCMS: RT=3.66 min; (ES): m/z (M+H)$^+$=436.4

HPLC Purity: 95/5 to 5/95 H$_2$O/CH$_3$CN/0.05% TFA, flow=0.5 mL/min, gradient=15 min Sunfire C$_{18}$ 3.5 um, 3.0×150 mm: RT=13.229 min; Purity @220 nm: 97.3%; @254 nm: 95.6%

Xbridge Phenyl 3.5 um, 3.0×150 mm: RT=12.198 min; Purity @220 nm: 93.9%; @254 nm: 92.7%

$^1$H NMR (400 MHz, Chloroform-d) δ 8.61 (d, J=8.4 Hz, 1H), 7.76 (d, J=1.1 Hz, 1H), 7.46 (dd, J=8.4, 1.5 Hz, 1H), 7.40 (d, J=1.3 Hz, 1H), 7.36-7.27 (m, 4H), 7.13 (dd, J=7.5, 2.0 Hz, 2H), 5.59 (s, 2H), 2.34 (s, 3H), 2.18 (s, 3H), 1.85 (s, 1H), 1.70 (s, 6H).

Example 185

9-Benzyl-2-(3,5-dimethyl-4-isoxazolyl)-7-(1-hydroxy-1-methylethyl)-9H-carbazole-4-carboxamide

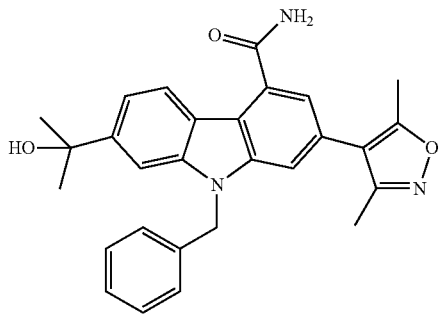 [SMILES: Cc1noc(C)c1-c1cc(C(N)=O)c2c3ccc(C(C)(C)O)cc3n(Cc3ccccc3)c2c1]

A solution of 9-benzyl-2-(3,5-dimethylisoxazol-4-yl)-7-(2-hydroxypropan-2-yl)-9H-carbazole-4-carbonitrile (38 mg, 0.087 mmol) in DMSO (2 mL) was treated with K$_2$CO$_3$ (36.2 mg, 0.262 mmol) and then dropwise with 50% aqueous H$_2$O$_2$ (0.160 mL, 2.62 mmol). The resulting mixture was stirred at room temperature. After 2 hours, the mixture was diluted with water and extracted into ethyl acetate. The combined organic fractions were then washed with water and concentrated. The crude product was chromatographed on an ISCO Companion 24 g silica gel column and eluted with EtOAc/Hexane gradient (50-100%) to give 9-benzyl-2-(3,5-dimethyl-4-isoxazolyl)-7-(1-hydroxy-1-methylethyl)-9H-carbazole-4-carboxamide (31 mg, 0.066 mmol, 75% yield) as an off-white solid.

LCMS: Waters Sunfire C18 2.1×30 mm 2.5 u (4 min grad) 0-100% B. Flow Rate=1 ml/min. Inj. Vol.=3 uL. Oven Temp.=40° C. Solvent A: 10% MeOH-90% H$_2$O-0.1% TFA. Solvent B: 90% MeOH-10% H$_2$O-0.1% TFA. LCMS: RT=3.03 min; (ES): m/z (M+H)±=MS 454.18.

HPLC Purity: 95/5 to 5/95 H$_2$O/CH$_3$CN/0.05% TFA, flow=0.5 mL/min, gradient=15 min Sunfire C$_{18}$ 3.5 um, 3.0×150 mm: RT=9.973 min; Purity @220 nm: 96.5%; @254 nm: 95.7%

Xbridge Phenyl 3.5 um, 3.0×150 mm: RT=9.848 min; Purity @220 nm: 96.7%; @254 nm: 94.8%.

$^1$H NMR (400 MHz, Chloroform-d) δ 8.51 (d, J=8.4 Hz, 1H), 7.70 (d, J=1.3 Hz, 1H), 7.36 (dd, J=8.6, 1.5 Hz, 1H), 7.32-7.25 (m, 4H), 7.22 (s, 1H), 7.13 (dd, J=7.7, 1.8 Hz, 2H), 6.11 (br. s., 1H), 5.93 (br. s., 1H), 5.59 (s, 2H), 2.33 (s, 3H), 2.18 (s, 3H), 1.86 (s, 1H), 1.68 (s, 6H).

Example 186

9-Benzyl-5-cyano-7-(3,5-dimethyl-4-isoxazolyl)-9H-carbazole-2-carboxylic acid

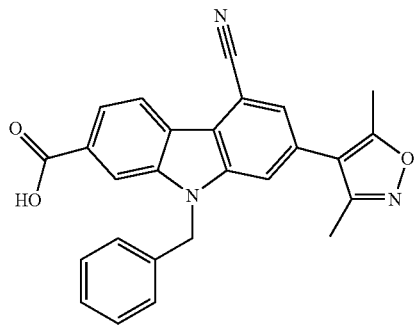 [SMILES: Cc1noc(C)c1-c1cc(C#N)c2c3ccc(C(=O)O)cc3n(Cc3ccccc3)c2c1]

A suspension of methyl 9-benzyl-5-cyano-7-(3,5-dimethylisoxazol-4-yl)-9H-carbazole-2-carboxylate (23 mg, 0.053 mmol) in MeOH (5 mL) was treated with 1 N aqueous NaOH (0.528 mL, 0.528 mmol). The resulting mixture was then heated at 80° C. in a heating block. After 1 hour, the clear solution was cooled to room temperature and concentrated on a rotary evaporator. The residue was made acidic with 1 N HCl and the resulting white suspension was extracted into ethyl acetate and concentrated to give a white solid. The crude material was then purified via preparative HPLC using the following conditions: Column: Waters XBridge C18, 19×200 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 0-100% B over 25 minutes, then a 5-minute hold at 100% B; Flow: 20 mL/min. Fractions containing the desired product were combined and dried via centrifugal evaporation to give 9-benzyl-5-cyano-7-(3,5-dimethyl-4-isoxazolyl)-9H-carbazole-2-carboxylic acid (4.4 mg, 20% yield). The estimated purity of the product by LCMS analysis was 99%.

Two analytical LCMS injections were used to determine the final purity.

Injection 1 conditions: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Injection 2 conditions: Column: Waters Acquity UPLC BEH C18, 2.1×50 mm, 1.7-µm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. Proton NMR was acquired in deuterated DMSO.

Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.11 mL/min.

LCMS: RT=1.363 min; (ES): m/z (M+H)$^+$=422.05

$^1$H NMR (500 MHz, DMSO-d$_6$) δ 8.52 (d, J=8.4 Hz, 1H), 8.37 (s, 1H), 8.15 (d, J=1.0 Hz, 1H), 8.04-7.97 (m, 1H), 7.86 (d, J=1.0 Hz, 1H), 7.34-7.27 (m, 2H), 7.25 (d, J=6.9 Hz, 1H), 7.19 (s, 2H), 5.92 (s, 2H), 2.45 (s, 3H), 2.27 (s, 3H).

Example 187

9-Benzyl-2-(3,5-dimethyl-4-isoxazolyl)-7-(morpholine-4-carbonyl)-9H-carbazole-4-carbonitrile

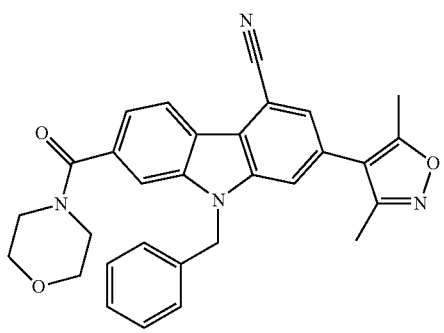 [SMILES: Cc1noc(C)c1-c1cc(C#N)c2c3ccc(C(=O)N4CCOCC4)cc3n(Cc3ccccc3)c2c1]

A solution of 9-benzyl-5-cyano-7-(3,5-dimethylisoxazol-4-yl)-9H-carbazole-2-carboxylic acid (80 mg, 0.190 mmol) in DMF (5 mL) was treated with TBTU (122 mg, 0.380 mmol), morpholine (33.1 mg, 0.380 mmol), and TEA (0.053 mL, 0.380 mmol). The resulting solution was then stirred at room temperature for 2 hours. Analysis by LCMS showed the reaction was complete. The mixture was diluted with water and extracted into ethyl acetate. The combined organic extracts were then washed with water and brine and concentrated. The crude product was chromatographed on an ISCO Companion 40 g silica gel column and eluted with EtOAc/Hexane gradient (40-100%) to give 9-benzyl-2-(3,5-dimethyl-4-isoxazolyl)-7-(morpholine-4-carbonyl)-9H-carbazole-4-carbonitrile (67 mg, 0.135 mmol, 71.2% yield) as a white solid which was triturated from DCM/hexanes.

LCMS: Waters Sunfire C18 2.1×30 mm 2.5 u (4 min grad) 0-100% B. Flow Rate=1 ml/min. Inj. Vol.=3 uL. Oven Temp.=40° C. Solvent A: 10% MeOH-90% H$_2$O-0.1% TFA. Solvent B: 90% MeOH-10% H$_2$O-0.1% TFA. LCMS: RT=3.39 min; (ES): m/z (M+H)$^+$=491.15.

HPLC Purity: 95/5 to 5/95 H$_2$O/CH$_3$CN/0.05% TFA, flow=0.5 mL/min, gradient=15 min Sunfire C$_{18}$ 3.5 um, 3.0×150 mm: RT=12.186 min; Purity @220 nm: 99.2%; @254 nm: 99.7%.

Xbridge Phenyl 3.5 um, 3.0×150 mm; RT=11.608 min; Purity @220 nm: 99.2%; @254 nm: 96.0%.

$^1$H NMR (400 MHz, Chloroform-d) δ 8.69 (d, J=8.1 Hz, 1H), 7.62 (s, 1H), 7.46 (d, J=1.3 Hz, 1H), 7.41 (dd, J=8.1, 1.3 Hz, 1H), 7.39 (d, J=1.1 Hz, 1H), 7.34-7.28 (m, 3H), 7.12 (dd, J=7.2, 2.3 Hz, 2H), 5.59 (s, 2H), 4.02-3.45 (m, 8H), 2.36 (s, 3H), 2.20 (s, 3H).

Example 188

9-Benzyl-2-(3,5-dimethyl-4-isoxazolyl)-7-(morpholine-4-carbonyl)-9H-carbazole-4-carboxamide

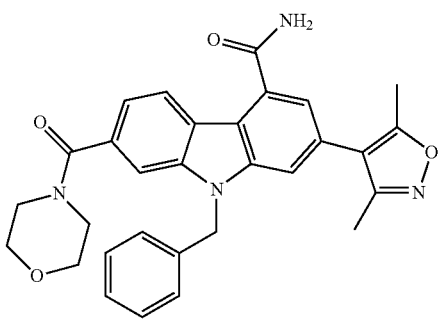 [SMILES: Cc1noc(C)c1-c1cc(C(N)=O)c2c3ccc(C(=O)N4CCOCC4)cc3n(Cc3ccccc3)c2c1]

A solution of 9-benzyl-2-(3,5-dimethylisoxazol-4-yl)-7-(morpholine-4-carbonyl)-9H-carbazole-4-carbonitrile (20 mg, 0.041 mmol) in DMSO (2 mL) was treated with K$_2$CO$_3$ (16.90 mg, 0.122 mmol) and 35% aqueous H$_2$O$_2$ (0.107 mL, 1.223 mmol). The resulting mixture was then stirred at room temperature. After 2 hours, analysis by LCMS showed complete reaction. The reaction was diluted with water and the white suspension was extracted into ethyl acetate. The combined organic fractions were washed with water and concentrated to give (after trituration from CHCl$_3$/Hexanes) 9-benzyl-2-(3,5-dimethyl-4-isoxazolyl)-7-(morpholine-4-carbonyl)-9H-carbazole-4-carboxamide (19 mg, 0.035 mmol, 87% yield) as a white solid.

LCMS: Waters Sunfire C18 2.1×30 mm 2.5 u (4 min grad) 0-100% B. Flow Rate=1 ml/min. Inj. Vol.=3 uL. Oven Temp.=40° C. Solvent A: 10% MeOH-90% H$_2$O-0.1% TFA. Solvent B: 90% MeOH-10% H$_2$O-0.1% TFA. LCMS: RT=2.78 min; (ES): m/z (M+H)$^+$=509.19.

HPLC Purity: 95/5 to 5/95 H$_2$O/CH$_3$CN/0.05% TFA, flow=0.5 mL/min, gradient=15 min Sunfire C$_{18}$ 3.5 um, 3.0×150 mm: RT=9.234 min; Purity @220 nm: 92.5%; 254 nm: 98.7%. Xbridge Phenyl 3.5 um, 3.0×150 mm: RT=9.328 min; Purity @220 nm: 96.5%; @254 nm: 97.1%.

$^1$H NMR (400 MHz, Chloroform-d) δ 8.57 (d, J=8.1 Hz, 1H), 7.59-7.51 (m, 1H), 7.35-7.31 (m, 1H), 7.31-7.26 (m, 5H), 7.11 (dd, J=7.3, 2.2 Hz, 2H), 6.21 (br. s., 1H), 5.98 (br. s., 1H), 5.58 (s, 2H), 4.02-3.27 (m, 8H), 2.35 (s, 3H), 2.21 (s, 3H).

Example 189

9-Benzyl-7-(3,5-dimethyl-4-isoxazolyl)-N~2~-methoxy-N~2~-methyl-9H-carbazole-2,5-dicarboxamide

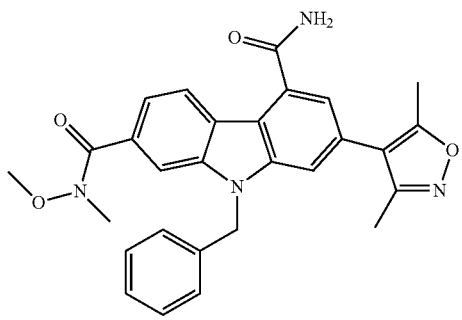 [SMILES: CON(C)C(=O)c1ccc2c3c(C(N)=O)cc(-c4c(C)noc4C)cc3n(Cc3ccccc3)c2c1]

Step 1: 9-Benzyl-5-cyano-7-(3,5-dimethylisoxazol-4-yl)-N-methoxy-N-methyl-9H-carbazole-2-carboxamide

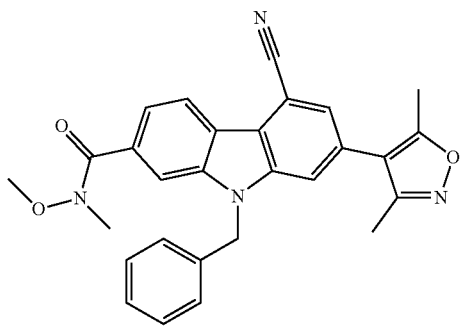 [SMILES: CON(C)C(=O)c1ccc2c3c(C#N)cc(-c4c(C)noc4C)cc3n(Cc3ccccc3)c2c1]

A mixture of 9-benzyl-5-cyano-7-(3,5-dimethylisoxazol-4-yl)-9H-carbazole-2-carboxylic acid (390 mg, 0.925 mmol), N,O-dimethylhydroxylamine HCl (181 mg, 1.851 mmol), EDC (222 mg, 1.157 mmol), HOBT (177 mg, 1.157 mmol), and TEA (0.516 mL, 3.70 mmol) in DMF (15 mL) was stirred at room temperature for 2 hours. Next, the reaction mixture was diluted with water and extracted into ethyl acetate. The combined organic extracts were washed with water and concentrated. The resulting product was chromatographed on an ISCO Companion 40 g silica gel column and eluted with EtOAc/Hexane gradient (50-100%) to give 9-benzyl-5-cyano-7-(3,5-dimethylisoxazol-4-yl)-N-methoxy-N-methyl-9H-carbazole-2-carboxamide (300 mg, 0.646 mmol, 69.8% yield) as a white solid.

LCMS: Waters Sunfire C18 2.1×30 mm 2.5 u (4 min grad) 0-100% B. Flow Rate=1 ml/min. Inj. Vol.=3 uL. Oven Temp.=40° C. Solvent A: 10% MeOH-90% $H_2O$-0.1% TFA. Solvent B: 90% MeOH-10% $H_2O$-0.1% TFA. LCMS: RT=3.56 min; (ES): m/z (M+H)$^+$=465.16

$^1$H NMR (400 MHz, Chloroform-d) δ 8.67 (d, J=8.1 Hz, 1H), 7.90 (s, 1H), 7.73 (dd, J=8.3, 1.2 Hz, 1H), 7.44 (d, J=1.3 Hz, 1H), 7.38 (d, J=1.1 Hz, 1H), 7.34-7.27 (m, 3H), 7.17-7.06 (m, 2H), 5.59 (s, 2H), 3.53 (s, 3H), 3.41 (s, 3H), 2.34 (s, 3H), 2.19 (s, 3H).

Step 2: 9-benzyl-7-(3,5-dimethyl-4-isoxazolyl)-N~2~-methoxy-N~2~-methyl-9H-carbazole-2,5-dicarboxamide A solution of 9-benzyl-5-cyano-7-(3,5-dimethylisoxazol-4-yl)-N-methoxy-N-methyl-9H-carbazole-2-carboxamide (300 mg, 0.646 mmol) in DMSO (5 mL) was treated with $K_2CO_3$ (268 mg, 1.938 mmol) and then dropwise with 50% aqueous $H_2O_2$ (1.187 mL, 19.38 mmol). The resulting mixture was then stirred at room temperature for 5 hours. [Note that the reaction was warm to the touch while adding the $H_2O_2$ solution]. The reaction was then diluted with water and extracted with ethyl acetate. The combined organic fractions were washed with water and concentrated to give a white solid.

A 15 mg sample of crude material was purified via preparative LCMS using the following conditions: Column: Waters XBridge C18, 19×150 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 15 minutes, then a 5-minute hold at 100% B; Flow: 20 mL/min. Fractions containing the desired product were combined and dried via centrifugal evaporation.

The material was further purified via preparative HPLC using the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-65% B over 25 minutes, then a 10-minute hold at 65% B; Flow: 25 mL/min. Fractions containing the desired product were combined and dried via centrifugal evaporation to give 8.1 mg of 9-benzyl-7-(3,5-dimethyl-4-isoxazolyl)-N~2~-methoxy-N~2~-methyl-9H-carbazole-2,5-dicarboxamide. The estimated purity of the product by LCMS analysis was 99%.

Two analytical LCMS injections were used to determine the final purity.

Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Injection 2 conditions: Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. Proton NMR was acquired in deuterated 1:1 methanol:chloroform.

LCMS: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

LCMS: RT=1.47 min; (ES): m/z (M+H)$^+$=483.20.

$^1$H NMR (500 MHz, $CDCl_3$/Methanol-$d_4$) δ 8.54 (d, J=8.4 Hz, 1H), 7.83 (s, 1H), 7.61 (s, 1H), 7.55 (d, J=8.4 Hz, 1H), 7.39 (d, J=1.5 Hz, 1H), 7.31-7.20 (m, 3H), 7.17-7.07 (m, 2H), 5.67 (s, 2H), 3.54 (s, 3H), 3.39 (s, 3H), 2.37 (s, 3H), 2.21 (s, 3H).

Example 190

9-Benzyl-2-(3,5-dimethyl-4-isoxazolyl)-7-(3-fluorobenzoyl)-9H-carbazole-4-carboxamide

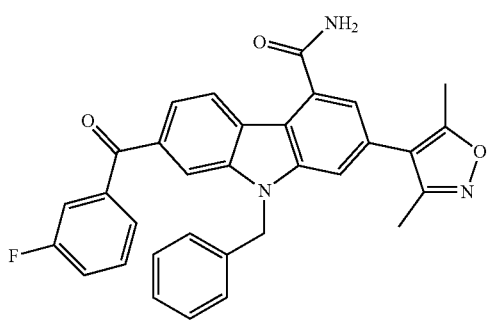 [SMILES: Cc1noc(C)c1-c1cc(C(N)=O)c2c3ccc(C(=O)c4cccc(F)c4)cc3n(Cc3ccccc3)c2c1]

A solution of 9-benzyl-7-(3,5-dimethylisoxazol-4-yl)-N2-methoxy-N2-methyl-9H-carbazole-2,5-dicarboxamide (32 mg, 0.066 mmol) in tetrahydrofuran (3 mL) in a scintillation vial with septum was cooled in ice bath and treated via syringe with (3-fluorophenyl)magnesium bromide 1 M in THF (0.199 mL, 0.199 mmol). The reaction was then stirred at 0° C. After almost 2 hours, more (3-fluorophenyl)magnesium bromide 1 M in THF (0.199 mL, 0.199 mmol) was added to the reaction mixture and stirring was continued. After another hour, more (3-fluorophenyl)magnesium bromide 1 M in THF (0.199 mL, 0.199 mmol) was added and stirring continued. After 40 minutes, the mixture was quenched with 1 N HCl and extracted into ethyl acetate. The combined organic extracts were washed well with water and concentrated. The material was then chromatographed on an ISCO Companion 40 g silica gel column and eluted with EtOAc/Hexane gradient (30-100%) to give 18 mg of a light yellow solid. The material was purified via preparative HPLC using the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 20 minutes, then a 5-minute hold at 100% B; Flow: 25 mL/min. Fractions containing the desired product were combined and dried via centrifugal evaporation to give 9-benzyl-2-(3,5-dimethyl-4-isoxazolyl)-7-(3-fluorobenzoyl)-9H-carbazole-4-carboxamide (9.6 mg, 27% yield). The estimated purity of the product by LCMS analysis was 95%.

Two analytical LCMS injections were used to determine the final purity.

Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Injection 2 conditions: Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. Proton NMR was acquired in deuterated 1:1 methanol:chloroform.

LCMS: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

HPLC Purity @ 220: 95%. LCMS: RT=1.92 min; (ES): m/z (M+H)$^+$=518.1.

$^1$H NMR (500 MHz, CDCl$_3$:Methanol-d$_4$) δ 8.61 (d, J=8.4 Hz, 1H), 7.97 (s, 1H), 7.72-7.65 (m, 1H), 7.62 (s, 1H), 7.59-7.52 (m, 1H), 7.49 (dd, J=7.9, 2.5 Hz, 2H), 7.44 (d, J=1.0 Hz, 1H), 7.40-7.32 (m, 2H), 7.31-7.25 (m, 2H), 7.16-7.06 (m, 2H), 5.68 (s, 2H), 2.39 (s, 3H), 2.22 (s, 3H).

Example 191

Methyl 5-cyano-7-(3,5-dimethyl-4-isoxazolyl)-9-(diphenylmethyl)-9H-carbazole-2-carboxylate

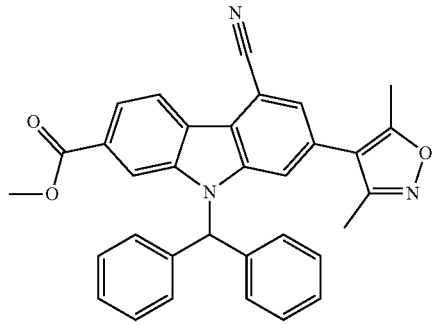 [SMILES: COC(=O)c1ccc2c3c(C#N)cc(-c4c(C)noc4C)cc3n(C(c3ccccc3)c3ccccc3)c2c1]

Step 1: Methyl 9-benzhydryl-7-bromo-5-cyano-9H-carbazole-2-carboxylate

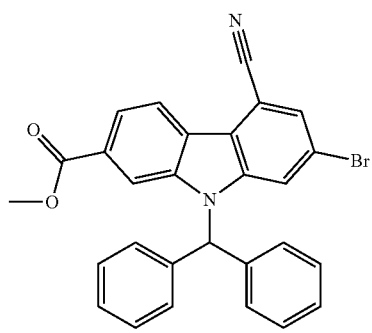 [SMILES: COC(=O)c1ccc2c3c(C#N)cc(Br)cc3n(C(c3ccccc3)c3ccccc3)c2c1]

A mixture of methyl 7-bromo-5-cyano-9H-carbazole-2-carboxylate (130 mg, 0.395 mmol), (bromomethylene)dibenzene (117 mg, 0.474 mmol), and Cs$_2$CO$_3$ (257 mg, 0.790 mmol) in DMF (5 mL) was stirred at room temperature overnight. The mixture was then diluted with water and extracted into ethyl acetate. The combined organic fractions were washed with water and brine, and concentrated to give an orange residue. The crude product was chromatographed on an ISCO Companion 40 g silica gel column and eluted with EtOAc/Hexane gradient (25-50%). The fractions containing product were combined, and the material was chromatographed a second time on an ISCO Companion 40 g silica gel column and eluted with EtOAc/Hexane gradient (0-30%) to give methyl 9-benzhydryl-7-bromo-5-cyano-9H-carbazole-2-carboxylate (85 mg, 0.172 mmol, 43.4% yield) as a white foam.

LCMS: Waters Sunfire C18 2.1×30 mm 2.5 u (4 min grad) 0-100% B. Flow Rate=1 ml/min. Inj. Vol.=3 uL. Oven Temp.=40° C. Solvent A: 10% MeOH-90% $H_2O$-0.1% TFA. Solvent B: 90% MeOH-10% $H_2O$-0.1% TFA. LCMS: RT=4.44 min; (ES): m/z $(M+H)^+$=495.05, 497.05.

Step 2: Methyl 5-cyano-7-(3,5-dimethyl-4-isoxazolyl)-9-(diphenylmethyl)-9H-carbazole-2-carboxylate A solution of methyl 9-benzhydryl-7-bromo-5-cyano-9H-carbazole-2-carboxylate (85 mg, 0.172 mmol) and 3,5-dimethyl-4-(4,4,5,5-tetramethyl-1,3,2-dioxaborolan-2-yl) isoxazole (77 mg, 0.343 mmol) in tetrahydrofuran (5 mL) in a scintillation vial was purged with nitrogen for several minutes. Next, 2 M aqueous tripotassium phosphate (0.257 mL, 0.515 mmol) and $PdCl_2$(dppf)-$CH_2Cl_2$ adduct (14.01 mg, 0.017 mmol) were added. The reaction was then purged with nitrogen for few more minutes. The vial was capped with a septum and then evacuated and purged with nitrogen several times before heating in a heating block at 80° C. for 3 hours. The mixture was then removed from the heating block and cooled to room temperature. The reaction was diluted with water and extracted into ethyl acetate. The combined organic extracts were washed with water and concentrated. The crude product was chromatographed on an ISCO Companion 40 g silica gel column and eluted with EtOAc/Hexane gradient (30-50%) to give methyl 5-cyano-7-(3,5-dimethyl-4-isoxazolyl)-9-(diphenylmethyl)-9H-carbazole-2-carboxylate (60 mg, 0.111 mmol, 64.9% yield) as a white solid.

LCMS: Waters Sunfire C18 2.1×30 mm 2.5 u (4 min grad) 0-100% B. Flow Rate=1 ml/min. Inj. Vol.=3 uL. Oven Temp.=40° C. Solvent A: 10% MeOH-90% $H_2O$-0.1% TFA. Solvent B: 90% MeOH-10% $H_2O$-0.1% TFA. LCMS: RT=4.15 min; (ES): m/z $(M+H)^+$=512.15.

HPLC Purity: 95/5 to 5/95 $H_2O$/$CH_3CN$/0.05% TFA, flow=0.5 mL/min, gradient=15 min. Xbridge Phenyl 3.5 um, 3.0×150 mm; RT=14.002 min; Purity @220 nm: >95%; purity @254 nm: >95%.

$^1$H NMR (400 MHz, Chloroform-d) δ 8.74 (d, J=8.4 Hz, 1H), 8.12 (s, 1H), 8.07 (dd, J=8.4, 1.3 Hz, 1H), 7.42 (d, J=1.3 Hz, 1H), 7.39-7.34 (m, 6H), 7.32 (s, 1H), 7.23-7.16 (m, 4H), 7.04 (d, J=1.3 Hz, 1H), 3.96 (s, 3H), 2.19 (s, 3H), 2.04 (s, 3H).

Example 192

Methyl 5-carbamoyl-7-(3,5-dimethyl-4-isoxazolyl)-9-(diphenylmethyl)-9H-carbazole-2-carboxylate

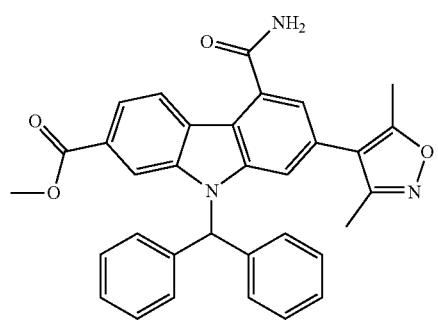 [SMILES: COC(=O)c1ccc2c3c(C(N)=O)cc(-c4c(C)noc4C)cc3n(C(c3ccccc3)c3ccccc3)c2c1]

A solution of methyl 9-benzhydryl-5-cyano-7-(3,5-dimethylisoxazol-4-yl)-9H-carbazole-2-carboxylate (50 mg, 0.098 mmol) in DMSO (3 mL) was treated with $K_2CO_3$ (40.5 mg, 0.293 mmol) and 50% aqueous $H_2O_2$ (0.180 mL, 2.93 mmol). The resulting mixture was then stirred at room temperature for 2 hours. The mixture was diluted with water and the resulting white suspension was extracted into ethyl acetate. The combined organic extracts were washed with water and concentrated to give a white solid. The product was placed under high vacuum and pumped on over the weekend to give methyl 5-carbamoyl-7-(3,5-dimethyl-4-isoxazolyl)-9-(diphenylmethyl)-9H-carbazole-2-carboxylate (30 mg, 0.054 mmol, 55.6% yield) as a white solid.

LCMS: Waters Sunfire C18 2.1×30 mm 2.5 u (4 min grad) 0-100% B. Flow Rate=1 ml/min. Inj. Vol.=3 uL. Oven Temp.=40° C. Solvent A: 10% MeOH-90% $H_2O$-0.1% TFA. Solvent B: 90% MeOH-10% $H_2O$-0.1% TFA. LCMS: RT=3.57 min; (ES): m/z $(M+H)^+$=530.12.

HPLC Purity: 95/5 to 5/95 $H_2O$/$CH_3CN$/0.05% TFA, flow=0.5 mL/min, gradient=15 min Sunfire $C_{18}$ 3.5 um, 3.0×150 mm: RT=12.454 min; Purity @220 nm: 95.8%; @254 nm: 98.4%.

Xbridge Phenyl 3.5 um, 3.0×150 mm: RT=11.976 min; Purity @220 nm: 96.3%; @254 nm: 97.7%.

$^1$H NMR (400 MHz, Chloroform-d) δ 8.55 (d, J=8.4 Hz, 1H), 8.07 (s, 1H), 7.95 (dd, J=8.5, 1.4 Hz, 1H), 7.39-7.30 (m, 6H), 7.25 (d, J=1.3 Hz, 1H), 7.21 (td, J=3.5, 2.3 Hz, 4H), 6.96 (d, J=1.3 Hz, 1H), 6.07 (br. s., 1H), 5.93 (br. s., 1H), 3.93 (s, 3H), 2.16 (s, 3H), 2.03 (s, 3H).

Example 193

5-Cyano-7-(3,5-dimethyl-4-isoxazolyl)-9-(diphenylmethyl)-9H-carbazole-2-carboxylic acid

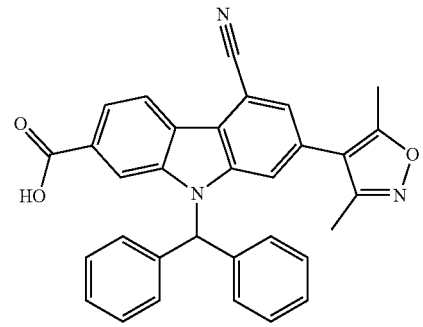

A suspension of methyl 9-benzhydryl-5-cyano-7-(3,5-dimethylisoxazol-4-yl)-9H-carbazole-2-carboxylate (225 mg, 0.440 mmol) in methanol (15 mL) in a round bottom flask equipped with a condenser was treated with 1 N aqueous NaOH (4.40 mL, 4.40 mmol) and heated to reflux. Gradually over time, the solution became clear. After 2 hours, the mixture was clear. LCMS analysis showed the reaction was complete. The mixture was allowed to cool to room temperature. The solvent was removed in vacuo on a rotary evaporator, and the residue was acidified with 1 N HCl and extracted into ethyl acetate. The combined organic extracts were washed with water and concentrated to give 5-cyano-7-(3,5-dimethyl-4-isoxazolyl)-9-(diphenylmethyl)-9H-carbazole-2-carboxylic acid (215 mg, 97% yield) as a white solid.

LCMS: Waters Sunfire C18 2.1×30 mm 2.5 u (4 min grad) 0-100% B. Flow Rate=1 ml/min. Inj. Vol.=3 uL. Oven Temp.=40° C. Solvent A: 10% MeOH-90% $H_2O$-0.1% TFA. Solvent B: 90% MeOH-10% $H_2O$-0.1% TFA. LCMS: RT=3.84 min; (ES): m/z $(M+H)^+$=498.07.

A 10 mg sample of the product was purified via preparative HPLC using the following conditions: Column: Waters XBridge C18, 19×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 10 minutes, then a 5-minute hold at 100% B; Flow: 20 mL/min. Fractions containing the desired product were combined and dried via centrifugal evaporation. The yield of the product was 9.8 mg, and its estimated purity by LCMS analysis was 100%. Two analytical LCMS injections were used to determine the final purity.

Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Injection 2 conditions: Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. Proton NMR was acquired in deuterated DMSO.

HPLC Purity @ 220: 100%. Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

LCMS: RT=1.55 min; (ES): m/z $(M+H)^+$=498.17

$^1$H NMR (500 MHz, DMSO-$d_6$) δ 8.54 (d, J=8.4 Hz, 1H), 8.06 (s, 1H), 7.97 (d, J=9.1 Hz, 1H), 7.82 (d, J=7.1 Hz, 2H), 7.54 (s, 1H), 7.46-7.34 (m, 6H), 7.24 (d, J=7.1 Hz, 4H), 2.29 (s, 3H), 2.11 (s, 3H).

Example 194

5-Cyano-7-(3,5-dimethyl-4-isoxazolyl)-9-(diphenylmethyl)-9H-carbazole-2-carboxamide

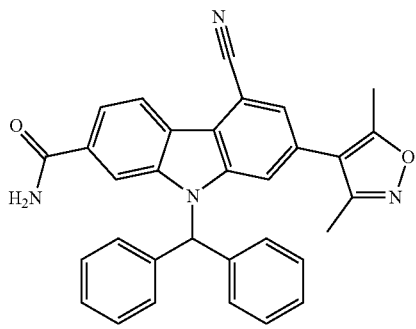 [SMILES: Cc1noc(C)c1-c1cc(C#N)c2c3ccc(C(=O)O)cc3n(C(c3ccccc3)c3ccccc3)c2c1]

A solution of 9-benzhydryl-5-cyano-7-(3,5-dimethylisoxazol-4-yl)-9H-carbazole-2-carboxylic acid (25 mg, 0.050 mmol) in DMF (1 mL) in a scintillation vial was treated with TBTU (32.3 mg, 0.100 mmol), 2 Molar ammonia in IPA (0.050 mL, 0.100 mmol) and TEA (0.014 mL, 0.100 mmol). The resulting mixture was then stirred at 25° C. After 3 hours, more TBTU and ammonia were added, and the mixture was stirred overnight. Next, the reaction mixture was diluted with water and extracted into ethyl acetate. The combined organic extracts were washed with water and brine and concentrated to give a white solid. Analysis by LCMS showed about 25% starting material remaining.

The crude product was purified via preparative HPLC using the following conditions: Column: Waters XBridge C18, 19×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 10 minutes, then a 5-minute hold at 100% B; Flow: 20 mL/min. Fractions containing the desired product were combined and dried via centrifugal evaporation to give 5-cyano-7-(3,5-dimethyl-4-isoxazolyl)-9-(diphenylmethyl)-9H-carbazole-2-carboxamide (13.4 mg, 53% yield). The estimated purity of the product by LCMS analysis was 99%.

Two analytical LCMS injections were used to determine the final purity.

Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Injection 2 conditions: Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. Proton NMR was acquired in deuterated DMSO.

HPLC Purity @ 220 nm: 99%.

LCMS: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

LCMS: RT=1.93 min; (ES): m/z $(M+H)^+$=497.19.

$^1$H NMR (500 MHz, DMSO-$d_6$) δ 8.50 (d, J=8.1 Hz, 1H), 8.15 (s, 1H), 8.07 (br. s., 1H), 7.91 (d, J=8.4 Hz, 1H), 7.80 (s, 1H), 7.73 (s, 1H), 7.50 (br. s., 1H), 7.44-7.32 (m, 7H), 7.25 (d, J=7.1 Hz, 4H), 2.25 (s, 3H), 2.08 (s, 3H).

Example 195

7-(3,5-Dimethyl-4-isoxazolyl)-9-(diphenylmethyl)-N~2~,N~2~-dimethyl-9H-carbazole-2,5-dicarboxamide

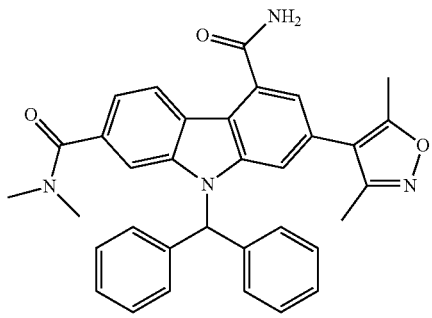 [SMILES: Cc1noc(C)c1-c1cc(C(N)=O)c2c3ccc(C(=O)N(C)C)cc3n(C(c3ccccc3)c3ccccc3)c2c1]

Step 1: 9-Benzhydryl-5-cyano-7-(3,5-dimethylisoxazol-4-yl)-N,N-dimethyl-9H-carbazole-2-carboxamide

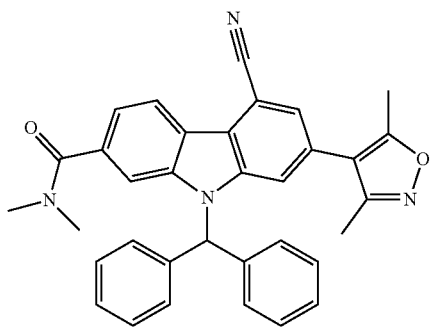 [SMILES: Cc1noc(C)c1-c1cc(C#N)c2c3ccc(C(=O)N(C)C)cc3n(C(c3ccccc3)c3ccccc3)c2c1]

A solution of 9-benzhydryl-5-cyano-7-(3,5-dimethylisoxazol-4-yl)-9H-carbazole-2-carboxylic acid (25 mg, 0.050 mmol) in DMF (1 mL) in a scintillation vial was treated with TBTU (32.3 mg, 0.100 mmol), 2 M dimethylamine in THF (0.050 mL, 0.100 mmol) and TEA (0.014 mL, 0.100 mmol). The resulting mixture was then stirred at 25° C. for 2 hours. The mixture was diluted with water and extracted into ethyl acetate. The combined organic extracts were washed with water and brine and concentrated to give 9-benzhydryl-5-cyano-7-(3,5-dimethylisoxazol-4-yl)-N,N-dimethyl-9H-carbazole-2-carboxamide (26 mg, 0.045 mmol, 90% yield) as a white solid.

LCMS: Waters Sunfire C18 2.1×30 mm 2.5 u (4 min grad) 0-100% B. Flow Rate=1 ml/min. Inj. Vol.=3 uL. Oven Temp.=40° C. Solvent A: 10% MeOH-90% $H_2O$-0.1% TFA. Solvent B: 90% MeOH-10% $H_2O$-0.1% TFA. LCMS: RT=3.67 min; (ES): m/z $(M+H)^+$=525.16

Step 2: 7-(3,5-Dimethyl-4-isoxazolyl)-9-(diphenylmethyl)-N~2~,N~2~-dimethyl-9H-carbazole-2,5-dicarboxamide A solution of 9-benzhydryl-5-cyano-7-(3,5-dimethylisoxazol-4-yl)-N,N-dimethyl-9H-carbazole-2-carboxamide (26 mg, 0.050 mmol) in DMSO (3 mL) was treated with $K_2CO_3$ (47.9 mg, 0.347 mmol) and 50% Aqueous $H_2O_2$ (0.304 mL, 4.96 mmol). The resulting mixture was then stirred at 25° C. for 1.5 hrs. Next, more 50% aqueous $H_2O_2$ (0.304 mL, 4.96 mmol) was added and stirring was continued for 1 hr to complete reaction. Next, the reaction was diluted with water and extracted into ethyl acetate. The combined organic extracts were washed with water and concentrated to give a white solid.

The crude material was purified via preparative HPLC using the following conditions: Column: Waters XBridge C18, 19×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 10 minutes, then a 5-minute hold at 100% B; Flow: 20 mL/min. Fractions containing the desired product were combined and dried via centrifugal evaporation to give 7-(3,5-dimethyl-4-isoxazolyl)-9-(diphenylmethyl)-N~2~,N~2~-dimethyl-9H-carbazole-2,5-dicarboxamide (26.5 mg, 96% yield). The estimated purity of the product by LCMS analysis was 100%.

Two analytical LCMS injections were used to determine the final purity.

Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Injection 2 conditions: Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. Proton NMR was acquired in deuterated DMSO.

HPLC Purity @ 220 nm: 100%. LCMS: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

LCMS: RT=1.70 min; (ES): m/z $(M+H)^+$=543.23.

$^1$H NMR (500 MHz, DMSO-$d_6$) δ 8.38 (d, J=7.9 Hz, 1H), 8.17 (s, 1H), 7.94 (s, 1H), 7.74 (s, 1H), 7.67 (s, 1H), 7.45-7.30 (m, 7H), 7.27-7.18 (m, 6H), 2.95 (br. s., 2H), 2.77 (br. s., 3H), 2.27 (s, 3H), 2.08 (s, 3H)

Example 196

2-(3,5-Dimethyl-4-isoxazolyl)-9-(diphenylmethyl)-7-(4-morpholinylcarbonyl)-9H-carbazole-4-carboxamide

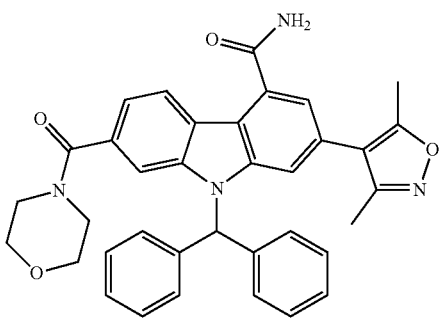 [SMILES: Cc1noc(C)c1-c1cc(C(N)=O)c2c3ccc(C(=O)N4CCOCC4)cc3n(C(c3ccccc3)c3ccccc3)c2c1]

Step 1: 9-Benzhydryl-2-(3,5-dimethylisoxazol-4-yl)-7-(morpholine-4-carbonyl)-9H-carbazole-4-carbonitrile

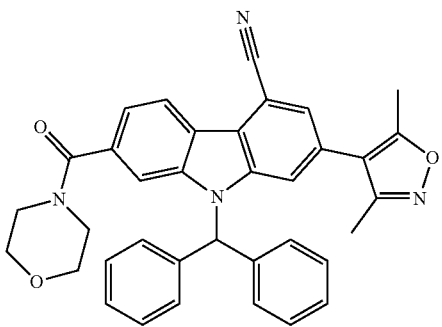 [SMILES: Cc1noc(C)c1-c1cc(C#N)c2c3ccc(C(=O)N4CCOCC4)cc3n(C(c3ccccc3)c3ccccc3)c2c1]

A solution of 9-benzhydryl-5-cyano-7-(3,5-dimethylisoxazol-4-yl)-9H-carbazole-2-carboxylic acid (25 mg, 0.050 mmol) in DMF (1 mL) in a scintillation vial was treated with TBTU (32.3 mg, 0.100 mmol), morpholine (8.76 µl, 0.100 mmol) and TEA (0.014 mL, 0.100 mmol) and stirred at 25° C. for 2 hours. The mixture was diluted with water and extracted into ethyl acetate. The combined organic extracts were washed with water and concentrated to give 9-benzhydryl-2-(3,5-dimethylisoxazol-4-yl)-7-(morpholine-4-carbonyl)-9H-carbazole-4-carbonitrile (28 mg, 0.047 mmol, 93% yield) as a white solid. LCMS: Waters Sunfire C18 2.1×30 mm 2.5 u (4 min grad) 0-100% B. Flow Rate=1 ml/min. Inj. Vol.=3 uL. Oven Temp.=40° C. Solvent A: 10% MeOH-90% H2O-0.1% TFA. Solvent B: 90% MeOH-10% H2O-0.1% TFA. LCMS: RT=3.66 min; (ES): m/z (M+H)$^+$=567.17.

Step 2: 9-benzhydryl-2-(3,5-dimethylisoxazol-4-yl)-7-(morpholine-4-carbonyl)-9H-carbazole-4-carboxamide A solution of 9-benzhydryl-2-(3,5-dimethylisoxazol-4-yl)-7-(morpholine-4-carbonyl)-9H-carbazole-4-carbonitrile (28 mg, 0.049 mmol) in DMSO (3 mL) was treated with $K_2CO_3$ (47.8 mg, 0.346 mmol) and 50% aqueous $H_2O_2$ (0.303 mL, 4.94 mmol). The mixture was then stirred at 25° C. for 2 hours. The mixture was diluted with water and extracted into ethyl acetate. The combined organic extracts were washed with water and concentrated to give a white solid.

The material was purified via preparative HPLC using the following conditions: Column: Waters XBridge C18, 19×100 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-100% B over 10 minutes, then a 5-minute hold at 100% B; Flow: 20 mL/min. Fractions containing the desired product were combined and dried via centrifugal evaporation to give 2-(3,5-dimethyl-4-isoxazolyl)-9-(diphenylmethyl)-7-(4-morpholinylcarbonyl)-9H-carbazole-4-carboxamide (25.1 mg, 86% yield). The estimated purity of the product by LCMS analysis was 100%.

Two analytical LCMS injections were used to determine the final purity.

Injection 1 conditions: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Injection 2 conditions: Column: Waters Acquity UPLC BEH C18, 2.1×50 mm, 1.7-µm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. Proton NMR was acquired in deuterated DMSO.

HPLC Purity @ 220 nm: 100%. LCMS: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

LCMS: RT=1.67 min; (ES): m/z (M+H)$^+$=585.23.

$^1$H NMR (500 MHz, DMSO-$d_6$) δ 8.41 (d, J=8.5 Hz, 1H), 8.18 (s, 1H), 7.95 (s, 1H), 7.75 (s, 1H), 7.69 (s, 1H), 7.46-7.33 (m, 7H), 7.30-7.19 (m, 6H), 3.7-3.3 (m, 8H), 2.29 (s, 3H), 2.10 (s, 3H).

Example 197

2-(3,5-dimethyl-4-isoxazolyl)-7-(1-hydroxy-1-methylethyl)-9-(tetrahydro-2H-pyran-4-ylmethyl)-9H-carbazole-4-carboxamide

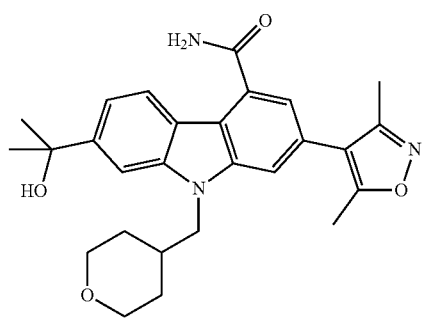 [SMILES: Cc1noc(C)c1-c1cc(C(N)=O)c2c3ccc(C(C)(C)O)cc3n(CC3CCOCC3)c2c1]

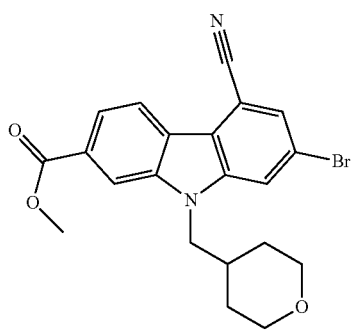 [SMILES: COC(=O)c1ccc2c3c(C#N)cc(Br)cc3n(CC3CCOCC3)c2c1]

Step 1. Methyl 7-bromo-5-cyano-9-((tetrahydro-2H-pyran-4-yl)methyl)-9H-carbazole-2-carboxylate In a 5 mL vial was methyl 7-bromo-5-cyano-9H-carbazole-2-carboxylate (50 mg, 0.152 mmol), 4-(bromomethyl)tetrahydro-2H-pyran (54.4 mg, 0.304 mmol), and $Cs_2CO_3$ (99 mg, 0.304 mmol) in DMF (0.5 mL). The mixture heated on a 70° C. heating block for 2 hours then cooled to room temperature. Water (3 mL) was added and the solid precipitate collected by filtration and rinsed with water. The solid was dried under vacuum to give 40.6 mg (70% yield) of methyl 7-bromo-5-cyano-9-((tetrahydro-2H-pyran-4-yl)methyl)-9H-carbazole-2-carboxylate as a white solid. HPLC: RT=3.498 min. ($H_2O$/MeOH with TFA, Chromolith ODS S5 4.6×50 mm, gradient=4 min, wavelength=220 nm). This was used without further purification in next reaction.

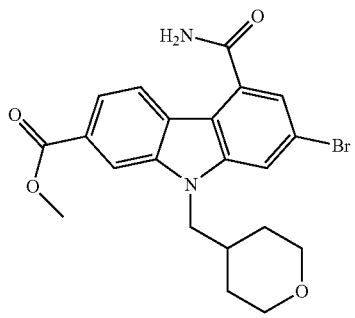 [SMILES: COC(=O)c1ccc2c3c(C(N)=O)cc(Br)cc3n(CC3CCOCC3)c2c1]

Step 2. Methyl 7-bromo-5-carbamoyl-9-((tetrahydro-2H-pyran-4-yl)methyl)-9H-carbazole-2-carboxylate In a 20 mL vial was methyl 7-bromo-5-cyano-9-((tetrahydro-2H-pyran-4-yl)methyl)-9H-carbazole-2-carboxylate (46 mg, 0.108 mmol) and $K_2CO_3$ (29.8 mg, 0.215 mmol) in DMSO (2 mL). To the mixture was added $H_2O_2$, 50% aq (0.198 mL, 3.23 mmol) and the reaction stirred at room temperature for 1 hour. Water (10 mL) was added and then extracted twice with EtOAc. The combined organic layers were concentrated and the crude material triturated with $CH_2Cl_2$. The solid was collected by filtration and dried under vacuum to give 23.3 mg (48% yield) of methyl 7-bromo-5-carbamoyl-9-((tetrahydro-2H-pyran-4-yl)methyl)-9H-carbazole-2-carboxylate as a white solid. MS (ES):m/z=445 [M+H$^+$]; HPLC: RT=2.500 min. ($H_2O$/MeOH with TFA, Chromolith ODS S5 4.6×50 mm, gradient=4 min, wavelength=220 nm). This was used without further purification in next reaction.

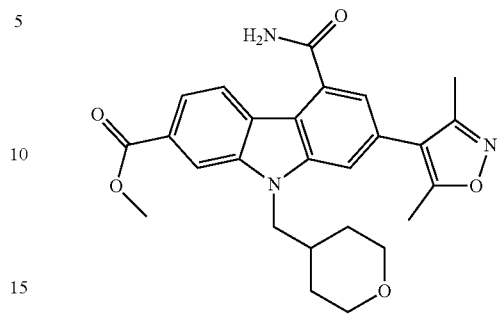

Step 3. Methyl 5-carbamoyl-7-(3,5-dimethylisoxazol-4-yl)-9-((tetrahydro-2H-pyran-4-yl)methyl)-9H-carbazole-2-carboxylate In a 5 mL vial was methyl 7-bromo-5-carbamoyl-9-((tetrahydro-2H-pyran-4-yl)methyl)-9H-carbazole-2-carboxylate (23 mg, 0.052 mmol), (3,5-dimethylisoxazol-4-yl)boronic acid (10.92 mg, 0.077 mmol), and tripotassium phosphate, 2M aq (0.077 mL, 0.155 mmol) in THF (0.5 mL). $PdCl_2$(dppf)-$CH_2Cl_2$Adduct (4.22 mg, 5.16 µmol) was added and N2 bubbled through reaction for 1 min. The reaction was sealed and heated on an 80° C. heating block for 1.5 hours. After cooling to room temperature the reaction was concentrated and purified directly on silica gel column (12 g) eluting with a gradient from 100% $CH_2Cl_2$ to 100% EtOAc. Fractions containing the product were collected, concentrated and dried under vacuum to give 21.8 mg (91% yield) of methyl 5-carbamoyl-7-(3,5-dimethylisoxazol-4-yl)-9-((tetrahydro-2H-pyran-4-yl)methyl)-9H-carbazole-2-carboxylate as a white solid. MS (ES):m/z=462 [M+H$^+$]; HPLC: RT=2.490 min. ($H_2O$/MeOH with TFA, Chromolith ODS S5 4.6×50 mm, gradient=4 min, wavelength=220 nm).

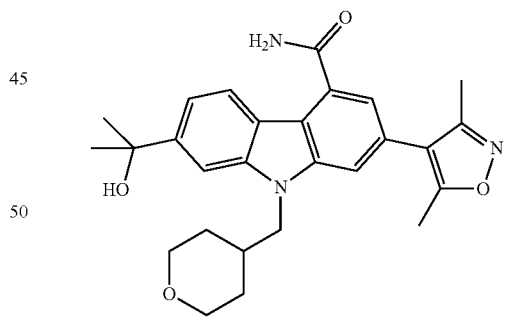

Step 4. 2-(3,5-dimethyl-4-isoxazolyl)-7-(1-hydroxy-1-methylethyl)-9-(tetrahydro-2H-pyran-4-ylmethyl)-9H-carbazole-4-carboxamide In a 5 mL vial was methyl 5-carbamoyl-7-(3,5-dimethylisoxazol-4-yl)-9-((tetrahydro-2H-pyran-4-yl)methyl)-9H-carbazole-2-carboxylate (21.8 mg, 0.047 mmol) in THF (2 mL). The mixture cooled in −78° C. bath then methyllithium, 1.6M in Et2O (0.177 mL, 0.283 mmol) was added dropwise. The reaction was stirred in −78° C. bath for 1.5 hours then it was quenched with saturated aqueous $NH_4Cl$ and warmed to room temperature. The mixture was extracted twice with EtOAc and the combined organic layers were concentrated. The crude material was purified on silica gel column (40 g) and eluted with a gradient from 100% CH₂Cl₂ to 5% MeOH/CH₂Cl₂. Fractions containing the product were collected, concentrated and dried to give 10.1 mg (44% yield) of 2-(3,5-dimethyl-4-isoxazolyl)-7-(1-hydroxy-1-methylethyl)-9-(tetrahydro-2H-pyran-4-ylmethyl)-9H-carbazole-4-carboxamide as a white solid.

MS (ES):m/z=462 [M+H⁺]; HPLC: RT=2.265 min. (H₂O/MeOH with TFA, Chromolith ODS S5 4.6×50 mm, gradient=4 min, wavelength=220 nm). ¹H NMRel18ell (500 MHz, CHLOROFORM-d) δ 8.47 (d, J=8.3 Hz, 1H), 7.67 (d, J=1.1 Hz, 1H), 7.35 (d, J=1.4 Hz, 1H), 7.33 (dd, J=8.5, 1.5 Hz, 1H), 7.30 (d, J=1.1 Hz, 1H), 6.13-5.82 (m, 2H), 4.26 (d, J=7.2 Hz, 2H), 3.97 (d, J=11.1 Hz, 2H), 3.31 (td, J=11.2, 3.5 Hz, 2H), 2.49 (s, 3H), 2.34 (s, 3H), 2.27 (d, J=4.7 Hz, 1H), 1.87 (s, 1H), 1.72 (s, 6H), 1.58-1.55 (m, 3H), 1.53-1.49 (m, 1H).

Example 198 & 199

2-(Dimethyl-1,2-oxazol-4-yl)-7-(2-hydroxypropan-2-yl)-9-[(R)-oxan-4-yl(phenyl)methyl]-9H-carbazole-4-carboxamide Enantiomer A, Example 198

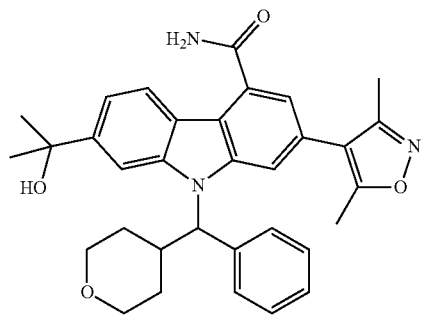

Enantiomer B, Example 199

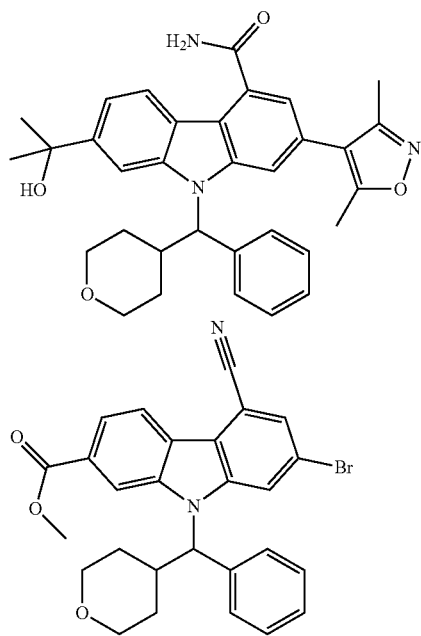

Step 1: Methyl 7-bromo-5-cyano-9-(phenyl(tetrahydro-2H-pyran-4-yl)methyl)-9H-carbazole-2-carboxylate To a 40 mL vial containing methyl 7-bromo-5-cyano-9H-carbazole-2-carboxylate (Step 2 of Example 182, 795 mg, 2.42 mmol) and phenyl(tetrahydro-2H-pyran-4-yl)methanol (methyl 7-bromo-5-cyano-9H-carbazole-2-carboxylate (795 mg, 2.42 mmol) [Orjales, A. et al. J. Med. Chem. 2003, 46, 5512-5532] in THF (16 mL) was added Ph₃P (1.27 g, 4.83 mmol) and DIAD (0.94 mL, 4.83 mmol) at 0° C. The resulting reaction mixture was stirred at room temperature for 2 h and then concentrated. The residue was purified using ISCO silica gel chromatography (220 g column, gradient from 0% to 20% EtOAc/CH₂Cl₂) to give the title compound (1.02 g, 84%) as an impure mixture which was carried on to the subsequent step without further purification. HPLC RT=3.72 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

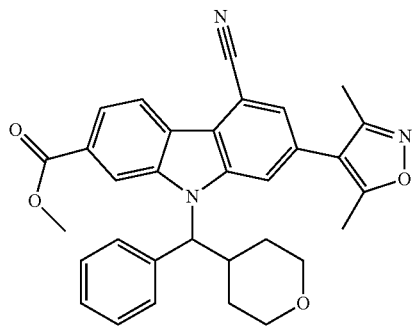 [SMILES: COC(=O)c1ccc2c3c(C#N)cc(-c4c(C)noc4C)cc3n(C(c3ccccc3)C3CCOCC3)c2c1]

Step 2: Methyl 5-cyano-7-(3,5-dimethylisoxazol-4-yl)-9-(phenyl(tetrahydro-2H-pyran-4-yl)methyl)-9H-carbazole-2-carboxylate To a 100 mL round bottom flask containing methyl 7-bromo-5-cyano-9-(phenyl(tetrahydro-2H-pyran-4-yl)methyl)-9H-carbazole-2-carboxylate (1.02 g, 2.03 mmol) and (3,5-dimethylisoxazol-4-yl)boronic acid (AOBChem, 0.43 g, 3.04 mmol) in THF (30 mL) was added tripotassium phosphate (2M aq., 3.0 mL, 6.08 mmol) to give a orange solution. Pd(dppf)Cl₂—CH₂Cl₂ (0.17 g, 0.20 mmol) was then added and N₂ was bubbled into the mixture for 4 min. The resulting reaction mixture was heated at 80° C. for 4 h, concentrated and purified directly using ISCO silica gel chromatography (120 g column, gradient from 0% to 50% EtOAc/CH₂Cl₂). Trituration with cold EtOAc gave the title compound (410 mg, 39%) as a tan solid. HPLC RT=3.52 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

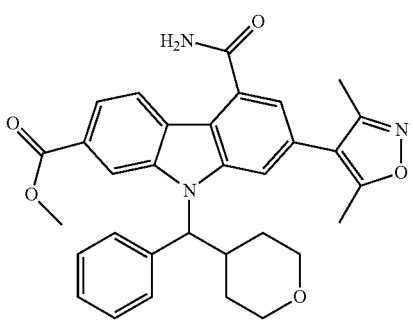 [SMILES: COC(=O)c1ccc2c3c(C(N)=O)cc(-c4c(C)noc4C)cc3n(C(c3ccccc3)C3CCOCC3)c2c1]

Step 3: Methyl 5-carbamoyl-7-(3,5-dimethylisoxazol-4-yl)-9-(phenyl(tetrahydro-2H-pyran-4-yl)methyl)-9H-carbazole-2-carboxylate Following a procedure analogous to that described for Example 187, methyl 5-cyano-7-(3,5-dimethylisoxazol-4-yl)-9-(phenyl(tetrahydro-2H-pyran-4-yl)methyl)-9H-carbazole-2-carboxylate (100 mg, 0.19 mmol) was converted to the title compound (97 mg, 94%). HPLC RT=2.78 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 4: 2-(Dimethyl-1,2-oxazol-4-yl)-7-(2-hydroxypropan-2-yl)-9-[-oxan-4-yl(phenyl)methyl]-9H-carbazole-4-carboxamide Following a procedure analogous to that described for Example 184, methyl 5-carbamoyl-7-(3,5-dimethylisoxazol-4-yl)-9-(phenyl(tetrahydro-2H-pyran-4-yl)methyl)-9H-carbazole-2-carboxylate (97 mg, 0.18 mmol) was converted to racemic 2-(dimethyl-1,2-oxazol-4-yl)-7-(2-hydroxypropan-2-yl)-9-[-oxan-4-yl(phenyl)methyl]-9H-carbazole-4-carboxamide (66 mg, 68%) which was separated using chiral prep SFC (Column: Chiral OJ-H 25×3 cm, 5 μm; Mobile Phase: 85/15 $CO_2$/MeOH; Flow: 85 mL/min) The faster eluting peak was concentrated to give a white solid which was assigned as Enantiomer A (30 mg, 43%). The slower eluting peak was treated in an identical manner and assigned as Enantiomer B (31 mg, 44%). Enantiomer A (2-(dimethyl-1,2-oxazol-4-yl)-7-(2-hydroxypropan-2-yl)-9-[(R)-oxan-4-yl(phenyl)methyl]-9H-carbazole-4-carboxamide): $^1$H NMR (500 MHz, CDCl$_3$) δ 8.43 (d, J=8.3 Hz, 1H), 7.88 (s, 1H), 7.44 (d, J=7.5 Hz, 2H), 7.37-7.29 (m, 4H), 7.22 (d, J=1.1 Hz, 1H), 6.07-5.80 (m, 2H), 5.63 (d, J=10.8 Hz, 1H), 4.06 (dd, J=11.7, 2.5 Hz, 1H), 3.87-3.79 (m, 1H), 3.57 (td, J=11.9, 1.9 Hz, 1H), 3.37-3.28 (m, 1H), 3.15 (d, J=10.8 Hz, 1H), 2.34 (br. s., 3H), 2.21 (s, 3H), 2.11 (d, J=13.6 Hz, 1H), 1.85 (s, 1H), 1.71 (s, 6H), 1.65 (d, J=9.4 Hz, 1H), 1.41-1.30 (m, 1H), 1.03 (d, J=11.9 Hz, 1H); LCMS (M+H)=538.4; HPLC RT=2.59 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=15.06 min (Column: Chiralcel OJ-H 250×4.6 mm, 5 μm; Mobile Phase: 85/15 $CO_2$/MeOH; Flow: 2 mL/min) Enantiomer B (2-(dimethyl-1,2-oxazol-4-yl)-7-(2-hydroxypropan-2-yl)-9-[(S)-oxan-4-yl(phenyl)methyl]-9H-carbazole-4-carboxamide): $^1$H NMR (500 MHz, CDCl$_3$) δ 8.43 (d, J=8.3 Hz, 1H), 7.88 (s, 1H), 7.44 (d, J=7.5 Hz, 2H), 7.38-7.29 (m, 4H), 7.22 (d, J=1.1 Hz, 1H), 6.08-5.79 (m, 2H), 5.63 (d, J=10.0 Hz, 1H), 4.06 (dd, J=11.8, 2.6 Hz, 1H), 3.83 (dd, J=11.8, 2.6 Hz, 1H), 3.57 (td, J=11.8, 1.9 Hz, 1H), 3.33 (td, J=11.9, 2.1 Hz, 1H), 3.15 (d, J=11.1 Hz, 1H), 2.34 (br. s., 3H), 2.21 (s, 3H), 2.11 (d, J=13.9 Hz, 1H), 1.85 (s, 1H), 1.71 (s, 6H), 1.68-1.59 (m, 1H), 1.41-1.30 (m, 1H), 1.03 (d, J=13.0 Hz, 1H); LCMS (M+H)=538.4; HPLC RT=2.59 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=17.33 min (Column: Chiralcel OJ-H 250×4.6 mm, 5 μm; Mobile Phase: 85/15 $CO_2$/MeOH; Flow: 2 mL/min) Note: Using a different chiral SFC conditions (Column: Chiral OD-H 25×3 cm, 5 μm; Mobile Phase: 60/40 $CO_2$/MeOH; Flow: 80 mL/min) the order of elution was reversed with Example 199 eluting first: SFC RT=3.55 min (Column: Chiralcel OD-H 250×4.6 mm, 5 μm; Mobile Phase: 60/40 $CO_2$/MeOH; Flow: 2 mL/min) and Example 198 eluting second: SFC RT=13.54 min (Column: Chiralcel OD-H 250×4.6 mm, 5 μm; Mobile Phase: 60/40 $CO_2$/MeOH; Flow: 2 mL/min).

Examples 200-218

The compounds in Table 12 were prepared according to the procedures described for Example 198:

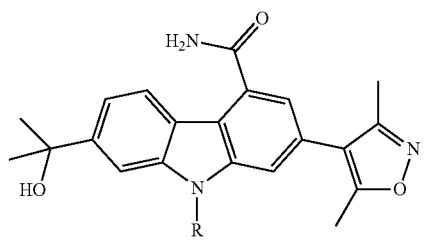

TABLE 12

| Example | R | LCMS (M + H) | HPLC RT (min) | HPLC Method |
|---|---|---|---|---|
| 200 Enantiomer A | ![](phenyl with CF3, CF3) | 618.4 | 9.45 | E |
| 201 Enantiomer B | ![](phenyl with CF3, CF3) | 618.4 | 11.72 | E |
| 202 Enantiomer A | ![](phenyl with Cl, CF3) | 584.3 | 3.98 | F |
| 203 Enantiomer B | ![](phenyl with Cl, CF3) | 584.3 | 6.03 | F |

TABLE 12-continued

| Example | R | LCMS (M + H) | HPLC RT (min) | HPLC Method |
|---|---|---|---|---|
| 204 Enantiomer A | 2,4,6-trifluorophenyl-(tetrahydropyran-4-yl)methyl | 592.3 | 5.39 | A |
| 205 Enantiomer B | 2,4,6-trifluorophenyl-(tetrahydropyran-4-yl)methyl | 592.3 | 7.67 | A |
| 206 Enantiomer A | 2,6-difluorophenyl-(tetrahydropyran-4-yl)methyl | 574.2 | 2.06 | G |
| 207 Enantiomer B | 2,6-difluorophenyl-(tetrahydropyran-4-yl)methyl | 574.2 | 3.46 | G |
| 208 Enantiomer A | 1-(pyridin-2-yl)-3,3,3-trifluoropropyl | 551.4 | 4.74 | B |
| 209 Enantiomer B | 1-(pyridin-2-yl)-3,3,3-trifluoropropyl | 551.4 | 5.86 | B |
| 210 Enantiomer A | 2-fluorophenyl-(tetrahydropyran-4-yl)methyl | 556.2 | 7.11 | A |
| 211 Enantiomer B | 2-fluorophenyl-(tetrahydropyran-4-yl)methyl | 556.2 | 9.38 | A |
| 212 Enantiomer A | 4-methoxyphenyl-(tetrahydropyran-4-yl)methyl | 569.5 | 5.89 | B |
| 213 Enantiomer B | 4-methoxyphenyl-(tetrahydropyran-4-yl)methyl | 569.5 | 13.30 | B |
| 214 Enantiomer A | 3-methoxyphenyl-(tetrahydropyran-4-yl)methyl | 569.5 | 4.97 | C |
| 215 Enantiomer B | 3-methoxyphenyl-(tetrahydropyran-4-yl)methyl | 569.5 | 11.10 | C |
| 216 Enantiomer A | 2,4-difluorophenyl-(tetrahydropyran-4-yl)methyl | 574.2 | 6.07 | A |
| 217 Enantiomer B | 2,4-difluorophenyl-(tetrahydropyran-4-yl)methyl | 574.2 | 7.72 | A |
| 218 | 1,1,1,5,5,5-hexafluoropentan-3-yl | 587.2 | 1.90 | D |

HPLC Conditions for Table 12:

Method A:

Column: Phenomenex Lux Cellulose 2, 250×4.6 mm, 5 μm particles; Mobile Phase: 60/40 $CO_2$/MeOH; Flow: 4 mL/min; Detection: UV at 220 nm.

Method B:

Column: Chiralcel OD-H 250×4.6 mm, 5 μm particles; Mobile Phase: 70/30 $CO_2$/MeOH; Flow: 2 mL/min; Detection: UV at 220 nm.

Method C:

Column: Chiralpak IB, 250×4.6 mm, 5 μm particles; Mobile Phase: 65/35 $CO_2$/MeOH; Flow: 2 mL/min; Detection: UV at 220 nm.

Method D:

Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-minute hold at 100% B; Flow: 1.11 mL/min; Detection: UV at 220 nm.

Method E:

Column: Regis Whelk-O R,R 250×4.6 mm ID, 5 μm particles; Mobile Phase: 75/25 $CO_2$/MeOH; Flow: 2 mL/min; Detection: UV at 220 nm.

Method F:

Column: Chiralcel OJ-H 250×4.6 mm, 5 μm particles; Mobile Phase: 80/20 $CO_2$/MeOH; Flow: 2 mL/min; Detection: UV at 220 nm.

Method G:

Column: Chiralcel OD-H 250×4.6 mm, 5 μm particles; Mobile Phase: 55/45 $CO_2$/(0.3% DEA in MeOH); Flow: 3 mL/min; Detection: UV at 249 nm.

Examples 219 & 220

2-(Dimethyl-1,2-oxazol-4-yl)-9-[(4-fluorophenyl)(oxan-4-yl)methyl]-7-(2-hydroxypropan-2-yl)-9H-carbazole-4-carboxamide Enantiomer A, Example 219

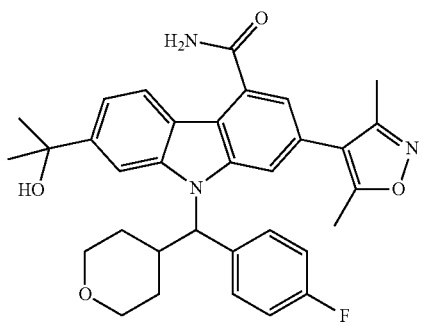

Enantiomer B, Example 220

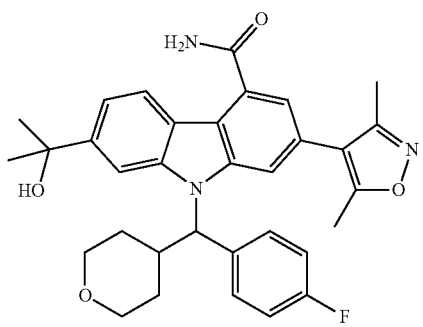

Step 1: (4-Fluorophenyl)(tetrahydro-2H-pyran-4-yl)methanol

To a 40 mL vial containing magnesium (0.39 g, 16.1 mmol) in THF (15 mL) was slowly added 4-bromotetrahydro-2H-pyran (PharmaBlock, 1.8 mL, 16.1 mmol) cooling in a water bath as needed. The resulting reaction mixture was stirred at room temperature for 1.5 h and then cooled in a water bath. 4-Fluorobenzaldehyde (Aldrich, 1.2 mL, 10.7 mmol) was added slowly. The resulting orange reaction mixture was removed from the water bath and quenched with sat. $NH_4Cl$ after 10 min. 10% LiCl solution was added and the mixture was extracted with $Et_2O$ (2×). The organic layer was dried over $MgSO_4$, filtered and concentrated. The residue was purified using ISCO silica gel chromatography (80 g column, gradient from 0% to 50% EtOAc/hexanes) to give the title compound (1.12 g, 33%) as a colorless oil. $^1$H NMR (500 MHz, CDCl$_3$) δ 7.31-7.27 (m, 2H), 7.08-7.02 (m, 2H), 4.37 (dd, J=7.7, 2.4 Hz, 1H), 4.06-3.99 (m, 1H), 3.94-3.87 (m, 1H), 3.37 (td, J=11.9, 2.2 Hz, 1H), 3.29 (td, J=11.8, 2.3 Hz, 1H), 1.94-1.87 (m, 2H), 1.81 (tdt, J=11.6, 7.7, 3.8 Hz, 1H), 1.45 (qd, J=12.3, 4.7 Hz, 1H), 1.36-1.27 (m, 1H), 1.16 (ddq, J=13.2, 3.9, 2.0 Hz, 1H); LCMS (M+H—H$_2$O)=193.1; HPLC RT=1.65 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 2: 2-(Dimethyl-1,2-oxazol-4-yl)-9-[(4-fluorophenyl)(oxan-4-yl)methyl]-7-(2-hydroxypropan-2-yl)-9H-carbazole-4-carboxamide Following procedures analogous to those described for Example 198, methyl 7-bromo-5-cyano-9H-carbazole-2-carboxylate (Step 2 of Example 182) and (4-fluorophenyl)(tetrahydro-2H-pyran-4-yl)methanol were converted to racemic 2-(dimethyl-1,2-oxazol-4-yl)-9-[(4-fluorophenyl)(oxan-4-yl)methyl]-7-(2-hydroxypropan-2-yl)-9H-carbazole-4-carboxamide which was separated by chiral prep SFC to give Enantiomer A and Enantiomer B. Enantiomer A: $^1$H NMR (400 MHz, CDCl$_3$) δ 8.44 (d, J=8.4 Hz, 1H), 7.87 (s, 1H), 7.43 (dd, J=8.7, 5.3 Hz, 2H), 7.37-7.31 (m, 2H), 7.25 (s, 1H), 7.06-6.98 (m, 2H), 6.05 (br. s., 1H), 5.91 (br. s., 1H), 5.60 (d, J=10.0 Hz, 1H), 4.13-4.03 (m, J=3.4 Hz, 1H), 3.88-3.79 (m, 1H), 3.62-3.53 (m, 1H), 3.38-3.29 (m, 1H), 3.12 (d, J=10.1 Hz, 1H), 2.38 (s, 3H), 2.24 (s, 3H), 2.07 (d, J=14.2 Hz, 1H), 1.89 (s, 1H), 1.72 (s, 6H), 1.65 (d, J=16.4 Hz, 1H), 1.41-1.31 (m, 1H), 1.06 (d, J=13.2 Hz, 1H); LCMS (M+H)=556.4; HPLC RT=2.59 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=8.80 min (Column: Chiralcel OD-H 250×4.6 mm, 5 μm; Mobile Phase: 75/25 CO$_2$/MeOH; Flow: 2 mL/min). Enantiomer B: $^1$H NMR (400 MHz, CDCl$_3$) δ 8.44 (d, J=8.4 Hz, 1H), 7.87 (s, 1H), 7.43 (dd, J=8.7, 5.3 Hz, 2H), 7.37-7.31 (m, 2H), 7.25 (s, 1H), 7.06-6.98 (m, 2H), 6.05 (br. s., 1H), 5.91 (br. s., 1H), 5.60 (d, J=10.0 Hz, 1H), 4.13-4.03 (m, J=3.4 Hz, 1H), 3.88-3.79 (m, 1H), 3.62-3.53 (m, 1H), 3.38-3.29 (m, 1H), 3.12 (d, J=10.1 Hz, 1H), 2.38 (s, 3H), 2.24 (s, 3H), 2.07 (d, J=14.2 Hz, 1H), 1.89 (s, 1H), 1.72 (s, 6H), 1.65 (d, J=16.4 Hz, 1H), 1.41-1.31 (m, 1H), 1.06 (d, J=13.2 Hz, 1H); LCMS (M+H)=556.4; HPLC RT=2.59 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=13.12 min (Column: Chiralcel OD-H 250×4.6 mm, 5 μm; Mobile Phase: 75/25 CO$_2$/MeOH; Flow: 2 mL/min).

Examples 221 & 222

2-(Dimethyl-1,2-oxazol-4-yl)-9-[(1-fluorocyclobutyl)(phenyl)methyl]-7-(2-hydroxypropan-2-yl)-9H-carbazole-4-carboxamide Enantiomer A, Example 221

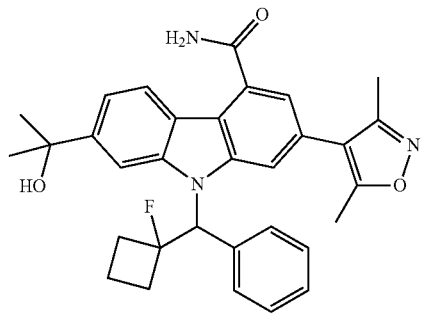

Enantiomer B, Example 222

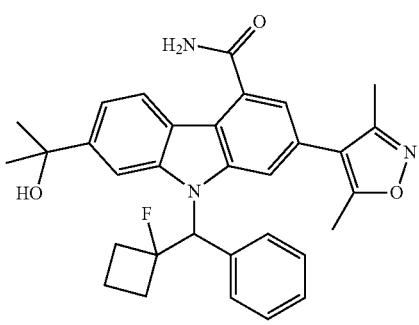

Step 1: (1-Fluorocyclobutyl)(phenyl)methanone

A suspension of Accufluor™ NFTh (Aldrich, 50% on alumina, 6.03 g, 9.36 mmol) and cyclobutyl(phenyl)methanone (0.75 g, 4.68 mmol) [Bauser, M. et al. PCT Int. Appl., 2005, WO2005039569] in MeOH (46.8 ml) was divided between two 40 mL pressure vials and stirred overnight at 70° C. Additional Accufluor™ NFTh (2.0 g) was added and heating was continued overnight. The reaction was cooled, then decanted and concentrated. $CH_2Cl_2$ was added, and the insoluble material was filtered off. The organic layer was washed sequentially with water and sat. NaCl, then dried with $Na_2SO_4$ and concentrated to give the crude title compound (600 mg, 72%), which was used in the subsequent step without further purification. $^1$H NMR (400 MHz, $CDCl_3$) δ 7.90-8.05 (2H, m), 7.52-7.63 (1H, m), 7.41-7.50 (2H, m), 2.71-2.91 (2H, m), 2.42-2.64 (2H, m), 2.00 (1H, dd, J=11.1, 3.7 Hz), 1.74 (1H, dtd, J=11.2, 8.9, 8.9, 2.3 Hz).

Step 2: 2-(Dimethyl-1,2-oxazol-4-yl)-9-[(1-fluorocyclobutyl)(phenyl)methyl]-7-(2-hydroxypropan-2-yl)-9H-carbazole-4-carboxamide Following procedures analogous to those described for Example 198, methyl 7-bromo-5-cyano-9H-carbazole-2-carboxylate (Step 2 of Example 182) and (1-fluorocyclobutyl)(phenyl)methanone were converted to racemic 2-(dimethyl-1,2-oxazol-4-yl)-9-[(1-fluorocyclobutyl)(phenyl)methyl]-7-(2-hydroxypropan-2-yl)-9H-carbazole-4-carboxamide which was separated by chiral prep SFC to give Enantiomer A and Enantiomer B. Enantiomer A: $^1$H NMR (400 MHz, $CD_3OD$) δ 8.37 (d, J=6.7 Hz, 1H), 8.05 (br s, 1H), 7.43 (d, J=8.1 Hz, 1H), 7.35-7.23 (m, 6H), 7.21 (br s, 1H), 6.59-6.46 (m, 1H), 2.91-2.76 (m, 2H), 2.34-2.16 (m, 5H), 2.04 (d, J=6.8 Hz, 5H), 1.69 (br s, 6H); LCMS (M+H)=526.5; SFC RT=5.28 min (Column: Chiralcel OD-H 250×4.6 mm, 5 μm; Mobile Phase: 70/30 $CO_2$/MeOH; Flow: 2 mL/min). Enantiomer B: $^1$H NMR (400 MHz, $CD_3OD$) δ 8.37 (br s, 1H), 8.05 (br s, 1H), 7.43 (d, J=6.8 Hz, 1H), 7.29 (br s, 6H), 7.21 (br s, 1H), 6.60-6.44 (m, 1H), 2.89-2.76 (m, 2H), 2.30-2.15 (m, 5H), 2.03 (br s, 5H), 1.69 (br s, 6H); LCMS (M+H)=526.5; SFC RT=14.56 min (Column: Chiralcel OD-H 250×4.6 mm, 5 μm; Mobile Phase: 75/25 $CO_2$/MeOH; Flow: 2 mL/min).

Examples 223 & 224

2-(Dimethyl-1,2-oxazol-4-yl)-8-fluoro-9-[(4-fluorophenyl)(oxan-4-yl)methyl]-7-(2-hydroxypropan-2-yl)-9H-carbazole-4-carboxamide Enantiomer A, Example 223

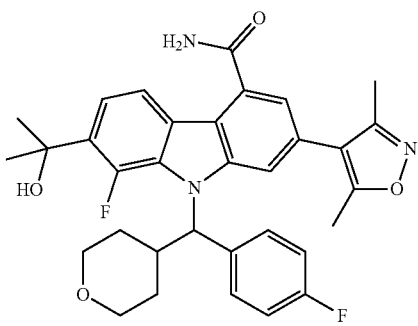

Enantiomer B, Example 224

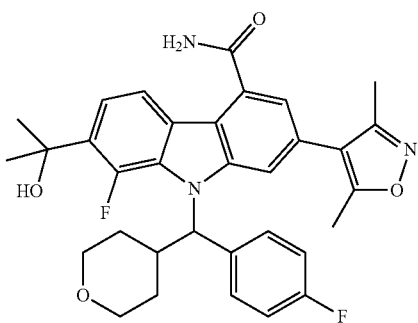

Step 1: Methyl 3-((3-cyano-5-(3,5-dimethylisoxazol-4-yl)phenyl)amino)-2-fluorobenzoate

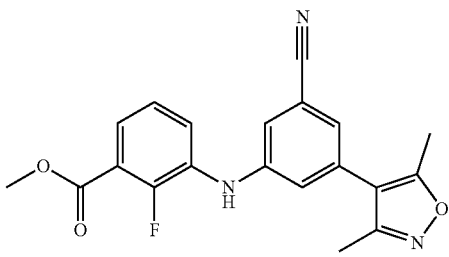 [SMILES: COC(=O)c1cccc(Nc2cc(C#N)cc(-c3c(C)noc3C)c2)c1F]

A mixture of was methyl 3-bromo-2-fluorobenzoate (5.20 g, 22.33 mmol), 3-amino-5-(3,5-dimethylisoxazol-4-yl)benzonitrile (5 g, 23.45 mmol), 2ND GENERATION XPHOS PRECATALYST (260 mg, 0.330 mmol), and $Cs_2CO_3$ (21.83 g, 67.0 mmol) in Toluene (150 mL) was added to a 25 ml screw top vial flask. Nitrogen was bubbled through the mixture for a few minutes and then it was sealed with a septum cap, evacuated and flushed with nitrogen several times. Next, the mixture was heated to 110° C. temperature. After 16 hours, 2ND GENERATION XPHOS PRECATALYST (100 mg, 0.127 mmol) was added and heating was continued at 110° C. overnight. After 40 hours, methyl 3-bromo-2-fluorobenzoate (2 g, 8.58 mmol) was added and heating was continued at 110° C. overnight. Analysis by LCMS showed reaction complete. The reaction mixture was evaporated to dryness and diluted with 50 ml ethyl acetate and 50 ml MeOH, filtered and concentrated. The residue was chromatographed on an ISCO Companion 40 g silica gel column and eluted with EtOAc/DCM (0-100%) to methyl 3-((3-cyano-5-(3,5-dimethylisoxazol-4-yl)phenyl)amino)-2-fluorobenzoate (7.5 g, 20.53 mmol, 92% yield) as a tan solid.

LCMS: Waters Acquity BEH C18 2×50 mm 1.7 u (1.5 min grad) 0-100% B. Flow Rate=1 ml/min. Inj. Vol.=1 uL. Oven Temp.=40C. Solvent A: 10% MeOH-90% $H_2O$-0.1% TFA. Solvent B: 90% MeOH-10% H2O-0.1% TFA. LCMS: RT=1.24 min; (ES): m/z (M+H)$^+$=366.25 $^1$H NMR (400 MHz, DMSO-$d_6$) δ 8.65 (s, 1H), 7.64 (td, J=7.8, 1.5 Hz, 1H), 7.52 (ddd, J=7.9, 6.4, 1.8 Hz, 1H), 7.35-7.23 (m, 3H), 7.19 (s, 1H), 3.88 (s, 3H), 2.43 (s, 3H), 2.25 (s, 3H)

Step 2: Methyl 5-cyano-7-(3,5-dimethylisoxazol-4-yl)-1-fluoro-9H-carbazole-2-carboxylate

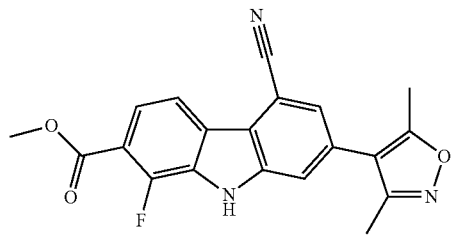 [SMILES: COC(=O)c1ccc2c([nH]c3cc(-c4c(C)noc4C)cc(C#N)c32)c1F]

A mixture of methyl 3-((3-cyano-5-(3,5-dimethylisoxazol-4-yl)phenyl)amino)-2-fluorobenzoate (7.5 g, 20.53 mmol), PdOAc$_2$ (0.922 g, 4.11 mmol), and $K_2CO_3$ (0.567 g, 4.11 mmol) in pivalic acid (103 ml) was heated to 110° C. with air bubbling through the solution for 24 hrs. PdOAc$_2$ (0.922 g, 4.11 mmol) and in pivalic acid (103 ml) was added and continued heating at 110° C. with air bubbling through the solution for 24 hrs. The reaction mixture is concentrate under reduced pressure and dried under high vacuum. The crude product was suspended in a 40 ml of THF/MeOH filtered. 30 g of silica gel was added and rotovap and chromatographed using a solid loading cartridge on an ISCO Companion 330 g silica gel column and eluted with EtOAc/DCM gradient (0-100%) to give methyl 5-cyano-7-(3,5-dimethylisoxazol-4-yl)-1-fluoro-9H-carbazole-2-carboxylate (2.86 g, 8.87 mmol, 38.3% yield) as a tan solid.

LCMS: Waters Acquity BEH C18 2×50 mm 1.7 u (1.5 min grad) 0-100% B. Flow Rate=1 ml/min. Inj. Vol.=1 uL. Oven Temp.=40C. Solvent A: 10% MeOH-90% $H_2O$-0.1% TFA. Solvent B: 90% MeOH-10% H2O-0.1% TFA. LCMS: RT=1.28 min; (ES): m/z (M+H)$^+$=364. $^1$H NMR (400 MHz, DMSO-$d_6$) δ 12.73 (s, 1H), 8.22 (d, J=8.4 Hz, 1H), 7.88-7.84 (m, 2H), 7.80 (dd, J=8.4, 6.4 Hz, 1H), 3.94 (s, 3H), 2.50 (s, 3H), 2.31 (s, 3H)

Step 3: 2-(Dimethyl-1,2-oxazol-4-yl)-8-fluoro-9-[(4-fluorophenyl)(oxan-4-yl)methyl]-7-(2-hydroxypropan-2-yl)-9H-carbazole-4-carboxamide Following procedures analogous to those described for Example 198, methyl 5-cyano-7-(3,5-dimethylisoxazol-4-yl)-1-fluoro-9H-carbazole-2-carboxylate and (4-fluorophenyl)(tetrahydro-2H-pyran-4-yl)methanol were converted to racemic 2-(dimethyl-1,2-oxazol-4-yl)-8-fluoro-9-[(4-fluorophenyl)(oxan-4-yl)methyl]-7-(2-hydroxypropan-2-yl)-9H-carbazole-4-carboxamide which was separated by chiral prep SFC to give Enantiomer A and Enantiomer B. Enantiomer A: $^1$H NMR (500 MHz, DMSO-$d_6$) δ 8.10 (br. s., 1H), 8.02 (d, J=8.4 Hz, 1H), 7.74-7.59 (m, 3H), 7.52-7.33 (m, 3H), 7.25-7.06 (m, 2H), 6.06 (br. s., 1H), 2.35 (br. s., 4H), 2.16 (br. s., 3H), 1.90 (d, J=12.5 Hz, 2H), 1.67 (d, J=5.4 Hz, 6H), 1.54 (br. s., 1H), 1.41 (br. s., 2H), 1.25 (d, J=12.8 Hz, 2H), 0.88 (br. s., 2H). LCMS: Waters Aquity UPLC BEH C18 2.1×50 mm 1.7 u (3 min grad) 0-100% B. Flow Rate=1 ml/min. Inj. Vol.=3 uL. Oven Temp.=50C. Solvent A: 5% ACN-95% $H_2O$-0.1% TFA. Solvent B: 95% ACN-15% H2O-0.1% TFA. LCMS: RT=1.73 min; (ES): m/z (M+H)$^+$=574.2; SFC RT=7.69 min (Column: Chiralpak IB, 250×4.6 mm, 5 µm particles; Mobile Phase: 65/35 $CO_2$/MeOH; Flow: 2 mL/min; Detection: UV at 220 nm. Enantiomer B: $^1$H NMR (500 MHz, DMSO-$d_6$) δ 8.10 (br. s., 1H), 8.02 (d, J=8.4 Hz, 1H), 7.74-7.59 (m, 3H), 7.52-7.33 (m, 3H), 7.25-7.06 (m, 2H), 6.06 (br. s., 1H), 2.35 (br. s., 4H), 2.16 (br. s., 3H), 1.90 (d, J=12.5 Hz, 2H), 1.67 (d, J=5.4 Hz, 6H), 1.54 (br. s., 1H), 1.41 (br. s., 2H), 1.25 (d, J=12.8 Hz, 2H), 0.88 (br. s., 2H). LCMS: LCMS: Waters Aquity UPLC BEH C18 2.1×50 mm 1.7 u (3 min grad) 0-100% B. Flow Rate=1 ml/min. Inj. Vol.=3 uL. Oven Temp.=50C. Solvent A: 5% ACN-95% $H_2O$-0.1% TFA. Solvent B: 95% ACN-15% H2O-0.1% TFA. LCMS: RT=1.73 min; (ES): m/z (M+H)$^+$=574.3; SFC RT=8.42 min (Column: Chiralpak IB, 250×4.6 mm, 5 µm particles; Mobile Phase: 65/35 $CO_2$/MeOH; Flow: 2 mL/min; Detection: UV at 220 nm.

Example 225 rel-2-(dimethyl-1,2-oxazol-4-yl)-9-{[(1R,2S,4S)-2-fluoro-7-oxabicyclo[2.2.1]heptan-2-yl]methyl}-7-(2-hydroxypropan-2-yl)-9H-carbazole-4-carboxamide

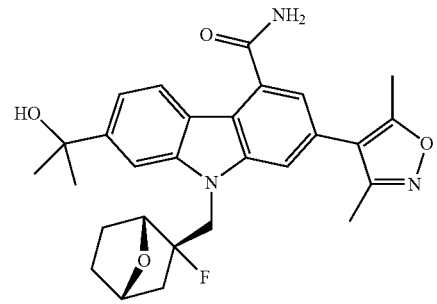 [SMILES: Cc1noc(C)c1-c1cc(C(N)=O)c2c3ccc(C(C)(C)O)cc3n(C[C@@]3(F)C[C@@H]4CC[C@H]3O4)c2c1]

Step 1: 2-bromo-7-(2-hydroxypropan-2-yl)-9H-carbazole-4-carbonitrile

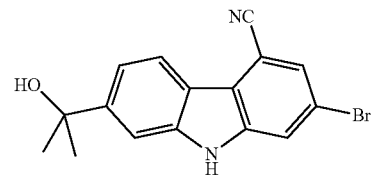 [SMILES: CC(C)(O)c1ccc2c(c1)[nH]c1cc(Br)cc(C#N)c12]

A solution of methyl 7-bromo-5-cyano-9H-carbazole-2-carboxylate (3 g, 9.11 mmol) in Tetrahydrofuran (75 mL) in a RB flask equipped with septum was cooled in bath to −78° C. and treated drop wise via syringe with methyllithium, 3 M in diethoxymethane (18.23 mL, 54.7 mmol) and then stirred in bath at −78° C. for 1 hour. The mixture was quenched with methanol, poured into aqueous sat'd NH$_4$Cl and extracted into ethyl acetate. Washed with water and brine and concentrated to give 2-bromo-7-(2-hydroxypropan-2-yl)-9H-carbazole-4-carbonitrile (2.95 g, 8.96 mmol, 98% yield) as a yellow-orange solid. This was used without further purification in next step.

HPLC: RT=2.96 min; (Column: Chromolith ODS S5 4.6×50 mm (4 min grad) 0-100% B. Flow Rate=4 ml/min. Inj. Vol.=10 uL. Wavelength=220. Oven Temp.=40. Solvent A: 10% MeOH-90% H2O-0.1% TFA. Solvent B: 90% MeOH-10% H2O-0.1% TFA).

LCMS: RT=0.96 min; (ES): m/z (M+H—H$_2$O)$^+$=311.1, 313.1 (Column: Waters Acquity SDS. Column: BEH C18 2.1×50 mm 17 u (1.6 min grad) 2-98% B. Flow Rate=0.8 ml/min. Solvent A: H2O-0.1% TFA. Solvent B: Acetonitrile-0.1% TFA).

Step 2. 2-bromo-7-(2-hydroxypropan-2-yl)-9H-carbazole-4-carboxamide

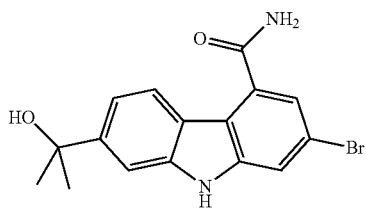 [SMILES: CC(C)(O)c1ccc2c(c1)[nH]c1cc(Br)cc(C(N)=O)c12]

A solution of 2-bromo-7-(2-hydroxypropan-2-yl)-9H-carbazole-4-carbonitrile (1.5 g, 4.56 mmol) in DMSO (15 mL) was treated with K$_2$CO$_3$ (1.889 g, 13.67 mmol) and the resulting mixture was cooled in an ice bath. Then added 50% aqueous H$_2$O$_2$ (8.38 mL, 137 mmol) drop wise to give very thick mixture and stirred in bath (added another 5 ml of DMSO) for 20 minutes and then stirred at room temperature for 1 hour. After hplc analysis showed reaction complete, the mixture was diluted with water and the resulting suspension was stirred for several minutes. The mixture was extracted into ethyl acetate and washed with water and concentrated to give yellow-orange solid. This was used without further purification in next step.

HPLC: RT=1.697 min; (Column: Chromolith ODS S5 4.6×50 mm (4 min grad) 0-100% B. Flow Rate=4 ml/min. Inj. Vol.=10 uL. Wavelength=220. Oven Temp.=40. Solvent A: 10% MeOH-90% H2O-0.1% TFA. Solvent B: 90% MeOH-10% H2O-0.1% TFA). LCMS: RT=0.69 min; (ES): m/z (M+H)+=347.2, 349.1 (Column: Waters Acquity SDS. Column: BEH C18 2.1×50 mm 17 u (1.6 min grad) 2-98% B. Flow Rate=0.8 ml/min. Solvent A: H2O-0.1% TFA. Solvent B: Acetonitrile-0.1% TFA).

$^1$H NMR (400 MHz, METHANOL-d4) δ 8.27 (d, J=8.4 Hz, 1H), 7.71 (d, J=1.8 Hz, 1H), 7.64 (d, J=1.1 Hz, 1H), 7.44 (d, J=1.8 Hz, 1H), 7.29 (dd, J=8.6, 1.5 Hz, 1H), 1.62 (s, 6H).

Step 3. 2-(3,5-dimethylisoxazol-4-yl)-7-(2-hydroxypropan-2-yl)-9H-carbazole-4-carboxamide

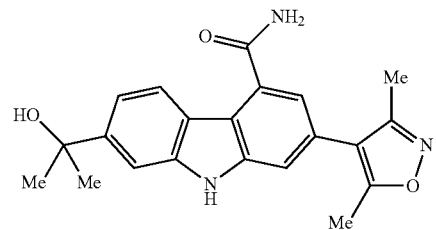 [SMILES: Cc1noc(C)c1-c1cc(C(N)=O)c2c(c1)[nH]c1cc(C(C)(C)O)ccc12]

A mixture of 2-bromo-7-(2-hydroxypropan-2-yl)-9H-carbazole-4-carboxamide (1.5 g, 4.32 mmol) and 3,5-dimethyl-4-(4,4,5,5-tetramethyl-1,3,2-dioxaborolan-2-yl)isoxazole (1.446 g, 6.48 mmol) in Tetrahydrofuran (20 mL) in a large vial was purged under a stream of nitrogen and then treated with 2 M aqueous TRIPOTASSIUM PHOSPHATE (6.48 mL, 12.96 mmol) and PdCl$_2$(dppf)-CH$_2$Cl$_2$ Adduct (0.353 g, 0.432 mmol). The vial was capped with septum and evacuated and purge with nitrogen 3 times and then heated in a heating block at 80° C. for 3 hours until analysis by lcms indicated reaction was complete. Cooled to room temperature and reaction solution was directly solid loaded on silica gel pre-column. Chromatographed on an ISCO Companion 40 g silica gel column and eluted with Ethyl acetate (100%) to give 2.2 g of dark solid which was triturated with DCM and filtered and rinsed with DCM to give 2-(3,5-dimethyl-isoxazol-4-yl)-7-(2-hydroxypropan-2-yl)-9H-carbazole-4-carboxamide (1.30 g, 3.58 mmol, 83% yield) as a tan solid. HPLC: RT=1.798 min; (Column: Chromolith ODS S5 4.6× 50 mm (4 min grad) 0-100% B. Flow Rate=4 ml/min. Inj. Vol.=10 uL. Wavelength=220. Oven Temp.=40. Solvent A: 10% MeOH-90% H2O-0.1% TFA. Solvent B: 90% MeOH-10% H2O-0.1% TFA). LCMS: RT=0.80 min; (ES): m/z (M+H)+=364.3 (Column: Waters Acquity SDS: BEH C18 2.1×50 mm, 1.7 u, aqueous MeCN/NH4OAc, 1 min gradient, monitoring at 220 nm). $^1$H NMR (400 MHz, DMSO-d$_6$) δ 11.40 (s, 1H), 8.28 (d, J=8.4 Hz, 1H), 7.98 (br. s., 1H), 7.63 (d, J=1.1 Hz, 1H), 7.56 (br. s., 1H), 7.51 (d, J=1.5 Hz, 1H), 7.24-7.16 (m, 2H), 5.07 (s, 1H), 2.48 (s, 3H), 2.30 (s, 3H), 1.51 (s, 6H).

Step 4. rel-(1R,2R,4R)-methyl 2-fluoro-7-oxabicyclo[2.2.1]hept-5-ene-2-carboxylate

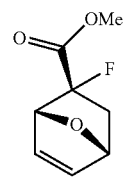 [SMILES: COC(=O)[C@@]1(F)C[C@@H]2C=C[C@H]1O2]

To a stirred mixture of furan (7.00 mL, 96 mmol) and methyl 2-fluoroacrylate (6.00 mL, 54.8 mmol) was added Zinc iodide (1.475 mL, 21.91 mmol). The mixture was heated at 55° C. in a heating block for 3 days. The mixture was diluted with 120 mL of EtOAc and washed successively with water, half-saturated Na$_2$S$_2$O$_3$ solution, water, then with brine. Dried over MgSO4, filtered and then concentrated to give rel-(1R,2R,4R)-methyl 2-fluoro-7-oxabicyclo

[2.2.1]hept-5-ene-2-carboxylate (2.30 g, 13.36 mmol, 24.40% yield) as a 3:1 endo/exo mixture. Endo isomer: $^1$H NMR (400 MHz, CHLOROFORM-d) δ 6.74-6.66 (m, 1H), 6.43 (dt, J=5.9, 1.7 Hz, 1H), 5.79-5.58 (m, 1H), 5.33 (dd, J=13.1, 3.2 Hz, 1H), 3.85 (s, 3H), 2.62 (td, J=12.2, 4.6 Hz, 1H), 1.61 (dd, J=19.9, 12.5 Hz, 1H). Exo isomer: $^1$H NMR (400 MHz, CHLOROFORM-d) δ 6.60 (dt, J=5.9, 1.5 Hz, 1H), 6.28-6.21 (m, 1H), 5.17-5.09 (m, 1H), 5.08-5.00 (m, 1H), 3.87 (s, 3H), 2.19 (d, J=4.2 Hz, 1H), 2.12 (d, J=2.3 Hz, 1H)

Step 5. rel-(1R,2R,4S)-methyl 2-fluoro-7-oxabicyclo[2.2.1]heptane-2-carboxylate

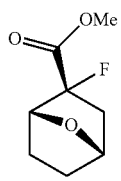 [SMILES: COC(=O)[C@@]1(F)C[C@@H]2CC[C@H]1O2]

To a stirred solution of methyl 2-fluoro-7-oxabicyclo[2.2.1]hept-5-ene-2-carboxylate (3:1 endo/exo mixture) (2.30 g, 13.36 mmol) in EtOAc (60 mL) was added 10% Pd/C (0.64 g, 13.36 mmol) and hydrogenated under an hydrogen atmosphere at room temperature for 24 hours. Filtered off the Pd catalyst through a 4 uM polycarbonate film and rinsed with DCM. The filtrate was concentrated to give rel-(1R,2R,4S)-methyl 2-fluoro-7-oxabicyclo[2.2.1]heptane-2-carboxylate (2.10 g, 12.06 mmol, 90% yield) as a 3:1 endo/exo mixture. Endo isomer: $^1$H NMR (400 MHz, CHLOROFORM-d) δ 4.72-4.64 (m, 1H), 4.12 (q, J=7.1 Hz, 1H), 3.83 (s, 3H), 2.59-2.46 (m, 1H), 2.24-2.15 (m, 1H), 1.91-1.82 (m, 1H), 1.76-1.64 (m, 3H). Exo isomer: $^1$H NMR (400 MHz, CHLOROFORM-d) δ 5.13-4.91 (m, 1H), 4.75 (t, J=5.3 Hz, 1H), 3.80 (s, 3H), 2.37 (dd, J=16.6, 13.6 Hz, 1H), 2.20-2.14 (m, 1H), 1.64-1.49 (m, 4H).

Step 6. rel-((1R,2S,4S)-(2-fluoro-7-oxabicyclo[2.2.1]heptan-2-yl)methanol

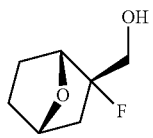

To a solution of methyl 2-fluoro-7-oxabicyclo[2.2.1]heptane-2-carboxylate (3:1 endo/exo mixture) (0.50 g, 2.87 mmol) in THF (10.0 mL) under nitrogen was cooled in an ice bath and treated with 2M LiAlH4/THF (7.18 mL, 14.35 mmol) dropwise over 10 min. The resulting mixture was stirred in an ice bath 1 hour and then allowed to warm to room temperature overnight. While cooling in an ice cooling bath the reaction was quenched with slow addition of 15 g Sodium Sulfate Decahydrate and then Celite. Diluted with 60 mL of ether and then stirred at room temperature for 3 hours. The mixture was filtered and rinsed with ether and the filtrate was concentrated to give rel-((1R,2S,4S)-(2-fluoro-7-oxabicyclo[2.2.1]heptan-2-yl)methanol as a 3:1 endo/exo mixture. This was used without further purification in next step.

Step 7. rel-(1R,2R,4S)-(2-fluoro-7-oxabicyclo[2.2.1]heptan-2-yl)methyl 4-methylbenzenesulfonate

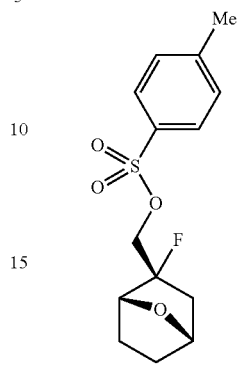

To a solution of (2-fluoro-7-oxabicyclo[2.2.1]heptan-2-yl)methanol (0.474 g, 3.24 mmol), and pyridine (2.62 mL, 32.4 mmol) in DCM (2.60 mL) was added Ts—Cl (2.349 g, 12.32 mmol) and the clear solution was stirred at room temperature overnight
The reaction mixture was diluted with 30 mL of saturated NaHCO$_3$ solution and extracted with DCM (3×40 mL) and washed with brine (1×20 mL). The extracts were dried (MgSO$_4$), filtered and concentrated and the residue was purified on ISCO 12 g silica gel column (Hexanes/EtOAc, 0 to 100% 15 min gradient, then to 100% in 5 min.) to give the major endo isomer rel-(1R,2R,4S)-(2-fluoro-7-oxabicyclo[2.2.1]heptan-2-yl)methyl 4-methylbenzenesulfonate (296 mg, 0.986 mmol, 30.4% yield). HPLC: RT=2.272 min (Chromolith SpeedROD column 4 6×50 mm, 10-90% aqueous methanol over 4 minutes containing 0.1% TFA, 4 mL/min, monitoring at 220 nm). HPLC: RT=0.91 min; (Waters Acquity SDS: BEH C18 2.1×50 mm, 1.7 u, aqueous MeCN/NH4OAc, 1 min gradient, monitoring at 220 nm). LC/MS: M+H=301.2. NMR:
$^1$H NMR (400 MHz, CHLOROFORM-d) δ 7.84-7.77 (m, 2H), 7.35 (d, J=8.1 Hz, 2H), 4.53 (t, J=5.4 Hz, 1H), 4.38 (d, J=5.0 Hz, 1H), 4.11 (s, 1H), 4.07 (d, J=2.6 Hz, 1H), 2.45 (s, 3H), 2.19-2.07 (m, 1H), 1.90-1.76 (m, 2H), 1.73-1.62 (m, 2H), 1.56 (d, J=8.2 Hz, 1H).

Step 8. rel-2-(dimethyl-1,2-oxazol-4-yl)-9-{[(1R,2S,4S)-2-fluoro-7-oxabicyclo[2.2.1]heptan-2-yl]methyl}-7-(2-hydroxypropan-2-yl)-9H-carbazole-4-carboxamide To a stirred mixture of 2-(3,5-dimethylisoxazol-4-yl)-7-(2-hydroxypropan-2-yl)-9H-carbazole-4-carboxamide (step 3) (60 mg, 0.165 mmol) and rel-((1R,2S,4S)-2-fluoro-7-oxabicyclo[2.2.1]heptan-2-yl)methyl 4-methylbenzenesulfonate (step 7) (55.0 mg, 0.182 mmoL) in DMF (1.00 mL) was added Cs$_2$CO$_3$ (161 mg, 0.495 mmol) and heated to 100° C. in a heating block for 24 hours. The mixture was cooled to room temperature and was purified via preparative HPLC with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 17-57% B over 20 minutes, then a 5-minute hold at 100% B; Flow: 20 mL/min. Fractions containing the desired product were combined and dried via centrifugal evaporation to give rel-2-(dimethyl-1,2-oxazol- 4-yl)-9-{[(1R,2S,4S)-2-fluoro-7-oxabicyclo[2.2.1]heptan-2-yl]methyl}-7-(2-hydroxypropan-2-yl)-9H-carbazole-4-carboxamide (39.4 mg, 0.080 mmol, 48.5% yield). LCMS: (M+H)+=492.2; LCMS: RT=1.43 min; (Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min).

$^1$H NMR (500 MHz, DMSO-d6) δ 8.29 (d, J=8.4 Hz, 1H), 8.08 (br. s., 1H), 7.73 (s, 1H), 7.67 (br. s., 1H), 7.61 (s, 1H), 7.34 (d, J=8.4 Hz, 1H), 7.26 (s, 1H), 5.15 (s, 1H), 4.73-4.66 (m, 1H), 4.31 (d, J=4.4 Hz, 1H), 2.50 (br. s., 3H), 2.32 (s, 3H), 2.20-2.08 (m, 1H), 1.90 (d, J=12.8 Hz, 1H), 1.53 (s, 6H).

Examples 226 & 227

9-[(4,4-difluorocyclohexyl)(phenyl)methyl]-2-(dimethyl-1,2-oxazol-4-yl)-8-fluoro-7-(2-hydroxypropan-2-yl)-9H-carbazole-4-carboxamide Enantiomer A, Example 226

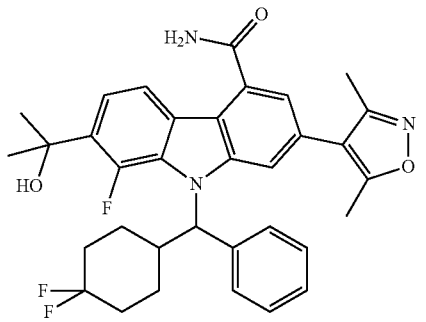

Enantiomer B, Example 227

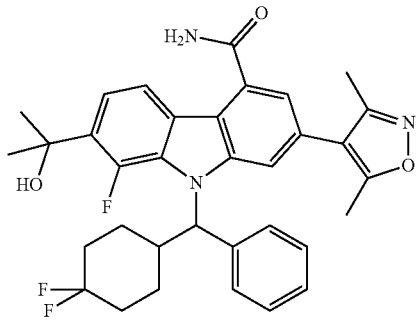

Following procedures analogous to those described for Example 223, methyl 5-cyano-7-(3,5-dimethylisoxazol-4-yl)-1-fluoro-9H-carbazole-2-carboxylate and (4,4-difluorocyclohexyl)-(phenyl)methanol were converted to racemic 9-[(4,4-difluorocyclohexyl)(phenyl)methyl]-2-(dimethyl-1,2-oxazol-4-yl)-8-fluoro-7-(2-hydroxypropan-2-yl)-9H-carbazole-4-carboxamide which was separated by chiral prep SFC to give Enantiomer A and Enantiomer B. Enantiomer A: $^1$H NMR (500 MHz, DMSO-d$_6$) δ 8.09 (br. s., 1H), 8.03 (d, J=8.4 Hz, 1H), 7.70 (br. s., 1H), 7.57 (br. s., 1H), 7.53-7.44 (m, 1H), 7.36 (br. s., 1H), 7.26 (br. s., 1H), 7.15 (br. s., 1H), 6.10 (br. s., 1H), 2.34 (br. s., 4H), 2.16 (br. s., 3H), 2.09 (br. s., 3H), 1.94 (br. s., 2H), 1.76 (br. s., 1H), 1.67 (d, J=13.8 Hz, 6H), 1.55 (br. s., 1H), 1.38 (br. s., 2H), 1.27 (d, J=10.8 Hz, 2H), 1.18 (br. s., 1H). LCMS: LCMS: LCMS: Waters Aquity UPLC BEH C18 2.1×50 mm 1.7 u (3 min grad) 0-100% B. Flow Rate=1 ml/min. Inj. Vol.=3 uL. Oven Temp.=50C. Solvent A: 5% ACN-95% H$_2$O-0.1% TFA. Solvent B: 95% ACN-15% H2O-0.1% TFA. LCMS: RT=1.95 min; (ES): m/z (M+H)$^+$=590.3; SFC RT=12.58 min (Column: Chiralcel OD-H 250×4.6 mm, 5 μm particles; Mobile Phase: 70/30 CO2/MeOH; Flow: 2 mL/min; Detection: UV at 220 nm).

Enantiomer B: $^1$H NMR (500 MHz, DMSO-d$_6$) δ 8.09 (br. s., 1H), 8.03 (d, J=8.4 Hz, 1H), 7.70 (br. s., 1H), 7.57 (br. s., 1H), 7.53-7.44 (m, 1H), 7.36 (br. s., 1H), 7.26 (br. s., 1H), 7.15 (br. s., 1H), 6.10 (br. s., 1H), 2.34 (br. s., 4H), 2.16 (br. s., 3H), 2.09 (br. s., 3H), 1.94 (br. s., 2H), 1.76 (br. s., 1H), 1.67 (d, J=13.8 Hz, 6H), 1.55 (br. s., 1H), 1.38 (br. s., 2H), 1.27 (d, J=10.8 Hz, 2H), 1.18 (br. s., 1H). LCMS: LCMS: Waters Aquity UPLC BEH C18 2.1×50 mm 1.7 u (3 min grad) 0-100% B. Flow Rate=1 ml/min. Inj. Vol.=3 uL. Oven Temp.=50C. Solvent A: 5% ACN-95% H$_2$O-0.1% TFA. Solvent B: 95% ACN-15% H2O-0.1% TFA. LCMS: RT=1.95 min; (ES): m/z (M+H)$^+$=590.3; SFC RT=16.11 min (Column: Chiralcel OD-H 250×4.6 mm, 5 μm particles; Mobile Phase: 70/30 CO2/MeOH; Flow: 2 mL/min; Detection: UV at 220 nm).

Example 228

2-(Dimethyl-1,2-oxazol-4-yl)-7-(2-methoxypropan-2-yl)-9-[(S)-oxan-4-yl(phenyl)methyl]-9H-carbazole-4-carboxamide

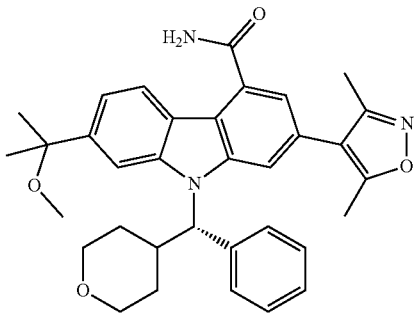 [SMILES: COC(C)(C)c1ccc2c3c(C(N)=O)cc(-c4c(C)noc4C)cc3n([C@H](c3ccccc3)C3CCOCC3)c2c1]

A solution of (S)-2-(3,5-dimethylisoxazol-4-yl)-7-(2-hydroxypropan-2-yl)-9-(phenyl(tetrahydro-2H-pyran-4-yl)methyl)-9H-carbazole-4-carboxamide (Example 199) (20 mg, 0.037 mmol) in Methanol (3 mL) was treated with 0.5 ml of TFA and stirred overnight at room temperature. Analysis by hplc showed reaction essentially complete. The mixture was concentrated on rotary evaporator and the residue was dissolved in methanol and the crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-85% B over 20 minutes, then a 7-minute hold at 100% B; Flow: 20 mL/min. Fractions containing the desired product were combined and dried via centrifugal evaporation. Obtained 2-(Dimethyl-1,2-oxazol-4-yl)-7-(2-methoxypropan-2-yl)-9-[(S)-oxan-4-yl(phenyl)methyl]-9H-carbazole-4-carboxamide (15 mg, 0.027 mmol, 72.4% yield). LCMS: (M+H)+=552.3; LCMS: RT=1.74 min; (Column: Waters Acquity UPLC BEH C18, 2.1×50 mm, 1.7-μm particles;

Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min).

$^1$H NMR (500 MHz, DMSO-d6) δ 8.26 (d, J=8.4 Hz, 1H), 8.06 (br. s., 1H), 7.96 (s, 1H), 7.66 (br. s., 1H), 7.60 (d, J=7.7 Hz, 2H), 7.33 (t, J=7.4 Hz, 2H), 7.27-7.13 (m, 4H), 5.90 (d, J=10.8 Hz, 1H), 3.90 (d, J=7.7 Hz, 1H), 3.72 (d, J=10.1 Hz, 1H), 3.52 (t, J=11.1 Hz, 1H), 3.43-3.37 (m, 1H), 3.29-3.14 (m, 1H), 2.99 (br. s., 3H), 2.43 (br. s., 3H), 2.30 (br. s., 3H), 1.82 (d, J=12.5 Hz, 1H), 1.63 (m, 1H), 1.25 (m, 1H), 0.92 (d, J=12.1 Hz, 1H).

Example 229

2-(Dimethyl-1,2-oxazol-4-yl)-9-[(S)-oxan-4-yl(phenyl)methyl]-7-(propan-2-yl)-9H-carbazole-4-carboxamide

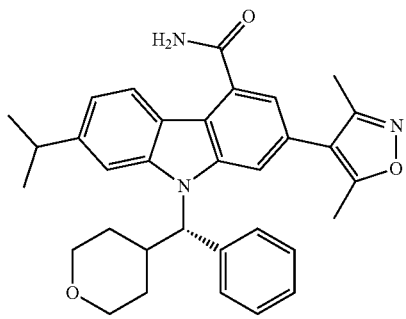 [SMILES: Cc1noc(C)c1-c1cc(C(N)=O)c2c3ccc(C(C)C)cc3n([C@H](c3ccccc3)C3CCOCC3)c2c1]

A solution of (S)-2-(3,5-dimethylisoxazol-4-yl)-7-(2-hydroxypropan-2-yl)-9-(phenyl(tetrahydro-2H-pyran-4-yl)methyl)-9H-carbazole-4-carboxamide (Example 199) (25 mg, 0.046 mmol) in Dichloromethane (1 mL) was treated TRIETHYLSILANE (0.074 mL, 0.465 mmol) and TFA (0.036 mL, 0.465 mmol) and the resulting light yellow solution was stirred at room temperature for 2 hours. The mixture was evaporated on rotary evaporator and the residue dissolved in 2 ml of methanol and the crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-85% B over 20 minutes, then a 7-minute hold at 100% B; Flow: 20 mL/min. Fractions containing the desired product were combined and dried via centrifugal evaporation. Obtained 2-(dimethyl-1,2-oxazol-4-yl)-9-[(S)-oxan-4-yl (phenyl)methyl]-7-(propan-2-yl)-9H-carbazole-4-carboxamide (23 mg, 0.044 mmol, 94% yield). LCMS: (M+H)+ =522.3; LCMS: RT=2.103 min; (Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min).

$^1$H NMR (500 MHz, DMSO-d6) δ 8.21 (d, J=8.1 Hz, 1H), 8.03 (br. s., 1H), 7.96 (s, 1H), 7.62 (d, J=8.1 Hz, 4H), 7.33 (t, J=7.6 Hz, 2H), 7.27-7.20 (m, 1H), 7.15 (br. s., 1H), 7.09 (br. s., 1H), 5.86 (d, J=11.1 Hz, 1H), 3.95-3.85 (m, 1H), 3.72 (d, J=8.8 Hz, 1H), 3.52 (t, J=11.3 Hz, 1H), 3.38 (br. s., 1H), 3.24 (t, J=11.6 Hz, 1H), 2.45 (br. s., 4H), 2.27 (br. s., 3H), 1.81 (d, J=10.8 Hz, 1H), 1.70-1.58 (m, 1H), 1.33 (br. s., 6H), 1.26 (d, J=13.1 Hz, 1H), 0.91 (d, J=12.8 Hz, 1H).

Examples 230 & 231

2-(dimethyl-1,2-oxazol-4-yl)-8-fluoro-7-(2-hydroxypropan-2-yl)-9-[4,4,4-trifluoro-1-phenylbutyl]-9H-carbazole-4-carboxamide Enantiomer A, Example 230

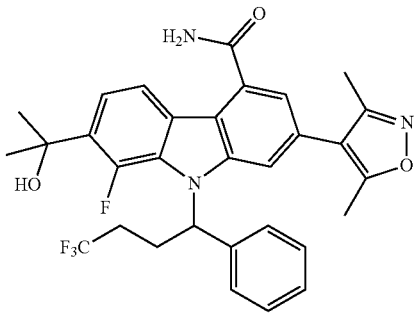

Enantiomer B, Example 231

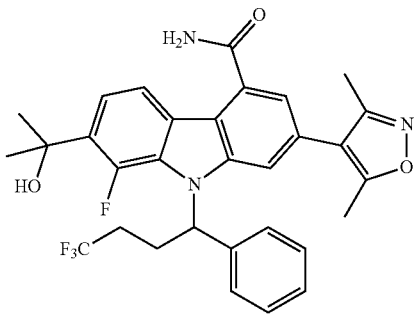

Following procedures analogous to those described for Example 223, methyl 5-cyano-7-(3,5-dimethylisoxazol-4-yl)-1-fluoro-9H-carbazole-2-carboxylate and 4,4,4-trifluoro-1-phenylbutan-1-ol were converted to racemic 2-(dimethyl-1,2-oxazol-4-yl)-8-fluoro-7-(2-hydroxypropan-2-yl)-9-[4,4,4-trifluoro-1-phenylbutyl]-9H-carbazole-4-carboxamide which was separated by chiral prep SFC to give Enantiomer A and Enantiomer B. Enantiomer A: $^1$H NMR (500 MHz, DMSO-d$_6$) δ 8.16 (br. s., 1H), 8.10 (d, J=8.4 Hz, 1H), 7.74 (br. s., 1H), 7.48 (br. s., 1H), 7.33 (br. s., 2H), 7.26 (d, J=7.7 Hz, 3H), 6.50 (br. s., 1H), 2.48-2.02 (m, 8H), 1.73 (br. s., 2H), 1.55 (br. s., 8H). LCMS: LCMS: Waters Aquity UPLC BEH C18 2.1×50 mm 1.7 u (3 min grad) 0-100% B. Flow Rate=1 ml/min. Inj. Vol.=3 uL. Oven Temp.=50C. Solvent A: 5% ACN-95% H$_2$O-0.1% TFA. Solvent B: 95% ACN-15% H2O-0.1% TFA. LCMS: RT=1.90 min; (ES): m/z (M+H)$^+$=568.2; SFC RT=7.67 min (Column: Chiralcel OD-H 250×4.6 mm, 5 μm particles; Mobile Phase: 70/30 CO2/MeOH; Flow: 2 mL/min; Detection: UV at 220 nm). Enantiomer B: $^1$H NMR (500 MHz, DMSO-d$_6$) δ 8.16 (br. s., 1H), 8.10 (d, J=8.4 Hz, 1H), 7.74 (br. s., 1H), 7.48 (br. s., 1H), 7.33 (br. s., 2H), 7.26 (d, J=7.7 Hz, 3H), 6.50 (br. s., 1H), 2.48-2.02 (m, 8H), 1.73 (br. s., 2H), 1.55 (br. s., 8H). LCMS: Waters Aquity UPLC BEH C18 2.1×50 mm 1.7 u (3 min grad) 0-100% B. Flow Rate=1 ml/min. Inj. Vol.=3 uL. Oven Temp.=50C. Solvent A: 5% ACN-95% H$_2$O-0.1% TFA. Solvent B: 95% ACN- 15% H2O-0.1% TFA. LCMS: RT=1.90 min; (ES): m/z (M+H)+=568.2; SFC RT=11.45 min (Column: Chiralcel OD-H 250×4.6 mm, 5 μm particles; Mobile Phase: 70/30 CO2/MeOH; Flow: 2 mL/min; Detection: UV at 220 nm).

Example 232 & 233

2-(1,4-Dimethyl-1H-1,2,3-triazol-5-yl)-7-(2-hydroxypropan-2-yl)-9-(phenyl(tetrahydro-2H-pyran-4-yl)methyl)-9H-carbazole-4-carboxamide

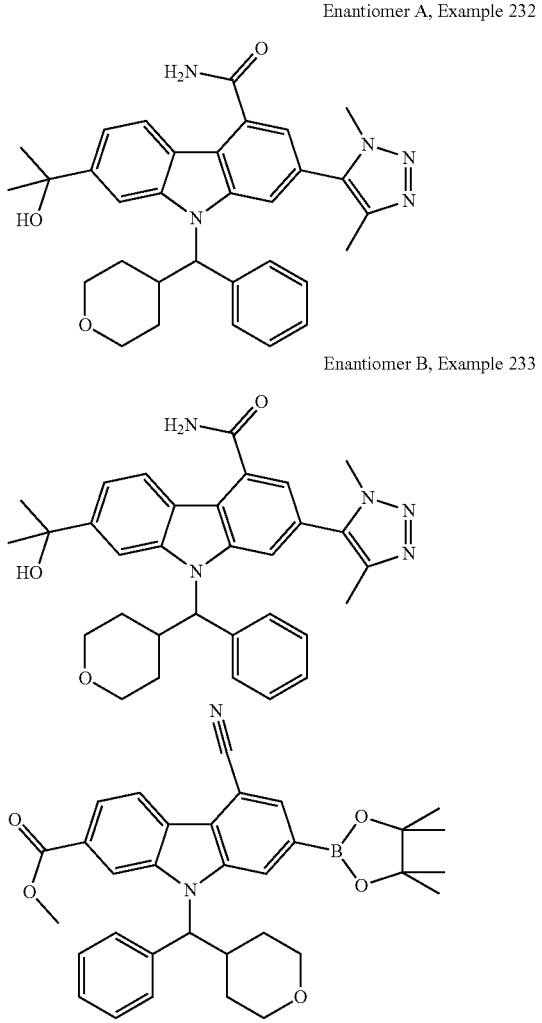

Enantiomer A, Example 232

Enantiomer B, Example 233

ISCO silica gel chromatography (40 g column, gradient from 0% to 100% EtOAc/CH₂Cl₂). Concentration of tubes containing product (211 mg, 102%) as an off white foam solid. HPLC RT=3.251 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

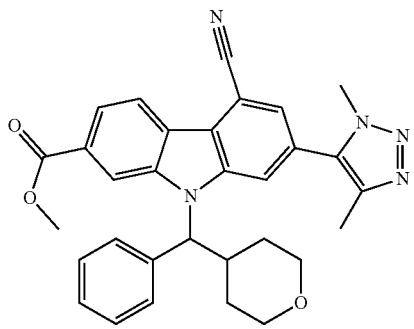 [SMILES: COC(=O)c1ccc2c3c(C#N)cc(-c4c(C)nnn4C)cc3n(C(c3ccccc3)C3CCOCC3)c2c1]

Step 2: Methyl 5-cyano-7-(1,4-Dimethyl-1H-1,2,3-triazol-5-yl)-9-(phenyl(tetrahydro-2H-pyran-4-yl)methyl)-9H-carbazole-2-carboxylate To a 40 mL pressure vial containing methyl 5-cyano-7-(4,4,5,5-tetramethyl-1,3,2-dioxaborolane-2-yl)-9-(phenyl(tetrahydro-2H-pyran-4-yl)methyl)-9H-carbazole-2-carboxylate (200 mg, 0.363 mmol), 5-iodo-1,4-dimethyl-1H-1,2,3-triazole (162 mg, 0.727 mmol) [Bunnage, M. E. et al. PCT International publication number WO2011/138751 A2] and K₂CO₃ (151 mg, 1.09 mmol) in dioxane (9 mL) and water (0.9 mL) was added Pd(dppf)Cl₂—CH₂Cl₂ (14.84 mg, 0.018 mmol) and N₂ was bubbled into the mixture for 1 min. The resulting reaction mixture was heated at 80° C. for 1 h, concentrated and purified directly using ISCO silica gel chromatography (40 g column, gradient from 0% to 100% EtOAc/CH₂Cl₂). Tubes containing product, overlapped with 5-iodo-1,4-dimethyl-1H-1,2,3-triazole, were collected (225.9 mg) to give an off white solid. HPLC RT=3.273 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min) LCMS (M+H) =520.1.

Step 1: Methyl 5-cyano-7-(4,4,5,5-tetramethyl-1,3,2-dioxaborolane-2-yl)-9-(phenyl(tetrahydro-2H-pyran-4-yl)methyl)-9H-carbazole-2-carboxylate To a 40 mL pressure vial containing methyl 7-bromo-5-cyano-9-(phenyl(tetrahydro-2H-pyran-4-yl)methyl)-9H-carbazole-2-carboxylate (190 mg, 0.377 mmol), 4,4,4',4',5,5,5',5'-octamethyl-2,2'-bi(1,3,2-dioxaborolane) (Aldrich, 192 mg, 0.755 mmol) and potassium acetate (111 mg, 1.132 mmol) in dioxane (3 mL) was added Pd(dppf)Cl₂—CH₂Cl₂ (15.41 mg, 0.019 mmol) and N₂ was bubbled into the mixture for 1 min. The resulting reaction mixture was heated at 80° C. for 2.5 h, concentrated and purified directly using

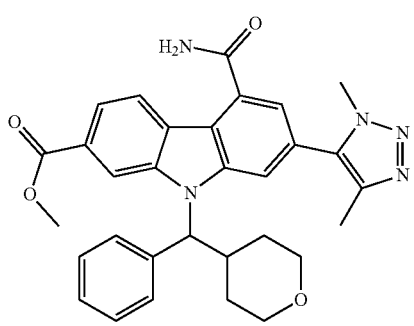 [SMILES: COC(=O)c1ccc2c3c(C(N)=O)cc(-c4c(C)nnn4C)cc3n(C(c3ccccc3)C3CCOCC3)c2c1]

Step 3: Methyl 5-carbamoyl-7-(1,4-Dimethyl-1H-1,2,3-triazol-5-yl)-9-(phenyl(tetrahydro-2H-pyran-4-yl)methyl)-9H-carbazole-2-carboxylate Following a procedure analogous to that described for Example 187, Methyl 5-cyano-7-(1,4-Dimethyl-1H-1,2,3-triazol-5-yl)-9-(phenyl(tetrahydro-2H-pyran-4-yl)methyl)-9H-carbazole-2-carboxylate (225 mg, 0.433 mmol) was converted to the title compound (58 mg, 25%). HPLC RT=2.558 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min) LCMS (M+H)=538.4.

Step 4: 2-(1,4-Dimethyl-1H-1,2,3-triazol-5-yl)-7-(2-hydroxypropan-2-yl)-9-(phenyl(tetrahydro-2H-pyran-4-yl)methyl)-9H-carbazole-4-carboxamide Following a procedure analogous to that described for Example 184, Methyl 5-carbamoyl-7-(1,4-Dimethyl-1H-1,2,3-triazol-5-yl)-9-(phenyl(tetrahydro-2H-pyran-4-yl)methyl)-9H-carbazole-2-carboxylate (57 mg, 0.106 mmol) was converted to racemic 2-(1,4-Dimethyl-1H-1,2,3-triazol-5-yl)-7-(2-hydroxypropan-2-yl)-9-[(R)-oxan-4-yl(phenyl)methyl]-9H-carbazole-4-carboxamide (41.3 mg, 68%) of which 38 mg was separated using chiral prep SFC (Column: Chiral OD-H 25×3 cm, 5 μm; Mobile Phase: 60/40 $CO_2$/MeOH; Flow: 80 mL/min). The faster eluting peak was concentrated to give a white solid which was assigned as Enantiomer A (18.9 mg, 47.7%). The slower eluting peak was treated in an identical manner and assigned as Enantiomer B (15.4 mg, 39.3%). Enantiomer A: $^1$H NMR (500 MHz, $CDCl_3$) δ 8.45 (d, J=8.3 Hz, 1H), 7.92 (s, 1H), 7.43 (d, J=7.5 Hz, 2H), 7.40-7.28 (m, 5H), 7.26 (d, J=1.1 Hz, 1H), 6.11-5.84 (m, 2H), 5.65 (d, J=10.8 Hz, 1H), 4.10-4.03 (m, 1H), 3.87-3.75 (m, 4H), 3.57 (td, J=11.8, 1.9 Hz, 1H), 3.33 (td, J=11.8, 1.9 Hz, 1H), 3.14 (d, J=11.1 Hz, 1H), 2.27 (s, 3H), 2.12 (d, J=13.0 Hz, 1H), 1.89 (s, 1H), 1.72 (s, 6H), 1.68-1.60 (m, 1H), 1.43-1.31 (m, 1H), 1.03 (d, J=12.5 Hz, 1H); LCMS (M+H)=538.4; HPLC RT=2.302 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=6.779 min (Column: Chiral OJ-H 250×4.6 mm, 5 μm; Mobile Phase: 80/20 $CO_2$/MeOH; Flow: 2 mL/min) Enantiomer B: $^1$H NMR (500 MHz, $CDCl_3$) δ8.45 (d, J=8.3 Hz, 1H), 7.92 (s, 1H), 7.43 (d, J=7.5 Hz, 2H), 7.40-7.28 (m, 5H), 7.26 (br. s., 1H), 6.08-5.84 (m, 2H), 5.65 (d, J=10.0 Hz, 1H), 4.06 (dd, J=11.5, 2.6 Hz, 1H), 3.88-3.77 (m, 4H), 3.57 (td, J=11.9, 1.9 Hz, 1H), 3.37-3.28 (m, 1H), 3.14 (d, J=11.4 Hz, 1H), 2.27 (s, 3H), 2.12 (d, J=13.6 Hz, 1H), 1.88 (s, 1H), 1.72 (s, 6H), 1.69-1.60 (m, 1H), 1.42-1.32 (m, 1H), 1.03 (d, J=12.8 Hz, 1H); LCMS (M+H)=538.4; HPLC RT=2.307 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=8.030 min (Column: Chiral OJ-H 250×4.6 mm, 5 μm; Mobile Phase: 80/20 $CO_2$/MeOH; Flow: 2 mL/min)

Evaluation of Biological Activity

Exemplary compounds were tested for inhibition of BRD2, BRD3, BRD4 and BRDT activity. Experimental procedures and results are provided below. Cloning, Expression, and Purification of Human Bromodomains for Thermal Shift Assays (TSA)

Recombinant DNA clones encoding bromodomains of human proteins were optimized for *E. coli* expression, chemically synthesized (GenScript, Piscataway N.J.), and inserted into a modified pET28 expression vector to construct tobacco vein mottling virus (TVMV) protease cleavable N-terminal hexahistidine fusions. The non-native amino acids (MGSSHHHHHHSSGETVRFQSM) (SEQ ID NO: 1) were immediately followed by bromodomain proteins with the amino acid residue sequences (followed by accessions referenced from and numbered according to the Uniprot Knowledgebase; Uniprot Consortium; www.uniprot.org) as follows:
CECR2(420-543), Q9BXF3-1; FALZ(2917-3037), Q12830-1; GCN5(731-837), Q92830-1; PCAF(715-831), Q92831-1; BRD2(24-472), P25440-1; BRD3(1-434), Q15059-1; BRD4(44-168), BRD4(333-460), BRD4(44-460), O60885-1; BRDT(1-383), Q58F21-1; BAZ1B(1340-1457), Q9UIG0-1; CREBBP(1081-1197), Q92793-1; EP300(1040-1161), Q09472-1; WDR9(1310-1430), Q9NSI6-1; ATAD2(981-1108), Q6PL18-1; BRD1(556-688), O95696-1; BRD7(129-236), Q9NPI1-1; BRD9(134-239), Q9H8M2-1; BRPF1(626-740), P55201-2; ATAD2B(952-1086), Q9ULI0-1; BAZ2B(2054-2168), Q9UIF8-1; SP140L(400-580), Q9H930-4; SP140(687-862), Q13342-1; TIF1(896-1014), O15164-1; TRIM28(619-805), Q13263-1; BRWD3(1295-1443), Q6R145-1; TAF1(1377-1503), TAF1(1501-1635), P21675-1; TAF1L(1402-1522), TAF1L(1523-1654), Q81ZX4-1; ASH1L(2433-2564), Q9NR48-1; PB1(43-156), PB1(178-291), PB1(388-494), PB1(645-766), PB1(773-917), Q86U86-1; SMARCA2(1367-1511), P51531-1; SMARCA2-2(1367-1493), P51531-2.

The recombinant vectors were transformed into *E. coli* BL21(DE3). The transformed cells were cultured in 1 L terrific broth in 2.5 L Thomson Ultra Yield shaker flasks at 37° C., 230 rpm and, at a cell density of OD600 nm=1.0, were induced with 0.5 mM IPTG and incubated in the shaker at 20° C. for 16-18 hours. The cell pellets were harvested by sedimentation and lysed by sonication in buffer containing 0.1 mg/ml lysozyme. Each sample was clarified by sedimentation, and the supernatant was loaded onto a HisTrap affinity column (GE Healthcare Life Sciences). The column was washed and then eluted with an imidazole gradient. The peak protein fractions containing the bromodomain protein were pooled, concentrated, and the protein was purified further by size exclusion chromatography on a Superdex 200 column (GE Healthcare Life Sciences) equilibrated with the final storage buffer (20 mM Tris-HCl pH 8.0, 200 mM NaCl, 5% glycerol, 2 mM DTT). The SEC peak fractions containing purified protein at 2-5 mg/ml were pooled, and the pool was divided into aliquots, flash frozen in liquid nitrogen, and store at −80° C.

Cloning, Expression, and Purification of Biotinylated Human Bromodomains for TR-FRET Assays Recombinant DNA clones encoding bromodomains of human BRD2, BRD3, BRD4 and BRDT were optimized for *E. coli* expression, chemically synthesized (GenScript, Piscataway N.J.), and inserted into a modified pET28 expression vector to construct tobacco vein mottling virus (TVMV) protease cleavable N-terminal hexahistidine fusions followed by a site specific biotinylation motif recognized by *E. coli* biotin ligase (BirA). The non-native amino acids (MGSSHHHHHHSSGETVRFQGLN-DIFEAQKIEWHEDTGHM) (SEQ ID NO: 2) were immediately followed by bromodomain constructs of BRD4 with the amino acid residue sequences (followed by the BRD4 accession referenced from and numbered according to the Uniprot Knowledgebase; Uniprot Consortium; www.uniprot.org) as follows: BRD4(44-168), BRD4(333-460), BRD4 (44-460), BRD4(1-477), O60885-1.

Each of the recombinant vectors were co-transformed into E. coli BL21 STAR (DE3) together with a plasmid encoding BirA under chloramphenicol selection. The transformed cells were cultured at 37° C. in 2.5 L Thomson Ultra Yield shaker flasks containing 1 L M9-CAS medium (Teknova) supplemented with 40 µg/ml kanamycin, 35 µg/ml chloramphenicol, and 100 µM biotin. At a cell density corresponding to an OD600 nm=0.6, the cultures were induced with 0.5 mM IPTG and incubated in the shaker for an additional 20 hours at 20° C. The cell pellets were harvested by sedimentation and lysed by sonication in buffer containing 0.1 mg/ml lysozyme. Each sample was clarified by sedimentation, and the supernatant was loaded onto a HisTrap affinity column. The column was washed and then eluted with an imidazole gradient. The peak protein fractions containing the bromodomain protein were pooled and incubated for 18 hours at 4° C. with purified His-TVMV protease (1:15 mass ratio of TVMV:BRD4 protein). The sample was exchanged into low imidazole buffer and passed through a HisTrap column to capture the cleaved His-tag and His-TVMV enzyme. The protein in the HisTrap column flow through was further purified and exchanged into the final storage buffer (PBS pH 7.0, 5% Glycerol, 1 mM DTT) by size exclusion chromatography on a Superdex 200 column. To improve purity, the BRD4(1-477) and BRD4(44-460) proteins were subjected to an additional cation exchange chromatography purification step prior to size exclusion chromatography. Essentially quantitative mono-biotinylation (+226 Da) of each protein was confirmed by electrospray ionization mass spectrometry analysis on the final sample. The purified samples were divided into aliquots, flash frozen in liquid nitrogen, and stored at −80° C.

Time Resolved Fluorescence Resonance Energy Transfer (TR-FRET) Assay

The binding of compounds to bromodomain BRD4 (44-168), BRD4 (333-460), and BRD4 (1-477 or 44-460) was assessed using a time resolved fluorescent resonance energy transfer binding assay (1), that measures the binding of a fluorescently labeled probe molecule to the bromodomain protein. The bromodomain protein, fluorescent probe molecule (either a biotinylated histone peptide or a fluorescently labeled small molecule), and dose-responsed test compound are incubated together to reach thermodynamic equilibrium. In the absence of a test compound, the bromodomain and small molecule are bound, resulting in a high fluorescent signal. In the presence of a sufficient concentration of inhibitor, this intercation is disrupted resulting in a lost of fluorescent resonance energy transfer.

All assay components were dissolved in buffer composition 20 mM Hepes pH 7.5, 150 mM NaCl, 5 mM DTT, 0.005% Tween 20, and 100 ug/ml BSA for BRD4 (1-477 and 44-460). The final concentrations of the bromodomain proteins are 1.6 nM BRD4(44-168), 1 nM BRD4(333-460), and 1 nM BRD4(1-477 or 44-460), and the fluorescent probe molecule is 100 nM, 50 nM, and 7.5 nM respectively. All proteins were biotinylated. A streptavidin labeled with terbium cryptate (Cisbio SA-Tb) was used as detection, and pre-mixed with the bromodomain protein at a final concentration of 0.2 nM. In some instances for BRD4 (44-460), anti-His terbium cryptate was used as a detection. 7.5 nl of dose-responsed test compound or dmso vehicle (0.0375%) was pre-spotted in a black Corning 384 well plate and 10 ul each of bromodomain/detection reagent and fluorescent small molecule solution were added to the plate, and the reaction incubated for 60 min at room temperature. Plates were then read on EnVision plate reader, ($\lambda$ex=340 nm, acceptor $\lambda$Em=520 nm, and donor $\lambda$Em=615 nm, LANCE D400 mirror). Time resolved fluorescence intensity measurements were made at both emissions, and the ratio of acceptor/donor was calculated and used for data analysis. All data was normalized to 16 high vehicle wells and 8 low reference control wells, and then a four parameter curve fit was applied:

$$Y=a+((b-a)/(1+(10x/10c)d)$$

Where 'a' is the minimum, 'b' is the Hill slope, 'c' is the $IC_{50}$, and 'd' is the maximum.

Histone peptide: Purchased from GenScript H4K5K8K12K16

(SEQ ID NO: 3)
Biotin-AHA-SGRGK(Ac)GGK(Ac)GLGK(Ac)GGAK(Ac)RHRKV

The fluorescently labeled small molecule used was a BRD4 inhibitor known in the art 1. F. Degorce, A. Card, S. Soh, E. Trinquet, G. P. Knapik and B. Xie, HTRF: A technology tailored for drug discovery—a review of theoretical aspects and recent applications. Current Chemical Genomics (2009) 3, 22-32

Thermal Shift Assay

The effect of compound binding on the thermal stability of the bromodomains was measured using a BioRad CFX real time PCR instrument by monitoring the fluorescence enhancement of an external probe (SYPRO orange) as it binds preferentially to the unfolded protein. The unfolding reactions were carried out in a 384-well plate in a 4 uL volume with 2-8 uM of bromodomain protein, 1-2% (v/v) DMSO in buffer containing 10 mM Hepes, pH 7.4, 500 mM NaCl. SYPRO orange dye was added at a dilution of 1:500. Compound concentrations ranged from 1.6-100 uM. Unfolding reactions were monitored by first equilibrating the instrument at 25° C. for 2.4 sec, followed by ramping the temperature in 0.5° C. increments from 25 to 95° C. with 60 s equilibration prior to a read at each temperature. Excitation and emission filters for the SYPRO orange dye were set to FRET with the excitation range from 450-490 nm and the emission range from 560-580 nm. The midpoint temperature was determined by calculating the inflection point using the second derivative. The observed temperature shifts were recorded as the difference between the midpoint between a reference well containing protein with dmso but no ligand and a well containing protein with compound.

The thermal shift assay is a biophysical technique that compares the change in unfolding transition temperature of a protein obtained in the presence and absence of a ligand (1). Typically, a fluorescent dye is used to monitor the protein unfolding as the protein is heated. During the unfolding process, hydrophobic regions of the protein are exposed, resulting in an increase in the dye binding and an increase in fluorescence intensity. The midpoint of the protein unfolding transition is defined as the Tm. A ligand that binds to the protein causes an increase in the protein thermal stability, thus increasing the Tm, proportionally to both the ligand concentration and its binding affinity.

1. M. W. Pantoliano, E. C. Petrella, J. D. Kwasnoski, V. S. Lobanov, J. Myslik, E. Graf, T. Carver, E. Asel, B. A. Springer, P. Lane, F. R. Salemme, High-density miniaturized thermal shift assays as a general strategy for drug discovery. J. Biomol. Screen 6 (2001) 429-440.
2. M. D. Cummings, M. A. Farnum, M. I. Nelen, Universal screening methods and application of ThermoFluor. J. Biomol. Screen 11 (2006) 854-863

MYC HCS Assay

Tumor cells in complete RPMI growth media (Gibco, 11875-085) supplemented with 10% FBS were harvested and plated into 384 black clear-bottom PDL cell culture plates in 30 ul media with 10,000 cells per well. After compound treatment at 37C for 4 hrs, cells were fixed in 4% Formaldehyde at room temperature for 30 minutes and subsequently permeabilized. After washing and blocking, the plates were then incubated with anti-myc primary antibody 1:1000 (Cell Signaling Technology, 5605) at RT overnight. The following day, cells were washed and blocked before adding secondary antibody Alexa 488 Goat-anti Rabbit 1:2000 (Invitrogen, A11034) at RT in the dark for 1 hr. Cells were subsequently washed and scanned on the Cellomics ArrayScan with 10× objective lens.

MTS Cell Proliferation Assay

Tumor cells were plated at certain seeding densities in 384-well black clear bottom Matrix plates at 40 ul per well and incubated overnight at 37° C. in 5% CO2 before assaying. On the next day, one set of cell plates (T0 plates) were used to determine time zero cell density, and 3-(4,5-dimethylthiazol-2-yl)-5-(3-carboxymethoxyphenyl)-2-(4-sulfophenyl)-2H-tetrazolium from the CellTiter 96 AQueous Non-Radioactive Cell proliferation Kit (Promega, G5440) was added at 4 μl/well into T0 plates followed by incubation at 37° C. in 5% CO2 for three hours. Absorbance at 490 nm was measured on an Envision reader (Perkin Elmer, Boston, Mass.). On the same day, the remaining cell plates (T72 plates) were treated with compounds at 37° C. in 5% CO2. After 72 hours, 4 ul MTS reagents were then added onto those cell plates. The plates were further incubated at 37° C. in 5% CO2 for three hours and the absorbance values at A490 were measured on an Envision reader.

Human Tumor Xenograft Models in Mice

All rodents were obtained from Jackson Laboratory. (Bar Harbor, Me.), and maintained in an ammonia-free environment in a defined and pathogen-free colony. All mice were quarantined approximately 1 week prior to their use for tumor propagation and drug efficacy testing. Mice were fed food and water ad libitum. The animal care program of Bristol-Myers Squibb Pharmaceutical Research Institute is fully accredited by the American Association for Accreditation of Laboratory Animal Care (AAALAC). All experiments were performed in accordance with Bristol-Myers Squibb (BMS) animal test methods and guidelines.

Tumor xenografts were grown and maintained subcutaneously (SC) in NSG (NOD scid IL2 receptor gamma chain knockout) mice (Jackson Lab). Tumors were propagated as subcutaneous transplants using tumor fragments obtained from donor mice.

Preclinical Chemotherapy Trials

The required numbers of animals needed to detect a meaningful response were pooled at the start of the experiment and each was given bilateral subcutaneous implants of two tumor fragments (~20 mg) with a 13-gauge trocar. Tumors were allowed to grow to the pre-determined size window (tumors outside the range were excluded) and animals were evenly distributed to various treatment and control groups. There were typically 6-8 mice per treatment and control groups, consisting of 10-12 tumors. Treatment of each animal was based on individual body weight. Treated animals were checked daily for treatment related toxicity/mortality. Each group of animals was weighed before the initiation of treatment ($Wt_1$) and then again following the last treatment dose ($Wt_2$). The difference in body weight ($Wt_2-Wt_1$) provides a measure of treatment-related toxicity.

Tumor response was determined by measurement of tumors with a caliper twice a week, until the tumors reached a predetermined "target" size of 0.5 gm or 1 gm depending on the tumor type. Tumor weights (mg) were estimated from the formula:

Tumor weight=(length×width)÷2

Tumor response criteria are expressed in terms of tumor growth inhibition (% TGI). Tumor growth delay is defined as the difference in time (days) required for the treated tumors (T) to reach a predetermined target size compared to those of the control group (C). For this purpose, the tumor weight of a group is expressed as medium tumor weight (MTW).

Tumor growth inhibition is calculated as follows:

$$\% \text{ Tumor Growth Inhibition} = \frac{\left(1 - \frac{T_t}{T_0} * \frac{C_0}{C_t}\right)}{\left(1 - \frac{C_0}{C_t}\right)}$$

where,
$C_t$=Median control tumor size at end of treatment
$C_0$=Median control tumor size at treatment initiation
$T_t$=Median tumor size of treated group at end of treatment
$T_0$=Median tumor size of treated group at treatment initiation Activity is defined as the achievement of durable tumor growth inhibition of 50% or greater (i.e. TGI ≥50%) for a period equivalent to at least 1 tumor volume doubling time and drug treatment must be for a period equivalent to at least 2 tumor volume doubling time.

Tumor response was also expressed in terms of tumor growth delay and expressed as log cell kill (LCK value), defined as the difference in time (days) required for the treated tumors (T) to reach a predetermined target size compared to those of the control group (C).

Whenever possible, antitumor activity was determined at a range of dose levels up to the maximum tolerated dose (MTD) which is defined as the dose level immediately below which excessive toxicity (i.e. more than one death) occurred. When death occurred, the day of death was recorded. Treated mice dying prior to having their tumors reach target size were considered to have died from drug toxicity. No control mice died bearing tumors less than target size. Treatment groups with more than one death caused by drug toxicity were considered to have had excessively toxic treatments and their data were not included in the evaluation of a compound's antitumor efficacy.

Potential drug toxicity interaction affecting treatment tolerability is an important consideration in combination chemotherapy trials. Interpretation of combination therapeutic results must be based on comparison of antitumor activity of the best possible response for the single agents versus the combination at comparably tolerated doses. Therefore, therapeutic synergism was defined as a therapeutic effect achieved with a tolerated regimen of the combined agents that exceeded the optimal effect achieved at any tolerated dose of monotherapy. Statistical evaluations of data were performed using Gehan's generalized Wilcoxon test. Statistical significance was declared at P<0.05.

Drug Administration

For administration of BET inhibitors to rodents, compounds were dissolved in 90% PEG300/10% TPGS/10% Ethanol. BET inhibitors were typically administered orally on a schedule of QDx7 or QDx10 (5 day-on-2 day-off), although other schedules had also been evaluated and shown to be efficacious Results:

FIG. 1 shows the results of one compound of the invention against the H187 Human Small Cell Carcinoma.

Results of the assays are shown in the Table below. The activity data is based on the use of one of the FRET assays described. Compounds with an IC50 less than 7.5 μM are shown with (+), compounds with an IC50 less than 500 nm are shown with (++) and those with an IC50 less than 50 nm are shown with (+++).

| Example # | FRET BRD4 IC$_{50}$ (uM) |
|---|---|
| Example 1 | ++ |
| Example 2 | ++ |
| Example 3 | ++ |
| Example 4 | ++ |
| Example 5 | ++ |
| Example 6 | ++ |
| Example 7 | ++ |
| Example 8 | ++ |
| Example 9 | +++ |
| Example 10 | ++ |
| Example 11 | ++ |
| Example 12 | ++ |
| Example 13 | ++ |
| Example 14 | ++ |
| Example 15 | ++ |
| Example 16 | + |
| Example 17 | ++ |
| Example 18 | ++ |
| Example 19 | ++ |
| Example 20 | ++ |
| Example 21 | ++ |
| Example 22 | ++ |
| Example 23 | + |
| Example 24 | ++ |
| Example 25 | ++ |
| Example 26 | +++ |
| Example 27 | +++ |
| Example 28 | +++ |
| Example 29 | ++ |
| Example 30 | +++ |
| Example 31 | +++ |
| Example 32 | +++ |
| Example 33 | +++ |
| Example 34 | +++ |
| Example 35 | +++ |
| Example 36 | +++ |
| Example 37 | +++ |
| Example 38 | ++ |
| Example 39 | +++ |
| Example 40 | +++ |
| Example 41 | +++ |
| Example 42 | +++ |
| Example 43 | +++ |
| Example 44 | +++ |
| Example 45 | + |
| Example 46 | ++ |
| Example 47 | +++ |
| Example 48 | +++ |
| Example 49 | + |
| Example 50 | +++ |
| Example 51 | +++ |
| Example 52 | +++ |
| Example 53 | +++ |
| Example 54 | +++ |
| Example 55 | +++ |
| Example 56 | +++ |
| Example 57 | +++ |
| Example 58 | +++ |
| Example 59 | +++ |
| Example 60 | +++ |
| Example 61 | +++ |
| Example 62 | +++ |
| Example 63 | +++ |
| Example 64 | +++ |
| Example 65 | +++ |
| Example 66 | +++ |
| Example 67 | +++ |
| Example 68 | +++ |
| Example 69 | +++ |
| Example 70 | +++ |
| Example 71 | +++ |
| Example 72 | +++ |
| Example 73 | +++ |
| Example 74 | +++ |
| Example 75 | +++ |
| Example 76 | +++ |
| Example 77 | +++ |
| Example 78 | +++ |
| Example 79 | +++ |
| Example 80 | +++ |
| Example 81 | +++ |
| Example 82 | +++ |
| Example 83 | +++ |
| Example 84 | +++ |
| Example 85 | +++ |
| Example 86 | +++ |
| Example 87 | +++ |
| Example 88 | +++ |
| Example 89 | +++ |
| Example 90 | +++ |
| Example 91 | +++ |
| Example 92 | +++ |
| Example 93 | +++ |
| Example 94 | +++ |
| Example 95 | +++ |
| Example 96 | +++ |
| Example 97 | +++ |
| Example 98 | +++ |
| Example 99 | ++ |
| Example 100 | ++ |
| Example 101 | ++ |
| Example 102 | +++ |
| Example 103 | +++ |
| Example 104 | +++ |
| Example 105 | +++ |
| Example 106 | ++ |
| Example 107 | +++ |
| Example 108 | +++ |
| Example 109 | +++ |
| Example 110 | +++ |
| Example 111 | +++ |
| Example 112 | ++ |
| Example 113 | +++ |
| Example 114 | +++ |
| Example 115 | +++ |
| Example 116 | +++ |
| Example 117 | +++ |
| Example 118 | ++ |
| Example 119 | +++ |
| Example 120 | ++ |
| Example 121 | ++ |
| Example 122 | +++ |
| Example 123 | ++ |
| Example 124 | +++ |
| Example 125 | +++ |
| Example 126 | +++ |
| Example 127 | + |
| Example 128 | ++ |
| Example 129 | ++ |
| Example 130 | +++ |
| Example 131 | +++ |
| Example 132 | +++ |
| Example 133 | +++ |
| Example 134 | +++ |
| Example 135 | +++ |
| Example 136 | +++ |

| Example # | FRET BRD4 IC$_{50}$ (uM) |
|---|---|
| Example 137 | +++ |
| Example 138 | +++ |
| Example 139 | +++ |
| Example 140 | +++ |
| Example 141 | +++ |
| Example 142 | +++ |
| Example 143 | +++ |
| Example 144 | +++ |
| Example 145 | +++ |
| Example 146 | +++ |
| Example 147 | +++ |
| Example 148 | +++ |
| Example 149 | +++ |
| Example 150 | ++ |
| Example 151 | +++ |
| Example 152 | +++ |
| Example 153 | +++ |
| Example 154 | + |
| Example 155 | + |
| Example 156 | +++ |
| Example 157 | +++ |
| Example 158 | +++ |
| Example 159 | +++ |
| Example 160 | +++ |
| Example 161 | +++ |
| Example 162 | +++ |
| Example 163 | +++ |
| Example 164 | ++ |
| Example 165 | ++ |
| Example 166 | + |
| Example 167 | +++ |
| Example 168 | ++ |
| Example 169 | +++ |
| Example 170 | +++ |
| Example 171 | +++ |
| Example 172 | +++ |
| Example 173 | + |
| Example 174 | +++ |
| Example 175 | +++ |
| Example 176 | +++ |
| Example 177 | +++ |
| Example 178 | +++ |
| Example 179 | +++ |
| Example 180 | +++ |
| Example 181 | +++ |
| Example 182 | + |
| Example 183 | +++ |
| Example 184 | ++ |
| Example 185 | +++ |
| Example 186 | +++ |
| Example 187 | ++ |
| Example 188 | +++ |
| Example 189 | +++ |
| Example 190 | ++ |
| Example 191 | +++ |
| Example 192 | +++ |
| Example 193 | +++ |
| Example 194 | +++ |
| Example 195 | +++ |
| Example 196 | +++ |
| Example 197 | +++ |
| Example 198 | +++ |
| Example 199 | +++ |
| Example 200 | +++ |
| Example 201 | +++ |
| Example 202 | +++ |
| Example 203 | +++ |
| Example 204 | +++ |
| Example 205 | +++ |
| Example 206 | +++ |
| Example 207 | +++ |
| Example 208 | +++ |
| Example 209 | +++ |
| Example 210 | +++ |
| Example 211 | +++ |
| Example 212 | +++ |
| Example 213 | +++ |
| Example 214 | +++ |
| Example 215 | +++ |
| Example 216 | +++ |
| Example 217 | +++ |
| Example 218 | +++ |
| Example 219 | +++ |
| Example 220 | +++ |
| Example 221 | +++ |
| Example 222 | +++ |
| Example 223 | +++ |
| Example 224 | +++ |
| Example 225 | +++ |
| Example 226 | +++ |
| Example 227 | +++ |
| Example 228 | +++ |
| Example 229 | +++ |
| Example 230 | +++ |
| Example 231 | +++ |
| Example 232 | +++ |
| Example 233 | +++ |

What is claimed is:

1. A compound of formula (I)

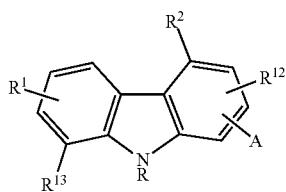

(I)

wherein:

A is an isoxazole, oxazole or triazole group substituted with 0-4 $R^{14}$;

R is optionally substituted $(C_1-C_6)$alkyl, optionally substituted $(C_3-C_8)$cycloalkyl$(C_1-C_6)$alkyl, optionally substituted aryl$(C_1-C_6)$alkyl, optionally substituted heteroaryl$(C_1-C_6)$alkyl, optionally substituted heterocyclo$(C_1-C_6)$alkyl, optionally substituted $(C_1-C_6)$alkyl-CO—, optionally substituted aryl-CO—, optionally substituted $(C_3-C_8)$cycloalkyl-CO—, optionally substituted heteroaryl, optionally substituted heterocyclo-CO—, optionally substituted aryl-SO$_2$—, optionally substituted $(C_1-C_6)$alkyl-SO$_2$—, optionally substituted $(C_3-C_8)$cycloalkyl-SO$_2$—, optionally substituted heteroaryl-SO$_2$—, optionally substituted $(C_1-C_6)$alkyl-OCO— or optionally substituted $(C_3-C_8)$cycloalkyl-OCO—; or R is

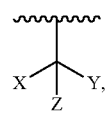

wherein

X and Y are independently selected from hydrogen, optionally substituted $(C_1-C_6)$alkyl, optionally substituted $(C_3-C_8)$cycloalkyl, optionally substituted aryl, optionally substituted heteroaryl or optionally substituted heterocyclo;

Z is hydrogen, halogen, —OH, $(C_1-C_6)$alkyl, $(C_1-C_6)$alkoxy, —NR$^3$R$^4$, —CONR$^3$R$^4$, —OCONR$^3$R$^4$, —NR$^6$OCOR$^3$, —NR$^6$CONR$^3$R$^4$, —NR$^6$SO$_2$NR$^3$R$^4$ or —NR$^6$SO$_2$R$^4$;

$R^1$ is halogen, —CN, OH, —NR$^3$R$^4$, —CONR$^3$R$^4$, —COOH, —OCONR$^3$R$^4$, —NHOCOR$^7$, —NHCONR$^7$R$^8$, —NHSO$_2$NR$^7$R$^8$, optionally substituted $(C_1-C_6)$alkyl, optionally substituted $(C_2-C_6)$alkenyl, optionally substituted $(C_2-C_6)$alkynyl, optionally substituted $(C_1-C_6)$alkoxy, optionally substituted $(C_3$-

$C_8$)cycloalkyl, optionally substituted ($C_3$-$C_8$)cycloalkyl-CO—, optionally substituted ($C_3$-$C_8$)cycloalkyl-$SO_2$—, optionally substituted aryl ($C_1$-$C_6$)alkoxy, optionally substituted ($C_3$-$C_8$)cycloalkyl ($C_1$-$C_6$)alkoxy, optionally substituted heterocyclyl-CO—, optionally substituted heterocyclyl, optionally substituted ($C_1$-$C_6$)alkyl-$SO_2$—, —$NHSO_2$-optionally substituted ($C_1$-$C_6$)alkyl, —$NHSO_2$-optionally substituted heterocyclo, optionally substituted ($C_1$-$C_6$)alkyl-$NHSO_2$— or optionally substituted heterocyclo-$NHSO_2$—;

$R^2$ is H, halogen, —CN, —COOH, —$CONR^7R^8$, —$NHCOR^3R^4$, —$OCONR^3R^4$, —$NHCOOR^3R^4$, optionally substituted ($C_1$-$C_6$)alkyl, optionally substituted ($C_2$-$C_6$)alkynyl, optionally substituted ($C_1$-$C_6$)alkoxy, optionally substituted heteroaryl or optionally substituted heterocyclo;

$R^3$ is hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy($C_1$-$C_6$)alkyl, optionally substituted aryl, optionally substituted aryl($C_1$-$C_6$)alkyl, optionally substituted aryloxy($C_1$-$C_6$)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl($C_1$-$C_6$)alkyl, $R^4$ is hydrogen, optionally substituted ($C_1$-$C_6$)alkyl or optionally substituted ($C_3$-$C_8$)cycloalkyl;

or $R^3$ and $R^4$ may be taken together with the nitrogen atom to which they are attached to form an optionally substituted ($C_4$-$C_8$) heteroaryl or ($C_4$-$C_8$) heterocyclic ring;

$R^6$ is hydrogen or optionally substituted ($C_1$-$C_6$)alkyl;

$R^7$ and $R^8$ are independently hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy($C_1$-$C_6$)alkyl, optionally substituted aryl, optionally substituted aryl($C_1$-$C_6$)alkyl, optionally substituted aryloxy($C_1$-$C_6$)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl($C_1$-$C_6$)alkyl;

or $R^7$ and $R^8$ may be taken together with the nitrogen atom to which they are attached to form an optionally substituted ($C_4$-$C_8$) heteroaryl or ($C_4$-$C_8$) heterocyclic ring;

$R^{12}$ and $R^{13}$ are independently hydrogen, halogen, —CN, OH, —$CONR^3R^4$, —$NHCOOR^4$, —$NHCONR^3R^4$, —$NHCOR^4$, —$NHSO_2R^7$, —$SO_2NR^3R^4$, —$NHSO_2NR^3R^4$, —$SO_2R^7$, optionally substituted ($C_1$-$C_6$)alkyl, optionally substituted ($C_3$-$C_8$)cycloalkyl, optionally substituted ($C_1$-$C_6$) alkoxy, optionally substituted aryl, optionally substituted heteroaryl or optionally substituted heterocyclo;

$R^{14}$ is hydrogen, optionally substituted ($C_1$-$C_6$)alkyl, ($C_1$-$C_6$)alkoxy, halogen, —CN, —$NR^3R^4$, OH, —$NHOCOR^7$, —$OCONR^7R^8$, —$NHCONR^7R^8$ or —$CF_3$;

or a pharmaceutically acceptable salt, tautomer or stereoisomer thereof.

2. A compound according to claim 1 of formula (II)

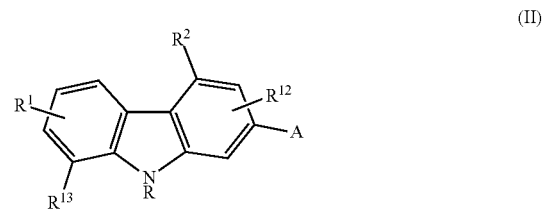

(II)

wherein:

A is an isoxazole, oxazole or triazole group substituted with 0-4 $R^{14}$;

R is optionally substituted ($C_1$-$C_6$)alkyl, optionally substituted ($C_3$-$C_8$)cycloalkyl($C_1$-$C_6$)alkyl, optionally substituted aryl($C_1$-$C_6$)alkyl, optionally substituted heteroaryl($C_1$-$C_6$)alkyl, optionally substituted heterocyclo ($C_1$-$C_6$)alkyl, optionally substituted ($C_1$-$C_6$)alkyl-CO—, optionally substituted aryl-CO—, optionally substituted ($C_3$-$C_8$)cycloalkyl-CO—, optionally substituted heteroaryl, optionally substituted heterocyclo-CO—, optionally substituted aryl-$SO_2$—, optionally substituted ($C_1$-$C_6$)alkyl-$SO_2$—, optionally substituted ($C_3$-$C_8$)cycloalkyl-$SO_2$—, optionally substituted heteroaryl-$SO_2$—, optionally substituted ($C_1$-$C_6$)alkyl-OCO— or optionally substituted ($C_3$-$C_8$)cycloalkyl-OCO—; or R is

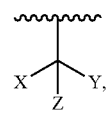

wherein

X and Y are independently selected from hydrogen, optionally substituted ($C_1$-$C_6$)alkyl, optionally substituted ($C_3$-$C_8$)cycloalkyl, optionally substituted aryl, optionally substituted heteroaryl or optionally substituted heterocyclo;

Z is hydrogen, halogen, —OH, ($C_1$-$C_6$)alkyl, ($C_1$-$C_6$) alkoxy, —$NR^3R^4$, —$CONR^3R^4$, —$OCONR^3R^4$, —$NR^6OCOR^3$, —$NR^6CONR^3R^4$, —$NR^6SO_2NR^3R^4$ or —$NR^6SO_2R^4$;

$R^1$ is halogen, —CN, OH, —$NR^3R^4$, —$CONR^3R^4$, —COOH, —$OCONR^3R^4$, —$NHOCOR^7$, —$NHCONR^7R^8$, —$NHSO_2NR^7R^8$, optionally substituted ($C_1$-$C_6$)alkyl, optionally substituted ($C_2$-$C_6$)alkenyl, optionally substituted ($C_2$-$C_6$)alkynyl, optionally substituted ($C_1$-$C_6$)alkoxy, optionally substituted ($C_3$-$C_8$)cycloalkyl, optionally substituted ($C_3$-$C_8$)cycloalkyl-CO—, optionally substituted ($C_3$-$C_8$)cycloalkyl-$SO_2$—, optionally substituted aryl ($C_1$-$C_6$)alkoxy, optionally substituted ($C_3$-$C_8$)cycloalkyl ($C_1$-$C_6$)alkoxy, optionally substituted heterocyclyl-CO—, optionally substituted heterocyclyl, optionally substituted ($C_1$-$C_6$)alkyl-$SO_2$—, —$NHSO_2$-optionally substituted ($C_1$-$C_6$)alkyl, —$NHSO_2$-optionally substituted heterocyclo, optionally substituted ($C_1$-$C_6$)alkyl-$NHSO_2$— or optionally substituted heterocyclo-$NHSO_2$—;

$R^2$ is H, halogen, —CN, —COOH, —$CONR^7R^8$, —$NHCOR^3R^4$, —$OCONR^3R^4$, —$NHCOOR^3R^4$, optionally substituted (C₁-C₆)alkyl, optionally substituted (C₂-C₆)alkynyl, optionally substituted (C₁-C₆) alkoxy, optionally substituted heteroaryl or optionally substituted heterocyclo;

R³ is hydrogen, optionally substituted (C₁-C₆)alkyl, optionally substituted (C₃-C₈)cycloalkyl, optionally substituted (C₂-C₆)alkenyl, optionally substituted (C₂-C₆)alkynyl, cyano(C₁-C₆)alkyl, hydroxy(C₁-C₆)alkyl, optionally substituted aryl, optionally substituted aryl (C₁-C₆)alkyl, optionally substituted aryloxy(C₁-C₆) alkyl, optionally substituted (C₁-C₆)alkyl-SO₂—, optionally substituted heterocyclyl, optionally substituted heterocyclyl(C₁-C₆)alkyl, optionally substituted heteroaryl or optionally substituted heteroaryl(C₁-C₆) alkyl, R⁴ is hydrogen, optionally substituted (C₁-C₆)alkyl or optionally substituted (C₃-C₈)cycloalkyl;

or R³ and R⁴ may be taken together with the nitrogen atom to which they are attached to form an optionally substituted (C₄-C₈) heteroaryl or (C₄-C₈) heterocyclic ring;

R⁶ is hydrogen or optionally substituted (C₁-C₆)alkyl;

R⁷ and R⁸ are independently hydrogen, optionally substituted (C₁-C₆)alkyl, optionally substituted (C₃-C₈)cycloalkyl, optionally substituted (C₂-C₆)alkenyl, optionally substituted (C₂-C₆)alkynyl, cyano(C₁-C₆)alkyl, hydroxy(C₁-C₆)alkyl, optionally substituted aryl, optionally substituted aryl(C₁-C₆)alkyl, optionally substituted aryloxy(C₁-C₆)alkyl, optionally substituted (C₁-C₆)alkyl-SO₂—, optionally substituted heterocyclyl, optionally substituted heterocyclyl(C₁-C₆)alkyl, optionally substituted heteroaryl or optionally substituted heteroaryl(C₁-C₆)alkyl;

or R⁷ and R⁸ may be taken together with the nitrogen atom to which they are attached to form an optionally substituted (C₄-C₈) heteroaryl or (C₄-C₈) heterocyclic ring;

R¹² and R¹³ are independently hydrogen, halogen, —CN, OH, —CONR³R⁴, —NHCOOR⁴, —NHCONR³R⁴, —NHCOR⁴, —NHSO₂R⁷, —SO₂NR³R⁴, —NHSO₂NR³R⁴, —SO₂R⁷, optionally substituted (C₁-C₆)alkyl, optionally substituted (C₃-C₈)cycloalkyl, optionally substituted (C₁-C₆) alkoxy, optionally substituted aryl, optionally substituted heteroaryl or optionally substituted heterocyclo;

R¹⁴ is hydrogen, optionally substituted (C₁-C₆)alkyl, (C₁-C₆)alkoxy, halogen, —CN, —NR³R⁴, OH, —NHOCOR⁷, —OCONR⁷R⁸, —NHCONR⁷R⁸ or —CF₃;

a pharmaceutically acceptable salt, tautomer or stereoisomer thereof.

3. A compound according to claim 2 of formula (II)

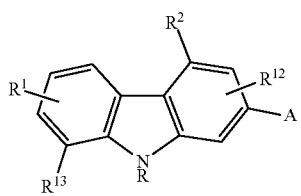

(II)

wherein:
A is an isoxazole, oxazole or triazole group substituted with 0-4 R¹⁴;

R is optionally substituted (C₁-C₆)alkyl, optionally substituted (C₃-C₈)cycloalkyl(C₁-C₆)alkyl, optionally substituted aryl(C₁-C₆)alkyl, optionally substituted heteroaryl(C₁-C₆)alkyl, optionally substituted heterocyclo (C₁-C₆)alkyl, optionally substituted (C₁-C₆)alkyl-CO—, optionally substituted aryl-CO—, optionally substituted (C₃-C₈)cycloalkyl-CO—, optionally substituted heteroaryl, optionally substituted heterocyclo-CO—, optionally substituted aryl-SO₂—, optionally substituted (C₁-C₆)alkyl-SO₂—, optionally substituted (C₃-C₈)cycloalkyl-SO₂—, optionally substituted heteroaryl-SO₂—, optionally substituted (C₁-C₆)alkyl-OCO— or optionally substituted (C₃-C₈)cycloalkyl-OCO—; or R is

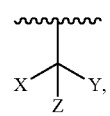

wherein
X and Y are independently selected from hydrogen, optionally substituted (C₁-C₆)alkyl, optionally substituted (C₃-C₈)cycloalkyl, optionally substituted aryl, optionally substituted heteroaryl or optionally substituted heterocyclo;

Z is hydrogen, halogen, —OH, (C₁-C₆)alkyl, (C₁-C₆) alkoxy, —NR³R⁴, —CONR³R⁴, —OCONR³R⁴, —NR⁶OCOR³, —NR⁶CONR³R⁴, —NR⁶SO₂NR³R⁴ or —NR⁶SO₂R⁴;

R¹ is halogen, —CN, OH, —NR³R⁴, —CONR³R⁴, —COOH, —OCONR³R⁴, —NHOCOR⁷, —NHCONR⁷R⁸, —NHSO₂NR⁷R⁸, optionally substituted (C₁-C₆)alkyl, optionally substituted (C₂-C₆)alkenyl, optionally substituted (C₂-C₆)alkynyl, optionally substituted (C₁-C₆)alkoxy, optionally substituted (C₃-C₈)cycloalkyl, optionally substituted (C₃-C₈)cycloalkyl-CO—, optionally substituted (C₃-C₈)cycloalkyl-SO₂—, optionally substituted aryl (C₁-C₆) alkoxy, optionally substituted (C₃-C₈)cycloalkyl (C₁-C₆)alkoxy, optionally substituted heterocyclyl-CO—, optionally substituted heterocyclyl, optionally substituted (C₁-C₆)alkyl-SO₂—, —NHSO₂-optionally substituted (C₁-C₆)alkyl, —NHSO₂-optionally substituted heterocyclo, optionally substituted (C₁-C₆)alkyl-NHSO₂— or optionally substituted heterocyclo-NHSO₂—;

R² is H, halogen, —CN, —COOH, —CONR⁷R⁸, —NHCOR³R⁴, —OCONR³R⁴, —NHCOOR³R⁴, optionally substituted (C₁-C₆)alkyl, optionally substituted (C₂-C₆)alkynyl, optionally substituted (C₁-C₆) alkoxy, optionally substituted heteroaryl or optionally substituted heterocyclo;

R³ is hydrogen, optionally substituted (C₁-C₆)alkyl, optionally substituted (C₃-C₈)cycloalkyl, optionally substituted (C₂-C₆)alkenyl, optionally substituted (C₂-C₆)alkynyl, cyano(C₁-C₆)alkyl, hydroxy(C₁-C₆)alkyl, optionally substituted aryl, optionally substituted aryl (C₁-C₆)alkyl, optionally substituted aryloxy(C₁-C₆) alkyl, optionally substituted (C₁-C₆)alkyl-SO₂—, optionally substituted heterocyclyl, optionally substituted heterocyclyl(C₁-C₆)alkyl, optionally substituted heteroaryl or optionally substituted heteroaryl(C₁-C₆) alkyl, R⁴ is hydrogen, optionally substituted (C₁-C₆)alkyl or optionally substituted (C₃-C₈)cycloalkyl;

or R³ and R⁴ may be taken together with the nitrogen atom to which they are attached to form an optionally substituted (C₄-C₈) heteroaryl or (C₄-C₈) heterocyclic ring;

R⁶ is hydrogen or optionally substituted (C₁-C₆)alkyl;

R⁷ and R⁸ are independently hydrogen, optionally substituted (C₁-C₆)alkyl, optionally substituted (C₃-C₈)cycloalkyl, optionally substituted (C₂-C₆)alkenyl, optionally substituted (C₂-C₆)alkynyl, cyano(C₁-C₆)alkyl, hydroxy(C₁-C₆)alkyl, optionally substituted aryl, optionally substituted aryl(C₁-C₆)alkyl, optionally substituted aryloxy(C₁-C₆)alkyl, optionally substituted (C₁-C₆)alkyl-SO₂—, optionally substituted heterocyclyl, optionally substituted heterocyclyl(C₁-C₆)alkyl, optionally substituted heteroaryl or optionally substituted heteroaryl(C₁-C₆)alkyl;

or R⁷ and R⁸ may be taken together with the nitrogen atom to which they are attached to form an optionally substituted (C₄-C₈) heteroaryl or (C₄-C₈) heterocyclic ring;

R¹² is hydrogen, halogen, —CN, optionally substituted (C₁-C₆)alkyl or optionally substituted (C₁-C₆) alkoxy;

R¹³ is hydrogen, halogen, —CN, OH, —CONR³R⁴, —NHCOOR⁴, —NHCONR³R⁴, —NHCOR⁴, —NHSO₂R⁷, —SO₂NR³R⁴, —NHSO₂NR³R⁴, —SO₂R⁷, optionally substituted (C₁-C₆)alkyl, optionally substituted (C₃-C₈)cycloalkyl, optionally substituted (C₁-C₆) alkoxy, optionally substituted aryl, optionally substituted heteroaryl or optionally substituted heterocyclo;

R¹⁴ is hydrogen, optionally substituted (C₁-C₆)alkyl, (C₁-C₆)alkoxy, halogen, —CN, —NR³R⁴, OH, —NHOCOR⁷, —OCONR⁷R⁸, —NHCONR⁷R⁸ or —CF₃;

or a pharmaceutically acceptable salt, tautomer or stereoisomer thereof.

4. A compound according to claim 3 of the formula

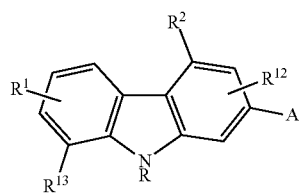

(II)

wherein:

A is an isoxazole, oxazole or triazole group substituted with 0-4 R¹⁴;

R is optionally substituted (C₁-C₆)alkyl, optionally substituted (C₃-C₈)cycloalkyl(C₁-C₆)alkyl, optionally substituted aryl(C₁-C₆)alkyl, optionally substituted heteroaryl(C₁-C₆)alkyl, optionally substituted heterocyclo(C₁-C₆)alkyl, optionally substituted (C₁-C₆)alkyl-CO—, optionally substituted aryl-CO—, optionally substituted (C₃-C₈)cycloalkyl-CO—, optionally substituted heteroaryl, optionally substituted heterocyclo-CO—, optionally substituted aryl-SO₂—, optionally substituted (C₁-C₆)alkyl-SO₂—, optionally substituted (C₃-C₈)cycloalkyl-SO₂—, optionally substituted heteroaryl-SO₂—, optionally substituted (C₁-C₆)alkyl-OCO— or optionally substituted (C₃-C₈)cycloalkyl-OCO—; or R is

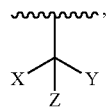

wherein

X and Y are independently selected from hydrogen, optionally substituted (C₁-C₆)alkyl, optionally substituted (C₃-C₈)cycloalkyl, optionally substituted aryl, optionally substituted heteroaryl or optionally substituted heterocyclo;

Z is hydrogen, halogen, —OH, (C₁-C₆)alkyl, (C₁-C₆) alkoxy, —NR³R⁴, —CONR³R⁴, —OCONR³R⁴, —NR⁶OCOR³, —NR⁶CONR³R⁴, —NR⁶SO₂NR³R⁴ or —NR⁶SO₂R⁴;

R¹ is halogen, —CN, OH, —NR³R⁴, —CONR³R⁴, —COOH, —OCONR³R⁴, —NHOCOR⁷, —NHCONR⁷R⁸, —NHSO₂NR⁷R⁸, optionally substituted (C₁-C₆)alkyl, optionally substituted (C₂-C₆)alkenyl, optionally substituted (C₂-C₆)alkynyl, optionally substituted (C₁-C₆)alkoxy, optionally substituted (C₃-C₈)cycloalkyl, optionally substituted (C₃-C₈)cycloalkyl-CO—, optionally substituted (C₃-C₈)cycloalkyl-SO₂—, optionally substituted aryl (C₁-C₆) alkoxy, optionally substituted (C₃-C₈)cycloalkyl (C₁-C₆)alkoxy, optionally substituted heterocyclyl-CO—, optionally substituted heterocyclyl, optionally substituted (C₁-C₆)alkyl-SO₂—, —NHSO₂-optionally substituted (C₁-C₆)alkyl, —NHSO₂-optionally substituted heterocyclo, optionally substituted (C₁-C₆)alkyl-NHSO₂— or optionally substituted heterocyclo-NHSO₂—;

R² is H, halogen, —CN, —COOH, —CONR⁷R⁸, —NHCOR³R⁴, —OCONR³R⁴, —NHCOOR³R⁴, optionally substituted (C₁-C₆)alkyl, optionally substituted (C₂-C₆)alkynyl, optionally substituted (C₁-C₆) alkoxy, optionally substituted heteroaryl or optionally substituted heterocyclo;

R³ is hydrogen, optionally substituted (C₁-C₆)alkyl, optionally substituted (C₃-C₈)cycloalkyl, optionally substituted (C₂-C₆)alkenyl, optionally substituted (C₂-C₆)alkynyl, cyano(C₁-C₆)alkyl, hydroxy(C₁-C₆)alkyl, optionally substituted aryl, optionally substituted aryl (C₁-C₆)alkyl, optionally substituted aryloxy(C₁-C₆) alkyl, optionally substituted (C₁-C₆)alkyl-SO₂—, optionally substituted heterocyclyl, optionally substituted heterocyclyl(C₁-C₆)alkyl, optionally substituted heteroaryl or optionally substituted heteroaryl(C₁-C₆)alkyl, R⁴ is hydrogen, optionally substituted (C₁-C₆)alkyl or optionally substituted (C₃-C₈)cycloalkyl;

or R³ and R⁴ may be taken together with the nitrogen atom to which they are attached to form an optionally substituted (C₄-C₈) heteroaryl or (C₄-C₈) heterocyclic ring;

R⁶ is hydrogen or optionally substituted (C₁-C₆)alkyl;

R⁷ and R⁸ are independently hydrogen, optionally substituted (C₁-C₆)alkyl, optionally substituted (C₃-C₈)cycloalkyl, optionally substituted (C₂-C₆)alkenyl, optionally substituted (C₂-C₆)alkynyl, cyano(C₁-C₆)alkyl, hydroxy(C₁-C₆)alkyl, optionally substituted aryl, optionally substituted aryl(C₁-C₆)alkyl, optionally substituted aryloxy(C₁-C₆)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl($C_1$-$C_6$)alkyl;

or $R^7$ and $R^8$ may be taken together with the nitrogen atom to which they are attached to form an optionally substituted ($C_4$-$C_8$) heteroaryl or ($C_4$-$C_8$) heterocyclic ring;

$R^{12}$ is hydrogen, halogen, —CN, optionally substituted ($C_1$-$C_6$)alkyl or optionally substituted ($C_1$-$C_6$) alkoxy;

$R^{13}$ is hydrogen, halogen, —CN, optionally substituted ($C_1$-$C_6$) alkoxy, —$NHSO_2R^7$ or —$SO_2R^7$;

$R^{14}$ is hydrogen, optionally substituted ($C_1$-$C_6$)alkyl, ($C_1$-$C_6$)alkoxy, halogen, —CN, —$NR^3R^4$, OH, —NHOCOR$^7$, —OCONR$^7R^8$, —NHCONR$^7R^8$ or —$CF_3$;

or a pharmaceutically acceptable salt, tautomer or stereoisomer thereof.

5. A compound according to claim 4 of the formula

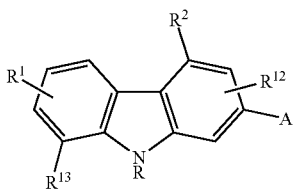

(II)

wherein:

A is an isoxazole, oxazole or triazole group substituted with 0-4 $R^{14}$;

R is optionally substituted ($C_1$-$C_6$)alkyl, optionally substituted ($C_3$-$C_8$)cycloalkyl($C_1$-$C_6$)alkyl, optionally substituted aryl($C_1$-$C_6$)alkyl, optionally substituted heteroaryl($C_1$-$C_6$)alkyl, optionally substituted heterocyclo($C_1$-$C_6$)alkyl, optionally substituted ($C_1$-$C_6$)alkyl-CO—, optionally substituted aryl-CO—, optionally substituted ($C_3$-$C_8$)cycloalkyl-CO—, optionally substituted heteroaryl, optionally substituted heterocyclo-CO—, optionally substituted aryl-$SO_2$—, optionally substituted ($C_1$-$C_6$)alkyl-$SO_2$—, optionally substituted ($C_3$-$C_8$)cycloalkyl-$SO_2$—, optionally substituted heteroaryl-$SO_2$—, optionally substituted ($C_1$-$C_6$)alkyl-OCO— or optionally substituted ($C_3$-$C_8$)cycloalkyl-OCO—; or R is

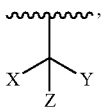

wherein

X and Y are independently selected from hydrogen, optionally substituted ($C_1$-$C_6$)alkyl, optionally substituted ($C_3$-$C_8$)cycloalkyl, optionally substituted aryl, optionally substituted heteroaryl or optionally substituted heterocyclo;

Z is hydrogen, halogen, —OH, ($C_1$-$C_6$)alkyl, ($C_1$-$C_6$) alkoxy, —$NR^3R^4$, —$CONR^3R^4$, —$OCONR^3R^4$, —$NR^6OCOR^3$, —$NR^6CONR^3R^4$, —$NR^6SO_2NR^3R^4$ or —$NR^6SO_2R^4$;

$R^1$ is halogen, —CN, OH, —$NR^3R^4$, —$CONR^3R^4$, —COOH, —$OCONR^3R^4$, —NHOCOR$^7$, —NHCONR$^7R^8$, —NHSO$_2$NR$^7R^8$, optionally substituted ($C_1$-$C_6$)alkyl, optionally substituted ($C_2$-$C_6$)alkenyl, optionally substituted ($C_2$-$C_6$)alkynyl, optionally substituted ($C_1$-$C_6$)alkoxy, optionally substituted ($C_3$-$C_8$)cycloalkyl, optionally substituted ($C_3$-$C_8$)cycloalkyl-CO—, optionally substituted ($C_3$-$C_8$)cycloalkyl-$SO_2$—, optionally substituted aryl ($C_1$-$C_6$)alkoxy, optionally substituted ($C_3$-$C_8$)cycloalkyl ($C_1$-$C_6$)alkoxy, optionally substituted heterocyclyl-CO—, optionally substituted heterocyclyl, optionally substituted ($C_1$-$C_6$)alkyl-$SO_2$—, —$NHSO_2$-optionally substituted ($C_1$-$C_6$)alkyl, —$NHSO_2$-optionally substituted heterocyclo, optionally substituted ($C_1$-$C_6$)alkyl-$NHSO_2$— or optionally substituted heterocyclo-$NHSO_2$—;

$R^2$ is H, halogen, —CN, —COOH, —$CONR^7R^8$, —$NHCOR^3R^4$, —$OCONR^3R^4$, —$NHCOOR^3R^4$, optionally substituted ($C_1$-$C_6$)alkyl, optionally substituted ($C_2$-$C_6$)alkynyl, optionally substituted ($C_1$-$C_6$) alkoxy, optionally substituted heteroaryl or optionally substituted heterocyclo;

$R^3$ is hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy($C_1$-$C_6$)alkyl, optionally substituted aryl, optionally substituted aryl ($C_1$-$C_6$)alkyl, optionally substituted aryloxy($C_1$-$C_6$) alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl($C_1$-$C_6$)alkyl, $R^4$ is hydrogen, optionally substituted ($C_1$-$C_6$)alkyl or optionally substituted ($C_3$-$C_8$)cycloalkyl;

or $R^3$ and $R^4$ may be taken together with the nitrogen atom to which they are attached to form an optionally substituted ($C_4$-$C_8$) heteroaryl or ($C_4$-$C_8$) heterocyclic ring;

$R^6$ is hydrogen or optionally substituted ($C_1$-$C_6$)alkyl;

$R^7$ and $R^8$ are independently hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy($C_1$-$C_6$)alkyl, optionally substituted aryl, optionally substituted aryl($C_1$-$C_6$)alkyl, optionally substituted aryloxy($C_1$-$C_6$)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl($C_1$-$C_6$)alkyl;

or $R^7$ and $R^8$ may be taken together with the nitrogen atom to which they are attached to form an optionally substituted ($C_4$-$C_8$) heteroaryl or ($C_4$-$C_8$) heterocyclic ring;

$R^{12}$ is hydrogen, halogen, —CN, optionally substituted ($C_1$-$C_6$)alkyl or optionally substituted ($C_1$-$C_6$) alkoxy;

$R^{13}$ is hydrogen, halogen, —CN, optionally substituted ($C_1$-$C_6$) alkoxy, —$NHSO_2R^7$ or —$SO_2R^7$;

$R^{14}$ is hydrogen or optionally substituted ($C_1$-$C_6$)alkyl;

or a pharmaceutically acceptable salt, tautomer or stereoisomer thereof.

6. A compound according to claim 5 of the formula

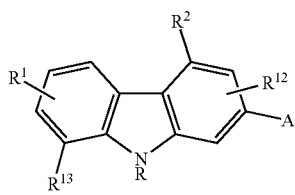

(II)

wherein:
A is an isoxazole, oxazole or triazole group substituted with 0-2 $R^{14}$;
R is optionally substituted $(C_1-C_6)$alkyl, optionally substituted $(C_3-C_8)$cycloalkyl$(C_1-C_6)$alkyl, optionally substituted aryl$(C_1-C_6)$alkyl, optionally substituted heteroaryl$(C_1-C_6)$alkyl, optionally substituted heterocyclo$(C_1-C_6)$alkyl, optionally substituted $(C_1-C_6)$alkyl-CO—, optionally substituted aryl-CO—, optionally substituted $(C_3-C_8)$cycloalkyl-CO—, optionally substituted heteroaryl, optionally substituted heterocyclo-CO—, optionally substituted aryl-SO$_2$—, optionally substituted $(C_1-C_6)$alkyl-SO$_2$—, optionally substituted $(C_3-C_8)$cycloalkyl-SO$_2$—, optionally substituted heteroaryl-SO$_2$—, optionally substituted $(C_1-C_6)$alkyl-OCO— or optionally substituted $(C_3-C_8)$cycloalkyl-OCO—; or
R is

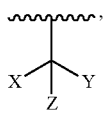

wherein
X and Y are independently selected from hydrogen, optionally substituted $(C_1-C_6)$alkyl, optionally substituted $(C_3-C_8)$cycloalkyl, optionally substituted aryl, optionally substituted heteroaryl or optionally substituted heterocyclo;
Z is hydrogen, halogen, —OH, $(C_1-C_6)$alkyl, $(C_1-C_6)$alkoxy, —NR$^3$R$^4$, —CONR$^3$R$^4$, —OCONR$^3$R$^4$, —NR$^6$OCOR$^3$, —NR$^6$CONR$^3$R$^4$, —NR$^6$SO$_2$NR$^3$R$^4$ or —NR$^6$SO$_2$R$^4$;
$R^1$ is halogen, —CN, OH, —NR$^3$R$^4$, —CONR$^3$R$^4$, —COOH, —OCONR$^3$R$^4$, —NHOCOR$^7$, —NHCONR$^7$R$^8$, —NHSO$_2$NR$^7$R$^8$, optionally substituted $(C_1-C_6)$alkyl, optionally substituted $(C_2-C_6)$alkenyl, optionally substituted $(C_2-C_6)$alkynyl, optionally substituted $(C_1-C_6)$alkoxy, optionally substituted $(C_3-C_8)$cycloalkyl, optionally substituted $(C_3-C_8)$cycloalkyl-CO—, optionally substituted $(C_3-C_8)$cycloalkyl-SO$_2$—, optionally substituted aryl $(C_1-C_6)$alkoxy, optionally substituted $(C_3-C_8)$cycloalkyl $(C_1-C_6)$alkoxy, optionally substituted heterocyclyl-CO—, optionally substituted heterocyclyl, optionally substituted $(C_1-C_6)$alkyl-SO$_2$—, —NHSO$_2$-optionally substituted $(C_1-C_6)$alkyl, —NHSO$_2$-optionally substituted heterocyclo, optionally substituted $(C_1-C_6)$alkyl-NHSO$_2$— or optionally substituted heterocyclo-NHSO$_2$—;

$R^2$ is H, —CN, —COOH or —CONR$^7$R$^8$;
$R^3$ is hydrogen, optionally substituted $(C_1-C_6)$alkyl, optionally substituted $(C_3-C_8)$cycloalkyl, optionally substituted $(C_2-C_6)$alkenyl, optionally substituted $(C_2-C_6)$alkynyl, cyano$(C_1-C_6)$alkyl, hydroxy$(C_1-C_6)$alkyl, optionally substituted aryl, optionally substituted aryl$(C_1-C_6)$alkyl, optionally substituted aryloxy$(C_1-C_6)$alkyl, optionally substituted $(C_1-C_6)$alkyl-SO$_2$—, optionally substituted heterocyclyl, optionally substituted heterocyclyl$(C_1-C_6)$alkyl, optionally substituted heteroaryl or optionally substituted heteroaryl$(C_1-C_6)$alkyl,
$R^4$ is hydrogen, optionally substituted $(C_1-C_6)$alkyl or optionally substituted $(C_3-C_8)$cycloalkyl;
or $R^3$ and $R^4$ may be taken together with the nitrogen atom to which they are attached to form an optionally substituted $(C_4-C_8)$ heteroaryl or $(C_4-C_8)$ heterocyclic ring;
$R^6$ is hydrogen or optionally substituted $(C_1-C_6)$alkyl;
$R^7$ and $R^8$ are independently hydrogen, optionally substituted $(C_1-C_6)$alkyl, optionally substituted $(C_3-C_8)$cycloalkyl, optionally substituted $(C_2-C_6)$alkenyl, optionally substituted $(C_2-C_6)$alkynyl, cyano$(C_1-C_6)$alkyl, hydroxy$(C_1-C_6)$alkyl, optionally substituted aryl, optionally substituted aryl$(C_1-C_6)$alkyl, optionally substituted aryloxy$(C_1-C_6)$alkyl, optionally substituted $(C_1-C_6)$alkyl-SO$_2$—, optionally substituted heterocyclyl, optionally substituted heterocyclyl$(C_1-C_6)$alkyl, optionally substituted heteroaryl or optionally substituted heteroaryl$(C_1-C_6)$alkyl;
or $R^7$ and $R^8$ may be taken together with the nitrogen atom to which they are attached to form an optionally substituted $(C_4-C_8)$ heteroaryl or $(C_4-C_8)$ heterocyclic ring;
$R^{12}$ is hydrogen, halogen, —CN, optionally substituted $(C_1-C_6)$alkyl or optionally substituted $(C_1-C_6)$ alkoxy;
$R^{13}$ is hydrogen, halogen, —CN, optionally substituted $(C_1-C_6)$ alkoxy, —NHSO$_2$R$^7$ or —SO$_2$R$^7$;
$R^{14}$ is hydrogen or optionally substituted $(C_1-C_6)$alkyl;
or a pharmaceutically acceptable salt, tautomer or stereoisomer thereof.

7. A compound according to claim 6 of the formula

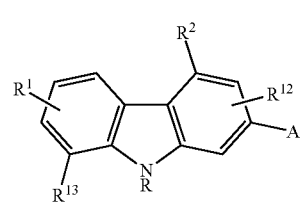

(II)

wherein:
A is an isoxazole, oxazole or triazole group substituted with 0-2 $R^{14}$;
R is optionally substituted $(C_1-C_6)$alkyl, optionally substituted $(C_3-C_8)$cycloalkyl$(C_1-C_6)$alkyl, optionally substituted aryl$(C_1-C_6)$alkyl, optionally substituted heteroaryl$(C_1-C_6)$alkyl, optionally substituted heterocyclo$(C_1-C_6)$alkyl, optionally substituted $(C_1-C_6)$alkyl-CO—, optionally substituted aryl-CO—, optionally substituted $(C_3-C_8)$cycloalkyl-CO—, optionally substituted heteroaryl, optionally substituted heterocyclo-CO—, optionally substituted aryl-SO$_2$—, optionally substituted $(C_1-C_6)$alkyl-SO$_2$—, optionally substituted ($C_3$-$C_8$)cycloalkyl-$SO_2$—, optionally substituted heteroaryl-$SO_2$—, optionally substituted ($C_1$-$C_6$)alkyl-OCO— or optionally substituted ($C_3$-$C_8$)cycloalkyl-OCO—; or R is

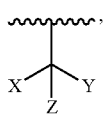

wherein

X and Y are independently selected from hydrogen, optionally substituted ($C_1$-$C_6$)alkyl, optionally substituted ($C_3$-$C_8$)cycloalkyl, optionally substituted aryl, optionally substituted heteroaryl or optionally substituted heterocyclo;

Z is hydrogen, halogen, —OH, ($C_1$-$C_6$)alkyl, ($C_1$-$C_6$)alkoxy, —$NR^3R^4$, —$CONR^3R^4$, —$OCONR^3R^4$, —$NR^6OCOR^3$, —$NR^6CONR^3R^4$, —$NR^6SO_2NR^3R^4$ or —$NR^6SO_2R^4$;

$R^1$ is optionally substituted ($C_1$-$C_6$)alkyl, optionally substituted ($C_1$-$C_6$)alkyl-$SO_2$—, optionally substituted ($C_3$-$C_8$)cycloalkyl-CO—, optionally substituted ($C_3$-$C_8$)cycloalkyl-$SO_2$— or optionally substituted heterocyclyl-CO—;

$R^2$ is H, —CN, —COOH or —$CONR^7R^8$;

$R^3$ is hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy($C_1$-$C_6$)alkyl, optionally substituted aryl, optionally substituted aryl ($C_1$-$C_6$)alkyl, optionally substituted aryloxy($C_1$-$C_6$)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl($C_1$-$C_6$)alkyl, $R^4$ is hydrogen, optionally substituted ($C_1$-$C_6$)alkyl or optionally substituted ($C_3$-$C_8$)cycloalkyl;

or $R^3$ and $R^4$ may be taken together with the nitrogen atom to which they are attached to form an optionally substituted ($C_4$-$C_8$) heteroaryl or ($C_4$-$C_8$) heterocyclic ring; $R^6$ is hydrogen or optionally substituted ($C_1$-$C_6$)alkyl;

$R^6$ is hydrogen or optionally substituted ($C_1$-$C_6$)alkyl;

$R^7$ and $R^8$ are independently hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy($C_1$-$C_6$)alkyl, optionally substituted aryl, optionally substituted aryl($C_1$-$C_6$)alkyl, optionally substituted aryloxy($C_1$-$C_6$)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl($C_1$-$C_6$)alkyl;

or $R^7$ and $R^8$ may be taken together with the nitrogen atom to which they are attached to form an optionally substituted ($C_4$-$C_8$) heteroaryl or ($C_4$-$C_8$) heterocyclic ring;

$R^{12}$ is hydrogen, halogen, —CN, optionally substituted ($C_1$-$C_6$)alkyl or optionally substituted ($C_1$-$C_6$) alkoxy;

$R^{13}$ is hydrogen, halogen, —CN, optionally substituted ($C_1$-$C_6$) alkoxy, —$NHSO_2R^7$ or —$SO_2R^7$;

$R^{14}$ is hydrogen or optionally substituted ($C_1$-$C_6$)alkyl;

or a pharmaceutically acceptable salt, tautomer or stereoisomer thereof.

8. A compound according to claim 7 of the formula

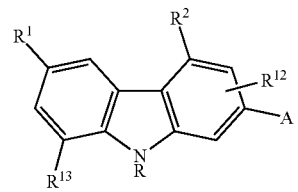

(III)

wherein:

A is an isoxazole, oxazole or triazole group substituted with 0-2 $R^{14}$;

R is optionally substituted ($C_1$-$C_6$)alkyl, optionally substituted ($C_3$-$C_8$)cycloalkyl($C_1$-$C_6$)alkyl, optionally substituted aryl($C_1$-$C_6$)alkyl, optionally substituted heteroaryl($C_1$-$C_6$)alkyl, optionally substituted heterocyclo($C_1$-$C_6$)alkyl, optionally substituted ($C_1$-$C_6$)alkyl-CO—, optionally substituted aryl-CO—, optionally substituted ($C_3$-$C_8$)cycloalkyl-CO—, optionally substituted heteroaryl, optionally substituted heterocyclo-CO—, optionally substituted aryl-$SO_2$—, optionally substituted ($C_1$-$C_6$)alkyl-$SO_2$—, optionally substituted ($C_3$-$C_8$)cycloalkyl-$SO_2$—, optionally substituted heteroaryl-$SO_2$—, optionally substituted ($C_1$-$C_6$)alkyl-OCO— or optionally substituted ($C_3$-$C_8$)cycloalkyl-OCO—; or R is

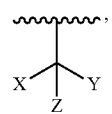

wherein

X and Y are independently selected from hydrogen, optionally substituted ($C_1$-$C_6$)alkyl, optionally substituted ($C_3$-$C_8$)cycloalkyl, optionally substituted aryl, optionally substituted heteroaryl or optionally substituted heterocyclo;

Z is hydrogen, halogen, —OH, ($C_1$-$C_6$)alkyl, ($C_1$-$C_6$) alkoxy, —$NR^3R^4$, —$CONR^3R^4$, —$OCONR^3R^4$, —$NR^6OCOR^3$, —$NR^6CONR^3R^4$, —$NR^6SO_2NR^3R^4$ or —$NR^6SO_2R^4$;

$R^1$ is optionally substituted ($C_1$-$C_6$)alkyl, optionally substituted ($C_1$-$C_6$)alkyl-$SO_2$—, optionally substituted ($C_3$-$C_8$)cycloalkyl-CO—, optionally substituted ($C_3$-$C_8$)cycloalkyl-$SO_2$— or optionally substituted heterocyclyl-CO—;

$R^2$ is H, —CN, —COOH or —$CONR^7R^8$;

$R^3$ is hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy($C_1$-$C_6$)alkyl, optionally substituted aryl, optionally substituted aryl ($C_1$-$C_6$)alkyl, optionally substituted aryloxy($C_1$-$C_6$) alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl($C_1$-$C_6$) alkyl, $R^4$ is hydrogen, optionally substituted ($C_1$-$C_6$)alkyl or optionally substituted ($C_3$-$C_8$)cycloalkyl;

or $R^3$ and $R^4$ may be taken together with the nitrogen atom to which they are attached to form an optionally substituted ($C_4$-$C_8$) heteroaryl or ($C_4$-$C_8$) heterocyclic ring;

$R^6$ is hydrogen or optionally substituted ($C_1$-$C_6$)alkyl;

$R^7$ and $R^8$ are independently hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy($C_1$-$C_6$)alkyl, optionally substituted aryl, optionally substituted aryl($C_1$-$C_6$)alkyl, optionally substituted aryloxy($C_1$-$C_6$)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl($C_1$-$C_6$)alkyl;

or $R^7$ and $R^8$ may be taken together with the nitrogen atom to which they are attached to form an optionally substituted ($C_4$-$C_8$) heteroaryl or ($C_4$-$C_8$) heterocyclic ring;

$R^{12}$ is hydrogen, halogen, —CN, optionally substituted ($C_1$-$C_6$)alkyl or optionally substituted ($C_1$-$C_6$) alkoxy;

$R^{13}$ is hydrogen, halogen, —CN, optionally substituted ($C_1$-$C_6$) alkoxy, —$NHSO_2R^7$ or —$SO_2R^7$;

$R^{14}$ is hydrogen or optionally substituted ($C_1$-$C_6$)alkyl;

or a pharmaceutically acceptable salt, tautomer or stereoisomer thereof.

9. A compound according to claim 8 of the formula

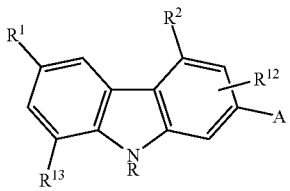

(III)

wherein:

A is an isoxazole, oxazole or triazole group substituted with 0-2 $R^{14}$;

R is optionally substituted ($C_1$-$C_6$)alkyl, optionally substituted ($C_3$-$C_8$)cycloalkyl($C_1$-$C_6$)alkyl, optionally substituted aryl($C_1$-$C_6$)alkyl, optionally substituted ($C_1$-$C_6$)alkyl-$SO_2$— or optionally substituted ($C_1$-$C_6$)alkyl-OCO—; or R is

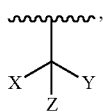

wherein

X and Y are independently selected from hydrogen, optionally substituted ($C_1$-$C_6$)alkyl, optionally substituted ($C_3$-$C_8$)cycloalkyl, optionally substituted aryl, optionally substituted heteroaryl or optionally substituted heterocyclo;

Z is hydrogen, halogen, —OH, ($C_1$-$C_6$)alkyl, ($C_1$-$C_6$) alkoxy, —$NR^3R^4$, —$CONR^3R^4$, —$OCONR^3R^4$, —$NR^6OCOR^3$, —$NR^6CONR^3R^4$, —$NR^6SO_2NR^3R^4$ or —$NR^6SO_2R^4$;

$R^1$ is optionally substituted ($C_1$-$C_6$)alkyl, optionally substituted ($C_1$-$C_6$)alkyl-$SO_2$—, optionally substituted ($C_3$-$C_8$)cycloalkyl-CO—, optionally substituted ($C_3$-$C_8$)cycloalkyl-$SO_2$— or optionally substituted heterocyclyl-CO—;

$R^2$ is H, —CN, —COOH or —$CONR^7R^8$;

$R^3$ is hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy($C_1$-$C_6$)alkyl, optionally substituted aryl, optionally substituted aryl($C_1$-$C_6$)alkyl, optionally substituted aryloxy($C_1$-$C_6$)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl($C_1$-$C_6$)alkyl, $R^4$ is hydrogen, optionally substituted ($C_1$-$C_6$)alkyl or optionally substituted ($C_3$-$C_8$)cycloalkyl;

or $R^3$ and $R^4$ may be taken together with the nitrogen atom to which they are attached to form an optionally substituted ($C_4$-$C_8$) heteroaryl or ($C_4$-$C_8$) heterocyclic ring;

$R^6$ is hydrogen or optionally substituted ($C_1$-$C_6$)alkyl;

$R^7$ and $R^8$ are independently hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy($C_1$-$C_6$)alkyl, optionally substituted aryl, optionally substituted aryl($C_1$-$C_6$)alkyl, optionally substituted aryloxy($C_1$-$C_6$)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl($C_1$-$C_6$)alkyl;

or $R^7$ and $R^8$ may be taken together with the nitrogen atom to which they are attached to form an optionally substituted ($C_4$-$C_8$) heteroaryl or ($C_4$-$C_8$) heterocyclic ring;

$R^{12}$ is hydrogen, halogen, —CN, optionally substituted ($C_1$-$C_6$)alkyl or optionally substituted ($C_1$-$C_6$) alkoxy;

$R^{13}$ is hydrogen, halogen, —CN, optionally substituted ($C_1$-$C_6$) alkoxy, —$NHSO_2R^7$ or —$SO_2R^7$;

$R^{14}$ is hydrogen or optionally substituted ($C_1$-$C_6$)alkyl;

or a pharmaceutically acceptable salt, tautomer or stereoisomer thereof.

10. A compound according to claim 9 of the formula

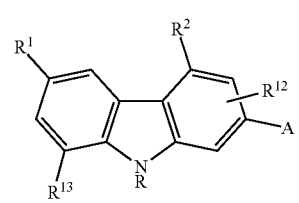

(III)

wherein:

A is

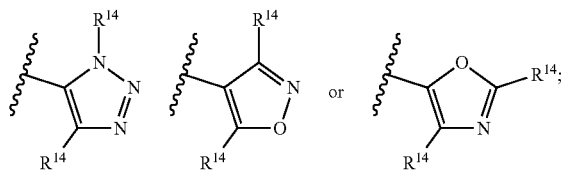

R is optionally substituted $(C_1-C_6)$alkyl, optionally substituted $(C_3-C_8)$cycloalkyl$(C_1-C_6)$alkyl, optionally substituted aryl$(C_1-C_6)$alkyl, optionally substituted $(C_1-C_6)$alkyl-$SO_2$— or optionally substituted $(C_1-C_6)$alkyl-OCO—; or R is

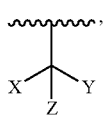

wherein

X and Y are independently selected from hydrogen, optionally substituted $(C_1-C_6)$alkyl, optionally substituted $(C_3-C_8)$cycloalkyl, optionally substituted aryl, optionally substituted heteroaryl or optionally substituted heterocyclo;

Z is hydrogen, halogen, —OH, $(C_1-C_6)$alkyl, $(C_1-C_6)$alkoxy, —$NR^3R^4$, —$CONR^3R^4$, —$OCONR^3R^4$, —$NR^6OCOR^3$, —$NR^6CONR^3R^4$, —$NR^6SO_2NR^3R^4$ or —$NR^6SO_2R^4$;

$R^1$ is optionally substituted $(C_1-C_6)$alkyl, optionally substituted $(C_1-C_6)$alkyl-$SO_2$—, optionally substituted $(C_3-C_8)$cycloalkyl-CO—, optionally substituted $(C_3-C_8)$cycloalkyl-$SO_2$— or optionally substituted heterocyclyl-CO—;

$R^2$ is H, —CN, —COOH or —$CONR^7R^8$;

$R^3$ is hydrogen, optionally substituted $(C_1-C_6)$alkyl, optionally substituted $(C_3-C_8)$cycloalkyl, optionally substituted $(C_2-C_6)$alkenyl, optionally substituted $(C_2-C_6)$alkynyl, cyano$(C_1-C_6)$alkyl, hydroxy$(C_1-C_6)$alkyl, optionally substituted aryl, optionally substituted aryl$(C_1-C_6)$alkyl, optionally substituted aryloxy$(C_1-C_6)$alkyl, optionally substituted $(C_1-C_6)$alkyl-$SO_2$—, optionally substituted heterocyclyl, optionally substituted heterocyclyl$(C_1-C_6)$alkyl, optionally substituted heteroaryl or optionally substituted heteroaryl$(C_1-C_6)$alkyl, $R^4$ is hydrogen, optionally substituted $(C_1-C_6)$alkyl or optionally substituted $(C_3-C_8)$cycloalkyl;

or $R^3$ and $R^4$ may be taken together with the nitrogen atom to which they are attached to form an optionally substituted $(C_4-C_8)$ heteroaryl or $(C_4-C_8)$ heterocyclic ring;

$R^6$ is hydrogen or optionally substituted $(C_1-C_6)$alkyl;

$R^7$ and $R^8$ are independently hydrogen, optionally substituted $(C_1-C_6)$alkyl, optionally substituted $(C_3-C_8)$cycloalkyl, optionally substituted $(C_2-C_6)$alkenyl, optionally substituted $(C_2-C_6)$alkynyl, cyano$(C_1-C_6)$alkyl, hydroxy$(C_1-C_6)$alkyl, optionally substituted aryl, optionally substituted aryl$(C_1-C_6)$alkyl, optionally substituted aryloxy$(C_1-C_6)$alkyl, optionally substituted $(C_1-C_6)$alkyl-$SO_2$—, optionally substituted heterocyclyl, optionally substituted heterocyclyl$(C_1-C_6)$alkyl, optionally substituted heteroaryl or optionally substituted heteroaryl$(C_1-C_6)$alkyl;

or $R^7$ and $R^8$ may be taken together with the nitrogen atom to which they are attached to form an optionally substituted $(C_4-C_8)$ heteroaryl or $(C_4-C_8)$ heterocyclic ring;

$R^{12}$ is hydrogen, halogen, —CN, optionally substituted $(C_1-C_6)$alkyl or optionally substituted $(C_1-C_6)$ alkoxy;

$R^{13}$ is hydrogen, halogen, —CN, optionally substituted $(C_1-C_6)$ alkoxy, —$NHSO_2R^7$ or —$SO_2R^7$;

$R^{14}$ is hydrogen or optionally substituted $(C_1-C_6)$alkyl;

or a pharmaceutically acceptable salt, tautomer or stereoisomer thereof.

11. A compound selected from the following 2-(3,5-dimethyl-4-isoxazolyl)-6-((cis-2,6-dimethyl-4-morpholinyl)carbonyl)-9-ethyl-9H-carbazole;

2-(dimethyl-1,2-oxazol-4-yl)-6-[(2R,6S)-2,6-dimethyl-morpholine-4-carbonyl]-9-propyl-9H-carbazole;

2-(dimethyl-1,2-oxazol-4-yl)-6-[(2R,6S)-2,6-dimethyl-morpholine-4-carbonyl]-9-(2-methylpropyl)-9H-carbazole;

9-(cyclopropylmethyl)-2-(dimethyl-1,2-oxazol-4-yl)-6-[(2R,6S)-2,6-dimethylmorpholine-4-carbonyl]-9H-carbazole;

2-(dimethyl-1,2-oxazol-4-yl)-6-[(2R,6S)-2,6-dimethyl-morpholine-4-carbonyl]-9-(2-fluoroethyl)-9H-carbazole;

9-(2,2-difluoroethyl)-2-(dimethyl-1,2-oxazol-4-yl)-6-[(2R,6S)-2,6-dimethylmorpholine-4-carbonyl]-9H-carbazole;

2-(dimethyl-1,2-oxazol-4-yl)-6-[(2R,6S)-2,6-dimethyl-morpholine-4-carbonyl]-9-(2-methoxyethyl)-9H-carbazole;

9-benzyl-2-(dimethyl-1,2-oxazol-4-yl)-6-[(2R,6S)-2,6-dimethylmorpholine-4-carbonyl]-9H-carbazole;

2-(dimethyl-1,2-oxazol-4-yl)-6-[(2R,6S)-2,6-dimethyl-morpholine-4-carbonyl]-9-(2-phenylethyl)-9H-carbazole;

9-[(2-chlorophenyl)methyl]-2-(dimethyl-1,2-oxazol-4-yl)-6-[(2R,6S)-2,6-dimethylmorpholine-4-carbonyl]-9H-carbazole;

9-[(4-chlorophenyl)methyl]-2-(dimethyl-1,2-oxazol-4-yl)-6-[(2R,6S)-2,6-dimethylmorpholine-4-carbonyl]-9H-carbazole;

9-[(3-chlorophenyl)methyl]-2-(dimethyl-1,2-oxazol-4-yl)-6-[(2R,6S)-2,6-dimethylmorpholine-4-carbonyl]-9H-carbazole;

2-(dimethyl-1,2-oxazol-4-yl)-6-[(2R,6S)-2,6-dimethyl-morpholine-4-carbonyl]-9-[(3-methoxyphenyl)methyl]-9H-carbazole;

2-(dimethyl-1,2-oxazol-4-yl)-6-[(2R,6S)-2,6-dimethyl-morpholine-4-carbonyl]-9-[(2-methoxyphenyl)methyl]-9H-carbazole;

2-(dimethyl-1,2-oxazol-4-yl)-6-[(2R,6S)-2,6-dimethyl-morpholine-4-carbonyl]-9-[(2-fluorophenyl)methyl]-9H-carbazole;

2-(dimethyl-1,2-oxazol-4-yl)-6-[(2R,6S)-2,6-dimethyl-morpholine-4-carbonyl]-9-[(3-fluorophenyl)methyl]-9H-carbazole;

2-(dimethyl-1,2-oxazol-4-yl)-6-[(2R,6S)-2,6-dimethyl-morpholine-4-carbonyl]-9-[(4-fluorophenyl)methyl]-9H-carbazole;

2-(dimethyl-1,2-oxazol-4-yl)-6-[(2R,6S)-2,6-dimethyl-morpholine-4-carbonyl]-9-[(2-methylphenyl)methyl]-9H-carbazole;

2-(dimethyl-1,2-oxazol-4-yl)-6-[(2R,6S)-2,6-dimethyl-morpholine-4-carbonyl]-9-[(3-methylphenyl)methyl]-9H-carbazole;

2-(dimethyl-1,2-oxazol-4-yl)-6-[(2R,6S)-2,6-dimethyl-morpholine-4-carbonyl]-9-[(4-methylphenyl)methyl]-9H-carbazole;

9-(cyclopropylmethyl)-2-(3,5-dimethyl-4-isoxazolyl)-6-(4-morpholinylcarbonyl)-9H-carbazole;

2-(3,5-dimethyl-4-isoxazolyl)-6-((cis-2,6-dimethyl-4-morpholinyl)carbonyl)-9-(methyl sulfonyl)-9H-carbazole;

9-benzoyl-2-(3,5-dimethyl-4-isoxazolyl)-6-((cis-2,6-dimethyl-4-morpholinyl)carbonyl)-9H-carbazole;

9-(cyclobutylmethyl)-2-(3,5-dimethyl-4-isoxazolyl)-6-((cis-2,6-dimethyl-4-morpholinyl)carbonyl)-9H-carbazole-4-carboxamide;

2-(dimethyl-1,2-oxazol-4-yl)-6-[(2R,6S)-2,6-dimethyl-morpholine-4-carbonyl]-9-(1,3-thiazol-4-ylmethyl)-9H-carbazole-4-carboxamide;

2-(dimethyl-1,2-oxazol-4-yl)-6-[(2R,6S)-2,6-dimethyl-morpholine-4-carbonyl]-9-[(4-methyl-1,3-thiazol-2-yl)methyl]-9H-carbazole-4-carboxamide;

2-(dimethyl-1,2-oxazol-4-yl)-6-[(2R,6S)-2,6-dimethyl-morpholine-4-carbonyl]-9-(1,3-oxazol-2-ylmethyl)-9H-carbazole-4-carboxamide;

2-(dimethyl-1,2-oxazol-4-yl)-6-[(2R,6S)-2,6-dimethyl-morpholine-4-carbonyl]-9-(1,3-thiazol-2-ylmethyl)-9H-carbazole-4-carboxamide;

2-(dimethyl-1,2-oxazol-4-yl)-6-[(2R,6S)-2,6-dimethyl-morpholine-4-carbonyl]-9-[(2-fluorophenyl)methyl]-9H-carbazole-4-carboxamide;

2-(dimethyl-1,2-oxazol-4-yl)-6-[(2R,6S)-2,6-dimethyl-morpholine-4-carbonyl]-9-[(4-fluorophenyl)methyl]-9H-carbazole-4-carboxamide;

9-[(2-chlorophenyl)methyl]-2-(dimethyl-1,2-oxazol-4-yl)-6-[(2R,6S)-2,6-dimethylmorpholine-4-carbonyl]-9H-carbazole-4-carboxamide;

9-[(3-chlorophenyl)methyl]-2-(dimethyl-1,2-oxazol-4-yl)-6-[(2R,6S)-2,6-dimethylmorpholine-4-carbonyl]-9H-carbazole-4-carboxamide;

9-[(4-chlorophenyl)methyl]-2-(dimethyl-1,2-oxazol-4-yl)-6-[(2R,6S)-2,6-dimethylmorpholine-4-carbonyl]-9H-carbazole-4-carboxamide;

9-[(2,4-difluorophenyl)methyl]-2-(dimethyl-1,2-oxazol-4-yl)-6-[(2R,6S)-2,6-dimethylmorpholine-4-carbonyl]-9H-carbazole-4-carboxamide;

9-[(4-cyanophenyl)methyl]-2-(dimethyl-1,2-oxazol-4-yl)-6-[(2R,6S)-2,6-dimethylmorpholine-4-carbonyl]-9H-carbazole-4-carboxamide;

2-(dimethyl-1,2-oxazol-4-yl)-6-[(2R,6S)-2,6-dimethyl-morpholine-4-carbonyl]-9-(pyrimidin-4-ylmethyl)-9H-carbazole-4-carboxamide;

2-(dimethyl-1,2-oxazol-4-yl)-6-[(2R,6S)-2,6-dimethyl-morpholine-4-carbonyl]-9-(1-phenylethyl)-9H-carbazole-4-carboxamide;

2-(dimethyl-1,2-oxazol-4-yl)-6-[(2R,6S)-2,6-dimethyl-morpholine-4-carbonyl]-9-[(2-methoxyphenyl)methyl]-9H-carbazole-4-carboxamide;

9-[(2,3-difluorophenyl)methyl]-2-(dimethyl-1,2-oxazol-4-yl)-6-[(2R,6S)-2,6-dimethylmorpholine-4-carbonyl]-9H-carbazole-4-carboxamide;

9-[(2,5-difluorophenyl)methyl]-2-(dimethyl-1,2-oxazol-4-yl)-6-[(2R,6S)-2,6-dimethylmorpholine-4-carbonyl]-9H-carbazole-4-carboxamide;

9-[(2-cyanophenyl)methyl]-2-(dimethyl-1,2-oxazol-4-yl)-6-[(2R,6S)-2,6-dimethylmorpholine-4-carbonyl]-9H-carbazole-4-carboxamide;

9-[(3-cyanophenyl)methyl]-2-(dimethyl-1,2-oxazol-4-yl)-6-[(2R,6S)-2,6-dimethylmorpholine-4-carbonyl]-9H-carbazole-4-carboxamide;

2-(3,5-dimethylisoxazol-4-yl)-6-(cis-2,6-dimethylmorpholine-4-carbonyl)-9-(phenylsulfonyl)-9H-carbazole-4-carboxamide;

9-benzoyl-2-(3,5-dimethylisoxazol-4-yl)-6-(cis-2,6-dimethylmorpholine-4-carbonyl)-9H-carbazole-4-carboxamide;

9-benzyl-2-(3,5-dimethyl-4-isoxazolyl)-6-(4-morpholinylcarbonyl)-9H-carbazole-4-carboxamide;

9-benzyl-7-(dimethyl-1,2-oxazol-4-yl)-3-N,3-N-dimethyl-9H-carbazole-3, 5-dicarboxamide;

9-benzyl-2-(dimethyl-1,2-oxazol-4-yl)-6-(3,3-dimethyl-morpholine-4-carbonyl)-9H-carbazole-4-carboxamide;

9-benzyl-2-(dimethyl-1,2-oxazol-4-yl)-6-(4-ethylpiperidine-1-carbonyl)-9H-carbazole-4-carboxamide;

9-benzyl-2-(dimethyl-1,2-oxazol-4-yl)-6-(4-hydroxy-4-methylpiperidine-1-carbonyl)-9H-carbazole-4-carboxamide;

9-benzyl-2-(dimethyl-1,2-oxazol-4-yl)-6-(3-methoxyazetidine-1-carbonyl)-9H-carbazole-4-carboxamide;

9-benzyl-2-(dimethyl-1,2-oxazol-4-yl)-6-(3-hydroxyazetidine-1-carbonyl)-9H-carbazole-4-carboxamide;

9-benzyl-2-(dimethyl-1,2-oxazol-4-yl)-6-(2-methylazetidine-1-carbonyl)-9H-carbazole-4-carboxamide;

9-benzyl-2-(dimethyl-1,2-oxazol-4-yl)-6-(2-methylmorpholine-4-carbonyl)-9H-carbazole-4-carboxamide;

9-benzyl-2-(dimethyl-1,2-oxazol-4-yl)-6-(1,4-oxazepane-4-carbonyl)-9H-carbazole-4-carboxamide;

9-benzyl-2-(dimethyl-1,2-oxazol-4-yl)-6-[(2S)-2-methylmorpholine-4-carbonyl]-9H-carbazole-4-carboxamide;

9-benzyl-2-(dimethyl-1,2-oxazol-4-yl)-6-(3,3-dimethyl-pyrrolidine-1-carbonyl)-9H-carbazole-4-carboxamide;

9-benzyl-2-(dimethyl-1,2-oxazol-4-yl)-6-[(3S)-3-fluoropyrrolidine-1-carbonyl]-9H-carbazole-4-carboxamide;

9-benzyl-2-(dimethyl-1,2-oxazol-4-yl)-6-[(3R)-3-fluoropyrrolidine-1-carbonyl]-9H-carbazole-4-carboxamide;

9-benzyl-6-(3,3-difluoropyrrolidine-1-carbonyl)-2-(dimethyl-1,2-oxazol-4-yl)-9H-carbazole-4-carboxamide;

9-benzyl-2-(dimethyl-1,2-oxazol-4-yl)-6-[(2R)-2-methylmorpholine-4-carbonyl]-9H-carbazole-4-carboxamide;

9-benzyl-2-(dimethyl-1,2-oxazol-4-yl)-6-(4-hydroxy-2,2,6,6-tetramethylpiperidine-1-carbonyl)-9H-carbazole-4-carboxamide;

9-benzyl-2-(dimethyl-1,2-oxazol-4-yl)-6-(4-hydroxy-2-methylpiperidine-1-carbonyl)-9H-carbazole-4-carboxamide;

9-benzyl-2-(dimethyl-1,2-oxazol-4-yl)-6-(3-fluoroazetidine-1-carbonyl)-9H-carbazole-4-carboxamide;

9-benzyl-2-(dimethyl-1,2-oxazol-4-yl)-6-(pyrrolidine-1-carbonyl)-9H-carbazole-4-carboxamide;

9-benzyl-2-(dimethyl-1,2-oxazol-4-yl)-6-(4-hydroxypiperidine-1-carbonyl)-9H-carbazole-4-carboxamide;

9-benzyl-2-(dimethyl-1,2-oxazol-4-yl)-6-[4-(hydroxymethyl)piperidine-1-carbonyl]-9H-carbazole-4-carboxamide;

9-benzyl-2-(dimethyl-1,2-oxazol-4-yl)-6-(2,6-dimethyl-morpholine-4-carbonyl)-9H-carbazole-4-carboxamide;

9-benzyl-2-(dimethyl-1,2-oxazol-4-yl)-6-(4-methoxypiperidine-1-carbonyl)-9H-carbazole-4-carboxamide;

6-(azetidine-1-carbonyl)-9-benzyl-2-(dimethyl-1,2-oxazol-4-yl)-9H-carbazole-4-carboxamide;

9-benzyl-2-(dimethyl-1,2-oxazol-4-yl)-6-(3,3-dimethyl-piperidine-1-carbonyl)-9H-carbazole-4-carboxamide;

9-benzyl-2-(dimethyl-1,2-oxazol-4-yl)-6-(2-methylpiperidine-1-carbonyl)-9H-carbazole-4-carboxamide;
9-benzyl-2-(dimethyl-1,2-oxazol-4-yl)-6-(4-methylpiperidine-1-carbonyl)-9H-carbazole-4-carboxamide;
9-benzyl-2-(dimethyl-1,2-oxazol-4-yl)-6-(4-methylpiperazine-1-carbonyl)-9H-carbazole-4-carboxamide;
9-benzyl-7-(dimethyl-1,2-oxazol-4-yl)-3-N-[2-(morpholin-4-yl)ethyl]-9H-carbazole-3,5-dicarboxamide;
9-benzyl-2-(dimethyl-1,2-oxazol-4-yl)-6-(4,4-dimethyl-1,3-oxazolidine-3-carbonyl)-9H-carbazole-4-carboxamide;
9-benzyl-6-(3,3-difluoroazetidine-1-carbonyl)-2-(dimethyl-1,2-oxazol-4-yl)-9H-carbazole-4-carboxamide;
9-(2,6-difluorobenzyl)-2-(3,5-dimethyl-4-isoxazolyl)-6-(((3S)-3-fluoro-1-pyrrolidinyl)carbonyl)-9H-carbazole-4-carboxamide;
9-[(4-chlorophenyl)methyl]-2-(dimethyl-1,2-oxazol-4-yl)-6-[(3S)-3-fluoropyrrolidine-1-carbonyl]-9H-carbazole-4-carboxamide;
2-(dimethyl-1,2-oxazol-4-yl)-9-[(3-fluorophenyl)methyl]-6-[(3S)-3-fluoropyrrolidine-1-carbonyl]-9H-carbazole-4-carboxamide;
2-(dimethyl-1,2-oxazol-4-yl)-6-[(3S)-3-fluoropyrrolidine-1-carbonyl]-9-[(2-methoxyphenyl)methyl]-9H-carbazole-4-carboxamide;
2-(dimethyl-1,2-oxazol-4-yl)-6-[(3S)-3-fluoropyrrolidine-1-carbonyl]-9-[(4-methyl-1,3-thiazol-2-yl)methyl]-9H-carbazole-4-carboxamide;
2-(dimethyl-1,2-oxazol-4-yl)-6-[(3S)-3-fluoropyrrolidine-1-carbonyl]-9-(1-phenylethyl)-9H-carbazole-4-carboxamide;
2-(3,5-dimethyl-4-isoxazolyl)-6-((3-fluoro-1-azetidinyl)carbonyl)-9-(1-phenylethyl)-9H-carbazole-4-carboxamide;
9-[(4-chloro-3-fluorophenyl)methyl]-2-(dimethyl-1,2-oxazol-4-yl)-6-(3-fluoroazetidine-1-carbonyl)-9H-carbazole-4-carboxamide;
9-[(4-chloro-2-fluorophenyl)methyl]-2-(dimethyl-1,2-oxazol-4-yl)-6-(3-fluoroazetidine-1-carbonyl)-9H-carbazole-4-carboxamide;
2-(dimethyl-1,2-oxazol-4-yl)-6-(3-fluoroazetidine-1-carbonyl)-9-{1-[3-(trifluoromethyl)phenyl]ethyl}-9H-carbazole-4-carboxamide;
2-(dimethyl-1,2-oxazol-4-yl)-6-(3-fluoroazetidine-1-carbonyl)-9-{1-[2-(trifluoromethyl)phenyl]ethyl}-9H-carbazole-4-carboxamide;
9-(cyclobutylmethyl)-2-(dimethyl-1,2-oxazol-4-yl)-6-(3-fluoroazetidine-1-carbonyl)-9H-carbazole-4-carboxamide;
2-(dimethyl-1,2-oxazol-4-yl)-6-(3-fluoroazetidine-1-carbonyl)-9-[1-(4-fluorophenyl)ethyl]-9H-carbazole-4-carboxamide;
9-(cyclopropylmethyl)-2-(dimethyl-1,2-oxazol-4-yl)-6-(3-fluoroazetidine-1-carbonyl)-9H-carbazole-4-carboxamide;
2-(dimethyl-1,2-oxazol-4-yl)-6-(3-fluoroazetidine-1-carbonyl)-9-[(4-fluorophenyl)methyl]-9H-carbazole-4-carboxamide;
9-(1-(4-chlorophenyl)ethyl)-2-(3,5-dimethyl-4-isoxazolyl)-6-((3-fluoro-1-azetidinyl)carbonyl)-9H-carbazole-4-carboxamide;
9-(4-chlorobenzyl)-6-((3,3-difluoro-1-azetidinyl)carbonyl)-2-(3,5-dimethyl-4-isoxazolyl)-9H-carbazole-4-carboxamide;
6-((3,3-difluoro-1-azetidinyl)carbonyl)-2-(3,5-dimethyl-4-isoxazolyl)-9-(1-phenylethyl)-9H-carbazole-4-carboxamide, racemic;
6-((3,3-difluoro-1-azetidinyl)carbonyl)-2-(3,5-dimethyl-4-isoxazolyl)-9-(1-phenylethyl)-9H-carbazole-4-carboxamide, Enantiomer 1;
6-((3,3-difluoro-1-azetidinyl)carbonyl)-2-(3,5-dimethyl-4-isoxazolyl)-9-(1-phenylethyl)-9H-carbazole-4-carboxamide, Enantiomer 2;
9-(4-chlorobenzyl)-6-(3,3-difluoroazetidine-1-carbonyl)-2-(3,5-dimethylisoxazol-4-yl)-N-methyl-9H-carbazole-4-carboxamide;
9-(4-chlorobenzyl)-2-(3,5-dimethylisoxazol-4-yl)-6-(3-fluoroazetidine-1-carbonyl)-N-methyl-9H-carbazole-4-carboxamide;
2-(dimethyl-1,2-oxazol-4-yl)-6-(3-fluoroazetidine-1-carbonyl)-9-[(4-fluorophenyl)methyl]-N-methyl-9H-carbazole-4-carboxamide;
2-(dimethyl-1,2-oxazol-4-yl)-6-(3-fluoroazetidine-1-carbonyl)-9-[(3-fluorophenyl)methyl]-N-methyl-9H-carbazole-4-carboxamide;
9-[(2,6-difluorophenyl)methyl]-2-(dimethyl-1,2-oxazol-4-yl)-6-(3-fluoroazetidine-1-carbonyl)-N-methyl-9H-carbazole-4-carboxamide;
9-[(2,4-difluorophenyl)methyl]-2-(dimethyl-1,2-oxazol-4-yl)-6-(3-fluoroazetidine-1-carbonyl)-N-methyl-9H-carbazole-4-carboxamide;
9-[(2,3-difluorophenyl)methyl]-2-(dimethyl-1,2-oxazol-4-yl)-6-(3-fluoroazetidine-1-carbonyl)-N-methyl-9H-carbazole-4-carboxamide;
9-[(4-cyanophenyl)methyl]-2-(dimethyl-1,2-oxazol-4-yl)-6-(3-fluoroazetidine-1-carbonyl)-N-methyl-9H-carbazole-4-carboxamide;
9-[(4-chloro-3-fluorophenyl)methyl]-2-(dimethyl-1,2-oxazol-4-yl)-6-(3-fluoroazetidine-1-carbonyl)-N-methyl-9H-carbazole-4-carboxamide;
9-[(4-chloro-2-fluorophenyl)methyl]-2-(dimethyl-1,2-oxazol-4-yl)-6-(3-fluoroazetidine-1-carbonyl)-N-methyl-9H-carbazole-4-carboxamide;
9-[1-(4-chlorophenyl)ethyl]-2-(dimethyl-1,2-oxazol-4-yl)-6-(3-fluoroazetidine-1-carbonyl)-N-methyl-9H-carbazole-4-carboxamide;
2-(dimethyl-1,2-oxazol-4-yl)-6-(3-fluoroazetidine-1-carbonyl)-9-[1-(4-fluorophenyl)ethyl]-N-methyl-9H-carbazole-4-carboxamide;
2-(dimethyl-1,2-oxazol-4-yl)-6-(3-fluoroazetidine-1-carbonyl)-N-methyl-9-(1-phenylethyl)-9H-carbazole-4-carboxamide;
9-(cyclobutylmethyl)-2-(dimethyl-1,2-oxazol-4-yl)-6-(3-fluoroazetidine-1-carbonyl)-N-methyl-9H-carbazole-4-carboxamide;
9-(cyclopropylmethyl)-2-(dimethyl-1,2-oxazol-4-yl)-6-(3-fluoroazetidine-1-carbonyl)-N-methyl-9H-carbazole-4-carboxamide;
2-(3,5-dimethylisoxazol-4-yl)-6-(3-fluoroazetidine-1-carbonyl)-N-methyl-9-(pyridin-2-ylmethyl)-9H-carbazole-4-carboxamide;
9-benzyl-2-(3,5-dimethylisoxazol-4-yl)-6-(cis-2,6-dimethylmorpholine-4-carbonyl)-N-methyl-9H-carbazole-4-carboxamide;
9-benzyl-2-(3,5-dimethylisoxazol-4-yl)-6-(cis-2,6-dimethylmorpholine-4-carbonyl)-N,N-dimethyl-9H-carbazole-4-carboxamide;
6-((3,3-difluoro-1-azetidinyl)carbonyl)-2-(3,5-dimethyl-4-isoxazolyl)-N-methyl-9-(1-phenylethyl)-9H-carbazole-4-carboxamide;
6-((3,3-difluoro-1-azetidinyl)carbonyl)-2-(3,5-dimethyl-4-isoxazolyl)-N,N-dimethyl-9-(1-phenylethyl)-9H-carbazole-4-carboxamide;

2-(3,5-dimethyl-4-isoxazolyl)-6-((3-fluoro-1-azetidinyl)carbonyl)-9-(3-fluorobenzyl)-9H-carbazole-4-carbonitrile;
9-(4-fluorobenzyl)-2-(3-methyl-4-isoxazolyl)-6-(4-morpholinylcarbonyl)-9H-carbazole-4-carboxamide;
9-(4-fluorobenzyl)-2-(5-methylisoxazol-4-yl)-6-(morpholine-4-carbonyl)-9H-carbazole-4-carboxamide;
2-(3,5-dimethyl-4-isoxazolyl)-6-((3-fluoro-1-azetidinyl)carbonyl)-9-(4-fluorobenzyl)-N-propyl-9H-carbazole-4-carboxamide;
N-cyclopropyl-2-(dimethyl-1,2-oxazol-4-yl)-6-(3-fluoroazetidine-1-carbonyl)-9-[(4-fluorophenyl)methyl]-9H-carbazole-4-carboxamide;
2-(dimethyl-1,2-oxazol-4-yl)-N-ethyl-6-(3-fluoroazetidine-1-carbonyl)-9-[(4-fluorophenyl)methyl]-9H-carbazole-4-carboxamide;
2-(dimethyl-1,2-oxazol-4-yl)-6-(3-fluoroazetidine-1-carbonyl)-9-[(4-fluorophenyl)methyl]-N-(propan-2-yl)-9H-carbazole-4-carboxamide;
2-(dimethyl-1,2-oxazol-4-yl)-6-(3-fluoroazetidine-1-carbonyl)-9-[(4-fluorophenyl)methyl]-N-(2-methylpropyl)-9H-carbazole-4-carboxamide;
2-(dimethyl-1,2-oxazol-4-yl)-4,6-bis(3-fluoroazetidine-1-carbonyl)-9-[(4-fluorophenyl)methyl]-9H-carbazole;
9-Benzyl-2-(3,5-dimethyl-4-isoxazolyl)-6-(methylamino)-9H-carbazole-4-carboxamide;
9-benzyl-2-(3,5-dimethylisoxazol-4-yl)-6-(N-methylacetamido)-9H-carbazole-4-carboxamide;
9-benzyl-2-(dimethyl-1,2-oxazol-4-yl)-N-methyl-6-(N-methylacetamido)-9H-carbazole-4-carboxamide;
9-benzyl-2-(dimethyl-1,2-oxazol-4-yl)-N-methyl-6-(methylamino)-9H-carbazole-4-carboxamide;
6-(acetyl(2-fluoroethyl)amino)-9-benzyl-2-(3,5-dimethyl-4-isoxazolyl)-9H-carbazole-4-carboxamide;
6-amino-9-benzyl-2-(3,5-dimethyl-4-isoxazolyl)-9H-carbazole-4-carboxamide;
9-benzyl-2-(3,5-dimethyl-4-isoxazolyl)-6-(2-fluoroethylamino)-9H-carbazole-4-carboxamide;
9-benzyl-2-(dimethyl-1,2-oxazol-4-yl)-6-[(2-hydroxyethyl)amino]-9H-carbazole-4-carboxamide;
9-benzyl-6-[(cyanomethyl)amino]-2-(dimethyl-1,2-oxazol-4-yl)-9H-carbazole-4-carboxamide;
9-benzyl-6-[(2,2-difluoroethyl)amino]-2-(dimethyl-1,2-oxazol-4-yl)-9H-carbazole-4-carboxamide;
9-benzyl-6-[bis(2-hydroxyethyl)amino]-2-(dimethyl-1,2-oxazol-4-yl)-9H-carbazole-4-carboxamide;
9-benzyl-2-(dimethyl-1,2-oxazol-4-yl)-6-(dimethylamino)-N-methyl-9H-carbazole-4-carboxamide;
6-acetamido-9-benzyl-2-(3,5-dimethyl-4-isoxazolyl)-9H-carbazole-4-carboxamide;
9-benzyl-2-(dimethyl-1,2-oxazol-4-yl)-6-methanesulfonamido-9H-carbazole-4-carboxamide;
methyl N-[9-benzyl-5-carbamoyl-7-(dimethyl-1,2-oxazol-4-yl)-9H-carbazol-3-yl]carbamate;
9-benzyl-2-(dimethyl-1,2-oxazol-4-yl)-6-(oxane-4-amido)-9H-carbazole-4-carboxamide;
9-benzyl-2-(dimethyl-1,2-oxazol-4-yl)-6-[(morpholine-4-carbonyl)amino]-9H-carbazole-4-carboxamide;
9-benzyl-2-(dimethyl-1,2-oxazol-4-yl)-6-[(dimethylcarbamoyl)amino]-9H-carbazole-4-carboxamide
9-benzyl-2-(dimethyl-1,2-oxazol-4-yl)-6-[(methylcarbamoyl)amino]-9H-carbazole-4-carboxamide;
9-benzyl-6-cyclopentaneamido-2-(dimethyl-1,2-oxazol-4-yl)-9H-carbazole-4-carboxamide;
2-(3,5-dimethyl-4-isoxazolyl)-9-(4-fluorobenzyl)-6-(2-oxo-1,3-oxazinan-3-yl)-9H-carbazole-4-carboxamide;
2-(3,5-dimethyl-4-isoxazolyl)-9-(4-fluorobenzyl)-6-(2-oxo-1,3-oxazolidin-3-yl)-9H-carbazole-4-carboxamide;
2-(3,5-dimethyl-4-isoxazolyl)-6-(5,5-dimethyl-2-oxo-1,3-oxazinan-3-yl)-9-(4-fluorobenzyl)-9H-carbazole-4-carboxamide;
2-(3,5-dimethyl-4-isoxazolyl)-N-ethyl-9-(4-fluorobenzyl)-6-(2-oxo-1,3-oxazinan-3-yl)-9H-carbazole-4-carboxamide;
9-benzyl-2-(3,5-dimethyl-4-isoxazolyl)-6-(2-oxo-1,3-oxazinan-3-yl)-9H-carbazole-4-carboxamide;
9-(4-chlorobenzyl)-2-(3,5-dimethyl-4-isoxazolyl)-6-(2-oxo-1,3-oxazinan-3-yl)-9H-carbazole-4-carboxamide;
2-(3,5-dimethyl-4-isoxazolyl)-6-(2-oxo-1,3-oxazinan-3-yl)-9-(1-phenylethyl)-9H-carbazole-4-carboxamide;
9-(2, 5-difluorobenzyl)-2-(3,5-dimethyl-4-isoxazolyl)-6-(2-oxo-1,3-oxazinan-3-yl)-9H-carbazole-4-carboxamide;
9-benzyl-2-(3,5-dimethyl-4-isoxazolyl)-6-(5, 5-dimethyl-2-oxo-1,3-oxazinan-3-yl)-9H-carbazole-4-carboxamide;
9-benzyl-2-(3,5-dimethyl-4-isoxazolyl)-6-(2-oxo-1,3-oxazolidin-3-yl)-9H-carbazole-4-carboxamide;
9-(4-chlorobenzyl)-2-(3,5-dimethyl-4-isoxazolyl)-6-(2-oxo-1,3-oxazolidin-3-yl)-9H-carbazole-4-carboxamide;
2-(3,5-dimethyl-4-isoxazolyl)-6-(2-oxo-1,3-oxazolidin-3-yl)-9-(1-phenylethyl)-9H-carbazole-4-carboxamide;
9-(4-chloro-3-fluorobenzyl)-2-(3,5-dimethyl-4-isoxazolyl)-6-(2-oxo-1,3-oxazolidin-3-yl)-9H-carbazole-4-carboxamide;
9-benzyl-2-(3,5-dimethyl-4-isoxazolyl)-N-ethyl-6-(2-oxo-1,3-oxazinan-3-yl)-9H-carbazole-4-carboxamide;
9-(4-chlorobenzyl)-2-(3,5-dimethyl-4-isoxazolyl)-N-ethyl-6-(2-oxo-1,3-oxazinan-3-yl)-9H-carbazole-4-carboxamide;
2-(3,5-dimethyl-4-isoxazolyl)-N-ethyl-6-(2-oxo-1,3-oxazinan-3-yl)-9-(1-phenylethyl)-9H-carbazole-4-carboxamide;
2-(3,5-dimethyl-4-isoxazolyl)-N-methyl-6-(2-oxo-1,3-oxazinan-3-yl)-9H-carbazole-4-carboxamide;
9-benzyl-2-(3,5-dimethyl-4-isoxazolyl)-N-methyl-6-(2-oxo-1,3-oxazinan-3-yl)-9H-carbazole-4-carboxamide;
9-(4-chlorobenzyl)-2-(3,5-dimethyl-4-isoxazolyl)-N-methyl-6-(2-oxo-1,3-oxazinan-3-yl)-9H-carbazole-4-carboxamide;
2-(3,5-dimethyl-4-isoxazolyl)-9-(4-fluorobenzyl)-N-methyl-6-(2-oxo-1,3-oxazinan-3-yl)-9H-carbazole-4-carboxamide;
9-(4-chloro-3-fluorobenzyl)-2-(3,5-dimethyl-4-isoxazolyl)-N-methyl-6-(2-oxo-1,3-oxazinan-3-yl)-9H-carbazole-4-carboxamide;
2-(3,5-dimethyl-4-isoxazolyl)-N-methyl-6-(2-oxo-1,3-oxazinan-3-yl)-9-(1-phenylethyl)-9H-carbazole-4-carboxamide;
2-(3,5-dimethyl-4-isoxazolyl)-6-(1,1-dioxido-2-isothiazolidinyl)-9-(4-fluorobenzyl)-9H-carbazole-4-carboxamide;
2-(3,5-dimethyl-4-isoxazolyl)-6-(1,1-dioxido-1,2-thiazinan-2-yl)-9-(4-fluorobenzyl)-9H-carbazole-4-carboxamide;
2-(3,5-dimethyl-4-isoxazolyl)-6-methoxy-9-(1-phenylethyl)-9H-carbazole-4-carboxamide;
9-benzyl-2-(3,5-dimethyl-4-isoxazolyl)-6-methoxy-9H-carbazole-4-carboxamide;
9-benzyl-2-(3,5-dimethyl-4-isoxazolyl)-6-hydroxy-9H-carbazole-4-carboxamide;

2-(3,5-dimethyl-4-isoxazolyl)-6-methoxy-9-(1-phenylethyl)-9H-carbazole-4-carboxamide, Enantiomer 1;
2-(3,5-dimethyl-4-isoxazolyl)-6-methoxy-9-(1-phenylethyl)-9H-carbazole-4-carboxamide, Enantiomer 2;
9-benzyl-2-(3,5-dimethyl-4-isoxazolyl)-6-(methylsulfonyl)-9H-carbazole-4-carboxamide;
Methyl 9-benzyl-5-cyano-7-(3,5-dimethyl-4-isoxazolyl)-9H-carbazole-2-carboxylate;
Methyl 9-benzyl-5-carbamoyl-7-(3,5-dimethyl-4-isoxazolyl)-9H-carbazole-2-carboxylate;
9-benzyl-2-(3,5-dimethyl-4-isoxazolyl)-7-(1-hydroxy-1-methylethyl)-9H-carbazole-4-carbonitrile;
9-Benzyl-2-(3,5-dimethyl-4-isoxazolyl)-7-(1-hydroxy-1-methylethyl)-9H-carbazole-4-carboxamide;
9-Benzyl-5-cyano-7-(3,5-dimethyl-4-isoxazolyl)-9H-carbazole-2-carboxylic acid;
9-Benzyl-2-(3,5-dimethyl-4-isoxazolyl)-7-(morpholine-4-carbonyl)-9H-carbazole-4-carbonitrile;
9-Benzyl-2-(3,5-dimethyl-4-isoxazolyl)-7-(morpholine-4-carbonyl)-9H-carbazole-4-carboxamide;
9-Benzyl-7-(3,5-dimethyl-4-isoxazolyl)-N~2~-methoxy-N~2~-methyl-9H-carbazole-2,5-dicarboxamide;
9-Benzyl-2-(3,5-dimethyl-4-isoxazolyl)-7-(3-fluorobenzoyl)-9H-carbazole-4-carboxamide;
5-cyano-7-(3,5-dimethyl-4-isoxazolyl)-9-(diphenylmethyl)-9H-carbazole-2-carboxylate;
Methyl 5-carbamoyl-7-(3,5-dimethyl-4-isoxazolyl)-9-(diphenylmethyl)-9H-carbazole-2-carboxylate;
5-Cyano-7-(3,5-dimethyl-4-isoxazolyl)-9-(diphenylmethyl)-9H-carbazole-2-carboxylic acid;
5-Cyano-7-(3,5-dimethyl-4-isoxazolyl)-9-(diphenylmethyl)-9H-carbazole-2-carboxamide;
7-(3,5-Dimethyl-4-isoxazolyl)-9-(diphenylmethyl)-N~2~,N~2~-dimethyl-9H-carbazole-2,5-dicarboxamide;
2-(3,5-Dimethyl-4-isoxazolyl)-9-(diphenylmethyl)-7-(4-morpholinylcarbonyl)-9H-carbazole-4-carboxamide;
2-(3,5-dimethyl-4-isoxazolyl)-7-(1-hydroxy-1-methylethyl)-9-(tetrahydro-2H-pyran-4-ylmethyl)-9H-carbazole-4-carboxamide;
2-(Dimethyl-1,2-oxazol-4-yl)-7-(2-hydroxypropan-2-yl)-9-[(R)-oxan-4-yl(phenyl)methyl]-9H-carbazole-4-carboxamide, Ent. A;
2-(Dimethyl-1,2-oxazol-4-yl)-7-(2-hydroxypropan-2-yl)-9-[(R)-oxan-4-yl(phenyl)methyl]-9H-carbazole-4-carboxamide, Ent. B;
2-(dimethyl-1,2-oxazol-4-yl)-7-(2-hydroxypropan-2-yl)-9-{4,4,4-trifluoro-1-[2-(trifluoromethyl)phenyl]butyl}-9H-carbazole-4-carboxamide,
2-(dimethyl-1,2-oxazol-4-yl)-7-(2-hydroxypropan-2-yl)-9-{4,4,4-trifluoro-1-[2-(trifluoromethyl)phenyl]butyl}-9H-carbazole-4-carboxamide;
9-[1-(2-chlorophenyl)-4,4,4-trifluorobutyl]-2-(dimethyl-1,2-oxazol-4-yl)-7-(2-hydroxypropan-2-yl)-9H-carbazole-4-carboxamide;
9-[1-(2-chlorophenyl)-4,4,4-trifluorobutyl]-2-(dimethyl-1,2-oxazol-4-yl)-7-(2-hydroxypropan-2-yl)-9H-carbazole-4-carboxamide;
2-(dimethyl-1,2-oxazol-4-yl)-7-(2-hydroxypropan-2-yl)-9-[oxan-4-yl(2,4,6-trifluorophenyl)methyl]-9H-carbazole-4-carboxamide;
2-(dimethyl-1,2-oxazol-4-yl)-7-(2-hydroxypropan-2-yl)-9-[oxan-4-yl(2,4,6-trifluorophenyl)methyl]-9H-carbazole-4-carboxamide;
9-[(2,6-difluorophenyl)(oxan-4-yl)methyl]-2-(dimethyl-1,2-oxazol-4-yl)-7-(2-hydroxypropan-2-yl)-9H-carbazole-4-carboxamide;
9-[(2,6-difluorophenyl)(oxan-4-yl)methyl]-2-(dimethyl-1,2-oxazol-4-yl)-7-(2-hydroxypropan-2-yl)-9H-carbazole-4-carboxamide;
2-(dimethyl-1,2-oxazol-4-yl)-7-(2-hydroxypropan-2-yl)-9-[4,4,4-trifluoro-1-(pyridin-2-yl)butyl]-9H-carbazole-4-carboxamide;
2-(dimethyl-1,2-oxazol-4-yl)-7-(2-hydroxypropan-2-yl)-9-[4,4,4-trifluoro-1-(pyridin-2-yl)butyl]-9H-carbazole-4-carboxamide;
2-(dimethyl-1,2-oxazol-4-yl)-9-[(2-fluorophenyl)(oxan-4-yl)methyl]-7-(2-hydroxypropan-2-yl)-9H-carbazole-4-carboxamide;
2-(dimethyl-1,2-oxazol-4-yl)-9-[(2-fluorophenyl)(oxan-4-yl)methyl]-7-(2-hydroxypropan-2-yl)-9H-carbazole-4-carboxamide;
2-(dimethyl-1,2-oxazol-4-yl)-7-(2-hydroxypropan-2-yl)-9-[(4-methoxyphenyl)(oxan-4-yl)methyl]-9H-carbazole-4-carboxamide;
2-(dimethyl-1,2-oxazol-4-yl)-7-(2-hydroxypropan-2-yl)-9-[(4-methoxyphenyl)(oxan-4-yl)methyl]-9H-carbazole-4-carboxamide;
2-(dimethyl-1,2-oxazol-4-yl)-7-(2-hydroxypropan-2-yl)-9-[(3-methoxyphenyl)(oxan-4-yl)methyl]-9H-carbazole-4-carboxamide;
2-(dimethyl-1,2-oxazol-4-yl)-7-(2-hydroxypropan-2-yl)-9-[(3-methoxyphenyl)(oxan-4-yl)methyl]-9H-carbazole-4-carboxamide;
9-[(2,4-difluorophenyl)(oxan-4-yl)methyl]-2-(dimethyl-1,2-oxazol-4-yl)-7-(2-hydroxypropan-2-yl)-9H-carbazole-4-carboxamide;
9-[(2,4-difluorophenyl)(oxan-4-yl)methyl]-2-(dimethyl-1,2-oxazol-4-yl)-7-(2-hydroxypropan-2-yl)-9H-carbazole-4-carboxamide;
2-(dimethyl-1,2-oxazol-4-yl)-8-fluoro-9-(1,1,1,7,7,7-hexafluoroheptan-4-yl)-7-(2-hydroxypropan-2-yl)-9H-carbazole-4-carboxamide;
(Dimethyl-1,2-oxazol-4-yl)-9-[(4-fluorophenyl)(oxan-4-yl)methyl]-7-(2-hydroxypropan-2-yl)-9H-carbazole-4-carboxamide, Ent. A;
(Dimethyl-1,2-oxazol-4-yl)-9-[(4-fluorophenyl)(oxan-4-yl)methyl]-7-(2-hydroxypropan-2-yl)-9H-carbazole-4-carboxamide, Ent. B;
2-(Dimethyl-1,2-oxazol-4-yl)-9-[(1-fluorocyclobutyl)(phenyl)methyl]-7-(2-hydroxypropan-2-yl)-9H-carbazole-4-carboxamide, Ent. A;
2-(Dimethyl-1,2-oxazol-4-yl)-9-[(1-fluorocyclobutyl)(phenyl)methyl]-7-(2-hydroxypropan-2-yl)-9H-carbazole-4-carboxamide, Ent. B; 2-(Dimethyl-1,2-oxazol-4-yl)-8-fluoro-9-[(4-fluorophenyl)(oxan-4-yl)methyl]-7-(2-hydroxypropan-2-yl)-9H-carbazole-4-carboxamide, Ent. A;
2-(Dimethyl-1,2-oxazol-4-yl)-8-fluoro-9-[(4-fluorophenyl)(oxan-4-yl)methyl]-7-(2-hydroxypropan-2-yl)-9H-carbazole-4-carboxamide, Ent. B;
rel-2-(dimethyl-1,2-oxazol-4-yl)-9-{[(1R,2S,4S)-2-fluoro-7-oxabicyclo[2.2.1]heptan-2-yl]methyl}-7-(2-hydroxypropan-2-yl)-9H-carbazole-4-carboxamide;
9-[(4,4-difluorocyclohexyl)(phenyl)methyl]-2-(dimethyl-1,2-oxazol-4-yl)-8-fluoro-7-(2-hydroxypropan-2-yl)-9H-carbazole-4-carboxamide, Ent. A;
9-[(4,4-difluorocyclohexyl)(phenyl)methyl]-2-(dimethyl-1,2-oxazol-4-yl)-8-fluoro-7-(2-hydroxypropan-2-yl)-9H-carbazole-4-carboxamide, Ent. B;
2-(Dimethyl-1,2-oxazol-4-yl)-7-(2-methoxypropan-2-yl)-9-[(S)-oxan-4-yl(phenyl)methyl]-9H-carbazole-4-carboxamide;

2-(Dimethyl-1,2-oxazol-4-yl)-9-[(S)-oxan-4-yl(phenyl)
methyl]-7-(propan-2-yl)-9H-carbazole-4-carboxamide;

2-(dimethyl-1,2-oxazol-4-yl)-8-fluoro-7-(2-hydroxypropan-2-yl)-9-[4,4,4-trifluoro-1-phenylbutyl]-9H-carbazole-4-carboxamide, Ent. A;

2-(dimethyl-1,2-oxazol-4-yl)-8-fluoro-7-(2-hydroxypropan-2-yl)-9-[4,4,4-trifluoro-1-phenylbutyl]-9H-carbazole-4-carboxamide, Ent. B;

2-(1,4-Dimethyl-1H-1,2,3-triazol-5-yl)-7-(2-hydroxypropan-2-yl)-9-(phenyl(tetrahydro-2H-pyran-4-yl)methyl)-9H-carbazole-4-carboxamide, Ent. A;

2-(1,4-Dimethyl-1H-1,2,3-triazol-5-yl)-7-(2-hydroxypropan-2-yl)-9-(phenyl(tetrahydro-2H-pyran-4-yl)methyl)-9H-carbazole-4-carboxamide, Ent. B;

or a pharmaceutically acceptable salt, tautomer or stereoisomer thereof.

12. A compound according to claim 1 wherein the IC50 in the FRET assay disclosed is less than 50 nm.

13. A pharmaceutical composition which comprises one or more compounds according to claim 1 or a pharmaceutically acceptable salt thereof and one or more pharmaceutically acceptable carriers, diluents or excipients.

14. A compound according to claim 1 or a pharmaceutically acceptable salt thereof for use in the treatment of diseases or conditions for which a bromodomain inhibitor is indicated.

15. A compound or a pharmaceutically acceptable salt thereof for use according to claim 14, wherein the disease or condition is small cell lung cancer.

* * * * *

UNITED STATES PATENT AND TRADEMARK OFFICE
CERTIFICATE OF CORRECTION

PATENT NO. : 9,492,460 B2  
APPLICATION NO. : 14/190477  
DATED : November 15, 2016  
INVENTOR(S) : Poss et al.

Page 1 of 1

It is certified that error appears in the above-identified patent and that said Letters Patent is hereby corrected as shown below:

In the Claims

Claim 2, In Column 217, Line 51:
Before "a" insert -- or --.

Claim 11, In Column 238, Line 49:
After "B;" delete "2-(Dimethyl-1,2-oxazol-" and insert the same on Column 238, Line 50 as a same line.

Signed and Sealed this
Twenty-third Day of May, 2017

Michelle K. Lee
*Director of the United States Patent and Trademark Office*